United States Patent
Edwards et al.

(10) Patent No.: US 7,977,352 B2
(45) Date of Patent: Jul. 12, 2011

(54) TRIAZOLOPYRIDINE COMPOUNDS USEFUL FOR THE TREATMENT OF DEGENERATIVE AND INFLAMMATORY DISEASES

(75) Inventors: Paul John Edwards, Laval (CA); Wolfgang Schmidt, Saffron Walden (GB); Veronique Birault, Hertford (GB); Friedrich Erich Karl Kroll, Mechelen (BE); Andrew Burritt, San Diego, CA (US); Xueliang Tao, San Diego, CA (US); Martin James Inglis Andrews, Mechelen (BE); Sébastien Laurent Xavier Martina, Mechelen (BE)

(73) Assignee: Galapagos NV, Mechelen (BE)

( * ) Notice: Subject to any disclaimer, the term of this patent is extended or adjusted under 35 U.S.C. 154(b) by 0 days.

(21) Appl. No.: 11/998,817

(22) Filed: Nov. 30, 2007

(65) Prior Publication Data
US 2009/0105242 A1 Apr. 23, 2009

Related U.S. Application Data

(60) Provisional application No. 60/868,144, filed on Dec. 1, 2006.

(51) Int. Cl.
*A61K 31/44* (2006.01)
(52) U.S. Cl. ........ 514/300; 544/127; 544/333; 544/362; 546/121; 546/268.1; 548/375.1; 548/503
(58) Field of Classification Search .................. 514/300; 544/127, 333, 362; 546/121, 268.1; 548/375.1, 548/503
See application file for complete search history.

(56) References Cited

U.S. PATENT DOCUMENTS

| 6,919,341 B2 | 7/2005 | Paruch et al. |
| 7,576,085 B2 | 8/2009 | Guzi et al. |
| 2007/0117804 A1 | 5/2007 | Zhao et al. |
| 2009/0048245 A1 | 2/2009 | Edwards et al. |

FOREIGN PATENT DOCUMENTS

| WO | 0117999 | 3/2001 |
| WO | 2004014908 | 2/2004 |
| WO | 2005070927 | 8/2005 |
| WO | 2006004702 | 1/2006 |
| WO | 2007131991 | 11/2007 |
| WO | 2007138072 | 12/2007 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, New York: John Wiley & Sons, 1996, vol. 1, 975-976.*

Andreakos E, et al. (2003). Arthritis Rheum. 48: 1901-12."Heterogeneous requirement of IkB kinase 2 for inflammatory cytokine and matrix metalloproteinase production in RA".
Blonska M. et al. (2005) J. Biol. Chem. 280: 43056-43063. "TAK1 Is Recruited to the Tumor Necrosis Factor-(TNF-) Receptor 1 Complex in a Receptor-interacting Protein (RIP) . . . ".
Boutros M. at al. (2002) Dev. Cell 3(5): 711-722. "Sequential activation of signaling pathways during innate immune responses in Drosophila.".
Choy EH, Panayi GS. (2001). N Engl J Med. 344: 907-16. "Cytokine pathways and joint inflammation in rheumatoid arthritis."
Coussens LM, et al. (2002). Science 295: 2387-92. "Matrix metalloproteinase inhibitors and cancer: trials and tribulations."
Creemers EE, et al. (2001). Circ Res. 2001 89:201-10. "Matrix metalloproteinase inhibition after myocardial infarction."
Cunnane G, et al. (2001). Arthritis Rheum 44: 2263-74. "Early joint erosions and serum levels of matrix metalloproteinase 1, matrix metalloproteinase 3, . . . ".
Dong W. et al. (2006). J. Biol. Chem. 281: 26029-26040. The IRAK-1-BCL10-MALT1-TRAF6-TAK1 Cascade Mediates Signaling to NF-B from Toll-like receptor 4.
Edwards J. C.W. et al. (2004) N Engl J Med. 350:2572-2581. "Efficacy of B-cell-targeted therapy with rituximab in patients with RA."
Firestein GS. (2003). Nature. 423:356-61. "Evolving concepts of rheumatoid arthritis."
Gapski R, et al. (2004). J Periodontol. 75:441-52. "Effect of Systemic Matrix Metalloproteinase Inhibition on Periodontal Wound Repair: A Proof of Concept Trial."
Gomez-Reino JJ et al. (2003). Arthritis Rheum. 48: 2122-7. "Treatment of rheumatoid arthritis with tumor necrosis factor inhibitors . . . ".
Huang H. et al. (2006). Cell Death Differ. 13:1879-1891. "Osteoclast differentiation requires TAK1 and MKK6 for NFATc1 induction and NF-κB transactivation by RANKL".
Irie T et al. (2000) FEBS Lett. 467:160-164. "TAK1 mediates an activation signal from toll-like receptor(s) to nuclear factor-κB in lipopolysaccharide-stimulated macrophages."
Klatt AR et al. (2006) Biomedicine&Pharmacotherapy 60:55-61. "TAK1 downregulation reduces IL-1β induced expression of MMP13, MMP1 and TNF-alpha."

(Continued)

*Primary Examiner* — James O Wilson
*Assistant Examiner* — Douglas M Willis
(74) *Attorney, Agent, or Firm* — Klauber & Jackson LLC

(57) ABSTRACT

Novel triazolopyridine compounds are disclosed that have a formula represented by the following:

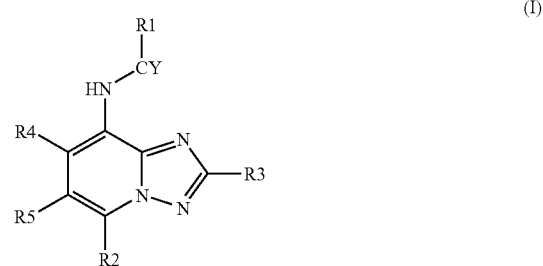

The compounds may be prepared as pharmaceutical compositions, and may be used for the prevention and treatment of a variety of conditions in mammals including humans, including by way of non-limiting example, ECM degradation, joint degradation and/or inflammation, and others.

32 Claims, 3 Drawing Sheets

OTHER PUBLICATIONS

Kremer JM. et al. (2003) N Engl J Med. 349:1907-1915. "Treatment of RA by selective inhibition of T-cell activation with fusion protein CTLA4Ig."

Lee DM, Weinblatt ME (2001). Lancet. 358: 903-11. "Rheumatoid arthritis."

Muzikami J. et al. (2002) Mol. Cell Biol. 22: 992-1000. "Receptor Activator of NF-B Ligand (RANKL) Activates TAK1 Mitogen-Activated Protein Kinase . . .".

New L. et al. (2003) Mol Biol Cell. 14(6):2603-16. "Regulation of PRAK subcellular location by p38 MAP kinases . . .".

Ninomiya-Tsuji J. et al. (1999). Nature 398: 252-256. "The kinase TAK1 can activate the NIK-IκB as well as the MAP kinase cascade in the IL-1 signalling pathway."

O'Dell JR et al. (2002). Arthritis Rheum. 46:1164-70. "Treatment of RA with methotrexate and hydroxychloroquine, methotrexate and sulfasalazine, . . .".

O'Dell JR. (2004) N Engl J Med. 350(25):2591-602. "Therapeutic strategies for rheumatoid arthritis."

Reif S. et al. (2005) Digestion. 71:124-130. "Matrix metalloproteinases 2 and 9 are markers of inflammation but not of the degree of fibrosis in chornic hepatitis C".

Rosenberg GA. (2002). Glia. 39:279-91. "Matrix metalloproteinases in neuroinflammation."

Sakurai H. et al. (1999). J. Biol. Chem. 274: 10641-10648. "Functional Interactions of Transforming Growth Factor—activated Kinase 1 with IB Kinases to Stimulate NF-B . . . ".

Sato S. et al. (2005) Nat. Immunol. 6: 1087-1095. "Essential function for the kinase TAK1 in innate and adaptive immune responses".

Schanstra JP. et al. (2002) J Clin Invest. 110:371-9. "In vivo bradykinin B2 receptor activation reduces renal fibrosis."

Shi Y et al. (2003). Mol Cell Biol. 23:7732-41. "Elimination of protein kinase MK5/PRAK activity by targeted homologous recombination."

Shibuya H. et al. (1998). EMBO J. 17: 1019-1028. "Role of TAK1 and TAB1 in BMP signaling in early Xenopus development."

Shim JH. et al. (2005) Genes Dev. 19:2668-2681. "TAK1, but not TAB1 or TAB2, plays an essential role in multiple signaling pathways in vivo."

Smolen JS, Steiner G. (2003). Nat Rev Drug Discov. 2: 473-88. "Therapeutic strategies for rheumatoid arthritis."

St. Clair E.W. et al. (2004). Arthritis Rheum. 50 :3432-43.Combination of infliximab and methotrexate therapy for early rheumatoid arthritis: a randomized, controlled trial.

Suzuki et al. (2004). Treat Respir Med. 3:17-27. "Matrix metalloproteinases in the pathogenesis of asthma and COPD."

Vidal S. et al. (2001). Genes & Dev. 15: 1900-1912. "Mutations in the Drosophila dTAK1 gene reveal a conserved function for MAPKKKs . . . ".

Wan YY. et al. (2006). Nat. Immunol. 7: 851-858. "The kinase TAK1 integrates antigen and cytokine receptor signaling for T cell development, survival and function."

Yamaguchi K et al. (1995). Science 270: 2008-2011. "Identification of a Member of the MAPKKK Family as a Potential Mediator of TGF-Signal Transduction."

Yang YH et al. (2004). Arthritis Rheum. 50:976-84."Modulation of inflammation and response to dexamethasone by Annexin 1 in antigen-induced arthritis."

\* cited by examiner

Increased expression of MMP1 by SFs triggered with cytokines involved in rheumatoid arthritis pathology.

TRIAZOLOPYRIDINE COMPOUNDS USEFUL FOR THE TREATMENT OF DEGENERATIVE AND INFLAMMATORY DISEASES

RELATED APPLICATIONS

The present application claims the benefit under 35 U.S.C. §119 of U.S. Provisional Application No. 60/868,144, filed Dec. 1, 2006, the contents of which is hereby incorporated by reference in its entirety.

BACKGROUND OF THE INVENTION

1. Field of Invention

The present invention relates to a class of triazolopyridine compounds capable of binding to the active site of a serine/threonine kinase, and which can be used to treat conditions involving the degradation of extra-cellular matrix (ECM), such as joint degeneration and diseases involving such degradation and/or inflammation.

2. Description of the Related Art

Diseases involving the degradation of extra-cellular matrix include, but are not limited to, psoriatic arthritis, juvenile arthritis, early arthritis, reactive arthritis, osteoarthritis, ankylosing spondylitis, osteoporosis, musculoskeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, and ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

It is widely accepted that RA is an auto-immune disease, the initial trigger(s) mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). As the disease progresses, the cellular activation and cytokine production cascade becomes self-perpetuating. At this early stage, the destruction of joint structures is already very clear. Thirty percent of the patients have radiographic evidence of bone erosions at the time of diagnosis and this proportion increases to 60 percent after two years.

Histological analysis of the joints of RA patients clearly evidences the mechanisms involved in the RA-associated degradative processes (FIG. 1). This analysis shows that the main effector responsible for RA-associated joint degradation is the pannus; whereas the synovial fibroblast (SF), by producing diverse proteolytic enzymes, is the prime driver of cartilage and bone erosion. A joint classically contains two adjacent bones that articulate on a cartilage layer, surrounded by the synovial membrane and joint capsule. In the advanced RA patient, the synovium of the joint increases in size to form the pannus, due to the proliferation of the synovial fibroblasts and the infiltration of mononuclear cells such as T-cells, B-cells, monocytes, macrophages and neutrophils. The pannus mediates the degradation of the adjacent cartilage, leading to the narrowing of the joint space, and has the potential to invade adjacent bone and cartilage. As bone and cartilage tissues are composed mainly of collagen type I or II, respectively, the pannus' destructive and invasive properties are mediated by the secretion of collagenolytic proteases, principally the matrix metalloproteinases (MMPs). The erosion of the bone under and adjacent to the cartilage is also part of the RA process, and results principally from the presence of osteoclasts at the interface of bone and pannus. Osteoclasts are multinucleated cells that, upon adhesion to the bone tissue, form a closed compartment, within which the osteoclasts secrete proteases (cathepsin K, MMP9) that degrade the bone tissue. The osteoclast population in the joint is abnormally increased by osteoclast formation from precursor cells induced by the secretion of the receptor activator of NFκB ligand (RANKL) by activated SFs and T-cells.

Various collagen types have a key role in defining the stability of the extracellular matrix (ECM). Collagen type I and collagen type II, for example, are the main components of bone and cartilage, respectively. Collagen proteins typically organize into multimeric structures referred to as collagen fibrils. Native collagen fibrils are very resistant to proteolytic cleavage. Only a few types of ECM-degrading proteins have been reported to have the capacity to degrade native collagen: MMPs and cathepsins. Among the cathepsins, cathepsin K, which is active mainly in osteoclasts, is the best characterized. Among the MMPs, MMP1, MMP2, MMP8 MMP13 and MMP14 are known to have collagenolytic properties. The correlation between an increased expression of MMP1 by SFs and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, musculoskeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reif et al., 2005), cardio-vascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

Transforming growth factor-β activated kinase 1 (TAK1), is a member of the mitogen-activated protein kinase kinase kinase (MAP3K) family, originally identified as a key regulator of MAP kinase activation in TGFβ/BMP signaling (Yamaguchi et al. 1995; Shibuya et al. 1998). Later studies have reported that Drosophila TAK1 is required for both c-jun N-terminal kinase and NFκB activation in response to immune challenge by gram-negative bacteria infection (Vidal et al., 2001; Boutros et al., 2002). TAK1 has also been shown to function as a critical upstream molecule of NFκB and MAPK signaling in various mammalian cell types after stimulation with IL1, TNF and lipopolysaccharide, which activates Toll-like receptor (TLR) signaling (Ninomiya-Tsuji et al., 1999; Sakurai et al., 1999; Irie et al., 2000; Blonska et al., 2005; Shim et al., 2005; Dong et al., 2006). In addition, TAK1 was shown to be required for RANKL induced osteoclast differentiation (Mizukami et al., 2002; Huang et al., 2006). In these signaling cascades, TAK1 is recruited to TRAF6 complexes in response to IL1R, TLR and RANKL signaling or to TRAF2 complexes in response to TNFR stimulation. Activated TAK1 phosphorylates MAPK kinases (MAP2K) MKK4 and MKK3/6, which in turn can activate JNK and p38 mitogen-activated protein kinase, leading to the activation of the activator protein 1 (AP1) transcription factor. Furthermore, TAK1 activates IκB kinase (IKK) signaling pathway, leading to the nuclear translocation of NFκB. Furthermore, studies with mice having B-cell specific or T-cell specific TAK1 deficiencies revealed that TAK1 was indispensable for cellular responses to B cell receptor cross-linking and T cell development, survival and function (Sato et al., 2005; Wan et al., 2006). It has also recently been shown that siRNA-mediated knock-down of TAK1 in the human SW1353 chondrosarcoma cell line significantly reduced IL1 triggered expression of MMP1 and MMP13, enzymes involved in ECM degradation in arthritis (Klatt et al. 2006). Taken together, these findings suggest critical roles for TAK1 in inflammatory and immunological responses.

Since TAK1 is a key molecule in pro-inflammatory signaling pathways, TAK1 inhibition can be expected to be effective in diseases associated with inflammation and tissue destruction such as rheumatoid arthritis.

The current therapies for RA are not satisfactory due to a limited efficacy (no adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

Accordingly, a need exists for the identification of new agents that can more effectively and reliably treat conditions such as RA, and it is in response to this need and toward its satisfaction, that the present invention is directed.

SUMMARY OF THE INVENTION

The present invention relates to a class of triazolopyridine compounds that inhibit pro-inflammatory cytokine-driven MMP1 expression in RA synovial fibroblasts and that are capable of inhibiting TAK1 kinase activity.

The present invention is based on the discovery that inhibitors of matrix metalloproteinase 1 (MMP1) expression, such as the compounds of the present invention, are useful for the treatment of diseases involving ECM degradation, joint degradation and/or inflammation, for example multiple sclerosis, rheumatoid arthritis and osteoarthritis. These compounds may also be described as inhibitors of TAK1 activity. The present invention also provides methods for the production of these compounds, pharmaceutical compositions comprising these compounds and methods for treating diseases involving ECM degradation, joint degradation and/or inflammation by administering a compound of the invention.

The present matrix metalloproteinase expression inhibiting compounds of the present invention are described generally as phenyl-[1,2,4]triazolo[1,5-a]pyridin-8-yl-amines substituted in the 5-position by an aromatic group capable of accepting electrons from, and an 8-amino substituent capable of donating electrons to, the [1,2,4]triazolo[1,5-a]pyridine ring.

More particularly, the present invention relates to compounds having anti-inflammatory properties in a mammalian cell, according to formula (I):

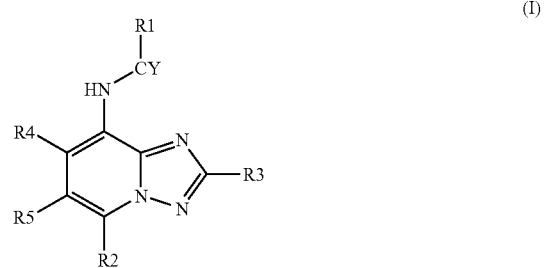

wherein:
CY represents an aryl or heteroaryl group optionally substituted with one or more groups selected from halogen, OH, $C_1$-$C_6$ alkyl, $C_1$-$C_6$ alkoxy, $NH_2$, $N(C_1$-$C_6$ alkyl)($C_1$-$C_6$alkyl), heterocycloalkyl, cycloalkyl and $CF_3$;

$R^1$ represents H, halogen, $C_1$-$C_6$ alkyl, $C_1$-$C_6$ alkoxy, $CF_3$, CN, a heterocycloalkyl group, a cycloalkyl group, a monocyclic aryl group, a monocyclic heteroaryl group, $CNHNR^aR^b$, $COR^a$, $OR^a$, $OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aN$-$R^aR^b$, $(CH_2)_aN(R^a)S(O)_2$—$C_1$-$C_6$ alkyl, $(CH_2)_aNR^aS(O)$—$C_1$-$C_6$ alkyl, $NR^aCO$—$R^b$, NH—CO—$OR^a$; each of which may be optionally substituted with one or more groups selected from halogen, OH, $C_1$-$C_6$ alkyl, $NH_2$, $N(C_1$-$C_6$ alkyl)($C_1$-$C_6$alkyl), optionally substituted heterocycloalkyl, optionally substituted cycloalkyl and $CF_3$;

$R^2$ represents an aryl or heteroaryl group optionally substituted with one or more groups selected from =O, hydroxy, halogen, CN, $C_1$-$C_6$ alkyl, $C_1$-$C_6$ alkoxy, $CNHNR^aR^b$, $COR^a$, $OR^a$, $OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aN$-$R^aR^b$, $(CH_2)_aN(R^a)S(O)_2$—$R^b$, $(CH_2)_aNR^aS(O)$—$C_1$-$C_6$ alkyl, $NR^aCO$—$R^b$, NH—CO—CO—$OR^a$, NH—CO—$NR^aR^b$, each of which may be optionally substituted with one or more groups selected from halogen, OH, $C_1$-$C_6$ alkyl, $NH_2$, $N(C_1$-$C_6$ alkyl)($C_1$-$C_6$alkyl), heterocycloalkyl, cycloalkyl and $CF_3$;

$R^3$, $R^4$ and $R^5$ each independently represent H, $C_1$-$C_6$ alkyl, halogen, $(CH_2)_a$-aryl or $(CH_2)_a$ heteroaryl; optionally substituted with one or more groups selected from =O, hydroxy, halogen, CN, $C_1$-$C_6$ alkyl, $C_1$-$C_6$ alkoxy, —CNHNR$^a$R$^b$, —COR$^a$, —OR$^a$, —OC(O)—C$_1$-C$_6$ alkyl, —(CH$_2$)$_a$COOR$^a$, —C(O)NR$^a$R$^b$, —S(O)$_2$(CH$_2$)$_a$N(R$^a$R$^b$), —SR$^a$, —SO(CH$_2$)$_a$NR$^a$R$^b$, —S(O)$_2$—R$^a$, —SOR$^a$, —(CH$_2$)$_a$NR$^a$R$^b$, —(CH$_2$)$_a$N(R$^a$)S(O)$_2$—R$^b$, —(CH$_2$)$_a$NR$^a$S(O)—C$_1$-C$_6$ alkyl, —NR$^a$CO—R$^b$, —NH—CO—CO—OR$^a$, —NH—CO—NR$^a$R$^b$, each of which may be optionally substituted with one or more groups selected from halogen, —OH, C$_1$-C$_6$ alkyl, —NH$_2$, —N(C$_1$-C$_6$ alkyl)(C$_1$-C$_6$alkyl), heterocycloalkyl, cycloalkyl or —CF$_3$;

R$^a$ and R$^b$ each independently represent H, halogen, C$_1$-C$_6$ alkyl, (CH$_2$)$_a$—N(C$_1$-C$_6$ alkyl)(C$_1$-C$_6$-alkyl), (CH$_2$)-monocyclic aryl, (CH$_2$)$_a$-monocyclic heteroaryl, (CH$_2$)$_a$-cycloalkyl or (CH$_2$)$_a$ heterocycloalkyl, each of which may be optionally substituted with one or more groups selected from halogen, —OH, C$_1$-C$_6$ alkyl, C$_1$-C$_6$ alkyl-O—C$_1$-C$_6$ alkyl, C$_1$-C$_6$ alkoxy, —NH$_2$, —NR$^c$R$^d$, NR$^c$COR$^d$, heteroaryl, heterocycloalkyl, substituted heterocycloalkyl or —CF$_3$; or R$^a$ and R$^b$ may, if joined to the same atom, represent together with the nitrogen to which they are attached a heterocycloalkyl group which may be optionally substituted with one or more groups selected from halogen, —OH, C$_1$-C$_6$ alkyl, C$_1$-C$_6$ alkoxy, —NH$_2$, —NR$^c$R$^d$, —NR$^c$COR$^d$, —C(O)NR$^c$R$^d$, optionally substituted aryl, optionally substituted aralkyl, optionally substituted heteroaryl, optionally substituted cycloalkyl or —CF$_3$;

R$^c$ and R$^d$ each independently represent H, C$_1$-C$_6$ alkyl; and

"a" is 0.1, 2 or 3;

or a pharmaceutically acceptable salt, hydrate, solvate or prodrug thereof.

The present invention also relates to compounds having anti-inflammatory properties in a mammalian cell, according to formula (II):

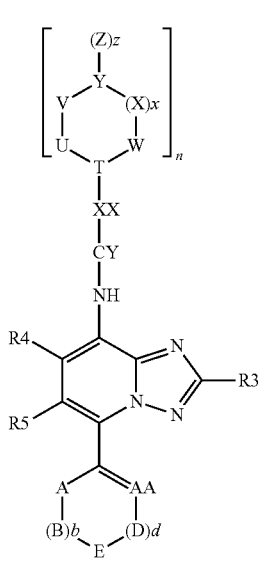

(II)

wherein:
A and B each independently represent CR$^g$R", NR", oxygen or sulphur;
AA represents CR$^g$ or N;
D represents C=O, CR$^g$R" or NR";
E represents N, CR"C(O)R$^g$ or CR"R$^g$;
T represents CR" or N;

U, V, W and X each independently represent CR"R$^h$ or NR";
R$^3$, R$^4$ and R$^5$ each independently represent H, C$_1$-C$_6$ alkyl, halogen, (CH$_2$)$_a$-aryl or (CH$_2$)$_a$ heteroaryl;
CY represents an aryl or heteroaryl group optionally substituted with one or more groups selected from halogen, OH, C$_1$-C$_6$ alkyl, C$_1$-C$_6$ alkoxy, NH$_2$, N(C$_1$-C$_6$ alkyl)(C$_1$-C$_6$alkyl), heterocycloalkyl, cycloalkyl and CF$_3$;
XX represents a linker group selected from a bond, —C(O)N(CH$_2$)$_c$—, —NC(O)(CH$_2$)$_c$—, S(O)$_2$N(CH$_2$)$_c$—, —NS(O)$_2$(CH$_2$)$_c$—, or XX represents a group selected from CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
Y represents CR", O or N; with the proviso that when Y represents O, z is 0;
Z represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl; (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
"b" and "d" each independently are 0 or 1; provided at least one of b or d is 1;
"c" is 0, 1, 2 or 3;
"n" is 0 or 1;
"z" is 0 or 1
R" represents H, F, or forms a double bond with an adjacent atom;
R$^e$ and R$^f$ each independently represent H, halogen, C$_1$-C$_6$ alkyl, (CH$_2$)$_c$—N(C$_1$-C$_6$ alkyl)(C$_1$-C$_6$-alkyl), (CH$_2$)$_c$-monocyclic aryl, (CH$_2$)$_c$-monocyclic heteroaryl, (CH$_2$)$_c$-cycloalkyl or (CH$_2$)$_c$-heterocycloalkyl or R$^e$ and R$^f$ may, if joined to the same atom, represent together with the nitrogen to which they are attached a heterocycloalkyl group; and
R$^g$ represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_e$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
R$^h$ independently represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, $(CH_2)_cNR^eS(O)$—$C_1$-$C_6$ alkyl, $NR^eCO$—$R^f$, NH—CO—CO—$OR^e$; each of which may be optionally substituted with one or more groups selected from halogen, OH, $C_1$-$C_6$ alkyl, $NH_2$, $N(C_1$-$C_6$ alkyl)($C_1$-$C_6$ alkyl), heterocycloalkyl, cycloalkyl and $CF_3$;

provided that where XX represents a linker group, then n represents 1, and where XX is not a linker group, then n represents 0; and further provided that the ring comprising A, B, AA, D and E is an aromatic system;

or a pharmaceutically acceptable salt, hydrate, solvate or prodrug thereof.

Another aspect of the present invention relates to compounds according to formula III:

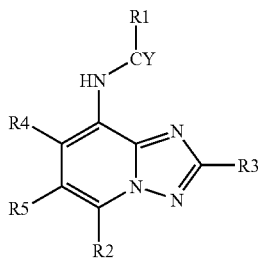

(III)

wherein $R^1$ represents H, halogen, $C_1$-$C_6$ alkyl, $C_1$-$C_6$ alkoxy, $CF_3$, CN, optionally substituted heterocycloalkyl, optionally substituted cycloalkyl, optionally substituted monocyclic aryl, optionally substituted monocyclic heteroaryl, $CNHNR^aR^b$, —$COR^a$, —$OR^a$, —OC(O)—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aNR^aR^b$, $(CH_2)_aN(R^a)S(O)_2$—$C_1$-$C_6$ alkyl, $(CH_2)_aNR^aS(O)$—$C_1$-$C_6$ alkyl, $NR^aCO$—$R^b$, NH—CO—CO—$OR^a$; each of which may be optionally substituted with one or more groups selected from halogen, OH, $C_1$-$C_6$ alkyl, $NH_2$, $N(C_1$-$C_6$ alkyl)($C_1$-$C_6$-alkyl), optionally substituted heterocycloalkyl, optionally substituted cycloalkyl and $CF_3$;

$R^2$ is selected from substituted or unsubstituted aryl, substituted or unsubstituted heteroaryl;

$R^3$, $R^4$ and $R^5$ are selected from H, OH, OMe, $OC_3H_5$, F, Cl, Me, Et, $SO_2Me$, $CF_3$ and $OCF_3$;

CY is selected from substituted or unsubstituted aryl, substituted or unsubstituted pyridyl, and substituted or unsubstituted pyrimidine;

$R^a$ and $R^b$ each independently represent H, halogen, $C_1$-$C_6$ alkyl, $(CH_2)_a$—$N(C_1$-$C_6$ alkyl)($C_1$-$C_6$-alkyl), $(CH_2)_a$-monocyclic aryl, $(CH_2)_a$-monocyclic heteroaryl, $(CH_2)_a$-cycloalkyl or $(CH_2)_a$-heterocycloalkyl, each of which may be optionally substituted with one or more groups selected from halogen, —OH, $C_1$-$C_6$ alkyl, $C_1$-$C_6$ alkyl-O—$C_1$-$C_6$ alkyl, $C_1$-$C_6$ alkoxy, —$NH_2$, —$NR^cR^d$, $NR^cCOR^d$, heteroaryl, heterocycloalkyl, substituted heterocycloalkyl or —$CF_3$; or $R^a$ and $R^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —C(O)$NR^cR^d$, optionally substituted aryl, optionally substituted aralkyl, optionally substituted heteroaryl, optionally substituted cycloalkyl or —$CF_3$;

$R^c$ and $R^d$ each independently represent H, $C_1$-$C_6$ alkyl; and

"a" is 0.1, 2 or 3;

or a pharmaceutically acceptable salt, solvate or prodrug thereof; or stereoisomers, isotopic variants or tautomers thereof.

Another aspect of this invention relates to the use of the present compound in a therapeutic method, a pharmaceutical composition, and the manufacture of such composition, useful for the treatment of a disease involving inflammation, and in particular, a disease characteristic of abnormal MMP expression. This invention also relates to processes for the preparation of the present compounds.

Other objects and advantages will become apparent from a consideration of the ensuing detailed description, which proceeds with reference to the following illustrative drawings.

DETAILED DESCRIPTION

Figure 1:
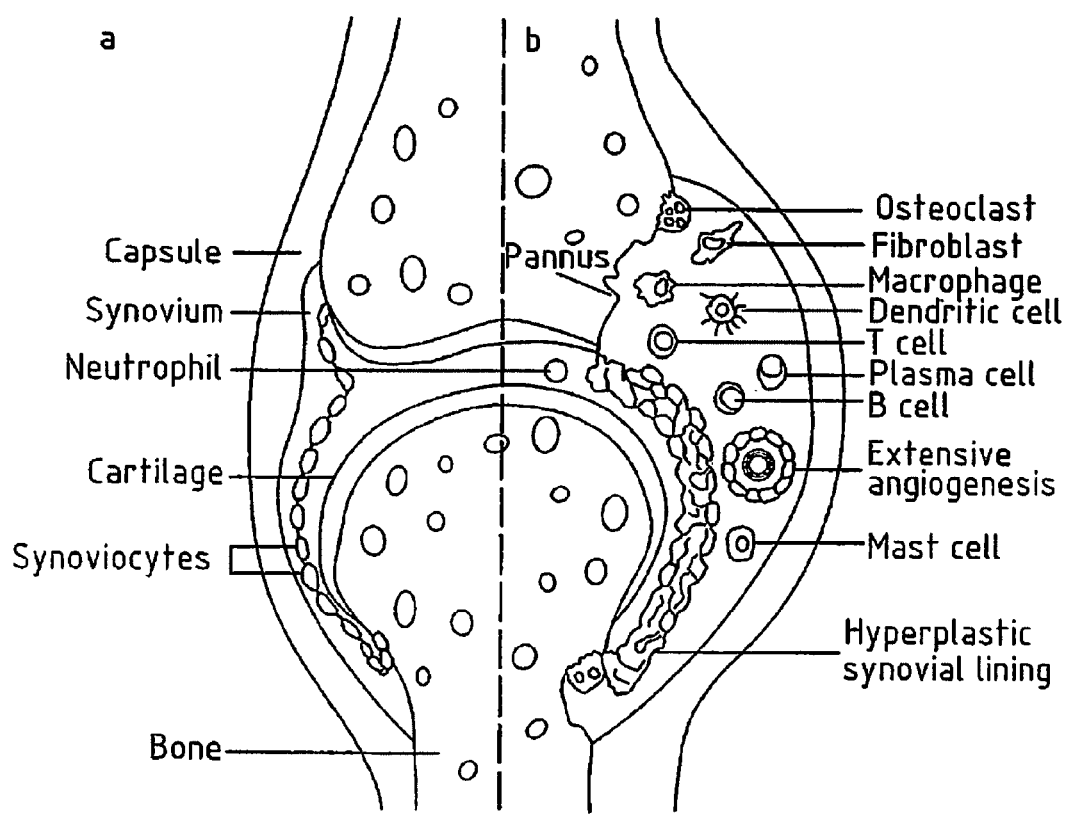
FIG. 1. This diagram shows the striking histological differences between a healthy joint and that of a RA patient.

The following terms are intended to have the meanings presented therewith below and are useful in understanding the description and intended scope of the present invention.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. By way of non-limiting example, such substituents may include e.g. halo (such as fluoro, chloro, bromo), —CN, —$CF_3$, —OH, —$OCF_3$, O—$CHF_2$, $C_1$-$C_6$ alkyl, $C_2$-$C_6$ alkenyl, $C_3$-$C_6$ alkynyl, $C_1$-$C_6$ alkoxy, aryl and di-$C_1$-$C_6$ alkylamino. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

'Acylamino' refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

'Acyloxy' refers to the group —OC(O)R$^{23}$ where R$^{23}$ is hydrogen, alkyl, aryl or cycloalkyl.

'Alkoxy' refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like. Particular alkoxy groups are lower alkoxy, i.e. with between 1 and 6 carbon atoms.

'Substituted alkoxy' includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkoxycarbonylamino' refers to the group —NR$^{25}$C(O)OR$^{26}$, where R$^{25}$ is hydrogen, alkyl, aryl or cycloalkyl, and R$^{26}$ is alkyl or cycloalkyl.

'Alkyl' means straight or branched aliphatic hydrocarbon having 1 to about 20 carbon atoms. Preferred alkyl has 1 to about 12 carbon atoms. More preferred is lower alkyl which has 1 to 6 carbon atoms. Most preferred are groups such as methyl, ethyl and propyl. Branched means that one or more lower alkyl groups such as methyl, ethyl or propyl is attached to a linear alkyl chain. The term C1-C6 alkyl includes both branched and straight chain groups, exemplary straight chain groups include ethyl, propyl, butyl, exemplary branched chain groups include isopropyl, isoamyl, and the like.

'Substituted alkyl' includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

'Alkylene' refers to divalent alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' includes those groups recited in the definition of 'substituted' herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically (unsaturated) hydrocarbon groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH$_2$), n-propenyl (—CH$_2$CH═CH$_2$), isopropenyl (—C(CH$_3$)═CH$_2$), vinyl and substituted vinyl, and the like.

'Substituted alkenyl' includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenylene' refers to divalent olefinically (unsaturated) hydrocarbon groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

'Alkynyl' refers to acetylenically or alkynically (unsaturated) hydrocarbon groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡H), propargyl (—CH$_2$C≡CH), and the like.

'Substituted alkynyl' includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkanoyl' or 'acyl' as used herein refers to the group R$^{27}$—C(O)—, where R$^{27}$ is hydrogen or alkyl as defined above.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly aryl groups include phenyl, naphthyl, indenyl, and tetrahydronaphthyl. The term 'aryl' includes 'bicycloaryl' as defined below.

'Bicycloaryl' refers to a monovalent aromatic hydrocarbon group derived by the removal of one hydrogen atom from a single carbon atom of a parent bicycloaromatic ring system.

Typical bicycloaryl groups include, but are not limited to, groups derived from indane, indene, naphthalene, tetrahydronaphthalene, and the like. Particularly, an aryl group comprises from 8 to 11 carbon atoms.

'Substituted Aryl' includes those groups recited in the definition of 'substituted' herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

'Fused Aryl' refers to an aryl having two of its ring carbon in common with a second aryl ring or with an aliphatic ring.

'Alkaryl' or 'arylalkyl' refers to an aryl group, as defined above, substituted with one or more alkyl groups, as defined above.

'Substituted Aralkyl' or 'substituted arylalkyl' refers to an alkyl group, as defined above, substituted with one or more aryl groups, as defined above.

'Aryloxy' refers to —O-aryl groups wherein 'aryl' is as defined above.

'Alkylamino' refers to the group alkyl-NR$^{28}$R$^{29}$, wherein each of R$^{28}$ and R$^{29}$ are independently selected from hydrogen and alkyl.

'Arylamino' refers to the group aryl-NR$^{30}$R$^{31}$, wherein each of R$^{30}$ and R$^{31}$ are independently selected from hydrogen, aryl and heteroaryl.

'Alkoxyamino' refers to a radical —N(H)OR$^{32}$ where R$^{32}$ represents an alkyl or cycloalkyl group as defined herein.

'Alkoxycarbonyl' refers to a radical —C(O)-alkoxy where alkoxy is as defined herein.

'Alkylarylamino' refers to a radical —NR$^{33}$R$^{34}$ where R$^{33}$ represents an alkyl or cycloalkyl group and R$^{34}$ is an aryl as defined herein.

'Alkylsulfonyl' refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

'Alkylsulfinyl' refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

'Alkylthio' refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

'Amino' refers to the radical —NH$_2$.

'Substituted amino' includes those groups recited in the definition of 'substituted' herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

'Aminocarbonyl' refers to the group —C(O)NR$^{37}$R$^{37}$ where each R$^{37}$ is independently hydrogen, alkyl, aryl and cycloalkyl, or where the R$^{37}$ groups are joined to form an alkylene group.

'Aminocarbonylamino' refers to the group —NR$^{38}$C(O)NR$^{38}$R$^{38}$ where each R$^{38}$ is independently hydrogen, alkyl, aryl or cycloalkyl, or where two R groups are joined to form an alkylene group.

'Aminocarbonyloxy' refers to the group —OC(O)NR$^{39}$R$^{39}$ where each R$^{39}$ is independently hydrogen, alkyl, aryl or cycloalkyl, or where the R groups are joined to form an alkylene group.

'Arylalkyloxy' refers to an —O-arylalkyl radical where arylalkyl is as defined herein.

'Arylamino' means a radical —NHR$^{40}$ where R$^{40}$ represents an aryl group as defined herein.

'Aryloxycarbonyl' refers to a radical —C(O)—O-aryl where aryl is as defined herein.

'Arylsulfonyl' refers to a radical —S(O)$_2$R$^{41}$ where R$^{41}$ is an aryl or heteroaryl group as defined herein.

'Azido' refers to the radical —N$_3$.

'Carbamoyl' refers to the radical —C(O)N(R$^{42}$)$_2$ where each R$^{42}$ group is independently hydrogen, alkyl, cycloalkyl or aryl, as defined herein, which may be optionally substituted as defined herein. A particular carbamoyl group is —C(O)NH$_2$.

'Carboxy' refers to the radical —C(O)OH.

'Carboxyamino' refers to the radical —N(H)C(O)OH.

'Cycloalkyl' refers to cyclic non-aromatic hydrocarbyl groups having from 4 to about 7 carbon atoms and having a single cyclic ring, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like.

'Substituted cycloalkyl' includes those groups recited in the definition of 'substituted' herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Cycloalkoxy' refers to the group —OR$^{43}$ where R$^{43}$ is cycloalkyl. Such cycloalkoxy groups include, by way of example, cyclopentoxy, cyclohexoxy and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Cyanato' refers to the radical —OCN.

'Cyano' refers to the radical —CN.

'Dialkylamino' means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

'Ethenyl' refers to substituted or unsubstituted —(C=C)—.

'Ethylene' refers to substituted or unsubstituted —(C—C)—.

'Ethynyl' refers to —(C≡C)—.

'Halo' or 'halogen' refers to fluoro (F), chloro (Cl), bromo (Br) and iodo (I). Preferred halo groups are either fluoro or chloro.

'Hydrogen' means in the context of a substituent that —H is present at the compound position and also includes its isotope, deuterium.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents include, but are not limited to —X, —R$^{46}$, —O$^-$, =O, —OR$^{46}$, —SR$^{46}$, —S$^-$, =S, —NR$^{46}$R$^{47}$, =NR$^{46}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

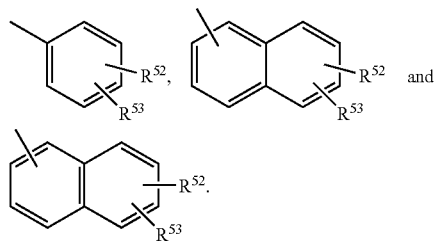

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

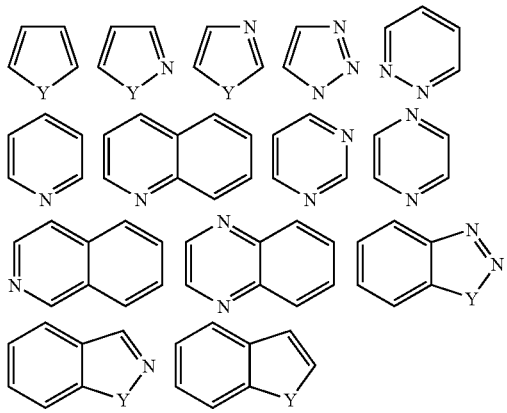

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like. The term 'heteroaryl' includes 'bicycloheteroaryl' as defined below.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoindolone, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

As used herein, the term 'heterocycloalkyl' refers to a 4-7 membered, stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

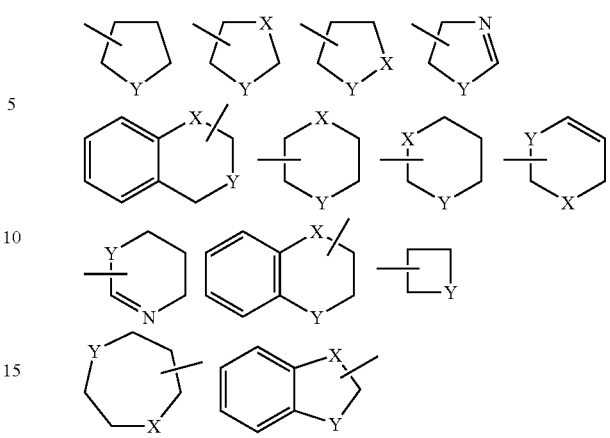

wherein each X is selected from CR$^{58}_2$, NR$^{58}$, O and S; and each Y is selected from NR$^{58}$, O and S; and R$^{58}$ is independently hydrogen, alkyl, cycloalkyl, heterocycloalkyl, aryl, heteroaryl, heteroalkyl or the like. These heterocycloalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. The term 'heterocycloalkyl' includes 'heterocycloalkenyl' as defined below.

Examples of representative heterocycloalkenyls include the following:

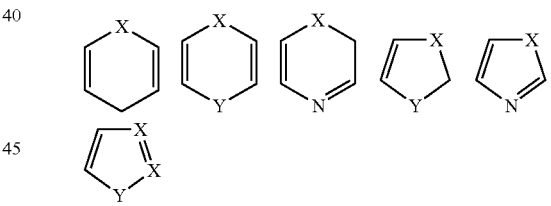

wherein each X is selected from CR$^{58}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

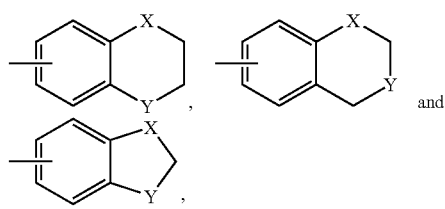

wherein each X is selected from C—R$^{58}_2$, NR$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

'Hetero substituent' refers to a halo, O, S or N atom-containing functionality that may be present as an R4 in a R4C group present as substituents directly on a ring atom of the compounds of this invention or may be present as a substituent in the "substituted" aryl and aliphatic groups present in the compounds.

Examples of hetero substituents include:
-halo,
—$NO_2$, —$NH_2$, —$NHR^{59}$, —$N(R^{59})_2$,
—NRCOR, —$NR^{59}SOR^{59}$, —$NR^{59}SO_2R^{59}$, OH, CN,
—$CO_2H$,
—$R^{59}$—OH, —O—$R^{59}$, —$COOR^{59}$,
—$CON(R^{59})_2$, —$CONROR^{59}$,
—$SO_3H$, —$R^{59}$—S, —$SO_2N(R^{59})_2$,
—$S(O)R^{59}$, —$S(O)_2R^{59}$
wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

'Hydrogen bond donor' group refers to a group containg O—H, N—H functionality. Examples of "hydrogen bond donor" groups include —OH, —$NH_2$, and —NH—$R^{59a}$ and wherein $R^{59a}$ is alkyl, cycloalkyl, aryl, or heteroaryl.

'Dihydroxyphosphoryl' refers to the radical —$PO(OH)_2$.

'Substituted dihydroxyphosphoryl' includes those groups recited in the definition of 'substituted' herein, and particularly refers to a dihydroxyphosphoryl radical wherein one or both of the hydroxyl groups are substituted. Suitable substituents are described in detail below.

'Aminohydroxyphosphoryl' refers to the radical —$PO(OH)NH_2$.

'Substituted aminohydroxyphosphoryl' includes those groups recited in the definition of 'substituted' herein, and particularly refers to an aminohydroxyphosphoryl wherein the amino group is substituted with one or two substituents. Suitable substituents are described in detail below. In certain embodiments, the hydroxyl group can also be substituted.

'Thioalkoxy' refers to the group —$SR^{60}$ where $R^{60}$ is alkyl.

'Substituted thioalkoxy' includes those groups recited in the definition of 'substituted' herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Sulfanyl' refers to the radical HS—. 'Substituted sulfanyl' refers to a radical such as RS— wherein R is any substituent described herein.

'Sulfonyl' refers to the divalent radical —$S(O_2)$—. 'Substituted sulfonyl' refers to a radical such as $R^{61}$—$(O_2)S$— wherein $R^{61}$ is any substituent described herein. "Aminosulfonyl" or "Sulfonamide" refers to the radical $H_2N(O_2)S$—, and "substituted aminosulfonyl" or "substituted sulfonamide" refers to a radical such as $R^{62}_2N(O_2)S$— wherein each $R^{62}$ is independently any substituent described herein.

'Sulfone' refers to the group —$SO_2R^{63}$. In particular embodiments, $R^{63}$ is selected from H, lower alkyl, alkyl, aryl and heteroaryl.

'Sulphonamide' refers to a group of compounds containing the chemical group —$SO_2NH_2$.

'Thioaryloxy' refers to the group —$SR^{64}$ where $R^{64}$ is aryl.

'Thioketo' refers to the group =S.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject that may be exposed to or predisposed to the disease but does not yet experience or display symptoms of the disease). This term encompasses the term 'prophylaxis', which means a measure taken for the prevention of a disease.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and insoluble solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated. In particular, with regard to treating an disease involving cartilage or joint degradation and/or inflammation, the terms "therapeutically effective amount" or "effective TAK1-inhibiting amount" is intended to mean that effective amount of an compound of the present invention that will bring about a biologically meaningful decrease in the production of TAK1 in the subject's disease affected tissues, such that cartilage or joint degradation and/or inflammation is meaningfully reduced. A compound having MMP1-inhibiting properties or a "MMP1-inhibiting compound" means a compound of the present invention that provided to a cell in effective amounts is able to cause a biologically meaningful decrease in the production of MMP1 in such cells.

'Treating' or 'treatment' of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

'Compounds of the present invention', and equivalent expressions, are meant to embrace compounds of Formula (I or II) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_s$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radio-isotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention relates to a class of triazolopyridine compounds capable of binding to the active site of a serine/threonine kinase, the expression of which is involved in the pathway resulting in the degradation of extra-cellular matrix (ECM), which is a causative factor in joint degeneration and diseases involving such degradation and/or inflammation.

In a general aspect, the invention relates to compounds of Formula I:

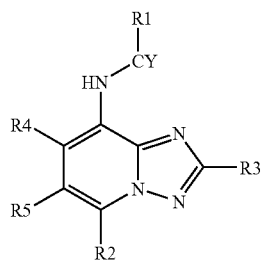

(I)

wherein:
CY represents an aryl or heteroaryl group optionally substituted with one or more groups selected from halogen, OH, $C_1$-$C_6$ alkyl, $C_1$-$C_6$ alkoxy, $NH_2$, $N(C_1$-$C_6$ alkyl)($C_1$-$C_6$alkyl), heterocycloalkyl, cycloalkyl and $CF_3$;

$R^1$ represents H, halogen, $C_1$-$C_6$ alkyl, $C_1$-$C_6$ alkoxy, $CF_3$, CN, a heterocycloalkyl group, a cycloalkyl group, a monocyclic aryl group, a monocyclic heteroaryl group, $CNHNR^aR^b$, $COR^a$, $OR^a$, $OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aNR^aR^b$, $(CH_2)_aN(R^a)S(O)_2$—$C_1$-$C_6$ alkyl, $(CH_2)_aNR^aS(O)$—$C_1$-$C_6$ alkyl, $NR^aCO$—$R^b$, NH—CO—CO—$OR^a$; each of which may be optionally substituted with one or more groups selected from halogen, OH, $C_1$-$C_6$ alkyl, $NH_2$, $N(C_1$-$C_6$ alkyl)($C_1$-$C_6$alkyl), optionally substituted heterocycloalkyl, optionally substituted cycloalkyl and $CF_3$;

$R^2$ represents an aryl or heteroaryl group optionally substituted with one or more groups selected from =O, hydroxy, halogen, CN, $C_1$-$C_6$ alkyl, $C_1$-$C_6$ alkoxy, $CNHNR^aR^b$, $COR^a$, $OR^a$, $OC(O)$—$C_1$-$C_6$ alkyl, $(CH_2)_aCOOR^a$, $C(O)NR^aR^b$, $S(O)_2(CH_2)_aN(R^aR^b)$, $SR^a$, $SO(CH_2)_aNR^aR^b$, $S(O)_2$—$R^a$, $SOR^a$, $(CH_2)_aN$-$R^aR^b$, $(CH_2)_aN(R^a)S(O)_2$—$R^b$, $(CH_2)_aNR^aS(O)$—$C_1$-$C_6$ alkyl, $NR^aCO$—$R^b$, NH—CO—CO—$OR^a$, NH—CO—$NR^aR^b$, each of which may be optionally substituted with one or more groups selected from halogen, OH, $C_1$-$C_6$ alkyl, $NH_2$, $N(C_1$-$C_6$ alkyl)($C_1$-$C_6$alkyl), heterocycloalkyl, cycloalkyl and $CF_3$;

$R^3$, $R^4$ and $R^5$ each independently represent H, $C_1$-$C_6$ alkyl, halogen, $(CH_2)_a$-aryl or $(CH_2)_a$ heteroaryl; optionally substituted with one or more groups selected from =O, hydroxy, halogen, CN, $C_1$-$C_6$ alkyl, $C_1$-$C_6$ alkoxy, —$CNHNR^aR^b$, —$COR^a$, —$OR^a$, —$OC(O)$—$C_1$-$C_6$ alkyl, —$(CH_2)_aCOOR^a$, —$C(O)NR^aR^b$, —$S(O)_2$ $(CH_2)_aN(R^aR^b)$, —$SR^a$, —$SO(CH_2)_aNR^aR^b$, —$S(O)_2$—$R^a$, —$SOR^a$, —$(CH_2)_aNR^aR^b$, —$(CH_2)_aN$ $(R^a)S(O)_2$—$R^b$, —$(CH_2)_aNR^aS(O)$—$C_1$-$C_6$ alkyl, —$NR^aCO$—$R^b$, —NH—CO—CO—$OR^a$, —NH—CO—$NR^aR^b$, each of which may be optionally substituted with one or more groups selected from halogen, —OH, $C_1$-$C_6$ alkyl, —$NH_2$, —$N(C_1$-$C_6$ alkyl)($C_1$-$C_6$alkyl), heterocycloalkyl, cycloalkyl or —$CF_3$;

$R^a$ and $R^b$ each independently represent H, halogen, $C_1$-$C_6$ alkyl, $(CH_2)_a$—$N(C_1$-$C_6$ alkyl)($C_1$-$C_6$-alkyl), $(CH_2)_a$-monocyclic aryl, $(CH_2)_a$-monocyclic heteroaryl, $(CH_2)_a$-cycloalkyl or $(CH_2)_a$-heterocycloalkyl, each of which may be optionally substituted with one or more groups selected from halogen, —OH, $C_1$-$C_6$ alkyl, $C_1$-$C_6$ alkyl-O—$C_1$-$C_6$ alkyl, $C_1$-$C_6$ alkoxy, —$NH_2$, —$NR^cR^d$, $NR^cCOR^d$, heteroaryl, heterocycloalkyl, substituted heterocycloalkyl or —$CF_3$; or $R^a$ and $R^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —$C(O)$ $NR^cR^d$, optionally substituted aryl, optionally substituted aralkyl, optionally substituted heteroaryl, optionally substituted cycloalkyl or —$CF_3$;

$R^c$ and $R^d$ each independently represent H, $C_1$-$C_6$ alkyl; and

"a" is 0.1, 2 or 3;

or a pharmaceutically acceptable salt, hydrate, solvate or prodrug thereof.

The present invention also relates to compounds having anti-inflammatory properties in a mammalian cell, according to formula (II):

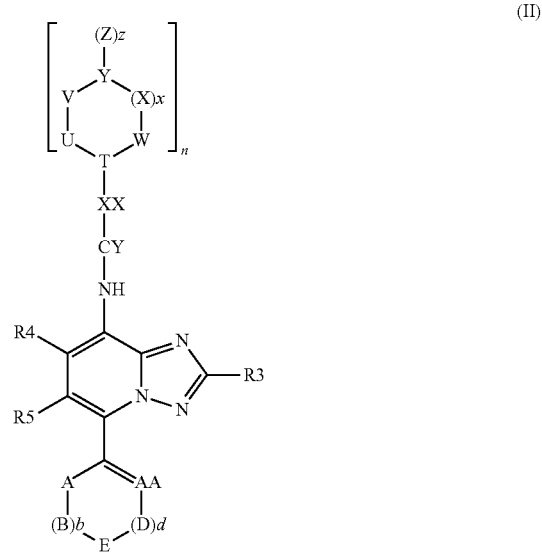

(II)

wherein:
A and B each independently represent CR$^g$R", NR", oxygen or sulphur;
AA represents CR$^g$ or N;
D represents C=O, CR$^g$R" or NR";
E represents N, CR"C(O)R$^g$ or CR"R$^g$;
T represents CR" or N;
U, V, W and X each independently represent CR"R$^h$ or NR";
R$^3$, R$^4$ and R$^5$ each independently represent H, C$_1$-C$_6$ alkyl, halogen, aryl or heteroaryl;
CY represents an aryl or heteroaryl group optionally substituted with one or more groups selected from halogen, OH, C$_1$-C$_6$ alkyl, C$_1$-C$_6$ alkoxy, NH$_2$, N(C$_1$-C$_6$ alkyl)(C$_1$-C$_6$alkyl), heterocycloalkyl, cycloalkyl and CF$_3$;
XX represents a linker group selected from a bond, —C(O)N(CH$_2$)c-, —NC(O)(CH$_2$)$_c$—, S(O)$_2$N(CH$_2$)$_c$—, —NS(O)$_2$(CH$_2$)$_c$—, or XX represents a group selected from CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
Y represents CR", O or N; with the proviso that when Y represents O, z is 0,
Z represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
"b" and "d" each independently are 0 or 1; provided at least one of b or d is 1;
"c" is 0, 1, 2 or 3;
"n" is 0 or 1;
"z" is 0 or 1;
R" represents H, F, or forms a double bond with an adjacent atom;
R$^e$ and R$^f$ each independently represent H, halogen, C$_1$-C$_6$ alkyl, (CH$_2$)$_c$—N(C$_1$-C$_6$ alkyl)(C$_1$-C$_6$-alkyl), (CH$_2$)$_c$-monocyclic aryl, (CH$_2$)$_c$-monocyclic heteroaryl, (CH$_2$)$_c$-cycloalkyl or (CH$_2$)$_c$-heterocycloalkyl or R$^e$ and R$^f$ may, if joined to the same atom, represent together with the nitrogen to which they are attached a heterocycloalkyl group; and
R$^g$ represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
R$^h$ independently represents H, halogen, C$_1$-C$_6$ alkyl, C$_1$-C$_6$ alkoxy, CF$_3$, CN, a heterocycloalkyl group, a cycloalkyl group, a monocyclic aryl group, a monocyclic heteroaryl group, CNHNR$^e$R$^f$, COR$^e$, OR$^e$, OC(O)—C$_1$-C$_6$ alkyl, (CH$_2$)$_c$COOR$^e$, C(O)NR$^e$R$^f$, S(O)$_2$(CH$_2$)$_c$N(R$^e$R$^f$), SR$^e$, SO(CH$_2$)$_c$NR$^e$R$^f$, S(O)$_2$—R$^e$, SOR$^e$, (CH$_2$)$_c$NR$^e$R$^f$, (CH$_2$)$_c$N(R$^e$)S(O)$_2$—C$_1$-C$_6$ alkyl, (CH$_2$)$_c$NR$^e$S(O)—C$_1$-C$_6$ alkyl, NR$^e$CO—R$^f$, NH—CO—CO—OR$^e$; each of which may be optionally substituted with one or more groups selected from halogen, OH, C$_1$-C$_6$ alkyl, NH$_2$, N(C$_1$-C$_6$ alkyl)(C$_1$-C$_6$ alkyl), heterocycloalkyl, cycloalkyl and CF$_3$;
provided that where XX represents a linker group, then n represents 1, and where XX is not a linker group, then n represents 0; and
further provided that the ring comprising A, B, AA, D and E is an aromatic system;
or a pharmaceutically acceptable salt, hydrate, solvate or prodrug thereof.

Another aspect of the present invention relates to compounds according to formula III:

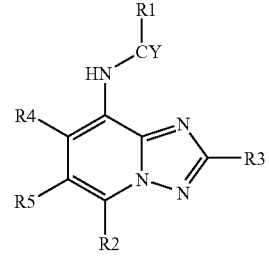

(III)

wherein
R$^1$ represents H, halogen, C$_1$-C$_6$ alkyl, C$_1$-C$_6$ alkoxy, CF$_3$, CN, optionally substituted heterocycloalkyl, optionally substituted cycloalkyl, optionally substituted monocyclic aryl, optionally substituted monocyclic heteroaryl, CNHNR$^a$R$^b$, —COR$^a$, —OR$^a$, —OC(O)—C$_1$-C$_6$ alkyl, (CH$_2$)$_a$COOR$^a$, C(O)NR$^a$R$^b$, S(O)$_2$(CH$_2$)$_a$N(R$^a$R$^b$), SR$^a$, SO(CH$_2$)$_a$NR$^a$R$^b$, S(O)$_2$—R$^a$, SOR$^a$, (CH$_2$)$_a$NR$^a$R$^b$, (CH$_2$)$_a$N(R$^a$)S(O)$_2$—C$_1$-C$_6$ alkyl, (CH$_2$)$_a$NR$^a$S(O)—C$_1$-C$_6$ alkyl, NR$^a$CO—R$^b$, NH—CO—CO—OR$^a$; each of which may be optionally substituted with one or more groups selected from H, halogen, OH, C$_1$-C$_6$ alkyl, NH$_2$, N(C$_1$-C$_6$ alkyl)(C$_1$-C$_6$ alkyl), optionally substituted heterocycloalkyl, optionally substituted cycloalkyl and CF$_3$;
R$^2$ is selected from substituted or unsubstituted aryl, substituted or unsubstituted heteroaryl;
R$^3$, R$^4$ and R$^5$ are selected from H, OH, OMe, OC$_3$H$_5$, F, Cl, Me, Et, SO$_2$Me, CF$_3$ and OCF$_3$;
CY is selected from substituted or unsubstituted aryl, substituted or unsubstituted pyridyl, and substituted or unsubstituted pyrimidine;
R$^a$ and R$^b$ each independently represent H, halogen, C$_1$-C$_6$ alkyl, (CH$_2$)$_a$—N(C$_1$-C$_6$ alkyl)(C$_1$-C$_6$-alkyl), (CH$_2$)$_a$-monocyclic aryl, (CH$_2$)$_a$-monocyclic heteroaryl, (CH$_2$)$_a$-cycloalkyl or (CH$_2$)$_a$ heterocycloalkyl, each of which may be optionally substituted with one or more groups selected from halogen, —OH, C$_1$-C$_6$ alkyl, C$_1$-C$_6$ alkyl-O—C$_1$-C$_6$ alkyl, C$_1$-C$_6$ alkoxy, —NH$_2$, —NR$^e$R$^d$, NR$^c$COR$^d$, heteroaryl, heterocycloalkyl, substituted heterocycloalkyl or —CF$_3$; or R$^a$ and R$^b$ may, if joined to the same atom, represent together with the nitrogen to which they are attached a heterocycloalkyl group which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —C(O)$NR^cR^d$, optionally substituted aryl, optionally substituted aralkyl, optionally substituted heteroaryl, optionally substituted cycloalkyl or —$CF_3$;

$R^c$ and $R^d$ each independently represent H, $C_1$-$C_6$ alkyl; and

"a" is 0.1, 2 or 3;

or a pharmaceutically acceptable salt, solvate or prodrug thereof; or stereoisomers, isotopic variants or tautomers thereof.

In one embodiment, with respect to compounds of formula III, CY is selected from substituted phenyl, substituted pyridyl, and substituted pyrimidine.

In one embodiment, with respect to compounds of formula III, CY is selected from:

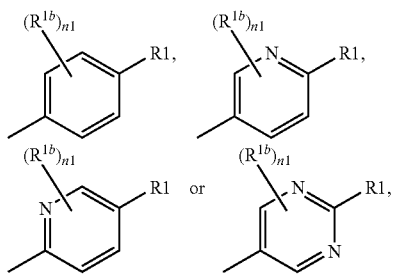

wherein $R^1$ is as described for formula III; the subscript n1 is selected from 1-4; and each $R^{1b}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, the subscript n1 is selected from 1-2; and each $R^{1b}$ is independently selected from hydrogen, $C_1$-$C_6$ alkyl, $C_1$-$C_6$ haloalkyl and halo.

In another embodiment, the subscript n1 is selected from 1-2; and each $R^{1b}$ is independently selected from hydrogen, Me, $CF_3$, Cl and F.

In one embodiment, with respect to compounds of formula III, CY is:

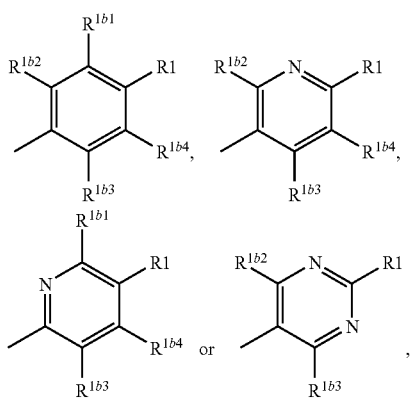

and wherein $R^1$ is as described for formula III; and each $R^{1b1}$, $R^{1b2}$, $R^{1b3}$, and $R^{1b4}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, each $R^{1b1}$, $R^{1b2}$, $R^{1b3}$, and $R^{1b4}$ is H.

In another embodiment, one of $R^{1b1}$, $R^{1b2}$, $R^{1b3}$, and $R^{1b4}$ is Me, Cl, F or $CF_3$; and the rest are H.

In another embodiment, two of $R^{1b1}$, $R^{1b2}$, $R^{1b3}$, and $R^{1b4}$ are Cl, or F; and the rest are H.

In one embodiment, with respect to compounds of formula III, $R^3$, $R^4$ and $R^5$ are all H.

In another embodiment, with respect to compounds of formula III, CY is selected from substituted phenyl, substituted pyridyl, and substituted pyrimidine; and $R^1$ is -L-$R^{1a}$; and wherein L is selected from a bond, alkylene, —CO—, and —$SO_2$—; and $R^{1a}$ is selected from substituted or unsubstituted alkyl, substituted or unsubstituted cycloalkyl, substituted or unsubstituted aryl, substituted or unsubstituted heterocycloalkyl, substituted or unsubstituted heteroaryl, substituted or unsubstituted amino, substituted or unsubstituted aralkyl, substituted or unsubstituted heteroarylalkyl and substituted or unsubstituted aminoalkyl.

In one embodiment, with respect to compounds of formula III, the compound is according to formula IIIa, IIIb, IIIc or IIId:

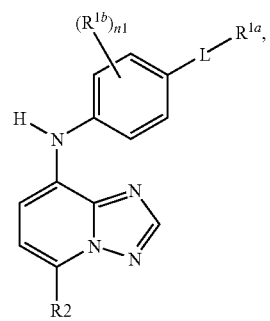

IIIa

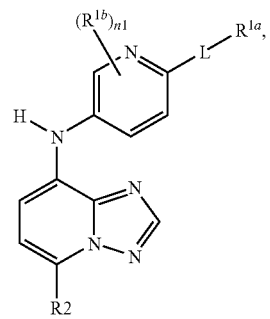

IIIb

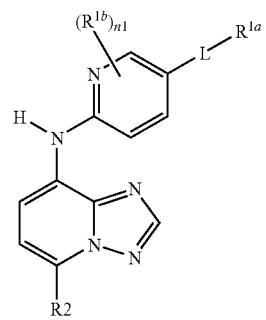

IIIc or

IIId

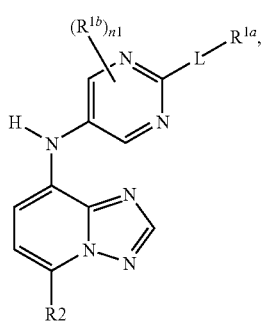

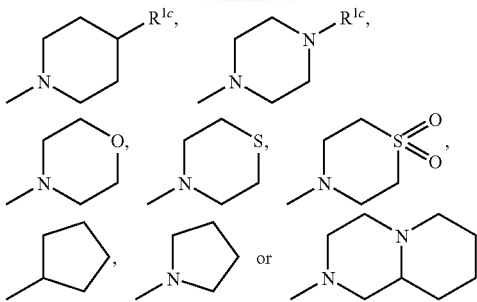

wherein L and $R^{1a}$ are as described above; the subscript n1 is selected from 1-4; and each $R^{1b}$ is independently selected from hydrogen, substituted or unsubstituted $C_1$-$C_6$ alkyl, $C_1$-$C_6$ alkoxy, $C_1$-$C_6$ haloalkyl, cyano, and halo.

In one embodiment, each $R^{1b}$ is independently selected from Me, Et, Pr, iso-Pr, Cl, F, CN, OMe, OEt, $CF_3$, $CF_2CF_3$ and $OCF_3$.

In one embodiment, with respect to compounds of formulae IIIa-IIId, L is —CO— or $SO_2$—; and $R^{1a}$ is selected from substituted or unsubstituted $C_1$-$C_6$ alkyl, substituted or unsubstituted cycloalkyl, substituted or unsubstituted aryl, substituted or unsubstituted heterocycloalkyl, substituted or unsubstituted heteroaryl, substituted or unsubstituted aralkyl, and substituted or unsubstituted heteroarylalkyl.

In one embodiment, with respect to compounds of formulae IIIa-IIId, L is —CO— or $SO_2$—; and $R^{1a}$ is substituted or unsubstituted amino.

In one embodiment, with respect to compounds of formulae IIIa-IIId, L is —CO— or $SO_2$—; and $R^{1a}$ is substituted or unsubstituted alkylamino, substituted or unsubstituted dialkylamino, substituted or unsubstituted cycloalkylamino, substituted or unsubstituted arylamino, substituted or unsubstituted aralkylamino, substituted or unsubstituted heteroarylamino, and substituted or unsubstituted heteroarylalkylamino.

In one embodiment, with respect to compounds of formulae IIIa-IIId, L is a bond, —CO—, $SO_2$, and —$(CH_2)_{m1}$—; the subscript m1 is selected from 1-4; and $R^{1a}$ is

and wherein the ring P is substituted or unsubstituted heterocycloalkyl.

In one embodiment the ring P is substituted or unsubstituted:

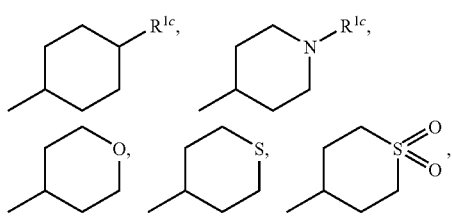

and wherein $R^{1c}$ is selected from hydrogen, halo, hydroxyl, substituted or unsubstituted alkyl, substituted or unsubstituted cycloalkyl or substituted or unsubstituted heterocycloalkyl; provided that $R^{1c}$ is other than halo or hydroxyl when it is attached to N.

In one embodiment, $R^{1c}$ is alkyl or haloalkyl. In another embodiment, $R^{1c}$ is Me, Et, i-Pr, n-Pr, 3-pentyl, 3-methylbutyl, $CF_3$, $CH_2CF_2$, $CH_2CH_2F$, 1-methylpropyl, cyclopropyl, cyclobutyl, or cyclohexyl.

In one embodiment, $R^{1c}$ is substituted or unsubstituted heterocycloalkyl.

In one embodiment, $R^{1c}$ is substituted or unsubstituted piperidine, piperazine, or pyrrolidine.

In one embodiment, $R^{1c}$ is substituted piperidine, piperazine, or pyrrolidine; and the substitution is selected from $C_1$-$C_6$ alkyl, hydroxyl or halo. In another embodiment, the substitution is selected from Me, OH, Cl and F.

In one embodiment, $R^{1c}$ is

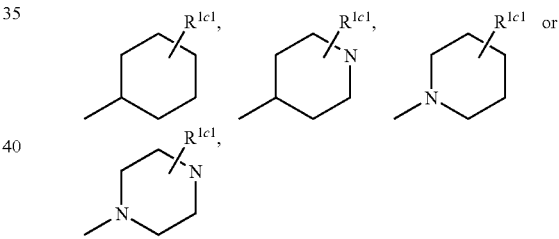

and wherein $R^{1c1}$ is selected from hydrogen, halo, hydroxyl, substituted or unsubstituted $C_1$-$C_6$ alkyl, provided that $R^{1c1}$ is other than halo or hydroxyl when it is attached to N.

In another embodiment, $R^{1c}$ is

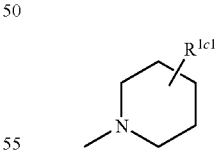

and wherein $R^{1c1}$ is selected from hydrogen, halo, hydroxyl, substituted or unsubstituted alkyl.

In another embodiment, $R^{1c}$ is

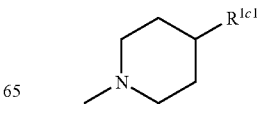

and wherein $R^{1c1}$ is selected from hydrogen, halo, hydroxyl, substituted or unsubstituted alkyl.

In one embodiment, $R^{1c1}$ is H, Me, Cl or F.

In one embodiment, with respect to compounds of formulae IIIa-IIId, $R^{1a}$ is ring P substituted with $(R^{1d})_{n2}$; and wherein each $R^{1d}$ is H, $C_1$-$C_6$ alkyl, halo, $C_1$-$C_6$ haloalkyl, CN, $C_1$-$C_6$ alkoxy or $C_1$-$C_6$ haloalkoxy and n2 is 0, 1, or 2.

In one embodiment, each $R^{1d}$ is independently selected from H, Me, Et, Pr, iso-Pr, Cl, F, CN, OMe, OEt, $CF_3$, $CF_2CF_3$ or $OCF_3$.

In one embodiment, with respect to compounds of formulae IIIa-IIId, $R^{1a}$ is

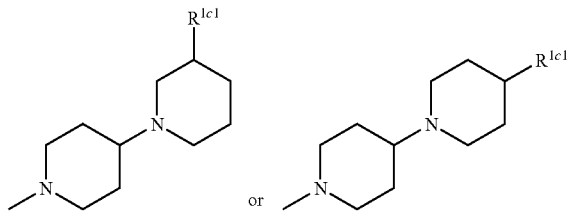

wherein $R^{1c1}$ is H, OH or Me.

In one embodiment, with respect to compounds of formulae IIIa-IIId, the compound is according to formula IVa, IVb, IVc, or IVd:

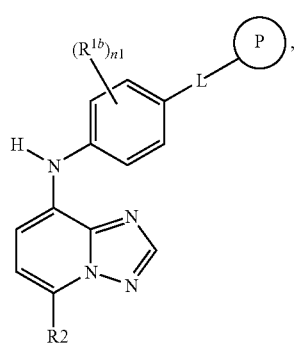

IVa

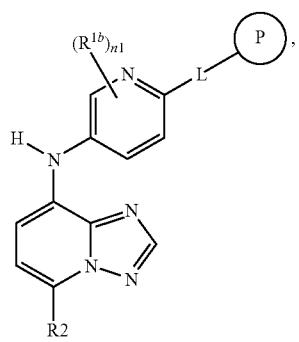

IVb

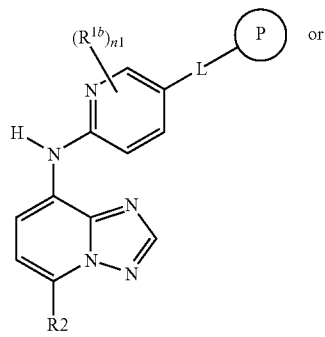

IVc or

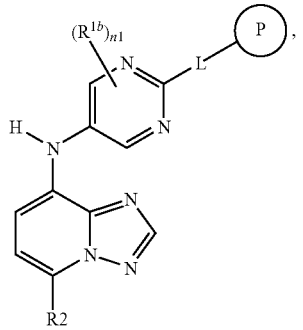

IVd and wherein L is bond, —CO—, $SO_2$, and —$(CH_2)_{m1}$—; the subscript m1 is selected from 1-4; the ring P is as described in the preceding paragraph; each $R^{1b}$ is independently selected from hydrogen, substituted or unsubstituted $C_1$-$C_6$ alkyl, $C_1$-$C_6$ alkoxy, cyano, and halo; the subscript n1 is selected from 1-4; and $R^2$ is independently selected from substituted or unsubstituted aryl and heteroaryl; or a pharmaceutically acceptable salt, solvate or prodrug thereof; and stereoisomers, isotopic variants and tautomers thereof.

In one embodiment, the compound is according to formula IVa.

In one embodiment, with respect to compounds of formulae IVa-IVd, L is a bond.

In another embodiment, with respect to compounds of formulae IVa-IVd, L is —CO—.

In another embodiment, with respect to compounds of formulae IVa-IVd, L is —$SO_2$—.

In another embodiment, with respect to compounds of formulae IVa-IVd, L is —$CH_2$—.

In one embodiment, with respect to compounds of formulae IVa-IVd, the ring P is substituted or unsubstituted pyrrolidine, thiomorpholine, piperidine, morpholine or piperazine.

In one embodiment, with respect to compounds of formulae IVa-IVd, the ring P is substituted or unsubstituted piperidine, morpholine or piperazine.

In one embodiment, with respect to compounds of formulae IVa-IVd, each $R^{1b}$ is H.

In another embodiment, with respect to compounds of formulae IVa-IVd, the subscript n1 is 1 and $R^{1b}$ is selected from Me, Et, Pr, iso-Pr, Cl, F, CN, OMe, or $CF_3$.

In another embodiment, with respect to compounds of formulae IVa-IVd, the compound is according to formula Va, Vb, Vc, Vd, Ve, Vf, Vg, Vh or Vi:

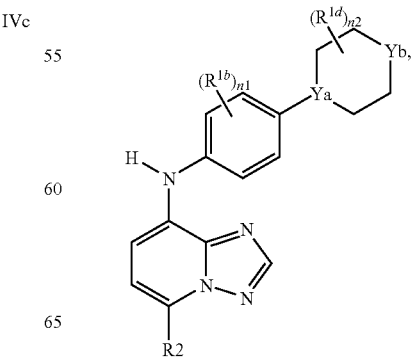

Va

-continued

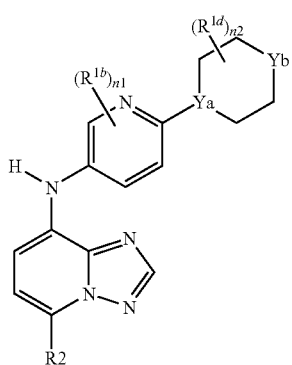
Vb

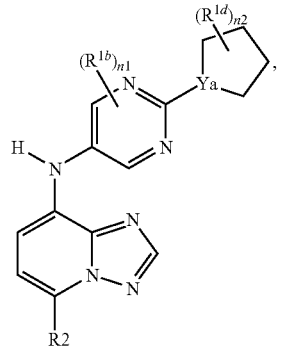
Vf

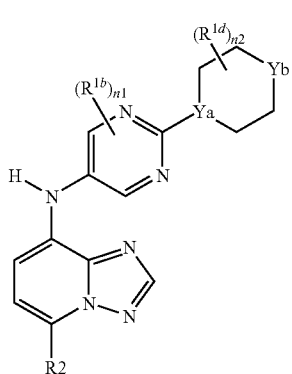
Vc

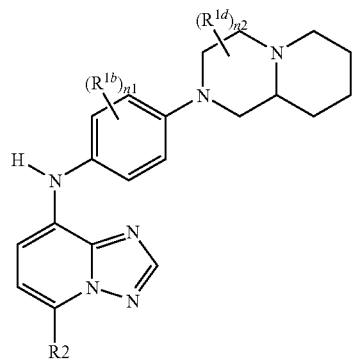
Vg

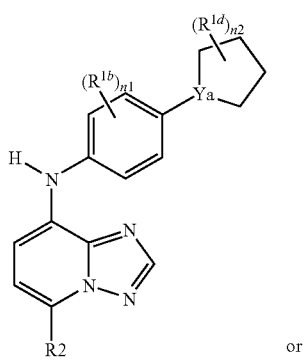
Vd

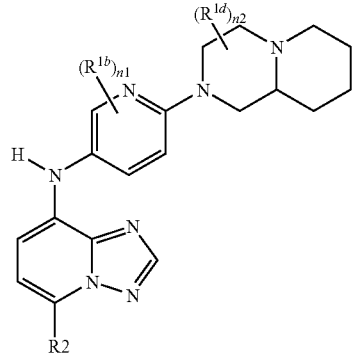
Vh or

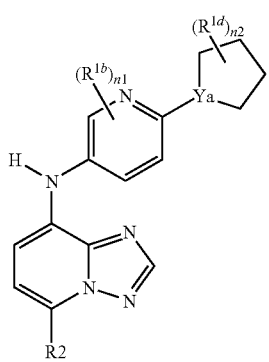
Ve

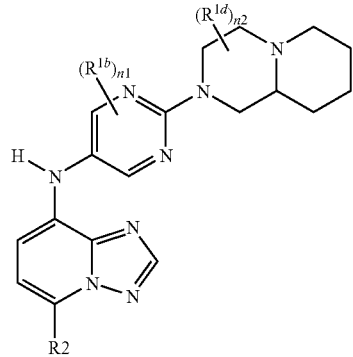
Vi and wherein $R^2$ is as described for formula III; Ya is C or N, Yb is C—$R^b$, O, S, $SO_2$ or N—$R^{1c}$, each $R^{1b}$ is independently selected from Me, Et, Pr, iso-Pr, Cl, F, CN, OMe, OEt, $CF_3$, $CF_2CF_3$ or $OCF_3$, $R^{1c}$ is hydrogen, substituted or unsubstituted $C_1$-$C_6$ alkyl or substituted or unsubstituted cycloalkyl, each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment, with respect to compounds of formulae Va-Vi, Ya is N.

In one embodiment, with respect to compounds of formulae Va-Vi, Yb is O.

In one embodiment, with respect to compounds of formulae Va-Vc, Yb is N—$R^{1c}$.

In one embodiment, with respect to compounds of formulae Va-Vc, Yb is $CR^{1c}$ and Ya is N.

In one embodiment, with respect to compounds of formulae Va-Vc, Ya is N, Yb is $CR^{1c}$ and $R^{1c}$ is substituted or unsubstituted piperidine.

In another embodiment, with respect to compounds of formulae Va-Ve, the compound is according to formula VIa, VIb, VIc, VId, Ve, VIf, VIg, VIh, VIi, VIj, VIk or Vll:

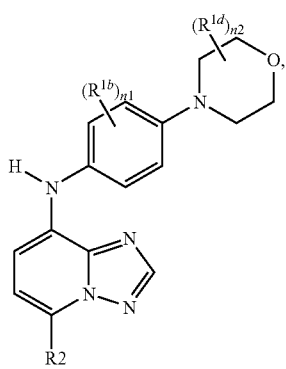
VIa

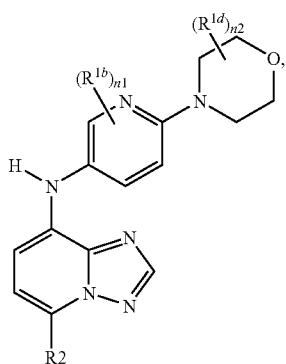
VIb

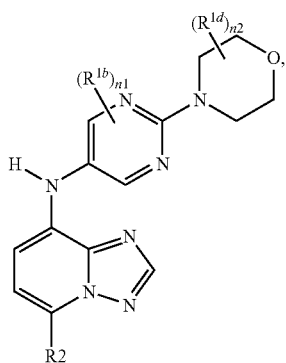
VIc

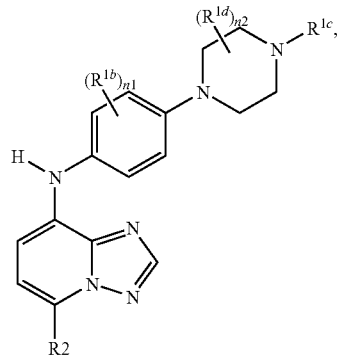
VId

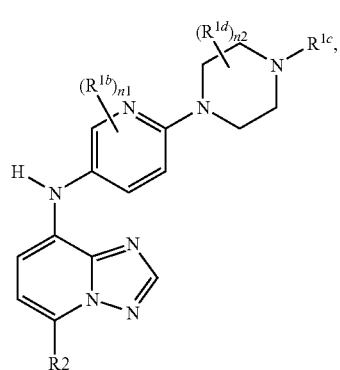
VIe

VIf

VIg

VIh 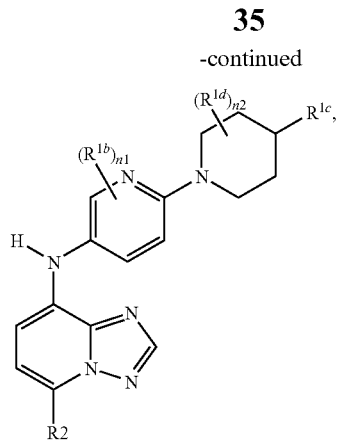

VIi 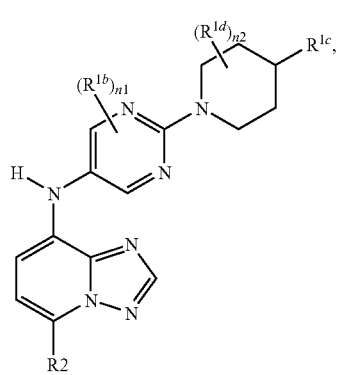

VIj 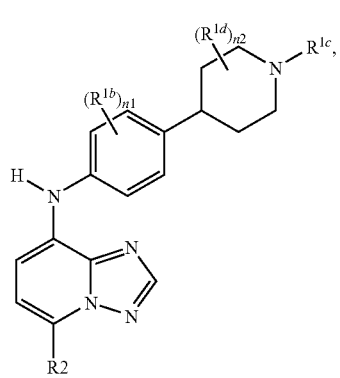

VIk 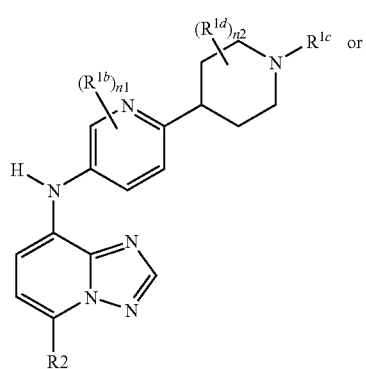

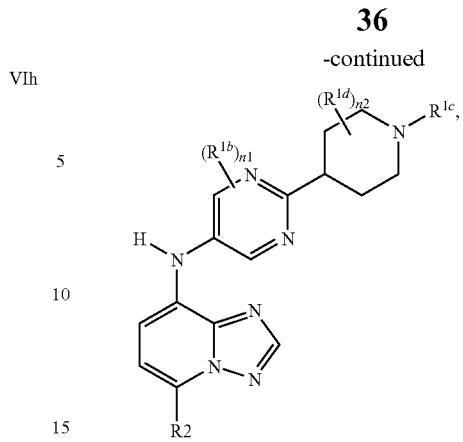
VIl and wherein $R^2$ is as described for formula III; each $R^{1b}$ is independently selected from Me, Et, Pr, iso-Pr, Cl, F, CN, OMe, OEt, $CF_3$, $CF_2CF_3$ or $OCF_3$ and $R^{1c}$ is selected from hydrogen, substituted or unsubstituted alkyl or substituted or unsubstituted cycloalkyl or substituted or unsubstituted heterocycloalkyl; each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment the compounds are according to formulae VIa, VId, VIg or VIh.

In one embodiment, with respect to compounds of formulae VId-VIl, $R^{1c}$ is H.

In another embodiment, with respect to compounds of formulae VId-VIl, $R^{1c}$ is substituted or unsubstituted $C_1$-$C_6$ alkyl, substituted or unsubstituted cycloalkyl or substituted or unsubstituted heterocycloalkyl.

In another embodiment, with respect to compounds of formulae VId-VIl, $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidine.

In another embodiment, with respect to compounds of formulae VId-VIl, $R^{1c}$ is piperidine substituted by one or more OH, Me or F.

In another embodiment, with respect to compounds of formulae VIg-VIi, $R^{1c}$ is piperidine substituted by one or more OH, Me or F.

In another embodiment, with respect to compounds of formulae Va-Ve, the compound is according to formula VIm, VIn, or VIo:

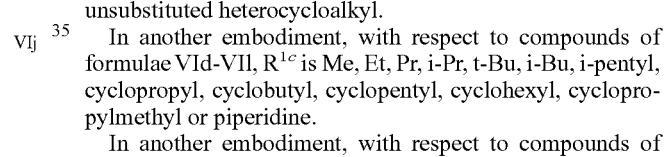

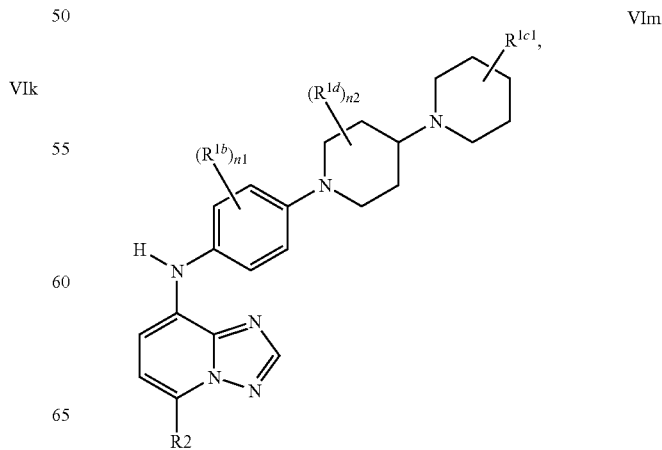
VIm

-continued
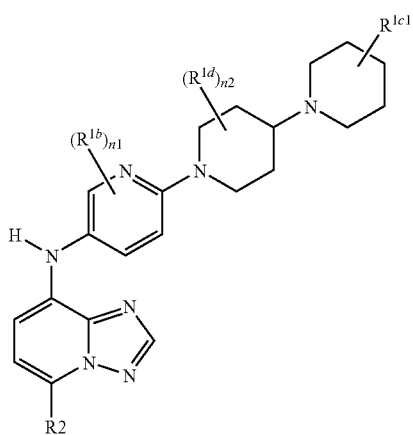
VIn
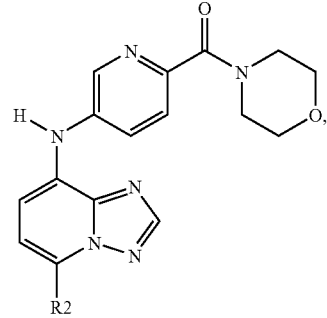
VIIb
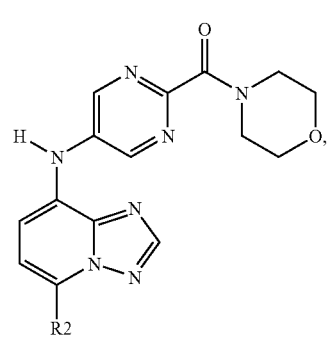
VIIc
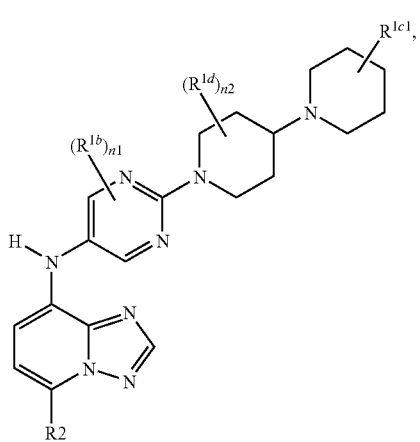
VIo
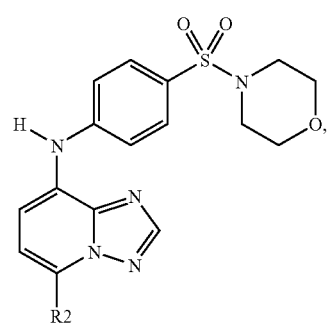
VIId
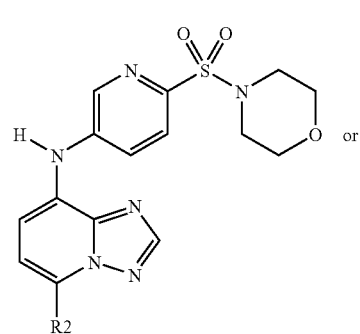
VIIe
and wherein R² is as described for formula III; $R^{1b}$, $R^{1d}$, n1 and n2 are as described for formulae Va-Vi; and $R^{1c1}$ is H, Me, F, Cl, or OH.
In another embodiment, with respect to compounds of formulae IVa-IVd, the compound is according to formula VIIa, VIIb, VIIc, VIId, VIIe, or VIf:
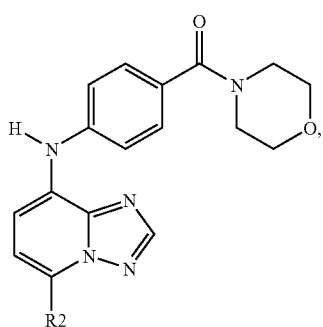
VIIa
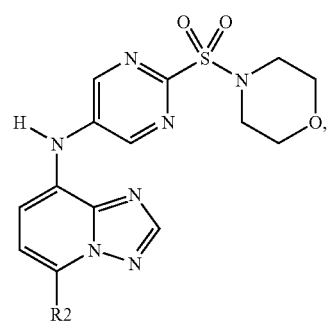
VIIf
and wherein R² is as described for formula III.

In one embodiment, the compound is according to Formula VIIa or VIId.
In another embodiment, with respect to compounds of formulae IVa-IVd, the compound is according to formula VIIIa, VIIIb, VIIIc, VIIId, VIIIe, VIIIf, VIIIh, VIIIi:
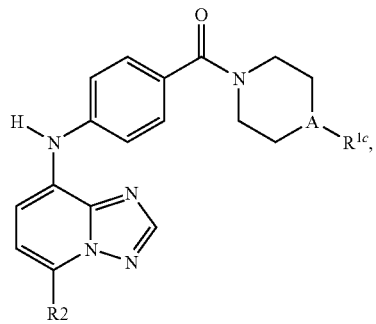
VIIIa
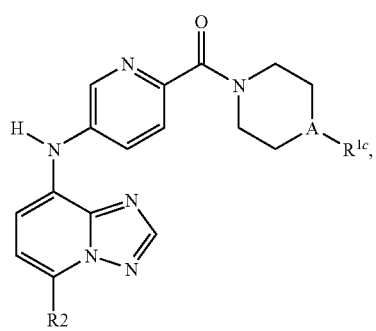
VIIIb
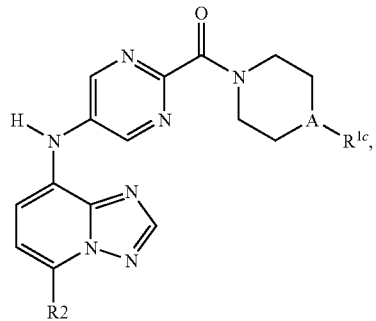
VIIIc
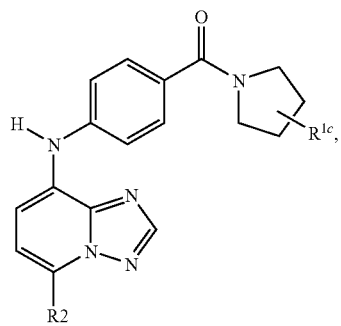
VIIId
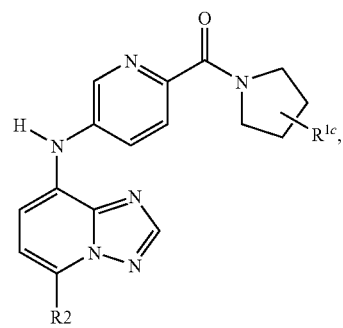
VIIIe
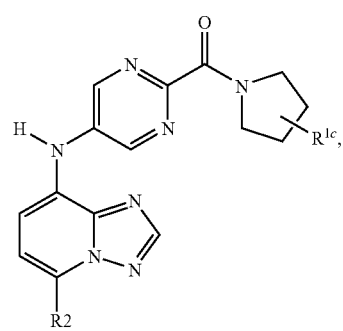
VIIIf
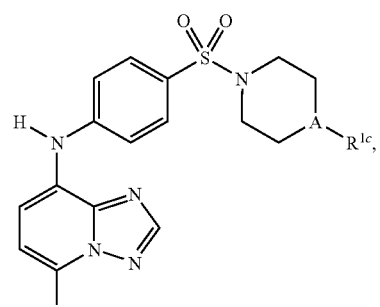
VIIIg
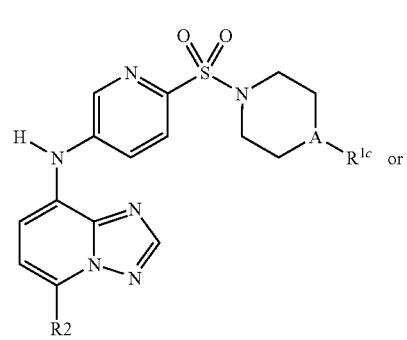
VIIIh or
VIIIi and wherein $R^2$ is as described for formula III; A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, the compounds are according to Formula VIIIa, VIIId or VIIIg.

In one embodiment, with respect to compounds of formulae VIIIa-VIIIi, $R^{1c}$ is H.

In another embodiment, with respect to compounds of formulae VIIIa-VIIIi, $R^{1c}$ is substituted or unsubstituted alkyl or substituted or unsubstituted cycloalkyl.

In another embodiment, with respect to compounds of formulae VIIIa-VIIIi, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae VIIIa-VIIIi, $R^{1c}$ is substituted or unsubstituted aryl, aralkyl or heteroaryl.

In another embodiment, with respect to compounds of formulae VIIIa-VIIIi, $R^{1c}$ is substituted or unsubstituted phenyl, benzyl or pyridyl.

In another embodiment, with respect to compounds of formula III, the compound is according to formula IXa or IXb:

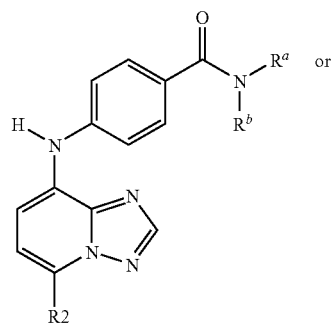

IXa

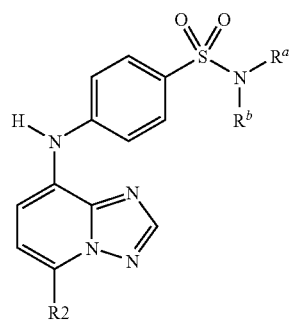

IXb and wherein $R^2$ is as described for formula III; each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae IXa-IXb, $R^a$ is H.

In another embodiment, with respect to compounds of formulae IXa-IXb, $R^a$ is Me, Et or n-Pr.

In another embodiment, with respect to compounds of formulae IXa-IXb, $R^b$ is substituted or unsubstituted alkyl or substituted or unsubstituted cycloalkyl.

In another embodiment, with respect to compounds of formulae IXa-IXb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment with respect to compounds of formulae IXa-IXb, $R^b$ is substituted or unsubstituted heterocycloalkyl.

In another embodiment with respect to compounds of formulae IXa-IXb, $R^b$ is substituted pyrrolidine.

In another embodiment with respect to compounds for formulae IXa, $R^b$ is pyrrolidine substituted by benzyl.

In another embodiment, with respect to compounds of formulae IXa-IXb, $R^b$ is substituted or unsubstituted aryl, aralkyl or heteroaryl.

In another embodiment, with respect to compounds of formulae IXa-IXb, $R^b$ is substituted or unsubstituted phenyl, benzyl or pyridyl.

In one embodiment, with respect to compounds of formulae III-IXb, $R^2$ is selected from substituted or unsubstituted aryl.

In another embodiment, with respect to compounds of formulae III-IXb, $R^2$ is selected from substituted or unsubstituted phenyl.

In another embodiment, with respect to compounds of formulae III-IXb, $R^2$ is selected from substituted or unsubstituted heteroaryl.

In another embodiment, with respect to compounds of formulae III-IXb, $R^2$ is selected from substituted or unsubstituted phenyl, pyridyl, indolyl, isoindolyl, pyrrolyl, furanyl, thienyl, pyrazolyl, oxazolyl, and thiazolyl.

In another embodiment, with respect to compounds of formulae III-IXb, $R^2$ is

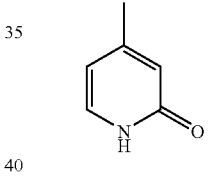

In another embodiment, with respect to compounds of formulae III-IXb, $R^2$ is

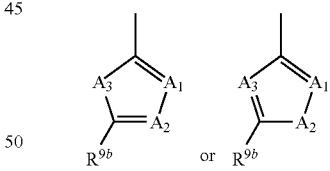

and each of $A^1$, $A^2$ and $A^3$ is independently selected from S, O, N, $NR^{9a}$, and $CR^{9a}$; each of $R^{9a}$ is independently H or substituted or unsubstituted $C_1$-$C_6$ alkyl; and $R^{9b}$ is $CONH_2$, CONHMe, or CN.

In another embodiment, with respect to compounds of formulae III-IXb, $R^2$ is

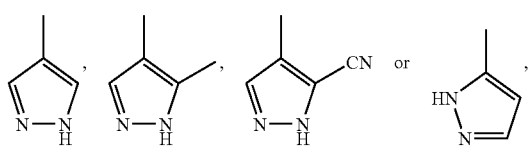

In another embodiment, with respect to compounds of formulae III-IXb, R² is

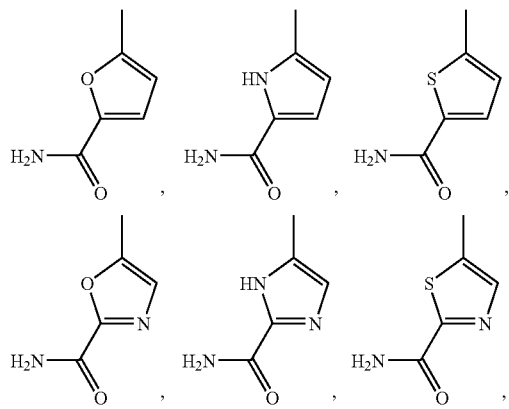

In another embodiment, with respect to compounds of formulae III-IXb, R² is

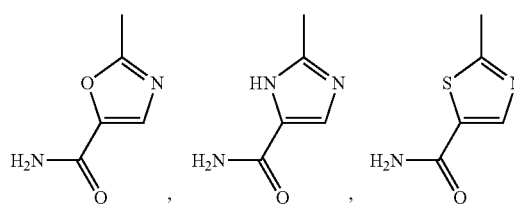

In another embodiment, with respect to compounds of formulae III-IXb, R² is

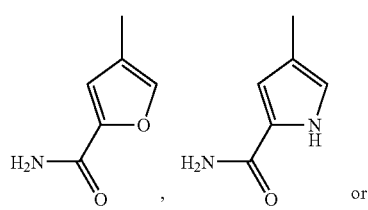

and wherein the subscript m is selected from 1-4 and each $R^{9d}$ is independently H, substituted or unsubstituted $C_1$-$C_6$ alkyl or halo.

In another embodiment, with respect to compounds of formulae III-IXb, R² is

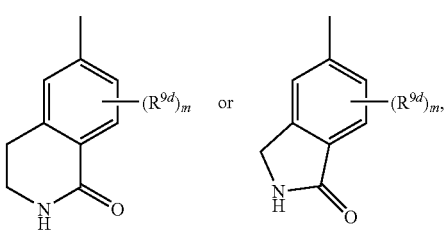

and wherein the subscript m is selected from 1-4 and each $R^{9d}$ is independently H, substituted or unsubstituted alkyl or halo.

In another embodiment, with respect to compounds of formulae III-IXb, R² is

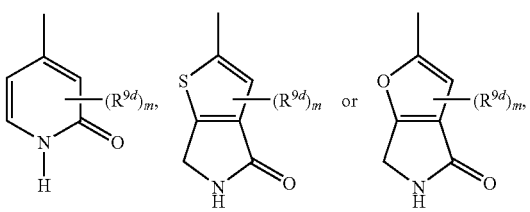

and wherein the subscript m is selected from 1-3 and each $R^{9d}$ is independently H, substituted or unsubstituted alkyl or halo.

In one embodiment, with respect to compounds of formulae III-IXb, R² is as described above and each $R^{9d}$ is H.

In another embodiment, with respect to compounds of formulae III-IXb, R² is as described above; and m is 1 or 2; and each $R^{9d}$ is Me, Cl or F.

In another embodiment, with respect to compounds of formula III, the compound is according to Formulae Xa, Xb or Xc:

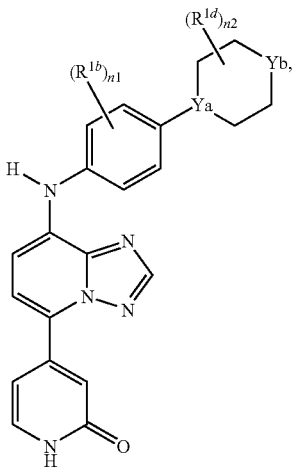

Xa

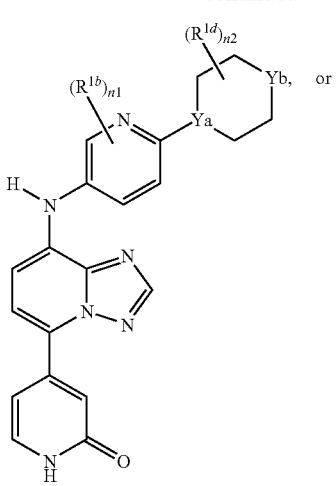

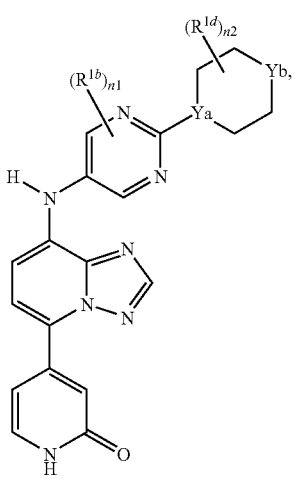

wherein Ya is C or N, Yb is C—R$^{1c}$, O, S, SO$_2$ or N—R$^{1c}$, each R$^{1b}$ is independently selected from Me, Et, Pr, iso-Pr, Cl, F, CN, OMe, OEt, CF$_3$, CF$_2$CF$_3$ or OCF$_3$ and R$^{1c}$ is selected from hydrogen, substituted or unsubstituted C$_1$-C$_6$ alkyl, substituted or unsubstituted cycloalkyl or substituted or unsubstituted heterocycloalkyl; each R$^{1d}$ is independently selected from H, Me, Et, Pr, iso-Pr, Cl, F, CN, OMe, OEt, CF$_3$, CF$_2$CF$_3$ or OCF$_3$, each n1 is independently an integer between 0 and 2 and each n2 is independently an integer between 0 and 2.

In another embodiment, with respect to compounds of Formula Xa-Xc, Ya is N.

In another embodiment, with respect to compounds of Formula Xa-Xc, Ya is C.

In one embodiment, with respect to compounds of formulae Xa-Xc, Yb is O.

In one embodiment, with respect to compounds of formulae Xa-Xc, Yb is N—R$^{1c}$.

In one embodiment, with respect to compounds of formulae Xa-Xc, Yb is CR$^{1c}$ and Ya is N.

In one embodiment, with respect to compounds of formulae Xa-Xc, Ya is N, Yb is CR$^{1c}$ and R$^{1c}$ is substituted or unsubstituted piperidine.

In another embodiment, with respect to compounds of formula III, the compound is according to formula XIa, XIb, XIc, XId, XIe, XIf, XIg, XIh, XIi, XIj, XIk or XII

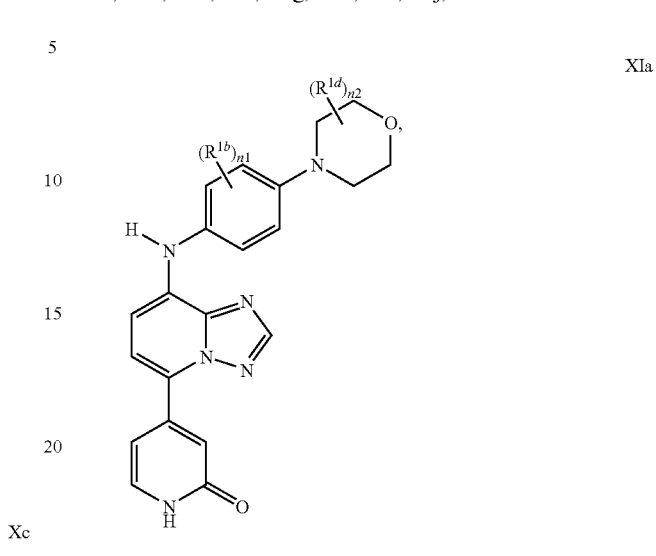

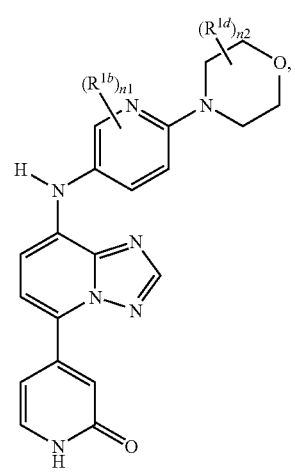

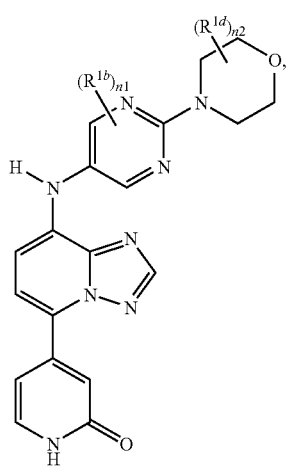

XId
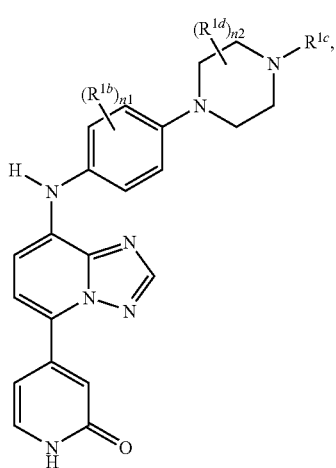
XIg
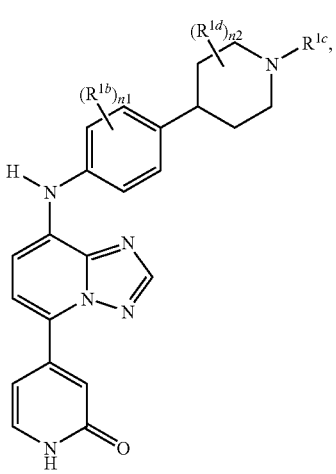
XIe
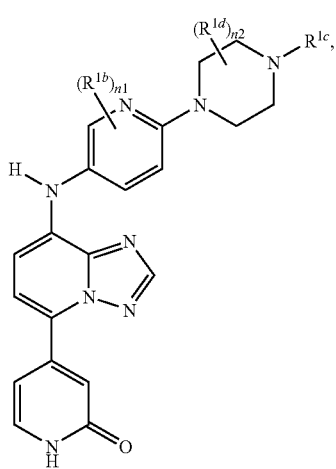
XIh
XIf
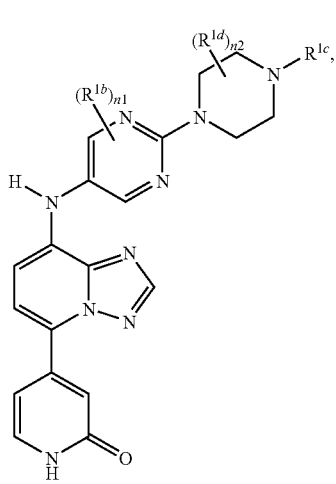
XIi

-continued

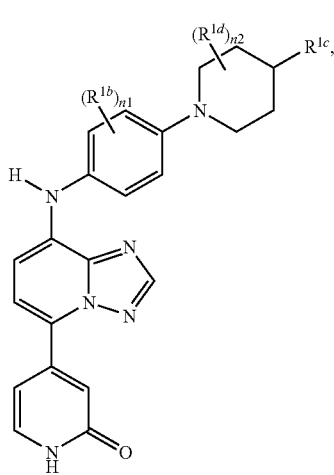

XIj

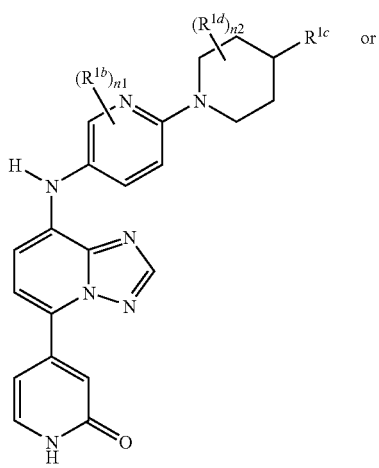

XIk

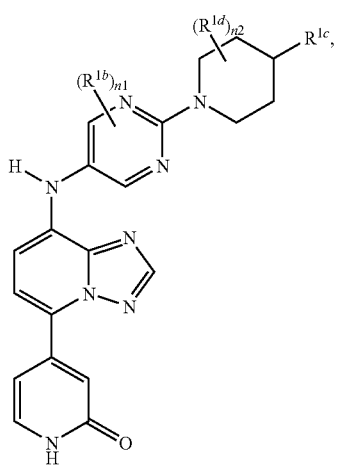

XII and wherein $R^{1c}$ is hydrogen, substituted or unsubstituted alkyl, substituted or unsubstituted cycloalkyl, or substituted or unsubstituted heterocycloalkyl and wherein each $R^{1b}$ is independently selected from Me, Et, Pr, iso-Pr, Cl, F, CN, OMe, OEt, $CF_3$, $CF_2CF_3$ or $OCF_3$, each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment, the compounds are according to formulae XIa, XId, XIg or XIj

In one embodiment, with respect to compounds of formulae XIc-XIl, $R^{1c}$ is H.

In another embodiment, with respect to compounds of formulae XIc-XIl, $R^{1c}$ is substituted or unsubstituted alkyl, substituted or unsubstituted cycloalkyl, or substituted or unsubstituted heterocycloalkyl.

In another embodiment, with respect to compounds of formulae IXa-IXf, $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidine.

In another embodiment, with respect to compounds of formulae XId-XIl, $R^{1c}$ is piperidine substituted by one or more OH, Me or F.

In another embodiment, with respect to compounds of formulae XIg-XIl, $R^{1c}$ is piperidine substituted by one or more OH, Me or F.

In another embodiment, with respect to compounds of formula III, the compound is according to formula XIm, XIn, or XIo,

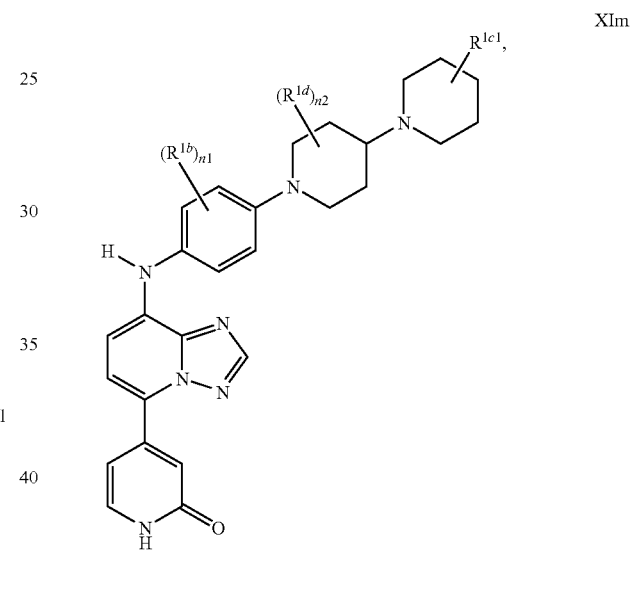

XIm

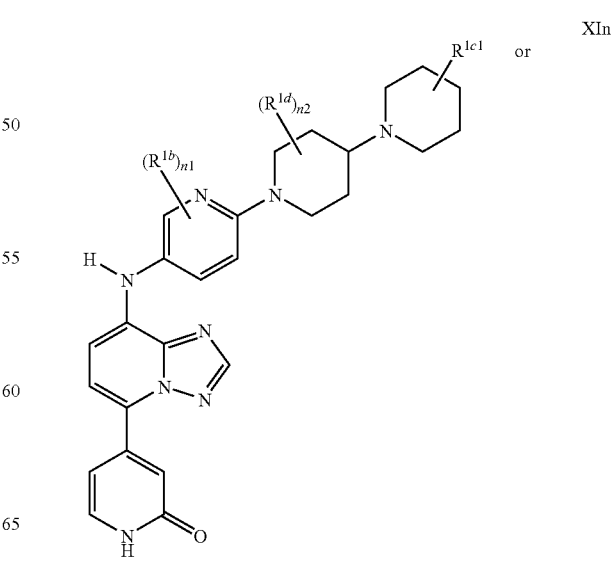

XIn

XIo
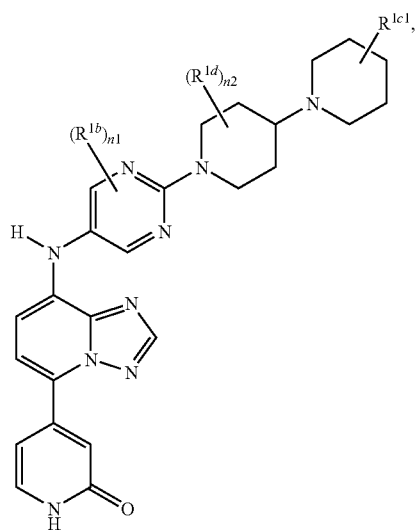
and wherein R² is as described for formula III; $R^{1b}$, $R^{1d}$, n1 and n2 are as described for formulae Va-Vi; and $R^{1C1}$ is H, Me, F, Cl, or OH.
In another embodiment, with respect to compounds of formula III, the compound is according to formula XIIa, XIIb, XIIc, XIId, XIIe, or XIIf:
XIIa
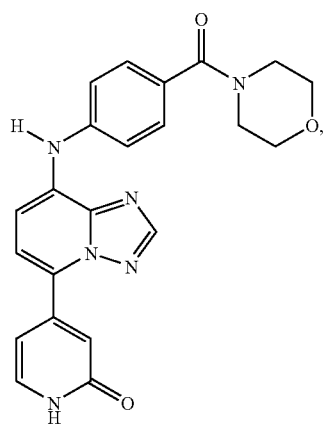
XIIb
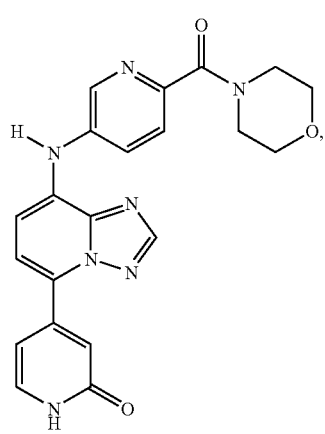
XIIc
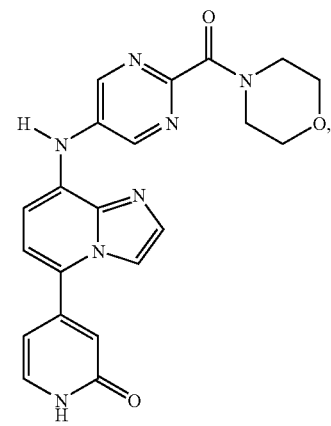
XIId
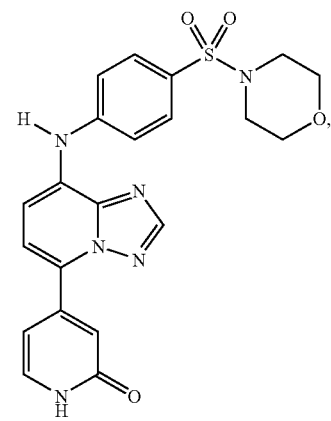
XIIe
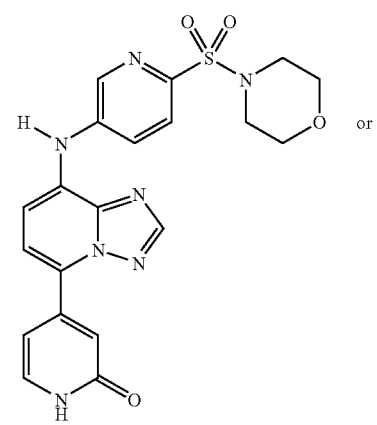
or
XIIf
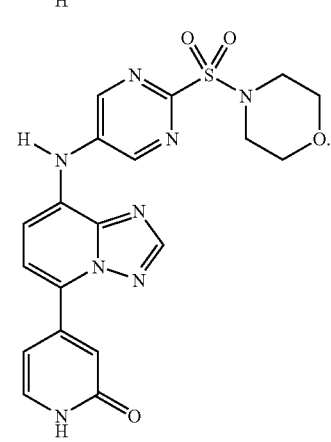

In one embodiment, the compounds are according to Formulae Xa or Xd.

In another embodiment, with respect to compounds of formula III, the compound is according to formula XIIIa, XIIIb, XIIIc, XIIId, XIIIe, or XIIIf:

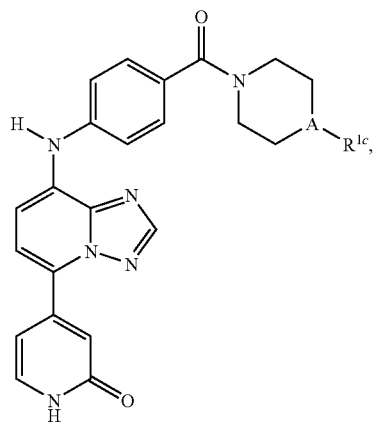

XIIIa

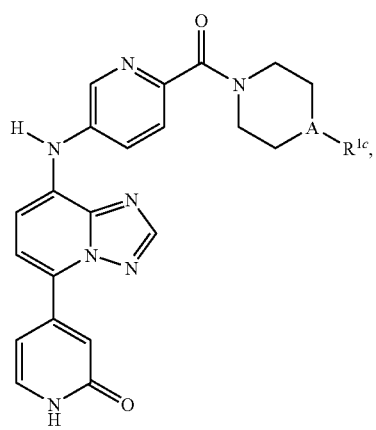

XIIIb

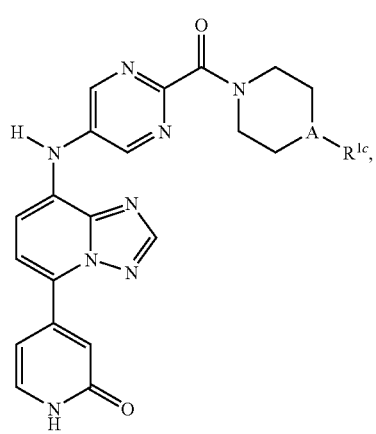

XIIIc

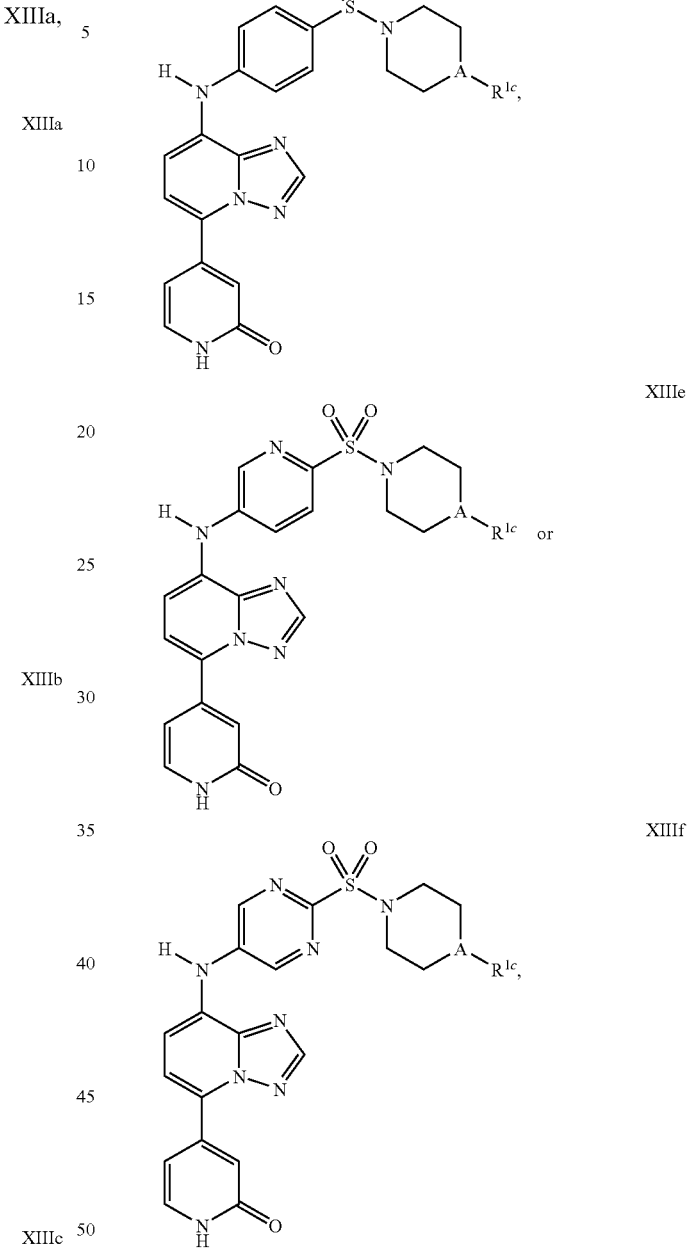

wherein A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, the compounds are according to formulae XIIa or XIId.

In one embodiment the compounds are according to formulae XIIIa or XIIId.

In one embodiment, with respect to compounds of formulae XIIa-XIIIf, $R^{1c}$ is H.

In another embodiment, with respect to compounds of formulae XIIa-XIIIf, $R^{1c}$ is substituted or unsubstituted $C_1$-$C_6$ alkyl or substituted or unsubstituted cycloalkyl.

In another embodiment, with respect to compounds of formulae XIIa-XIIIf, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XIIa-XIIIf, $R^{1c}$ is substituted or unsubstituted aryl, aralkyl or heteroaryl.

In another embodiment, with respect to compounds of formulae XIIa-XIIIf, $R^{1c}$ is substituted or unsubstituted phenyl, benzyl or pyridyl.

In another embodiment, with respect to compounds of formula III, the compound is according to formula XIVa, or XIVb:

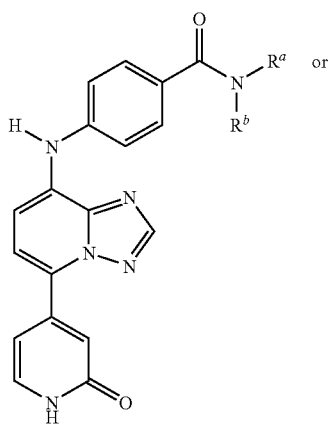

XIVa

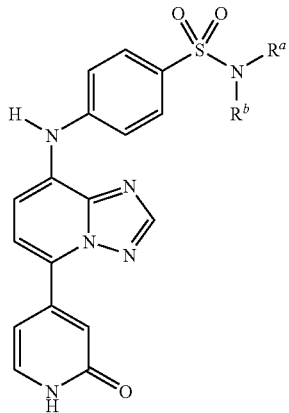

XIVb and wherein each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae XIVa-XIVb, $R^a$ is H.

In another embodiment, with respect to compounds of formulae XIVa-XIVb, $R^a$ is Me, Et or n-Pr.

In another embodiment, with respect to compounds of formulae XIVa-XIVb, $R^b$ is substituted or unsubstituted alkyl or substituted or unsubstituted cycloalkyl.

In another embodiment, with respect to compounds of formulae XIVa-XIVb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XIVa-XIVb, $R^b$ is substituted or unsubstituted aryl, aralkyl or heteroaryl.

In another embodiment, with respect to compounds of formulae XIVa-XIVb, $R^b$ is substituted or unsubstituted phenyl, benzyl or pyridyl.

In another embodiment with respect to compounds of formulae XIVa-XIVb, $R^b$ is substituted or unsubstituted heterocycloalkyl.

In another embodiment with respect to compounds of formulae XIVa-XIVb, $R^b$ is substituted pyrrolidine.

In another embodiment with respect to compounds for formulae XIVa, Rb is pyrrolidine substituted by benzyl.

In another embodiment, with respect to compounds of formula III, the compound is according to formula XVa, XVb, XVc, XVd, XVe, XVf, XVg, XVh, XVi, XVj, XVk or XVI:

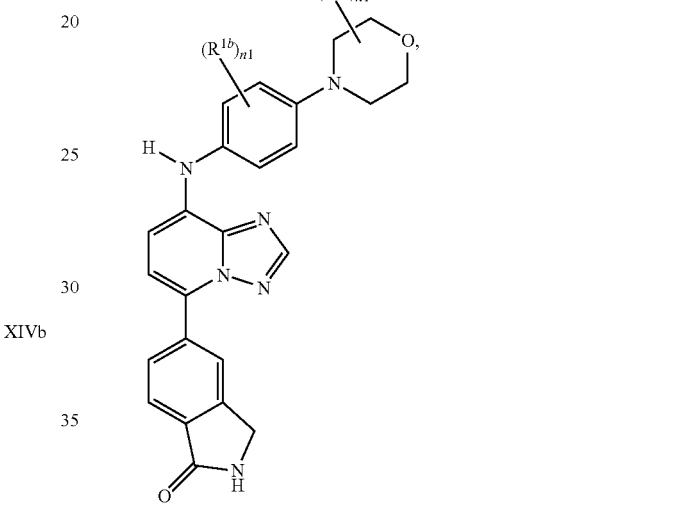

XVa

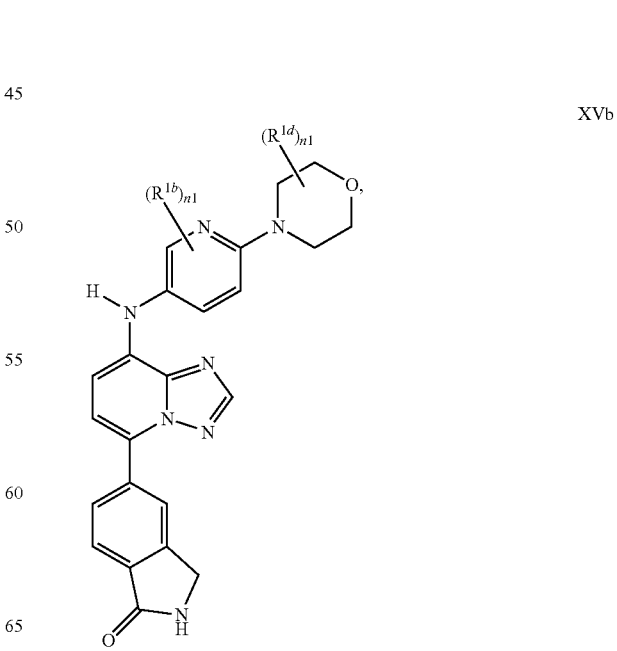

XVb

XVc
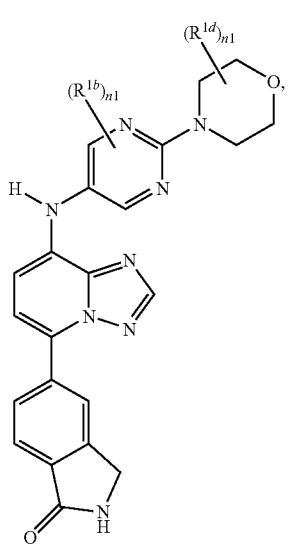
XVd
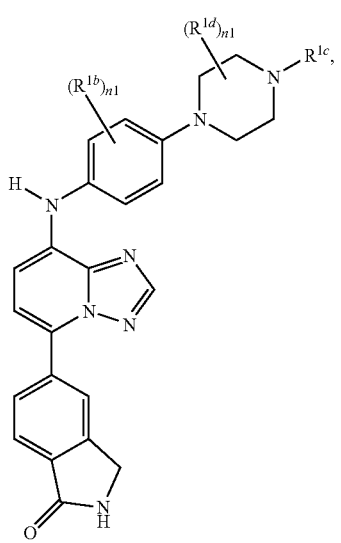
XVe
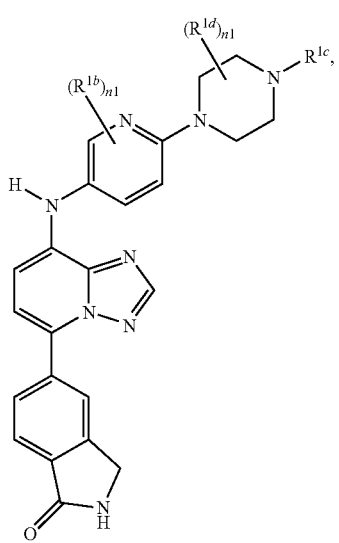
XVf
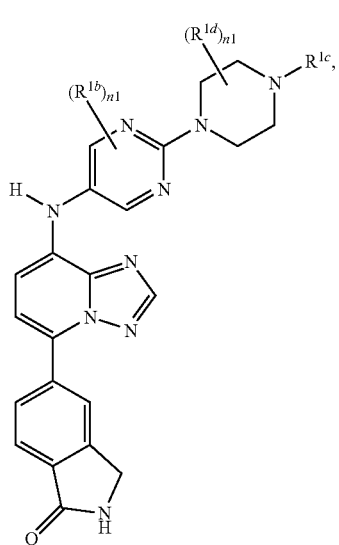
XVg
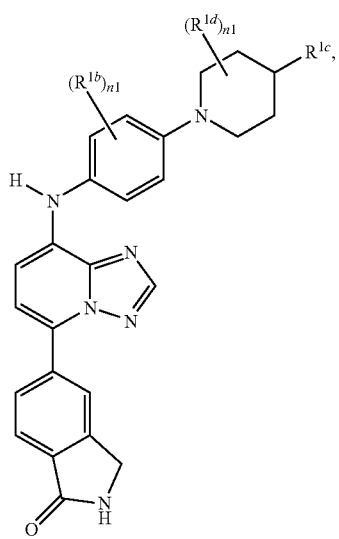
XVh
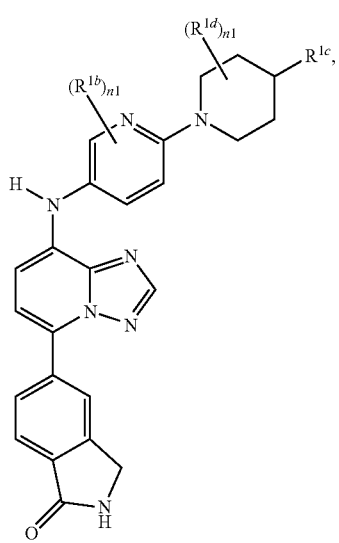

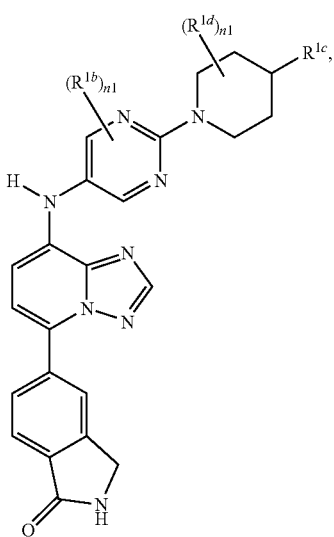

XVi

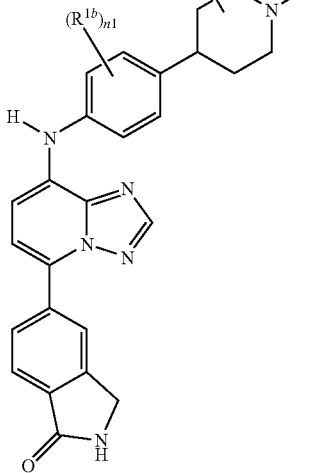

XVj

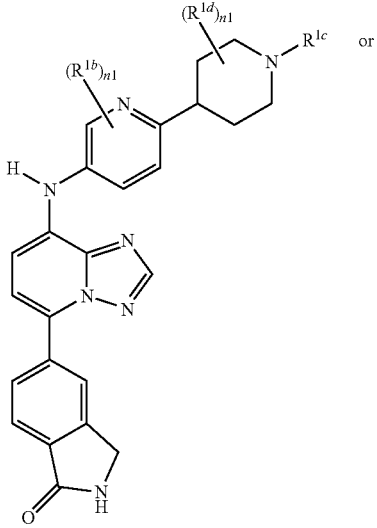

XVk

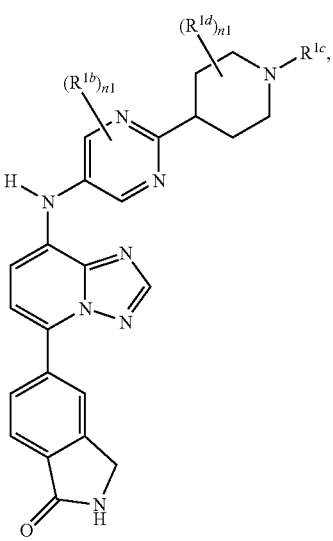

XVl and wherein $R^{1b}$ is selected from Me, Et, Pr, iso-Pr, Cl, F, CN, OMe, OEt, $CF_3$, $CF_2CF_3$ or $OCF_3$, $R^{1c}$ is hydrogen, substituted or unsubstituted alkyl or substituted or unsubstituted cycloalkyl, each $R^{1d}$ is independently selected from H, Me, Et, Pr, iso-Pr, Cl, F, CN, OMe, OEt, $CF_3$, $CF_2CF_3$ or $OCF_3$, each n1 is independently an integer between 0 and 2 and each n2 is independently an integer between 0 and 2.

In one embodiment, the compounds are according to formulae XVa, XVd, XVg or XVj.

In one embodiment, with respect to compounds of formulae XVa-XVf, $R^{1c}$ is H.

In another embodiment, with respect to compounds of formulae XVa-XVf, $R^{1c}$ is substituted or unsubstituted alkyl, substituted or unsubstituted cycloalkyl or substituted or unsubstituted heterocycloalkyl.

In another embodiment, with respect to compounds of formulae XIIIa-XIIIf, $R^{1c}$ is Me, Et, Pr, i-Pr, t-Bu, i-Bu, i-pentyl, cyclopropyl, cyclobutyl, cyclopentyl, cyclohexyl, cyclopropylmethyl or piperidine.

In another embodiment, with respect to compounds of formulae XVd-XVl, $R^{1c}$ is piperidine substituted by one or more OH, Me or F.

In another embodiment, with respect to compounds of formulae XVg-XVi, $R^{1c}$ is piperidine substituted by one or more OH, Me or F.

In another embodiment, with respect to compounds of formula III, the compound is according to formula XVm, XVn, or XVo,

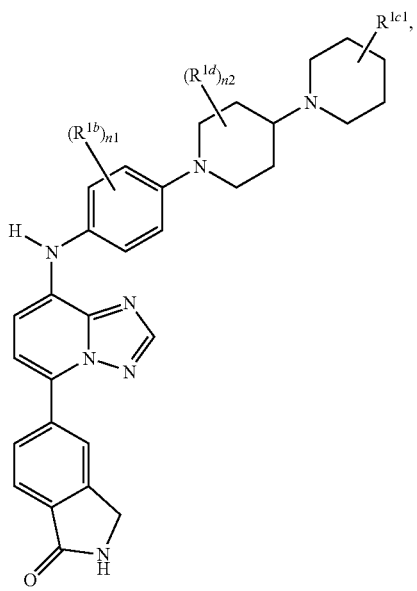
XVm
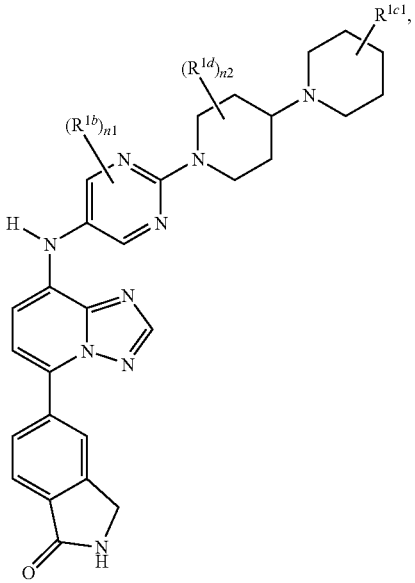
XVo
and wherein $R^2$ is as described for formula III; $R^{1b}$, $R^{1d}$, n1 and n2 are as described for formulae Va-Vi; and $R^{1c1}$ is H, Me, F, Cl, or OH.
In another embodiment, with respect to compounds of formula III, the compound is according to formula XVIa, XVI, XVIc, XVId, XVIe, or XVIf:
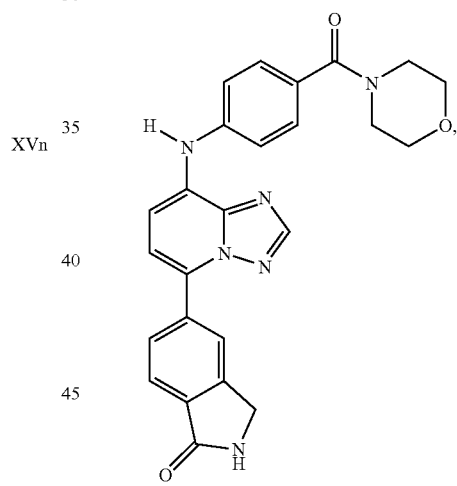
XVIa
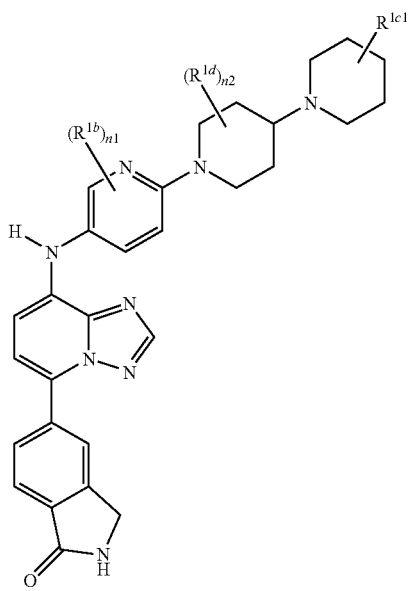 or
XVn
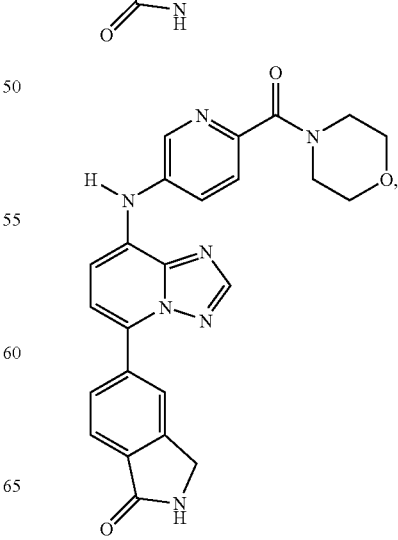
XVIb XVIc
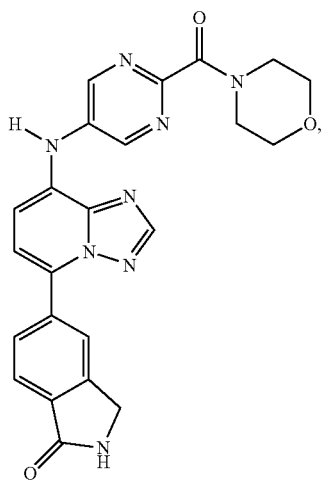
XVId
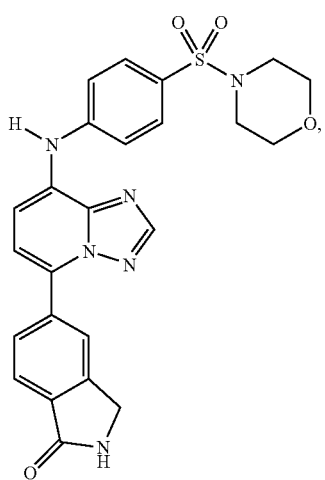
XVIe
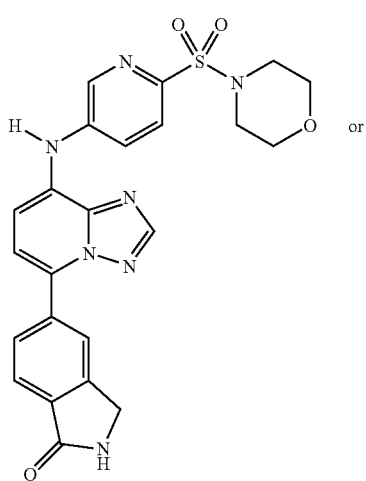
XVIf
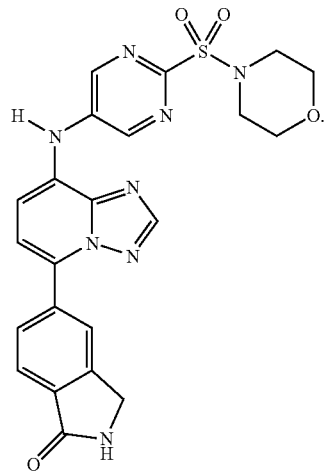
In another embodiment, with respect to compounds of formula III, the compound is according to formula XVIIa, XVIIb, XVIIc, XVIId, XVIIe, or XVIIf:
XVIIa
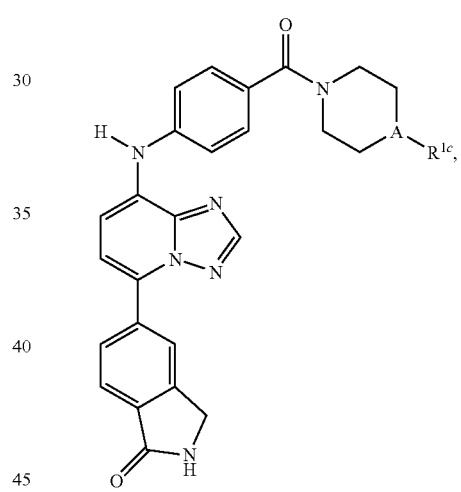
XVIIb
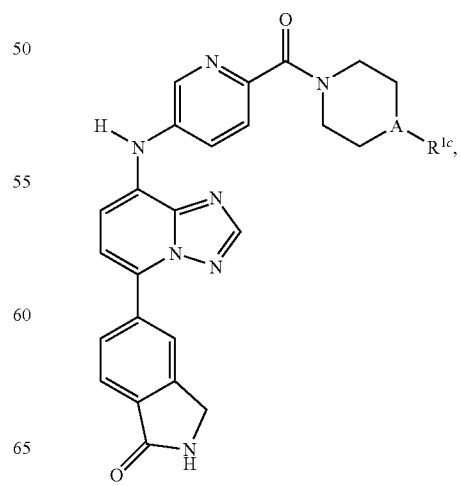

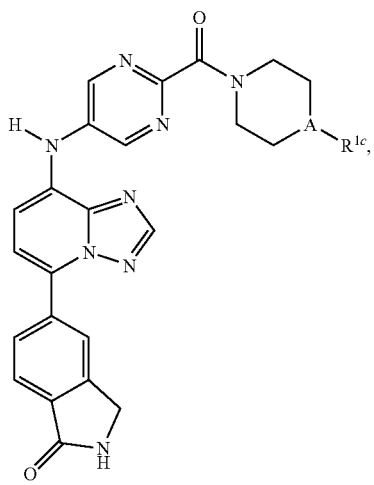

XVIIc

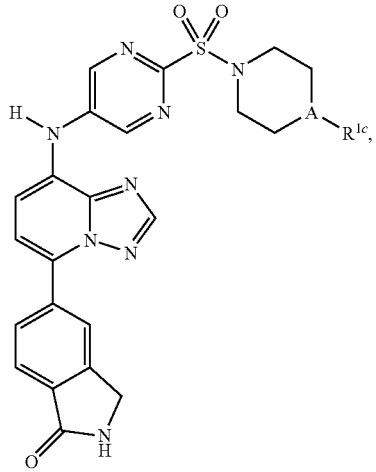

XVIIf

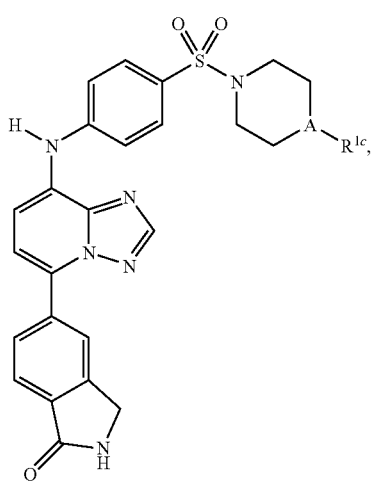

XVIId

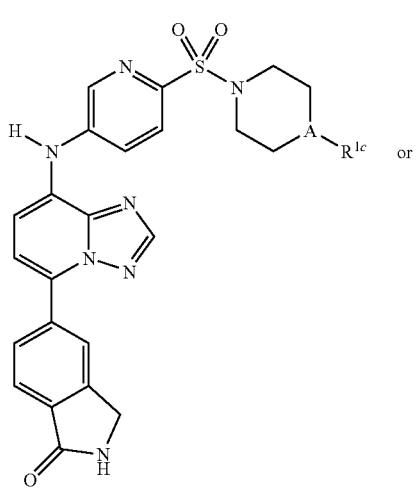

XVIIe wherein A is CH or N; and $R^{1c}$ is hydrogen, substituted or unsubstituted alkyl, substituted or unsubstituted aryl, substituted or unsubstituted aralkyl, substituted or unsubstituted heteroaryl or substituted or unsubstituted cyclo alkyl.

In one embodiment the compounds are according to formulae XVIa or XVId.

In one embodiment the compounds are according to formulae XVIIa or XVIId.

In one embodiment, with respect to compounds of formulae XVIa-XVIIf, $R^{1c}$ is H.

In another embodiment, with respect to compounds of formulae XVIa-XVIIf, $R^{1c}$ is substituted or unsubstituted $C_1$-$C_6$ alkyl or substituted or unsubstituted cycloalkyl.

In another embodiment, with respect to compounds of formulae XVIa-XVIIf, $R^{1c}$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XVIa-XVIIf, $R^{1c}$ is substituted or unsubstituted aryl, aralkyl or heteroaryl.

In another embodiment, with respect to compounds of formulae XVIa-XVIIf, $R^{1c}$ is substituted or unsubstituted phenyl, benzyl or pyridyl.

In another embodiment, with respect to compounds of formula III, the compound is according to formula XVIIIa, or XVIIIb:

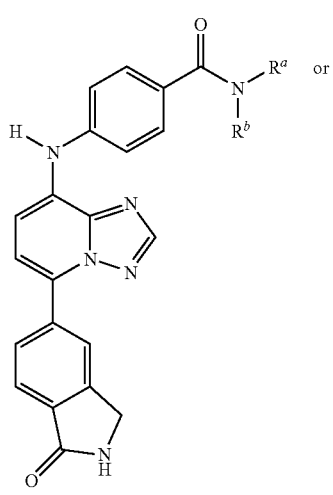

XVIIIa

XVIIIb

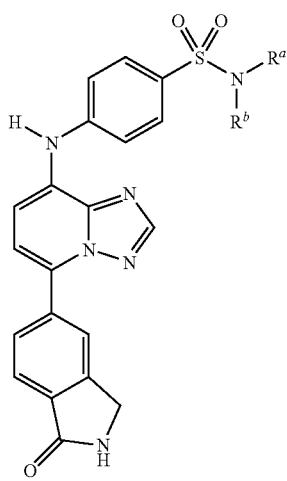

XIXa

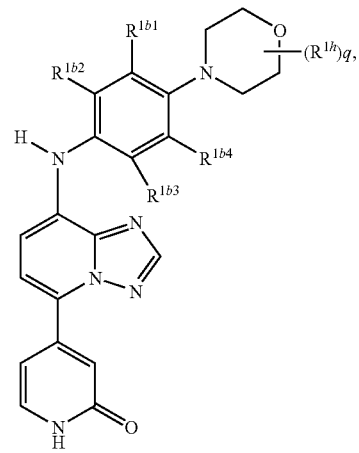

and wherein each $R^a$ and $R^b$ is independently hydrogen, substituted or unsubstituted alkyl, substituted or unsubstituted aryl, substituted or unsubstituted aralkyl, substituted or unsubstituted heteroaryl or substituted or unsubstituted cycloalkyl.

In one embodiment, with respect to compounds of formulae XVIa-XVIb, $R^a$ is H.

In another embodiment, with respect to compounds of formulae XVIa-XVIb, $R^a$ is Me, Et or n-Pr.

In another embodiment, with respect to compounds of formulae XVIa-XVIb, $R^b$ is substituted or unsubstituted $C_1$-$C_6$ alkyl or substituted or unsubstituted cycloalkyl.

In another embodiment, with respect to compounds of formulae XVIa-XVIb, $R^b$ is Me, Et, Pr, i-Pr, t-Bu, i-Bu, i-pentyl, cyclopropyl, cyclobutyl, cyclopentyl, cyclohexyl, or cyclopropylmethyl.

In another embodiment, with respect to compounds of formulae XVIa-XVIb, $R^b$ is substituted or unsubstituted aryl, aralkyl or heteroaryl.

In another embodiment, with respect to compounds of formulae XVIa-XVIb, $R^b$ is substituted or unsubstituted phenyl, benzyl or pyridyl.

In another embodiment with respect to compounds of formulae XIVa-XIVb, $R^b$ is substituted or unsubstituted heterocycloalkyl.

In another embodiment with respect to compounds of formulae XIVa-XIVb, $R^b$ is substituted pyrrolidine.

In another embodiment with respect to compounds for formulae XIVa, $R^b$ is pyrrolidine substituted by benzyl.

In another embodiment, with respect to compounds of formula III, the compound is according to formula XIXa, XIXb, XIXc, XIXd, XIXe, XIXf, XIXg or XIXh:

XIXb

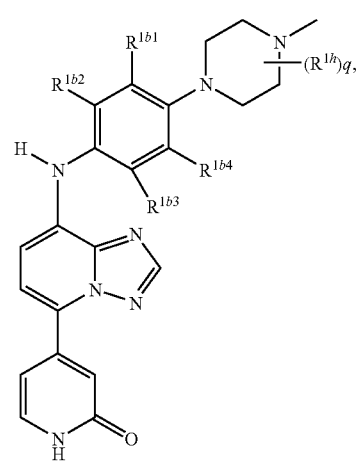

XIXc

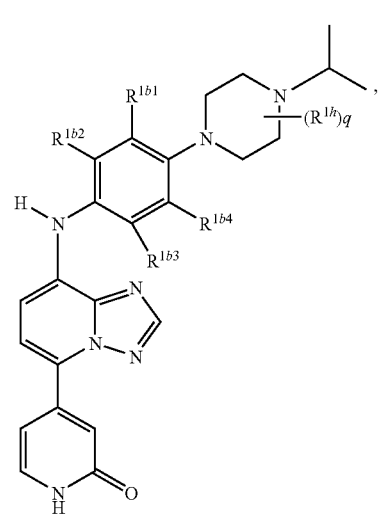

-continued
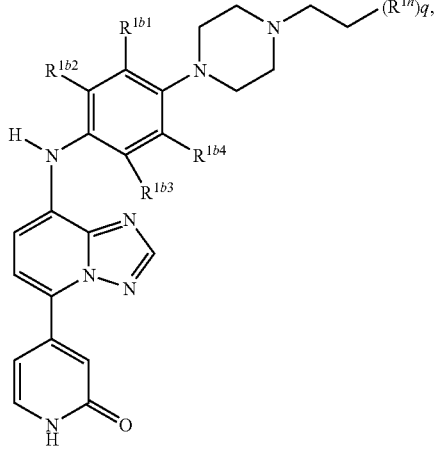
XIXd
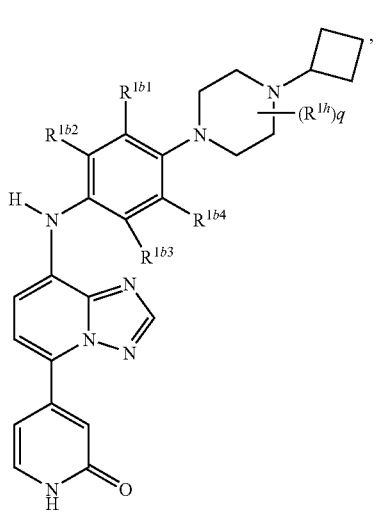
XIXe
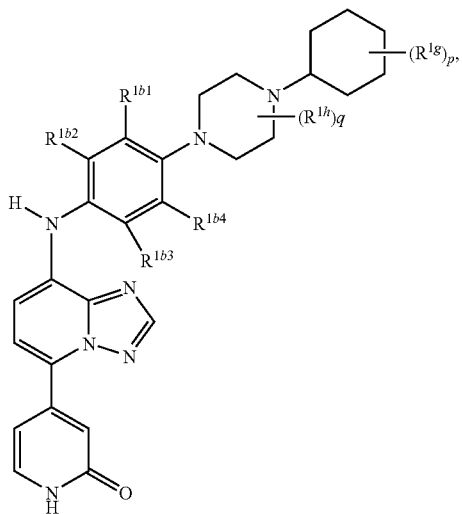
XIXf
-continued
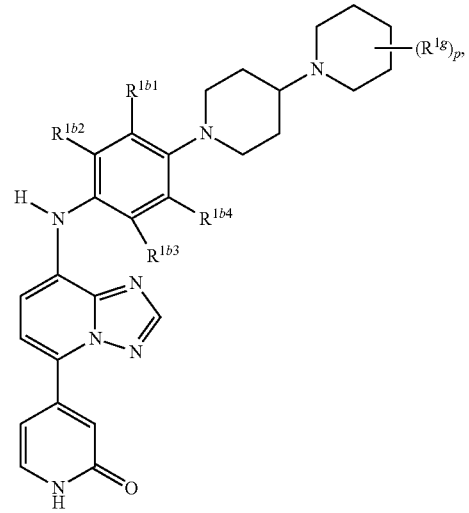
XIXg
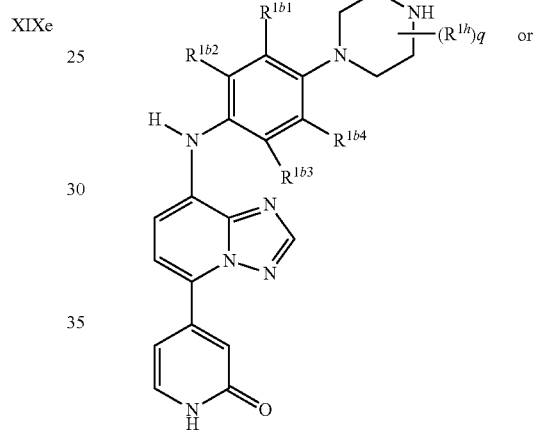
XIXh or
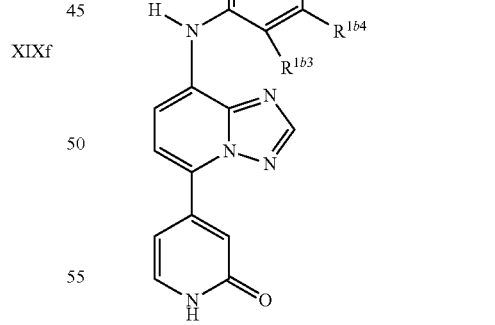
XIXi
and wherein each $R^{1b1}$, $R^{1b2}$, $R^{1b3}$ and $R^{1b4}$ is independently hydrogen, F or $CF_3$, each $R^{1g}$ is independently H, OH or Me, each $R^{1h}$ is independently H, Me or F, p is 0, 1 or 2 and q is 0, 1 or 2.
In one embodiment, with respect to compounds of formulae XIXa-XIXi, at least two of $R^{1b1}$, $R^{1b2}$, $R^{1b3}$ and $R^{1b4}$ are H.

In one embodiment, with respect to compounds of formulae XIXa-XIXi, at least three of $R^{1b1}$, $R^{1b2}$, $R^{1b3}$ and $R^{1b4}$ are H.

In one embodiment, with respect to compounds of formulae XIXa-XIXi, all of $R^{1b1}$, $R^{1b2}$, $R^{1b3}$ and $R^{1b4}$ are H.

In one embodiment with respect to compounds of formula XIXa or XIXh, $R^{1h}$ is Me and q is 2.

In one embodiment with respect to compounds of formula XIXa or XIXh q is 0.

In one embodiment with respect to compounds of formula XIXg, p is 1 and $R^{1g}$ is OH or Me.

In one embodiment with respect to compounds of formula XIXi, q is 1 or 2 and $R^{1g}$ is Me or F.

In another embodiment, with respect to compounds of formula III, the compound is according to formula XXa, XXb, XXc, XXd, or XXe:

XXa
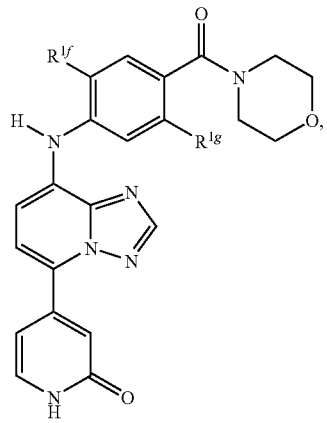

XXb
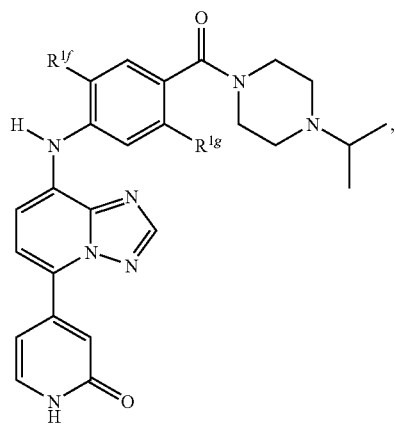

XXc
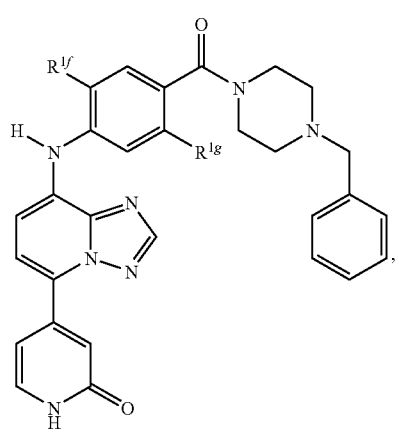

XXd
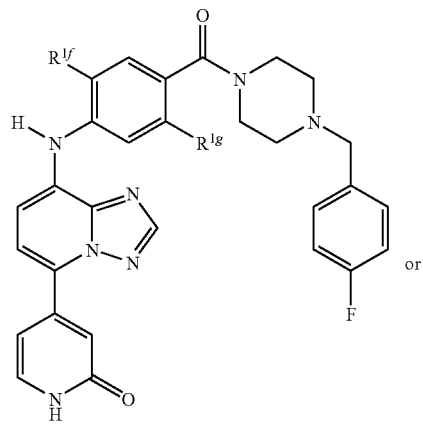

XXe
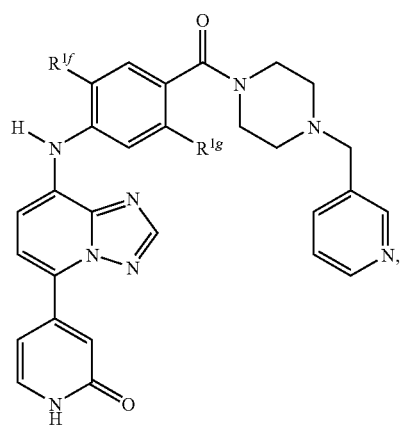

and wherein each $R^{1f}$ and $R^{1g}$ is hydrogen or F.

In another embodiment, with respect to compounds of formula III, the compound is according to formula XXIa, XXIb, XXIc, XXId, XXIe, or XXIf:

XXIa
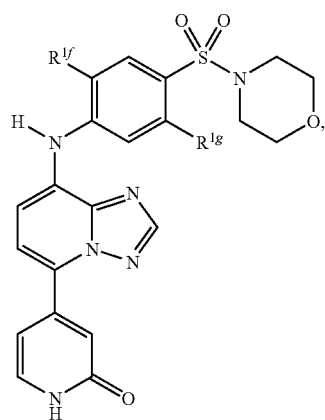

XXIb 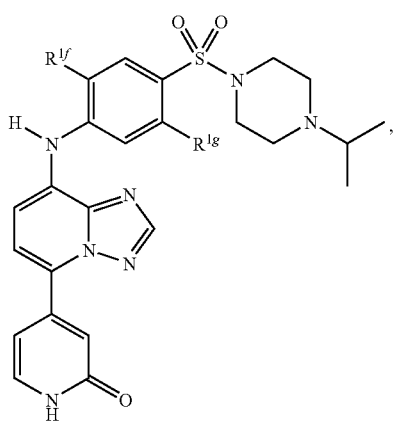
XXIc 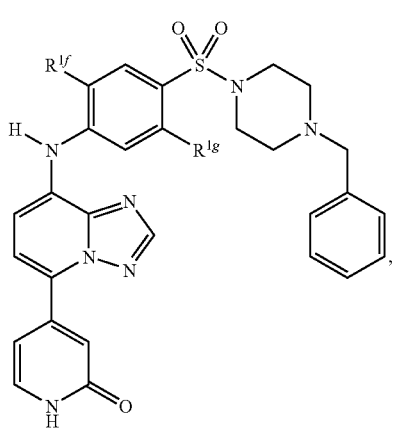
XXId 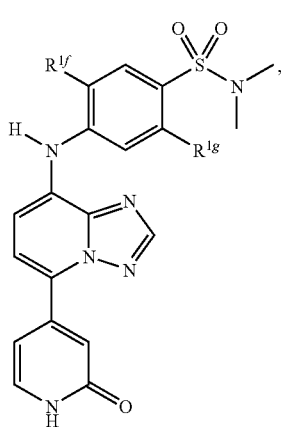
XXIe 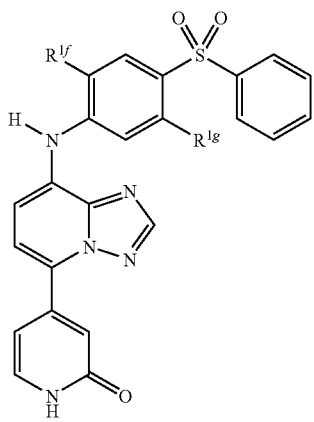
or
XXIf 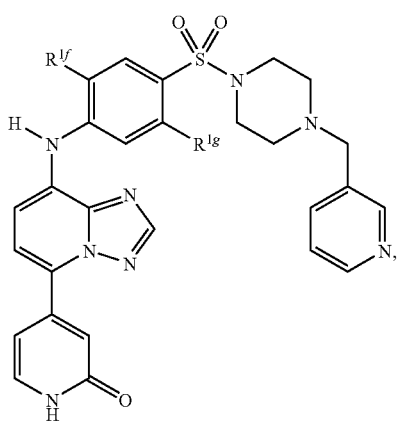
and wherein each $R^{1f}$ and $R^{1g}$ is hydrogen or F.
In another embodiment, with respect to compounds of formula III, the compound is according to formula XXIIa, XXIIb, XXIIc, XXIId, XXIIe, or XXIIf:
XXIIa 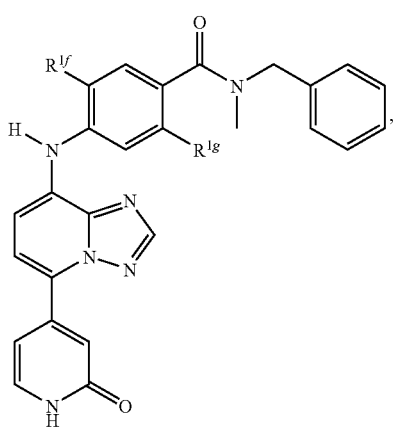

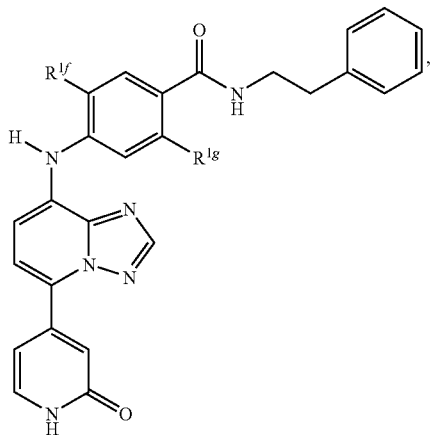

XXIIb

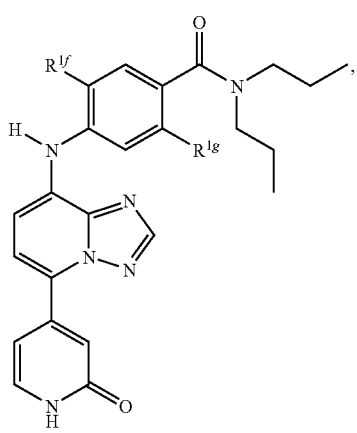

XXIIc

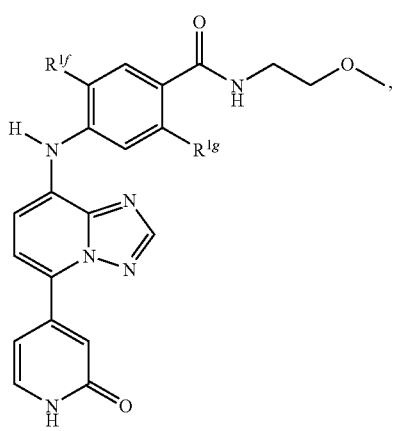

XXIId

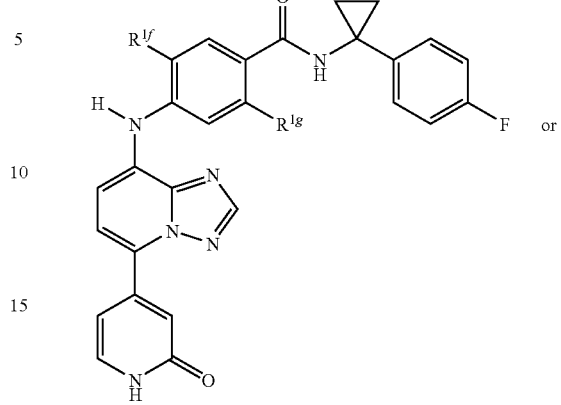

XXIIe

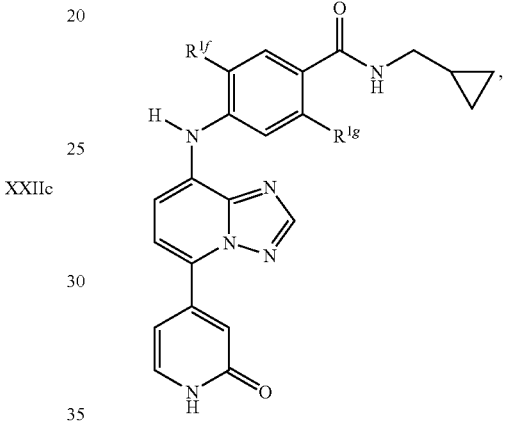

XXIIf and wherein each $R^{1f}$ and $R^{1g}$ is hydrogen or F.

In one embodiment, with respect to compounds of formulae XXa-XXIIf, each $R^{1f}$ and $R^{1g}$ is H.

In another embodiment, with respect to compounds of formulae XXa-XXIIf, $R^{1f}$ is F and $R^{1g}$ is H.

In another embodiment, with respect to compounds of formulae XXa-XXIIf, $R^{1f}$ is H and $R^{1g}$ is F.

In one embodiment the compounds are selected from:

4-[8-({3-fluoro-4-[(3R,5S)-3,4,5-trimethylpiperazin-1-yl]phenyl}amino)[1,2,4]triazolo[1,5-a]pyridin-5-yl]pyridin-2(1H)-one rel-4-[8-({4-[(2R,5S)-2,4,5-trimethylpiperazin-1-yl]phenyl}amino) [1,2,4]triazolo[1,5-a]pyridin-5-yl]pyridin-2(1H)-one rel-4-[8-({3-fluoro-4-[(2R,5S)-2,4,5-trimethylpiperazin-1-yl]phenyl}amino)[1,2,4]triazolo[1,5-a]pyridin-5-yl]pyridin-2(1H)-one 4-(8-{[4-(4-ethylpiperazin-1-yl)phenyl]amino}[1,2,4]triazolo[1,5-a]pyridin-5-yl)benzamide 4-(8-{[4-(4-propylpiperazin-1-yl)phenyl]amino}[1,2,4]triazolo[1,5-a]pyridin-5-yl)benzamide 4-[8-({4-[4-(1-ethylpropyl)piperazin-1-yl]phenyl}amino)[1,2,4]triazolo[1,5-a]pyridin-5-yl]benzamide 4-[8-({4-[4-(3-methylbutyl)piperazin-1-yl]phenyl}amino)[1,2,4]triazolo[1,5-a]pyridin-5-yl]benzamide 4-(8-{[4-(4-cyclobutylpiperazin-1-yl)phenyl]amino}[1,2,4]triazolo[1,5-a]pyridin-5-yl)benzamide 4-(8-{[4-(4-cyclohexylpiperazin-1-yl)phenyl]amino}[1,2,4]triazolo[1,5-a]pyridin-5-yl)benzamide 4-(8-{[4-(4-cyclopropylpiperazin-1-yl)phenyl]amino}[1,2,4]triazolo[1,5-a]pyridin-5-yl)benzamide 4-(8-{[4-(4-ethylpiperazin-1-yl)phenyl]amino}[1,2,4]tria-zolo[1,5-a]pyridin-5-yl)pyridin-2(1H)-one
4-(8-{[4-(4-propylpiperazin-1-yl)phenyl]amino}[1,2,4]tria-zolo[1,5-a]pyridin-5-yl)pyridin-2(1H)-one
4-[8-({4-[4-(1-ethylpropyl)piperazin-1-yl]phenyl}amino)[1,2,4]triazolo[1,5-a]pyridin-5-yl]pyridin-2(1H)-one
4-[8-({4-[4-(3-methylbutyl)piperazin-1-yl]phenyl}amino)[1,2,4]triazolo[1,5-a]pyridin-5-yl]pyridin-2(1H)-one
4-(8-{[4-(4-cyclopropylpiperazin-1-yl)phenyl]amino}[1,2,4]triazolo[1,5-a]pyridin-5-yl)pyridin-2(1H)-one
4-(8-{[4-(4-cyclobutylpiperazin-1-yl)phenyl]amino}[1,2,4]triazolo[1,5-a]pyridin-5-yl)pyridin-2(1H)-one
4-(8-{[4-(4-cyclohexylpiperazin-1-yl)phenyl]amino}[1,2,4]triazolo[1,5-a]pyridin-5-yl)pyridin-2(1H)-one
N-[4-(4-ethylpiperazin-1-yl)phenyl]-5-(2-methoxypyridin-4-yl)[1,2,4]triazolo[1,5-a]pyridin-8-amine
5-(2-methoxypyridin-4-yl)-N-[4-(4-propylpiperazin-1-yl)phenyl][1,2,4]triazolo[1,5-a]pyridin-8-amine
N-{4-[4-(1-ethylpropyl)piperazin-1-yl]phenyl}-5-(2-methoxypyridin-4-yl)[1,2,4]triazolo[1,5-a]pyridin-8-amine
5-(2-methoxypyridin-4-yl)-N-{4-[4-(3-methylbutyl)piperazin-1-yl]phenyl}[1,2,4]triazolo[1,5-a]pyridin-8-amine
N-[4-(4-cyclopropylpiperazin-1-yl)phenyl]-5-(2-methoxypyridin-4-yl)[1,2,4]triazolo[1,5-a]pyridin-8-amine
N-[4-(4-cyclobutylpiperazin-1-yl)phenyl]-5-(2-methoxypyridin-4-yl) [1,2,4]triazolo[1,5-a]pyridin-8-amine
N-[4-(4-cyclohexylpiperazin-1-yl)phenyl]-5-(2-methoxypyridin-4-yl)[1,2,4]triazolo[1,5-a]pyridin-8-amine
4-{8-[(4-piperazin-1-ylphenyl)amino][1,2,4]triazolo[1,5-a]pyridin-5-yl}pyridin-2(1H)-one
N-{4-[4-(1-ethylpropyl)piperazin-1-yl]phenyl}-5-(1H-pyrazol-4-yl)[1,2,4]triazolo[1,5-a]pyridin-8-amine
N-[4-(4-cyclobutylpiperazin-1-yl)phenyl]-5-(1H-pyrazol-4-yl)[1,2,4]triazolo[1,5-a]pyridin-8-amine
N-[4-(4-methylpiperazin-1-yl)phenyl]-5-(1H-pyrazol-4-yl)[1,2,4]triazolo[1,5-a]pyridin-8-amine
4-{[5-(1H-pyrazol-4-yl)[1,2,4]triazolo[1,5-a]pyridin-8-yl]amino}-N-(pyridin-3-ylmethyl)benzamide
N-(4-morpholin-4-ylphenyl)-5-(1H-pyrazol-4-yl)[1,2,4]triazolo[1,5-a]pyridin-8-amine
5-(5-methyl-1H-pyrazol-4-yl)-N-(4-morpholin-4-ylphenyl)[1,2,4]triazolo[1,5-a]pyridin-8-amine
4-(8-{[4-(4-methylpiperazin-1-yl)phenyl]amino}[1,2,4]triazolo[1,5-a]pyridin-5-yl)pyridin-2(1H)-one
4-{[5-(2-oxo-1,2-dihydropyridin-4-yl)[1,2,4]triazolo[1,5-a]pyridin-8-yl]amino}-N-(pyridin-3-ylmethyl)benzamide
2-fluoro-4-(8-{[4-(4-methylpiperazin-1-yl)phenyl]amino}[1,2,4]triazolo[1,5-a]pyridin-5-yl)benzamide
3-{8-[(4-morpholin-4-ylphenyl)amino][1,2,4]triazolo[1,5-a]pyridin-5-yl} benzamide
3-(8-{[4-(4-isopropylpiperazin-1-yl)phenyl]amino}[1,2,4]triazolo[1,5-a]pyridin-5-yl)benzamide
2-fluoro-5-{8-[(4-morpholin-4-ylphenyl)amino][1,2,4]triazolo[1,5-a]pyridin-5-yl}benzamide
2-fluoro-5-(8-{[4-(4-isopropylpiperazin-1-yl)phenyl]amino}[1,2,4]triazolo[1,5-a]pyridin-5-yl)benzamide
5-{8-[(4-morpholin-4-ylphenyl)amino][1,2,4]triazolo[1,5-a]pyridin-5-yl}pyrimidine-2,4(1H,3H)-dione
5-(1H-indol-4-yl)-N-(4-morpholin-4-ylphenyl)[1,2,4]triazolo[1,5-a]pyridin-8-amine
5-(1H-indol-4-yl)-N-[4-(4-isopropylpiperazin-1-yl)phenyl][1,2,4]triazolo[1,5-a]pyridin-8-amine
5-(1H-indol-5-yl)-N-(4-morpholin-4-ylphenyl)[1,2,4]triazolo[1,5-a]pyridin-8-amine
5-(1H-indol-5-yl)-N-[4-(4-isopropylpiperazin-1-yl)phenyl][1,2,4]triazolo[1,5-a]pyridin-8-amine
5-(1H-indol-6-yl)-N-(4-morpholin-4-ylphenyl)[1,2,4]triazolo[1,5-a]pyridin-8-amine
5-(1H-indol-6-yl)-N-[4-(4-isopropylpiperazin-1-yl)phenyl][1,2,4]triazolo[1,5-a]pyridin-8-amine
5-(2,4-dimethoxypyrimidin-5-yl)-N-(4-morpholin-4-ylphenyl)[1,2,4]triazolo[1,5-a]pyridin-8-amine
5-(8-{[4-(4-isopropylpiperazin-1-yl)phenyl]amino}[1,2,4]triazolo[1,5-a]pyridin-5-yl)pyrimidine-2,4(1H,3H)-dione
5-(2,4-dimethoxypyrimidin-5-yl)-N-[4-(4-isopropylpiperazin-1-yl)phenyl][1,2,4]triazolo[1,5-a]pyridin-8-amine
4-[8-({4-[(3R,5S)-3,4,5-trimethylpiperazin-1-yl]phenyl}amino)[1,2,4]triazolo[1,5-a]pyridin-5-yl]pyridin-2(1H)-one.

A compound for use according to the invention may contain one or more asymmetric carbon atoms and may exist in racemic and optically active forms. It will be understood by a person of skill in the art that the present invention includes both the racemic mixture and each enantiomer in isolated form. A compound according to an embodiment of the invention may be in trans or cis form.

The present invention also extends to a prodrug of a compound according to an embodiment of the invention such as an ester or amide thereof. A prodrug is a compound that may be converted under physiological conditions or by solvolysis to a compound according to an embodiment of the invention or to a pharmaceutically acceptable salt of a compound according to an embodiment of the invention. A prodrug may be inactive when administered to a subject but is converted in vivo to an active compound of the invention. "Pharmaceutically acceptable prodrugs" as used herein refers to those prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as prodrugs. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E.B. Roche, ed., American Pharmaceutical Association and Pergamon Press, 1987, which are incorporated herein by reference.

The present invention relates also to a method of treatment or prevention of inflammatory diseases, which comprises administering to a subject in need thereof, a therapeutically effective amount of compound of the invention.

The present invention relates also to a method of treatment or prevention of inflammatory diseases, which comprises administering to a subject in need thereof, a therapeutically effective amount of an inhibitor of TAK1 according to Formula I, II or III.

Another aspect of the present method invention relates to a method of treatment or prophylaxis of a condition characterized by abnormal MMP1 expression, which comprises administering a therapeutically effective amount of a compound which inhibits MMP1 expression according to Formula I, II or III.

A further aspect of the present method invention is a method of treatment or prophylaxis of a condition selected from diseases involving degradation of extra-cellular matrix, which comprises administering a therapeutically effective MMP1 expression-inhibiting amount of a compound according to Formula I, II or III.

A yet further aspect of the present method invention is a method of treatment or prophylaxis of a condition selected from diseases involving abnormal cellular expression of MMP1, which comprises administering a therapeutically effective MMP expression-inhibiting amount of a compound according to Formula I, II or III.

A special embodiment of the present method invention is a method of treatment or prevention of RA, which comprises administering to a subject in need thereof, a therapeutically effective amount of a compound according to Formula I, II or III.

This invention also relates to the use of the present compounds in the manufacture of a medicament for treatment or prophylaxis of a condition prevented, ameliorated or eliminated by administration of an inhibitor of TAK1 which is a compound of the invention, or a condition characterized by abnormal collagenase activity, or a condition selected from diseases involving inflammation, most preferably in for the treatment of rheumatoid arthritis.

Administration of the compound of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The compound of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammation, of an effective matrix metalloprotease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective MMP1 expression-inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A preferred therapeutically effective amount of the compound of the present invention to administer to a subject patient is about 0.1 mg/kg to about 10 mg/kg administered from once to three times a day. For example, an effective regimen of the present method may administer about 5 mg to about 1000 mg of said compound of the present invention from once to three times a day. It will be understood, however, that the specific dose level for any particular subject patient will depend upon a variety of factors including the age, body weight, general health, sex, diet, time of administration, route of administration, rate of excretion, drug combination and the severity of the particular inflammatory condition. A consideration of these factors is well within the purview of the ordinarily skilled clinician for the purpose of determining the therapeutically effective or prophylactically effective dosage amount needed to prevent, counter, or arrest the progress of the condition.

Compounds of the invention can be incorporated into pharmaceutical compositions suitable for administration. Such compositions typically comprise at least one compound of the invention and at least one pharmaceutically acceptable carrier. As used herein the language "pharmaceutically acceptable carrier" is intended to include solid carriers such as lactose, magnesium stearate, terra alba, sucrose, talc, stearic acid, gelatin, agar, pectin, acacia or the like; and liquids such as vegetable oils, arachis oil and sterile water, or the like, any and all solvents, dispersion media, coatings, antibacterial and antifungal agents, isotonic and absorption delaying agents, and the like, compatible with pharmaceutical administration. This listing of pharmaceutically acceptable carriers is not to be construed as limiting. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

A compound according to an embodiment of the invention may be provided as a salt, preferably as a pharmaceutically acceptable salt of compounds of formula I, II or III. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts of compounds according to an embodiment of the invention may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

It will be appreciated by those skilled in the art that the foregoing description is exemplary and explanatory in nature, and is intended to illustrate the invention and its preferred embodiments. Through routine experimentation, an artisan will recognize apparent modifications and variations that may be made without departing from the spirit of the invention. Thus, the invention is intended to be defined not by the above description, but by the following claims and their equivalents.

The present invention will now be described in detail with reference to specific examples of compounds and methods for their production. Within this specification embodiments have been described in a way that enables a clear and concise specification to be written, but it will be appreciated that embodiments may be variously combined or separated without parting from the invention.

EXAMPLES

Analytical Methods

LC-MS Analysis

LC-MS/UV/ELS analysis was performed on instrumentation consisting of Shimadzu LC-10AD vp series HPLC pumps and dual wavelength UV detector, a Gilson 215 autosampler, a Sedex 75c evaporative light scattering (ELS) detector, and a PE/Sciex API 150EX mass spectrometer. The ELS detector was set to a temperature of 40° C. and a $N_2$ pressure of 3.3 atm. The gain setting on the ELS detector was varied as necessary, in order to keep the output signal within a quantifiable range. The Turbo IonSpray source was employed on the API 150 with an ion spray voltage of 5 kV, a temperature of 300° C., and orifice and ring voltages of 5 V and 175 V respectively. Positive ions were scanned in Q1 from 160 to 650 m/z. 5.0 µL injections were performed for each sample, on either a 4.6×50 mm or 4.6×100 mm Phenomenex Gemini 5 µm C18 column.

Two analyses of each crude compound were carried out with different mobile modifiers in order to identify the best system for preparative separation. The first mobile phase system consisted of 10.0 mM ammonium carbonate in HPLC grade water (A) and neat HPLC grade acetonitrile (B). The second system consisted of 0.1% formic acid in HPLC grade water (A) and 0.075% formic acid in HPLC grade acetonitrile (B). These mobile phases were approximately pH 8.5 and 3.8 respectively. Gradients used with each method are shown in Tables 1 and 2. Various issues arose during purification and analysis of these compounds, including apparent degradation under basic conditions, and lack of retention under acidic conditions. Therefore, several different methods were employed. As above, crude product analyses were done in both ammonium carbonate and formic acid, with the gradients listed in Tables 1 and 2 respectively. Analysis of collected fractions was performed with formic acid with the gradients listed in Table 2. Final product analysis was carried out using one of the gradients listed in tables 1, 2, 3, 4, or 5.

Analytical data were processed and analyzed using proprietary automation routines, including integration via PE/Sciex Anlayst software, and organization of data via Microsoft Excel. Correlation was performed between MS and UV chromatograms through the creation of an extracted ion chromatogram (XIC) for the mass of interest with a width of 1.0 m/z. The intensity of a peak in the XIC was required to be at least 1,000,000 counts per scan (cps) in order to be identified as representing the designed compound. The retention time of this XIC peak was then compared to the integration of the UV chromatogram, and the purity assigned as representative of the designed product, if the offset of the UV peak from the XIC retention time was ≦0.06 minutes.

TABLE 1

$(NH_4)_2CO_3$ Gradient (Crude/FInal)

| Time (min) | Flow (mL/min) | % A | % B |
|---|---|---|---|
| 0.00 | 2.0 | 95 | 5 |
| 4.00 | 2.0 | 5 | 95 |
| 5.80 | 2.0 | 5 | 95 |
| 6.00 | 2.0 | 95 | 5 |
| 7.00 | 2.0 | 95 | 5 |

TABLE 2

HCOOH Gradient (Crude/Fraction/Final)

| Time (min) | Flow (mL/min) | % A | % B |
|---|---|---|---|
| 0.00 | 2.0 | 95 | 5 |
| 4.00 | 2.0 | 0 | 100 |
| 5.80 | 2.0 | 0 | 100 |
| 6.00 | 2.0 | 95 | 5 |
| 7.00 | 2.0 | 95 | 5 |

TABLE 3

HCOOH Gradient (Final)

| Time (min) | Flow (mL/min) | % A | % B |
|---|---|---|---|
| 0.00 | 2.0 | 98 | 2 |
| 1.00 | 2.0 | 90 | 10 |

85

TABLE 3-continued

| HCOOH Gradient (Final) | | | |
|---|---|---|---|
| Time (min) | Flow (mL/min) | % A | % B |
| 5.00 | 2.0 | 0 | 100 |
| 5.80 | 2.0 | 0 | 100 |
| 6.00 | 2.0 | 95 | 2 |
| 7.00 | 2.0 | 95 | 2 |

TABLE 4

| HCOOH Gradient (Final) | | | |
|---|---|---|---|
| Time (min) | Flow (mL/min) | % A | % B |
| 0.00 | 2.0 | 95 | 5 |
| 5.00 | 2.0 | 0 | 100 |
| 7.80 | 2.0 | 0 | 100 |
| 8.00 | 2.0 | 95 | 5 |
| 9.50 | 2.0 | 95 | 5 |

TABLE 5

| HCOOH Gradient (Final) | | | |
|---|---|---|---|
| Time (min) | Flow (mL/min) | % A | % B |
| 0.00 | 2.0 | 95 | 5 |
| 1.00 | 2.0 | 95 | 5 |
| 5.00 | 2.0 | 0 | 100 |
| 5.80 | 2.0 | 0 | 100 |
| 6.00 | 2.0 | 95 | 5 |
| 7.00 | 2.0 | 95 | 5 |

Synthetic Preparation of Compounds of the Invention

A compound according to the present invention can be produced according to the following scheme.

General Synthetic Route A

86

A. Intermediates

A.1 3-Bromo-6-chloro-pyridin-2-ylamine

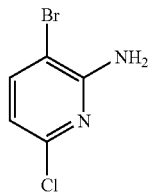

6-Chloro-pyridin-2-ylamine (5 g, 38.89 mmol) is dissolved in chloroform (250 mL) and a solution of bromine (1.33 mL, 26 mmol) in chloroform (50 mL) is slowly added over a one hour period. During the addition a precipitate (hydrobromide salt of the starting material) forms. After stirring overnight the reaction mixture is filtered, the filtrate is evaporated and the residue is partitioned between ethyl acetate and 1 M sodium carbonate solution. The organic phase is separated, evaporated and the solid residue purified by flash chromatography (silica gel, 15% ethyl acetate in petroleum ether) affording the title compound (1.44 g, 17%) as a solid. The material is carried through the next three reaction steps.

A.2 N'-(3-Bromo-6-chloro-pyridin-2-yl)-N,N-dimethyl-formamidine[2]

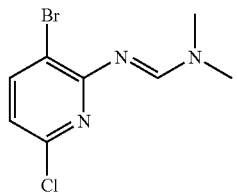

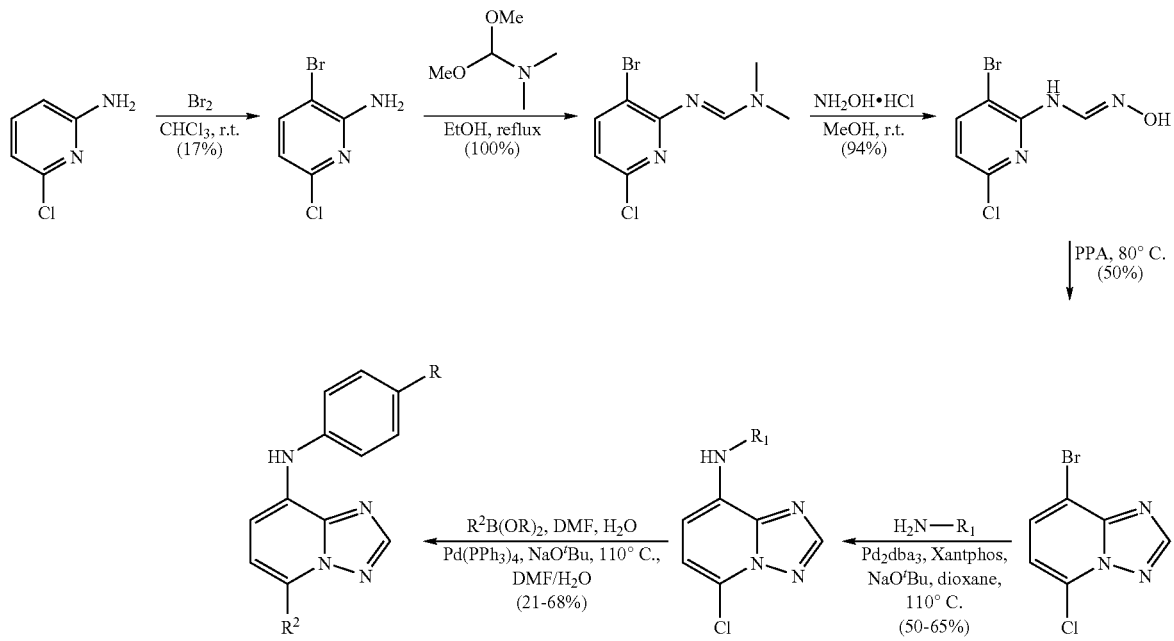

A mixture of 3-bromo-6-chloro-pyridin-2-ylamine (1.43 g, 6.89 mmol) and N,N-dimethylformamide dimethyl acetal (1.14 mL, 8.62 mmol), dissolved in ethanol (35 mL), is refluxed for 75 minutes. The reaction mixture is evaporated in vacuo affording the title compound (1.89 g, 100%).

A.3 N-(3-Bromo-6-chloro-pyridin-2-yl)-N'-hydroxyformamidine

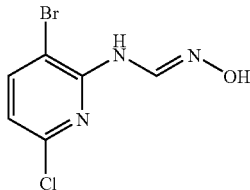

To a solution of N'-(3-bromo-6-chloro-pyridin-2-yl)-N,N-dimethyl-formamidine (1.89 g, 6.89 mmol) in methanol (30 mL) is added hydroxylamine hydrochloride (0.67 g, 9.65 mmol) in one portion. The reaction is stirred at room temperature for 1 hour. The solvent is evaporated and the solid residue is treated with cold (ice cooling) water and collected by filtration. The precipitate is washed with water (2×) and petroleum ether (2×) and dried in vacuo yielding the title compound (1.62 g, 94%) as a white solid.

A.4 8-Bromo-5-chloro-[1,2,4]-triazolo[1,5-a]pyridine

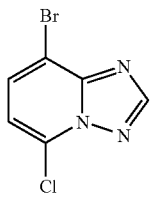

N-(3-Bromo-6-chloro-pyridin-2-yl)-N'-hydroxyformamidine (1.62 g, 6.47 mmol) is treated for one hour and 45 minutes with polyphosphoric acid (20 g) at 80° C. After cooling to room temperature, water (200 mL) is added to the reaction mixture. The resulting solution is brought to pH 8 by careful addition of solid NaHCO₃ in small portions. The clear solution is extracted three times with dichloromethane. The organic phase is dried over MgSO₄, filtered and evaporated. The solid residue (1.44 g) is purified by flash chromatography (silica gel, 4:4:0.7 petroleum ether: dichloromethane: ethyl acetate) to give the title compound (0.75 g) as a solid.

A.5 (5-Chloro-[1,2,4]-triazolo[1,5-a]pyridin-8-yl)-(4-morpholin-4-yl-phenyl)-amine

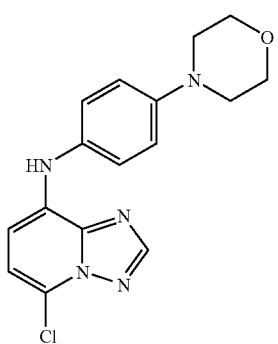

A suspension of 8-bromo-5-chloro-[1,2,4]triazolo[1,5-a]pyridine (160 mg, 0.69 mmol), 4-morpholin-4-yl-phenylamine (135 mg, 0.76 mmol), sodium-tert-butoxide (93 mg, 0.96 mmol), tris(dibenzylideneacetone)dipalladium (0) (13 mg, 13.76 µmol) and Xantphos (16 mg, 27.52 µmol) in dry toluene is heated at 90° C. in a sealed tube under a nitrogen atmosphere for 16 hours. The reaction mixture is evaporated to dryness and the residue partitioned between dichloromethane and 10% aqueous citric acid. The organic phase is further washed with water (1×) and brine (1×), dried over magnesium sulfate, filtered and evaporated. The solid residue (207 mg) is purified by flash chromatography (silica gel, dichloromethane/methanol 97:3) affording the title compound (70 mg) as a solid.

A.6 (5-Chloro-[1,2,4]triazolo[1,5-a]pyridin-8-yl)-[4-(4-methyl-piperazin-1-yl)-phenyl]-amine

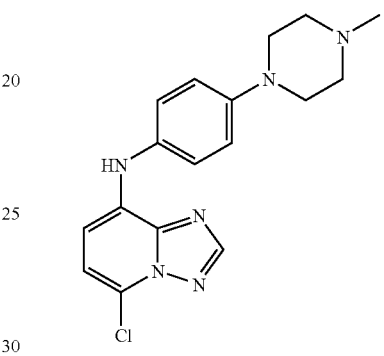

A solution of 8-bromo-5-chloro-[1,2,4]triazolo[1,5-a]pyridine (100 mg, 0.43 mmol), 4-(4-methyl-piperazin-1-yl)-phenylamine (91 mg, 0.47 mmol), sodium-tert-butoxide (58 mg, 0.6 mmol), tris(dibenzylideneacetone)dipalladium (0) (39 mg, 40 µmol) and Xantphos (50 mg, 90 µmol) in dioxane is degassed for one minute by nitrogen bubbling and irradiated in a sealed tube in a microwave (CEM Explorer) under a nitrogen atmosphere for 45 minutes at 110° C. After addition of dichloromethane the suspension is filtered through a plug of silica and the filtrate evaporated and stripped twice with dichloromethane. The residue is purified by flash chromatography (silica gel, dichloromethane/7N NH₃ in methanol 95:5) affording the title compound (95 mg) as a foam.

A.7 4-Amino-N-pyridin-3-ylmethyl-benzamide

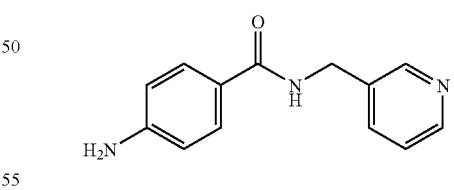

In a round-bottom flask a suspension of 4-amino-benzoic acid (2 g, 14.58 mmol), C-pyridin-3-yl-methylamine (1.48 mL, 14.58 mmol), hydroxybenzotriazole (HOBt, 2.17 g, 16.04 mmol) and triethylamine (4.06 mL, 29.16 mmol) in dichloromethane (150 mL) is cooled to 0° C. and EDCI*HCl (3.08 g, 16.04 mmol) is added. The reaction mixture is stirred at room temperature for 20 hours. The solvent is removed in vacuo and ice cooled water is added. The precipitate is collected by filtration, washed once with 1 N NaOH, three times with water, two times with petroleum ether and dried in vacuo to give the title compound (2.56 g) as a solid.

A.8 4-(5-Chloro-[1,2,4]-triazolo[1,5-a]pyridin-8-ylamino)-N-pyridin-3-ylmethyl-benzamide

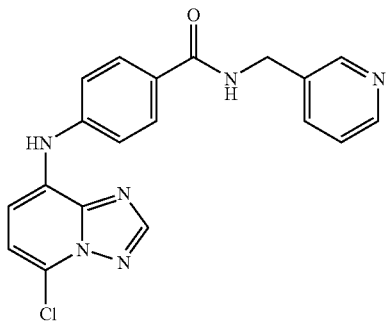

A solution of 8-bromo-5-chloro-[1,2,4]triazolo[1,5-a]pyridine (100 mg, 0.43 mmol), 4-Amino-N-pyridin-3-ylmethyl-benzamide (108 mg, 0.48 mmol), sodium-tert-butoxide (58 mg, 0.6 mmol), tris(dibenzylideneacetone)dipalladium (0) (39 mg, 40 µmol) and Xantphos (50 mg, 90 µmol) in dioxane is degassed for one minute by nitrogen bubbling and then irradiated in a sealed tube in a microwave (CEM Explorer) under a nitrogen atmosphere for 30 minutes at 110° C. The solvent is evaporated and the crude is dissolved in dichloromethane and filtered in order to remove the palladium catalyst. The residue is purified by flash chromatography (silica gel, dichloromethane/7N $NH_3$ in methanol 95:5) affording the title compound (117 mg) as a solid.

General Synthetic Route B

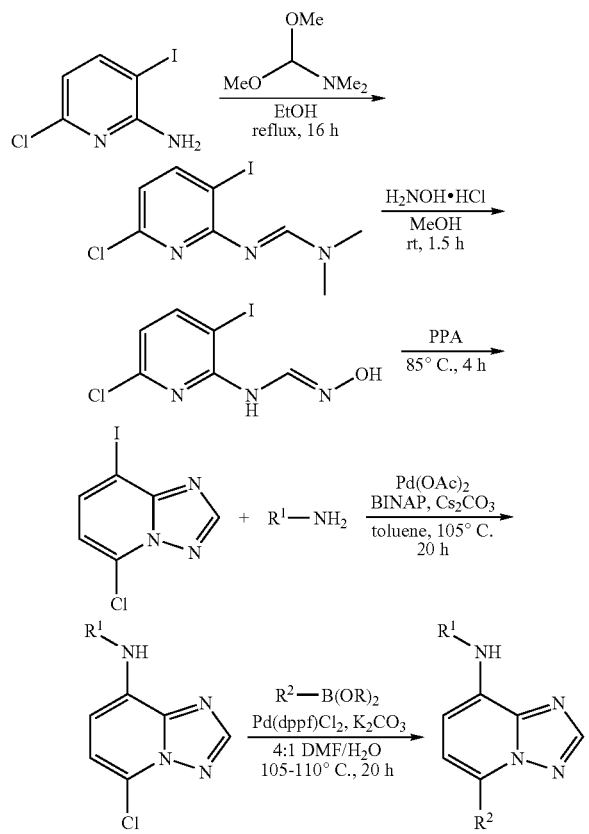

B: Scaffold Synthesis

Example Procedures

B.1 N-(6-chloro-3-iodopyridin-2-yl)pivalamide

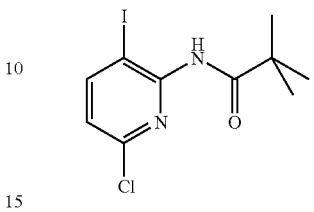

To a solution of N-(6-chloropyridin-2-yl)pivalamide (15.8 g, 74.2 mmol) in anhydrous THF (150 mL) at −78° C. under a nitrogen atmosphere, is added 1.7 M t-butyllithium in pentane (96 mL, 163 mmol, 2.2 eq.) dropwise (dropping funnel) over 0.5 h. The reaction mixture is then stirred at −78° C. for 3 h before iodine (22.6 g, 89 mmol, 1.2 eq.) in THF (60 mL) is slowly added in one portion. After 10 min., the cooling bath is removed and the reaction is allowed to warm to rt and stirred for 2 h. Hydrochloric acid (1 M, 75 mL) is then added to the reaction mixture. The reaction mixture is concentrated in vacuo (rotary evaporator) to remove the THF, the resulting mixture is extracted with ethyl acetate (800 mL). The phases are separated and the organic layer is washed with aqueous 1 M $Na_2S_2O_3$ (100 mL), brine (300 mL×2), water (300 mL), dried over $MgSO_4$, and evaporated. The crude product is recrystallized from DCM/hexanes (1:4) and the solid that forms collected by filtration to provide N-(6-chloro-3-iodopyridin-2-yl)pivalamide as a white crystalline solid (17.2 g). The filtrate is evaporated and the residue chromatographed on a silica gel column (hexanes/EtOAc, 9/1) to provide an additional product (2.5 g). Overall 19.7 g (78% yield) of N-(6-chloro-3-iodopyridin-2-yl)pivalamide is obtained. $^1$H NMR (300 MHz, DMSO-$d_6$), δ 9.86 (s, 1H), 8.30 (d, J=8.4 Hz, 1H), 7.20 (d, J=8.4 Hz, 1H), 1.23 (s, 9H). LCMS-ESI (m/z): calcd for $C_{10}H_{12}Cl_1N_2O$ 337.9; [M+H]$^+$ found 339.0.

B.2 6-Chloro-3-iodopyridine-2-amine

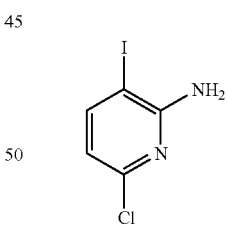

To a solution of N-(6-chloro-3-iodopyridin-2-yl)pivalamide (17.0 g, 50.2 mmol) in dioxane (80 mL) is added 2 N aqueous HCl (50 mL) and the resulting mixture is stirred at 105° C. for 2 h. After cooling to RT, the reaction mixture is slowly poured into a saturated aqueous $NaHCO_3$ solution (200 mL) and the resulting mixture is extracted with ethyl acetate (400 mL×3). The combined organic extracts are washed with brine (300 mL×3), dried over $MgSO_4$, and solvent is evaporated on a rotary evaporator to provide 6-chloro-3-iodopyridine-2-amine as light brown solid (12.8 g, yield 100%). $^1$H NMR (300 MHz, DMSO-$d_6$), δ 7.85 (d, J=8.1 Hz, 1H), 6.36 (d, J=8.1 Hz, 1H), 6.50 (br s, 2H). LCMS-ESI (m/z): calcd for $C_5H_4ClIN_2$ 253.9; [M+H]$^+$ found 255.3.

B.3 (E)-N-(6-chloro-3-iodopyridin-2-yl)-N'-hydroxy-formimidamide

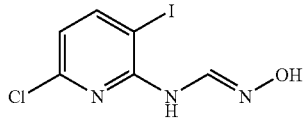

6-Chloro-3-iodopyridin-2-amine (22.4 g, 0.088 mol) and N,N-dimethylformamide dimethyl acetal (19.5 mL, 0.147 mol) are dissolved in ethanol (300 mL). The mixture is stirred and refluxed at 95° C. for 16 h after which time the solvent is evaporated to provide an oily residue (27.2 g, 99% recovery) that may be used in the next step without further purification. LCMS Purity: 95% by UV 254 nm detection; LCMS-ESI (m/z): calcd for $C_8H_9ClIN_3$ 308.9; [M+H]$^+$ found 309.9.

The residue is dissolved in methanol (300 mL) and treated with hydroxylamine hydrochloride (9.2 g, 0.132 mol) at rt for 1.5 h. (E)-N-(6-chloro-3-iodopyridin-2-yl)-N'-hydroxy-formimidamide is precipitated from the reaction mixture and is collected by filtration. The filtrate is concentrated to approximately half of the original volume, and a second crop of the product is isolated by filtration. The two precipitates are combined to provide (E)-N-(6-chloro-3-iodopyridin-2-yl)-N'-hydroxy-formimidamide (13.8 g, 53%) as an off-white solid. LCMS Purity: 100% by UV 254 nm detection; LCMS-ESI (m/z): calcd for $C_6H_5ClIN_3O$ 296.9; [M+H]$^+$ found 298.2.

B.4 5-Chloro-8-iodo-[1,2,4]-triazolo[1,5-a]pyridine

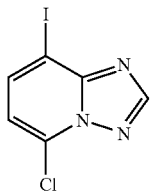

(E)-N-(6-chloro-3-iodopyridin-2-yl)-N'-hydroxyformimidamide (6.0 g, 0.02 mol) is treated with polyphosphoric acid (40 g) at 80° C. for 4 h with stirring. The reaction mixture is diluted with cold water (100 mL), and then neutralized with 10 N aq. sodium hydroxide solution to pH 8. The aqueous solution is extracted with dichloromethane (100 mL×3). The combined organic extracts are washed with saturated aq. sodium bicarbonate solution (50 mL), brine (30 mL×3), dried over sodium sulfate, filtered, and filtrate concentrated to afford 5-Chloro-8-iodo-[1,2,4]triazolo[1,5-a]pyridine (5.6 g, 94%) as an off-white solid. LCMS Purity: 95% by UV 254 nm detection; LCMS-ESI (m/z): calcd for $C_6H_3ClIN_3$, 278.9; [M+H]$^+$ found, 279.9. $^1$H NMR (300 MHz, DMSO-d$_6$) δ 8.63 (s, 1H), 8.15 (d, J=7.8 Hz, 1H), 7.29 (d, J=7.8 Hz, 1H).

C: Buchwald Reactions

C.1 5-Chloro-N-(4-morpholinophenyl)-[1,2,4]triazolo[1,5-a]pyridin-8-amine

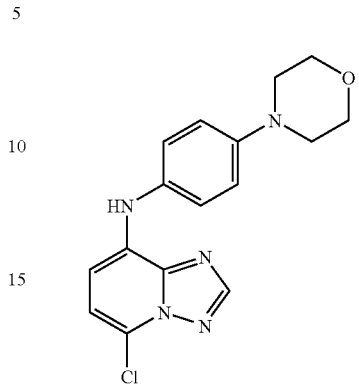

To a mixture of 5-chloro-8-iodo-[1,2,4]triazolo[1,5-a]pyridine (5.00 g, 17.9 mmol), 4-morpholinoaniline (3.51 g, 19.6 mmol, 1.1 eq), BINAP (1.11 g, 1.79 mmol, 0.1 eq.) and cesium carbonate (23.3 g, 71.6 mmol, 4 eq.) in toluene (200 mL) under a nitrogen atmosphere, is added palladium acetate (401 mg, 1.79 mmol, 0.1 eq.). The reaction mixture is stirred at 105° C. overnight (20 h). After cooling to rt, the reaction mixture is filtered, and the solids are washed with DCM/MeOH (9:1, 100 mL). The combined organic solution is evaporated to provide a black residue that is purified by silica gel column chromatography (hexanes/DCM/EtOAc/2N NH$_3$ in MeOH, 25:20:5:1 elution) to afford the product as a light brown solid (4.51 g, 76%). $^1$H NMR (300 MHz, DMSO-d$_6$) δ 8.53 (s, 1H), 8.50 (s, 1H), 7.21 (d, J=9.0 Hz, 2H), 6.95 (d, J=9.0 Hz, 2H), 7.15 (d, J=8.1 Hz, 1H), 6.86 (d, J=8.1 Hz, 1H), 3.74 (m, 4H), 3.07 (m, 4H). LCMS-ESI (m/z): calcd for $C_{16}H_{16}ClN_5O$ 329.1; [M+H]$^+$ found, 330.4.

C.2 5-Chloro-N-(4-(4-ethylpiperazin-1-yl))phenyl)-[1,2,4]-triazolo[1,5-a]pyridin-8-amine

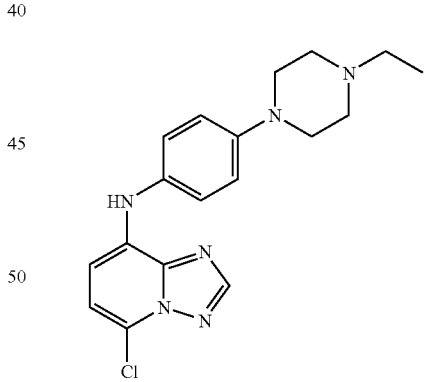

To a mixture of 5-chloro-8-iodo-[1,2,4]triazolo[1,5-a]pyridine (279.5 mg, 1.0 mmol), 4-(4-ethylpiperazin-1-yl) aniline (246 mg, 1.2 mmol, 1.2 eq), BINAP (62.3 mg, 0.1 mmol, 0.1 eq.) and cesium carbonate (1.3 g, 4.0 mmol, 4 eq.) in toluene (10 mL) under an argon atmosphere, is added palladium acetate (22.4 mg, 0.10 mmol, 0.1 eq.). The reaction mixture is stirred at 110° C. overnight (20 h). After cooling to rt, the reaction mixture is filtered, and the solids are washed with DCM/MeOH (9:1, 20 mL). The combined organic solution is evaporated to provide a black residue that is purified by silica gel column chromatography (1-3% 2N NH$_3$ in MeOH/DCM) to afford the title product as a grey solid (228 mg, yield 63.8%). ¹H NMR (300 MHz, DMSO-d₆): δ 8.56 (s, 1H), 8.49 (s, 1H), 7.21 (d, J=9.0 Hz, 2H), 7.16 (d, J=8.4 Hz, 1H), 6.95 (d, J=9.0 Hz, 2H), 6.86 (d, J=8.1 Hz, 1H), 3.11 (m, 4H), 2.45 (m, 4H), 2.39 (q, J=7.2 Hz, 2H), 1.04 (t, J=7.2 Hz, 3H); LCMS-ESI (m/z): calcd for $C_{18}H_{21}ClN_6$ $C_{16}H_{16}ClN_5O$ 356.1; [M+H]⁺ found, 357.2.

The following compounds were synthesised according to the procedure described above in C.2 of the Buchwald reaction:

C.3 5-Chloro-N-(4-(4-propylpiperazin-1-yl)phenyl)-[1,2,4]triazolo[1,5-a]pyridin-8-amine

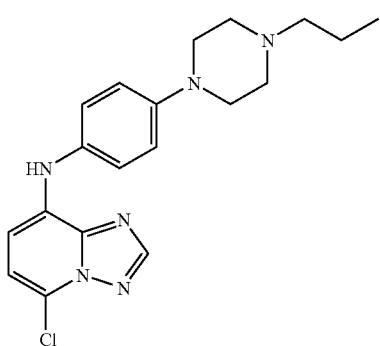

300 mg, yield 80%. ¹H NMR (300 MHz, DMSO-d₆): δ 8.56 (s, 1H), 8.49 (s, 1H), 7.22 (d, J=9.0 Hz, 2H), 7.16 (d, J=8.4 Hz, 1H), 6.95 (d, J=9.0 Hz, 2H), 6.86 (d, J=8.4 Hz, 1H), 3.10 (m, 4H), 2.45 (m, 4H), 2.27 (t, J=7.2 Hz, 2H), 1.46 (sextet, J=7.2 Hz, 2H), 0.87 (t, J=7.2 Hz, 3H); ESI-MS m/z 371.2 (M+1)⁺.

C.4 5-Chloro-N-(4-(4-(pentan-3-yl)piperazin-1-yl)phenyl)-[1,2,4]triazolo[1,5-a]pyridin-8-amine

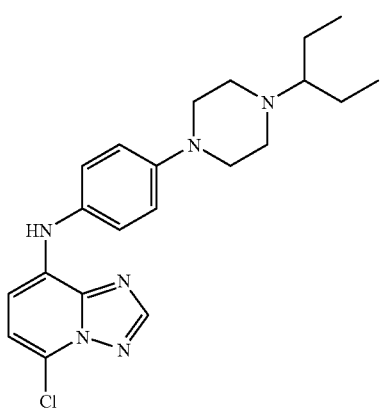

290 mg, yield 72.7%; LCMS-ESI (m/z): calcd for $C_{21}H_{27}ClN_6$, 398; [M+H]⁺ found, 399.

C.5 5-Chloro-N-(4-(4-isopentylpiperazin-1-yl)phenyl)-[1,2,4]triazolo[1,5-a]pyridin-8-amine

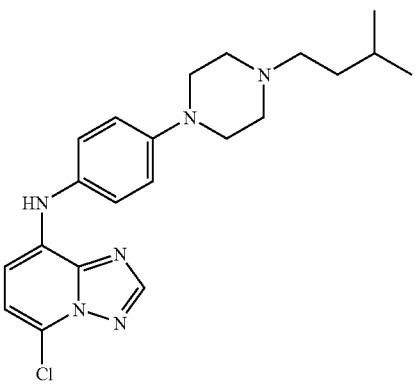

310 mg, yield 77.7%; ¹H NMR (300 MHz, DMSO-d₆): δ 8.55 (s, 1H), 8.49 (s, 1H), 7.21 (d, J=9.0 Hz, 2H), 7.16 (d, J=8.4 Hz, 1H), 6.95 (d, J=9.0 Hz, 2H), 6.86 (d, J=8.4 Hz, 1H), 3.09 (m, 4H), 2.45 (m, 4H), 2.32 (t, J=7.5 Hz, 2H), 1.60 (m, 1H), 1.35 (m, 2H), 0.88 (d, J=6.9 Hz, 6H); LCMS-ESI (m/z): calcd for $C_{21}H_{27}ClN_6$, 398; [M+H]⁺ found, 399.

C.6 5-Chloro-N-(4-(4-cyclopropylpiperazin-1-yl)phenyl)-[1,2,4]-triazolo[1,5-a]pyridin-8-amine

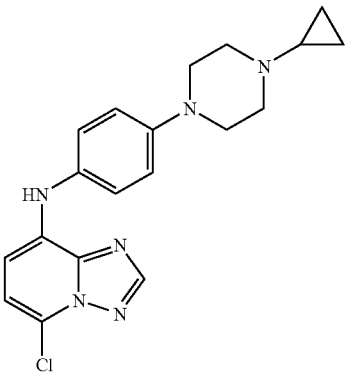

¹H NMR (300 MHz, DMSO-d₆): δ 8.55 (s, 1H), 8.49 (s, 1H), 7.21 (d, J=9.0 Hz, 2H), 7.16 (d, J=8.4 Hz, 1H), 6.95 (d, J=9.0 Hz, 2H), 6.86 (d, J=8.4 Hz, 1H), 3.06 (m, 4H), 2.68 (m, 4H), 1.66 (m, 1H), 0.5-0.4 (m, 2H), 0.4-0.3 (m, 2H); LCMS-ESI (m/z): calcd for $C_{19}H_{21}ClN_6$, 368; [M+H]⁺ found, 369.

C.7 5-Chloro-N-(4-(4-cyclobutylpiperazin-1-yl)phenyl)-[1,2,4]triazolo[1,5-a]pyridin-8-amine

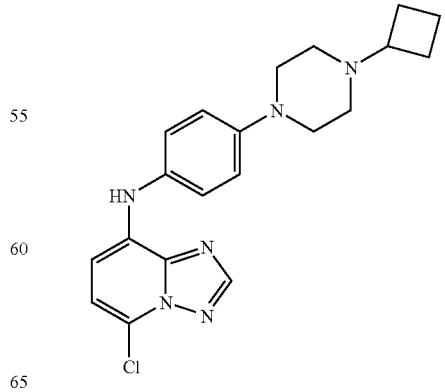

Yield 76%; LCMS-ESI (m/z): calcd for $C_{20}H_{23}ClN_6$, 382; [M+H]⁺ found, 383.

C.8 5-Chloro-N-(4-(4-cyclohexylpiperazin-1-yl)phenyl)-[1,2,4]triazolo[1,5-a]pyridin-8-amine

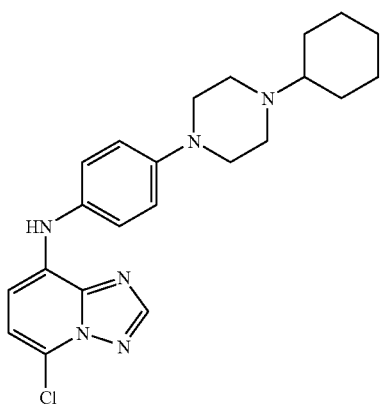

Yield 56%. $^1$H NMR (300 MHz, DMSO-$d_6$): δ 8.55 (s, 1H), 8.48 (s, 1H), 7.21 (d, J=9.0 Hz, 2H), 7.16 (d, J=8.7 Hz, 1H), 6.94 (d, J=9.0 Hz, 2H), 6.86 (d, J=8.1 Hz, 1H), 3.08 (m, 4H), 2.63 (m, 4H), 2.26 (m, 1H), 1.85-1.70 (m, 4H), 1.65-1.50 (m, 1H), 1.25-1.10 (m, 5H); LCMS-ESI (m/z): calcd for $C_{22}H_{27}ClN_6$, 410; [M+H]$^+$ found, 411.

D: Example Suzuki Reactions

D.1 [5-(1H-Indol-4-yl)-[1,2,4]triazolo[1,5-a]pyridin-8-yl]-(4-morpholin-4-yl-phenyl)-amine

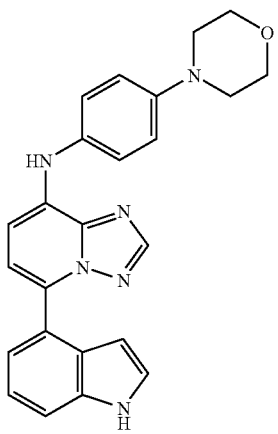

To a vial (40-mL), is added 5-chloro-N-(4-morpholinophenyl)-[1,2,4]triazolo[1,5-c]pyridin-8-amine (99 mg, 0.3 mmol), potassium carbonate (207 mg, 1.5 mmol, 5 eq.), 1H-indol-4-ylboronic acid (72 mg, 0.45 mmol, 1.5 eq), Pd(dppf)Cl$_2$ (0.03 mmol, 22 mg, 0.1 eq.), DMF (4 mL), and water (1 mL). The reaction mixture is deoxygenated by flushing with argon and then heated at 105-110° C. for 20 h. After cooling to rt, ethyl acetate (10 mL) is added, the phases are separated, and the organic extract is filtered through a pad of Celite. The filtrate is evaporated and the residue is purified by silica gel column chromatography (1-5% 7 N NH$_3$ in MeOH/DCM) to provide [5-(1H-indol-4-yl)-[1,2,4]triazolo[1,5-c]pyridin-8-yl]-(4-morpholin-4-yl-phenyl)-amine (70 mg, 57%). $^1$H NMR (300 MHz, DMSO-$d_6$), δ 11.27 (s, 1H), 8.39 (s, 1H), 8.38 (s, 1H), 7.48 (d, J=8.4 Hz, 1H), 7.42 (dd, J=0.9, 6.9 Hz, 1H), 7.37 (t, J=3.0 Hz, 1H), 7.28 (d, J=9.0 Hz, 2H), 7.19 (d, J=8.1 Hz, 1H), 7.13 (d, J=8.1 Hz, 1H), 7.02 (d, J=7.8 Hz, 1H), 6.96 (d, J=9.0 Hz, 2H), 6.24 (m, 1H), 3.74 (m, 4H), 3.07 (m, 4H). LCMS Purity: 99% by UV 220 nm detection; LCMS-ESI (m/z): calcd for $C_{24}H_{22}N_6O$, 410.1; [M+H]$^+$ found, 411.4.

D.2 4-(8-(4-(4-propylpiperazin-1-yl)phenylamino)-[1,2,4]triazolo[1,5-a]pyridin-5-yl)benzamide

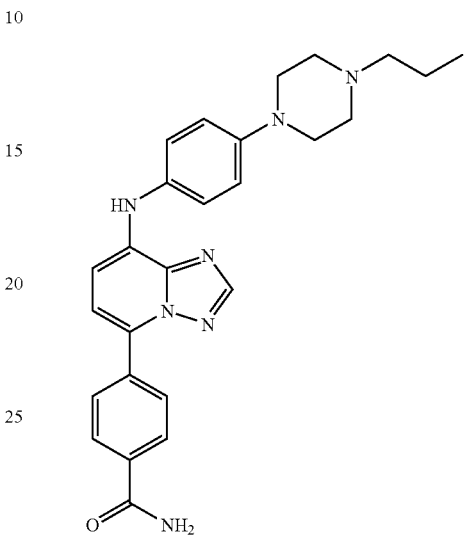

To a reaction vial (40 mL), is added 5-chloro-N-(4-(4-propylpiperazin-1-yl)phenyl)-[1,2,4]triazolo[1,5-a]pyridin-8-amine (55 mg, 0.15 mmol), potassium carbonate (104 mg, 0.75 mmol, 5 eq.), 4-carbamoylphenylboronic acid (50 mg, 0.30 mmol, 2 eq), PddppfCl$_2$ (20 mg, 15%), dioxane (4.0 mL) and water (1.0 mL). The reaction mixture is degassed and filled with argon. The reaction is heated at 105-110° C. for 20 h. After cooling to rt, ethyl acetate (10 mL) is added to each reaction vial. The organic phase was filtered through a pat of celite and then is evaporated to give a dry residue that was purified by preparatory HPLC to give the title compound, 28.9 mg, yield 42.2%; LCMS-ESI (m/z): calcd for $C_{26}H_{29}N_7O$, 455; [M+H]$^+$ found, 456.

D.3 N-(4-(4-Ethylpiperazin-1-yl)phenyl)-5-(2-methoxypyridin-4-yl)-[1,2,4]triazolo[1,5-a]pyridin-8-amine

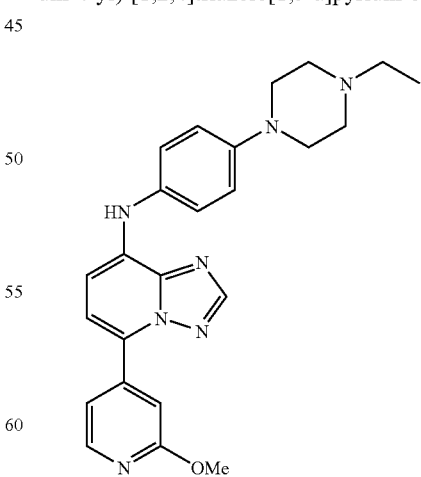

To a reaction vial (40 mL), is added 5-chloro-N-(4-(4-ethylpiperazin-1-yl)phenyl)-[1,2,4]triazolo[1,5-a]pyridin-8-amine (110 mg, 0.3 mmol), potassium carbonate (207 mg, 1.5 mmol, 5 eq.), 2-methoxypyridin-4-ylboronic acid (70 mg, 0.45 mmol, 1.5 eq), PddppfCl$_2$ (44 mg, 20%), dioxane (4.0 mL) and water (1.0 mL). The reaction mixture is degassed and filled with argon. The reaction is heated at 105-110° C. for 20 h. After cooling to rt, ethyl acetate (10 mL) is added to each reaction vial. The organic phase is filtered through a pat of celite and then is evaporated to give a residue that is purified by silica gel column chromatography (1-3% 2N NH$_3$ in MeOH/DCM) to give the title compound as a light yellow solid (90 mg, yield, 69.8%). $^1$H NMR (300 MHz, DMSO-d$_6$): δ 8.75 (s, 1H), 8.56 (s, 1H), 8.26 (d, J=6.0 Hz, 1H), 7.60 (d, J=4.8 Hz), 7.58 (s, 1H), 7.46 (d, J=8.4 Hz, 1H), 7.25 (d, J=9.0 Hz, 2H), 6.96 (d, J=9.0 Hz, 2H), 6.93 (d, J=8.4 Hz, 1H), 3.91 (s, 3H), 3.12 (m, 4H), 2.50 (m, 4H), 2.36 (q, J=6.9, 2H), 1.04 (t, J=6.9 Hz, 3H); LCMS-ESI (m/z): calcd for C$_{24}$H$_{27}$N$_7$O, 429; [M+H]$^+$ found, 430.

Following the procedure described above in D.3 of the Suzuki reaction, the following compounds were synthesised:

D.4 5-(2-methoxypyridin-4-yl)-N-(4-(4-propylpiperazin-1-yl)phenyl)-[1,2,4]triazolo[1,5-a]pyridin-8-amine

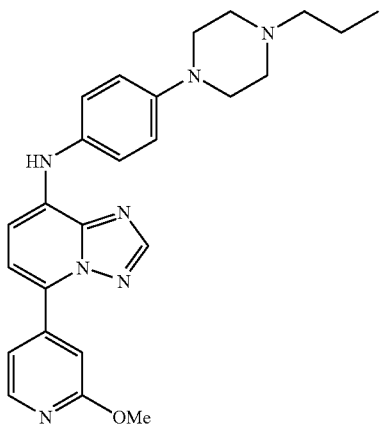

The title compound is obtained as a light yellow solid (84 mg, yield 63%). $^1$H NMR (300 MHz, DMSO-d$_6$): δ 8.75 (s, 1H), 8.56 (s, 1H), 8.26 (dd, J=0.6, 6.0 Hz, 1H), 7.60 (dd, J=1.5, 4.2 Hz, 1H), 7.58 (s, 1H), 7.46 (d, J=8.1 Hz, 1H), 7.25 (d, J=9.0 Hz, 2H), 6.96 (d, J=9.0 Hz, 2H), 6.93 (d, J=8.4 Hz, 1H), 3.91 (s, 3H), 3.11 (m, 4H), 2.50 (m, 4H), 2.28 (t, J=7.2 Hz, 2H), 1.47 (sextet, J=7.2 Hz, 2H), 0.88 (t, J=7.2 Hz, 3H); LCMS-ESI (m/z): calcd for C$_{25}$H$_{29}$N$_7$O, 443; [M+H]$^+$ found, 444.

D.5 5-(2-methoxypyridin-4-yl)-N-(4-(4-(pentan-3-yl)piperazin-1-yl)phenyl)-[1,2,4]triazolo[1,5-a]pyridin-8-amine

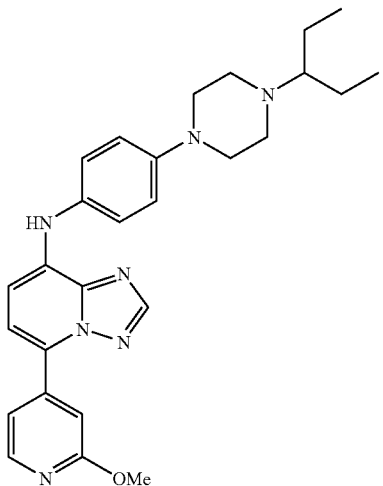

The title compound is obtained as a light yellow solid (110 mg, yield 77.7%). $^1$H NMR (300 MHz, DMSO-d$_6$): δ 8.75 (s, 1H), 8.56 (s, 1H), 8.26 (dd, J=0.9, 5.1 Hz, 1H), 7.60 (dd, J=1.2, 5.1 Hz, 1H), 7.58 (s, 1H), 7.47 (d, J=8.1 Hz, 1H), 7.25 (d, J=9.0 Hz, 2H), 6.96 (d, J=9.0 Hz, 2H), 6.93 (d, J=8.1 Hz, 1H), 3.91 (s, 3H), 3.08 (m, 4H), 2.59 (m, 4H), 2.19 (quintet, J=6.6 Hz, 1H), 1.54-1.40 (m, 2H), 1.34-1.20 (m, 2H), 0.88 (t, J=7.2 Hz, 3H); LCMS-ESI (m/z): calcd for C$_{27}$H$_{33}$N$_7$O, 471; [M+H]$^+$ found, 472.

D.6 N-(4-(4-isopentylpiperazin-1-yl)phenyl)-5-(2-methoxypyridin-4-yl)-[1,2,4]triazolo[1,5-a]pyridin-8-amine

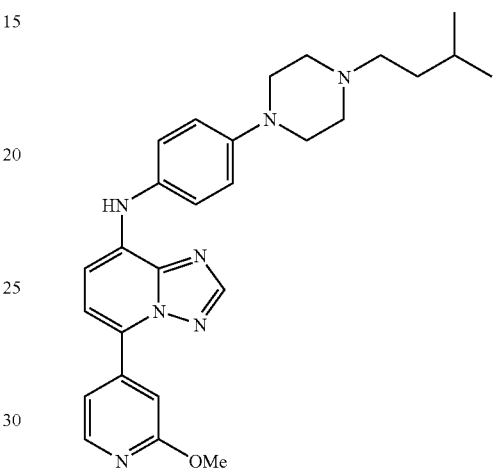

The title compound is obtained as a light greenish yellow solid (89 mg, yield 62.9%). $^1$H NMR (300 MHz, DMSO-d$_6$): δ 8.75 (s, 1H), 8.56 (s, 1H), 8.26 (d, J=5.4 Hz, 1H), 7.60 (dd, J=1.2, 5.7 Hz, 1H), 7.58 (s, 1H), 7.47 (d, J=8.1 Hz, 1H), 7.25 (d, J=9.0 Hz, 2H), 6.97 (d, J=9.0 Hz, 2H), 6.93 (d, J=8.1 Hz, 1H), 3.91 (s, 3H), 3.11 (m, 4H), 2.50 (m, 4H), 2.32 (t, J=7.5 Hz, 1H), 1.60 (m, 1H), 1.35 (q, J=6.6 Hz, 2H), 0.89 (d, J=6.6 Hz, 6H); LCMS-ESI (m/z): calcd for C$_{27}$H$_{33}$N$_7$O, 471; [M+H]$^+$ found, 472.

D.7 N-(4-(4-cyclopropylpiperazin-1-yl)phenyl)-5-(2-methoxypyridin-4-yl)-[1,2,4]triazolo[1,5-a]pyridin-8-amine

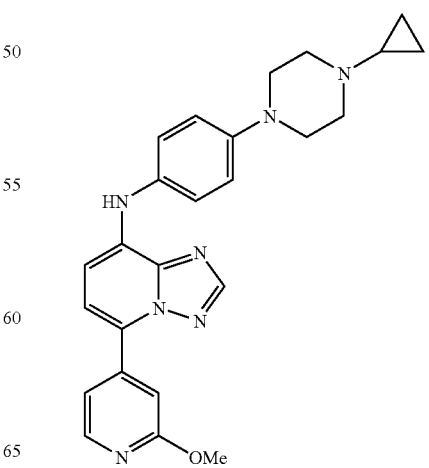

The title compound is obtained as a light yellow solid (85 mg, yield 64%). ¹H NMR (300 MHz, DMSO-d₆): δ 8.75 (s, 1H), 8.56 (s, 1H), 8.26 (d, J=6.0 Hz, 1H), 7.60 (dd, J=1.2, 6.0 Hz, 1H), 7.58 (s, 1H), 7.47 (d, J=8.1 Hz, 1H), 7.25 (d, J=9.0 Hz, 2H), 6.97 (d, J=9.0 Hz, 2H), 6.93 (d, J=8.1 Hz, 1H), 3.91 (s, 3H), 3.09 (m, 4H), 2.68 (m, 4H), 1.66 (m, 1H), 0.50-0.40 (m, 2H), 0.40-0.30 (m, 2H); LCMS-ESI (m/z): calcd for $C_{25}H_{27}N_7O$, 441; $[M+H]^+$ found, 442.

D.8 N-(4-(4-cyclobutylpiperazin-1-yl)phenyl)-5-(2-methoxypyridin-4-yl)-[1,2,4]triazolo[1,5-a]pyridin-8-amine

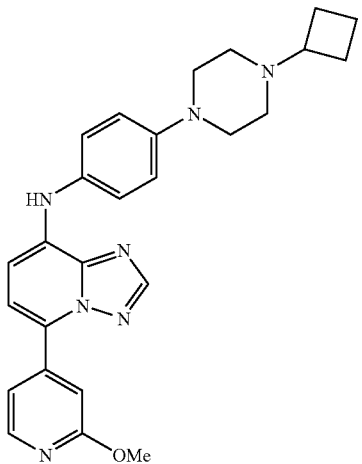

The title compound is obtained as a light yellow solid (95 mg, yield 69.5%). NMR (300 MHz, DMSO-d₆): δ 8.75 (s, 1H), 8.56 (s, 1H), 8.26 (dd, J=5.4, 1.2 Hz, 1H), 7.60 (dd, J=1.2, 5.4 Hz, 1H), 7.58 (s, 1H), 7.47 (d, J=8.1 Hz, 1H), 7.25 (d, J=9.0 Hz, 2H), 6.97 (d, J=9.0 Hz, 2H), 6.93 (d, J=8.1 Hz, 1H), 3.91 (s, 3H), 3.11 (m, 4H), 2.73 (m, 1H), 2.38 (m, 4H), 2.05-1.90 (m, 2H), 1.86-1.72 (m, 2H), 1.70-1.60 (m, 2H); LCMS-ESI (m/z): calcd for $C_{26}H_{29}N_7O$, 455; $[M+H]^+$ found, 456.

D.9 N-(4-(4-cyclohexylpiperazin-1-yl)phenyl)-5-(2-methoxypyridin-4-yl)-[1,2,4]triazolo[1,5-a]pyridin-8-amine

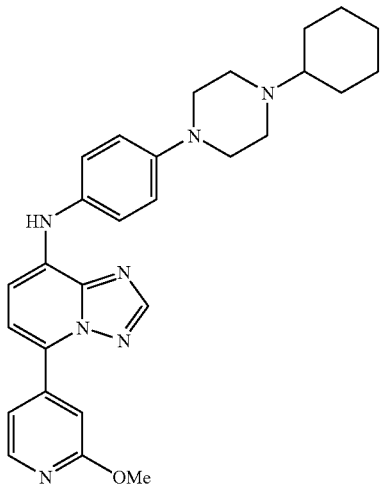

The title compound is obtained as a light yellow solid (68 mg, yield 46.8%). NMR (300 MHz, DMSO-d₆): δ 8.75 (s, 1H), 8.56 (s, 1H), 8.26 (dd, J=5.1, 0.6 Hz, 1H), 7.60 (dd, J=1.2, 5.4 Hz, 1H), 7.58 (s, 1H), 7.47 (d, J=8.1 Hz, 1H), 7.25 (d, J=9.0 Hz, 2H), 6.97 (d, J=9.0 Hz, 2H), 6.93 (d, J=8.1 Hz, 1H), 3.91 (s, 3H), 3.10 (m, 4H), 2.64 (m, 4H), 2.27 (m, 1H), 1.90-1.70 (m, 4H), 1.60-1.50 (m, 1H), 1.30-1.10 (m, 5H); LCMS-ESI (m/z): calcd for $C_{28}H_{33}N_7O$, 483; $[M+H]^+$ found, 484.

E. Boronic Ester Synthesis

E.1 2-Fluoro-4-(4,4,5,5-tetramethyl-1,3,2-dioxaborolan-2-yl)benzamide

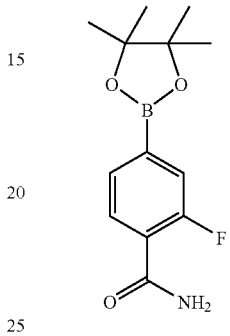

Pd(dppf)Cl₂ (21 mg, 0.028 mmol, 0.03 eq), potassium acetate (277 mg, 1.03 mmol, 2.82 mmol, 3 eq), 4,4,4',4',5,5,5',5'-octamethyl-2,2'-bi(1,3,2-dioxaborolane) (263 mg, 1.1 eq), and 4-bromo-2-fluorobenzamide (205 mg, 0.94 mmol, 1.0 eq) are suspended in anhydrous dioxane (2 mL) in a 5-mL microwave vial and the mixture is purged with nitrogen for 1 min. The resulting slurry is heated for 20 min at 90° C. in a microwave (Biotage Initiator, Absorption high). DCM (2 mL) is added to the dark brown reaction mixture and the resulting suspension is filtered. The precipitate collected on the frit is washed with DCM (2×5 mL) and the solid residue remaining in the microwave tube is washed with DCM (2×2 mL). The DCM washes and filtrates are combined. Celite (1.5 g) is added to the organic extracts and the solvent is evaporated on a rotary evaporator to provide a free-flowing powder. The Celite/compound mixture was loaded onto a prepacked silica column (10 g of silica) and the column eluted with 1:1 hexane/ethyl acetate to provide the crude 2-fluoro-4-(4,4,5,5-tetramethyl-1,3,2-dioxaborolan-2-yl)benzamide (307 mg, 124% recovery). The product was used in the next step without further purification. LCMS Purity: 78% by UV 254 nm detection); LCMS-ESI (m/z): calcd for $C_{13}H_{17}BFNO_3$, 265.1; $[M+H]^+$ found, 266.1.

F. Aniline Syntheses

F.1 racemic-1-(2-fluoro-4-nitrophenyl)-trans-2,5-dimethylpiperazine

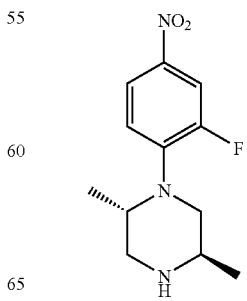

trans-2,5-Dimethylpiperazine (4.81 g, 42.1 mmol) and 1,2-difluoro-4-nitrobenzene (10.00 g, 62.9 mmol) are dissolved in 60 mL of dry acetonitrile and refluxed for 3 h, upon which a yellow precipitate forms on the bottom of the flask. The crude reaction mixture is concentrated in vacuo and the residue is chromatographed (silica gel, 10% MeOH in $CH_2Cl_2$) to give 4.32 g (17.0 mmol, 40%) of racemic-1-(2-fluoro-4-nitrophenyl)-trans-2,5-dimethylpiperazine as a yellow solid. $^1$H NMR (300 MHz, $CDCl_3$) δ 1.01 (d, J=6.0 Hz, 3H), 1.09 (d, J=6.3 Hz, 3H), 2.45 (dd, J=11.5, 9.0 Hz, 1H), 2.72 (dd, J=12.1, 9.0 Hz, 1H), 3.05-3.12 (m, 1H), 3.15 (dd, J=12.1, 3.3 Hz, 1H), 3.26 (dd, 2H), 7.12 (t, J=8.5 Hz, 1H), 7.91 (dd, J=11.2, 2.4 Hz, 1H), 7.95-8.01 (m, 1H). LCMS-ESI (m/z): calcd for $C_{12}H_{16}FN_3O_2$, 253.1; $[M+H]^+$ found, 254.4.

F.2 cis-3,5-Dimethyl-1-(4-nitrophenyl)piperazine

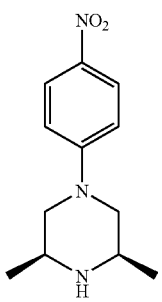

Crude cis-3,5-Dimethyl-1-(4-nitrophenyl)piperazine (4.91 g, 95% recovery) is prepared according to the method described above for the synthesis of racemic-1-(2-fluoro-4-nitrophenyl)-trans-2,5-dimethylpiperazine by treatment of 1-fluoro-4-nitrobenzene (3.08 g, 21.8 mmol) with cis-2,6-dimethylpiperazine (2.50 g, 21.8 mmol). The crude product is used in the next step without chromatographic purification. LCMS-ESI (m/z): calcd for $C_{12}H_{17}N_3O_2$, 235; $[M+H]^+$ found, 236.

F.3 1-(2-Fluoro-4-nitrophenyl)-cis-3,5-dimethylpiperazine

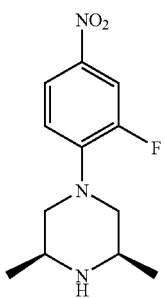

Crude 1-(2-fluoro-4-nitrophenyl)-cis-3,5-dimethylpiperazine (5.71 g, 103% recovery) is prepared according to the method described above for the synthesis of racemic-1-(2-fluoro-4-nitrophenyl)-trans-2,5-dimethylpiperazine by treatment of 1,2-difluoro-4-nitrobenzene (3.48 g, 21.8 mmol) with cis-2,6-dimethylpiperazine (2.50 g, 21.8 mmol). The crude product is used in the next step without chromatographic purification. LCMS-ESI (m/z): calcd for $C_{12}H_{16}FN_3O_2$, 253; $[M+H]^+$ found, 254.

F.4 racemic-[trans-2,5-dimethyl-1-(4-nitrophenyl)piperazine]

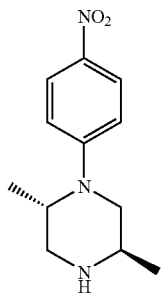

Racemic-[trans-2,5-dimethyl-1-(4-nitrophenyl)piperazine] (6.34 g, 31%) is prepared according to the method described above for the synthesis of racemic-1-(2-fluoro-4-nitrophenyl)-trans-2,5-dimethylpiperazine by treatment of 1-fluoro-4-nitrobenzene (12.3 g, 87.5 mmol) with trans-2,5-dimethylpiperazine (10.0 g, 87.5 mmol). LCMS-ESI (m/z): calcd for $C_{12}H_{17}N_3O_2$, $[M+H]^+$235; found, 236.

F.5 Racemic-1-(2-Fluoro-4-nitrophenyl)-trans-2,4,5-trimethylpiperazine

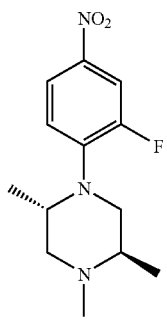

Racemic-1-(2-Fluoro-4-nitrophenyl)-trans-2,5-dimethylpiperazine (5.71 g, 24.3 mmol) and formalin (24 mL) are dissolved in 70 mL of acetonitrile. The solution is cooled to 0° C. and 2.44 g of $NaBH_3CN$ (38.8 mmol) is added in small portions. Acetic acid (2 mL) is added until no further effervescence is observed. The crude reaction mixture is then filtered through a thick plug of silica gel that is rinsed with 10% MeOH in $CH_2Cl_2$. Concentration in vacuo gives a yellow solid that is further purified by addition of ethyl acetate and filtration. Concentration in vacuo of the filtrate gave 6.1 g of racemic-1-(2-fluoro-4-nitrophenyl)-trans-2,4,5-trimethylpiperazine as an off-white solid (24.3 mmol, 100%). $^1$H NMR (300 MHz, $CDCl_3$) δ 1.04 (d, J=4.9 Hz, 1H), 1.07 (d, J=5.2 Hz, 1H), 2.20 (dd, J=11.5, 8.8 Hz, 1H), 2.32 (s, 3H), 2.41-2.50 (m, 1H), 2.65 (dd, J=11.6, 8.9 Hz, 1H), 2.90 (dd, J=11.5, 3.3 Hz, 1H), 3.25 (dd, J=11.8, 3.0 Hz, 1H), 3.44-3.53 (m, 1H), 7.10 (t, J=8.5 Hz, 1H), 7.90 (dd, J=11.5, 2.7 Hz, 1H), 7.95-8.00 (m, 1H). LCMS-ESI (m/z): calcd for $C_{13}H_{18}FN_3O_2$, 267.14; $[M+H]^+$ found, 268.2.

F.6 cis-1,2,6-Trimethyl-4-(4-nitrophenyl)piperazine

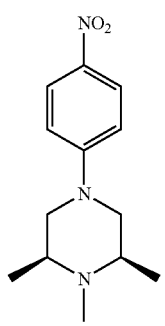

Crude cis-1,2,6-trimethyl-4-(4-nitrophenyl)piperazine (5.55 g, 106% recovery) is prepared according to the method described above for the synthesis of racemic-1-(2-fluoro-4-nitrophenyl)-trans-2,4,5-trimethylpiperazine from cis-3,5-Dimethyl-1-(4-nitrophenyl)piperazine (4.91 g, 20.8 mmol). LCMS-ESI (m/z): calcd for $C_{13}H_{19}N_3O_2$, 249; $[M+H]^+$ found, 250.

F.7 racemic-trans-[1,2,5-Trimethyl-4-(4-nitrophenyl)piperazine]

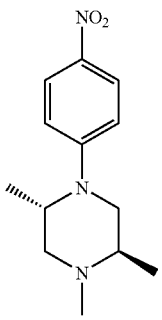

Crude racemic-trans-[1,2,5-trimethyl-4-(4-nitrophenyl) piperazine] (7.48 g, 111% recovery) is prepared according to the method described above for the synthesis of racemic-1-(2-fluoro-4-nitrophenyl)-trans-2,4,5-trimethylpiperazine from racemic-[trans-2,5-dimethyl-1-(4-nitrophenyl)-piperazine] (6.34 g, 25.0 mmol). LCMS-ESI (m/z): calcd for $C_{13}H_{19}N_3O_2$, 249; $[M+H]^+$ found, 250.

F.8 cis-4-(2-Fluoro-4-nitrophenyl)-1,2,6-trimethylpiperazine

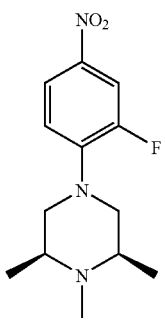

Crude cis-4-(2-Fluoro-4-nitrophenyl)-1,2,6-trimethylpiperazine (6.1 g, 100% recovery) is prepared according to the method described above for the synthesis of racemic-1-(2-fluoro-4-nitrophenyl)-trans-2,4,5-trimethylpiperazine from 1-(2-fluoro-4-nitrophenyl)-cis-3,5-dimethylpiperazine (5.71 g, 24.2 mmol). LCMS-ESI (m/z): calcd for $C_{13}H_{18}FN_3O_2$, 267; $[M+H]^+$ found, 268.

F.9 racemic-3-Fluoro-4-(trans-2,4,5-trimethylpiperazin-1-yl)aniline

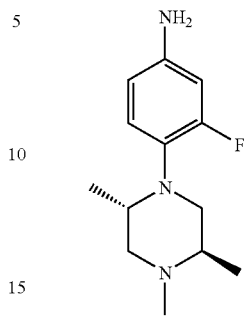

To a solution of racemic-1-(2-fluoro-4-nitrophenyl)-trans-2,4,5-trimethylpiperazine (0.10 g, 0.4 mmol) in 4 mL EtOH is added 0.04 g of 5% Pd/C. The atmosphere over the reaction is evacuated and replaced with $H_2$ thrice and then fitted with a balloon filled with $H_2$ gas. After stirring 12 h, the crude reaction mixture is filtered through Celite, rinsed with EtOH, concentrated in vacuo and chromatographed (silica gel, 10% MeOH in $CH_2Cl_2$) to give 0.027 g (0.12 mmol, 32%) of racemic-3-fluoro-4-(trans-2,4,5-trimethylpiperazin-1-yl) aniline as a yellow liquid. $^1$H NMR (300 MHz, $CDCl_3$) δ 0.86 (d, J=6.0 Hz, 3H), 1.07 (d, J=6.0 Hz, 3H), 2.16 (t, J=10.8 Hz, 2H), 2.34 (s, 3H), 2.72 (t, 1H), 2.83-2.92 (m, 2H), 3.19 (br. s., 1H), 3.58 (br. s., 2H), 6.32-6.40 (m, 2H), 6.92-7.00 (m, 1H). LCMS-ESI (m/z): calcd for $C_{13}H_{20}FN_3$, 237.1; $[M+H]^+$ found, 238.2.

F.10 racemic-4-(trans-2,4,5-Trimethyl-piperazin-1-yl)-phenylamine

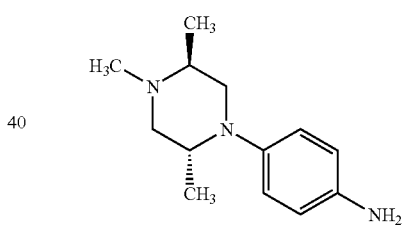

To a 250-mL round bottom flasked is added 10% Pd/C (150 mg). The flask is sealed with a septum, and flushed with a slow stream of $N_2$. racemic-trans-[1,2,5-Trimethyl-4-(4-nitrophenyl)piperazine] (1.28 g, 5.13 mmol) is dissolved in EtOH (30 mL) and transferred via syringe into the flask. The flask is again flushed with $N_2$ and then fitted with a balloon of hydrogen. An outlet needle is inserted through the septum and the flask is flushed with hydrogen before the outlet needle is removed. The resulting slurry is stirred vigorously under the $H_2$ atmosphere at rt. After 24 h the yellow color of the solution dissipates and the hydrogen balloon is removed. The flask is flushed with nitrogen, DCM (24 mL) is added to the reaction mixture, and the resulting slurry is stirred at rt for 24 h. The reaction is filtered through a filtration tube packed with a short column of Celite, the Celite is washed with DCM (2×25 mL), and the combined filtrate evaporated to dryness on a rotary evaporator to provide crude racemic 4-(trans-2,4,5-trimethyl-piperazin-1-yl)-phenylamine (1.11 g, 98% recovery, 97% purity as determined by LC/MS analysis @ UV 254 nm detection). The crude product is used in the next step without further purification. LCMS-ESI (m/z): calcd for $C_{13}H_{21}N_3$, 219; $[M+H]^+$ found, 220.

F.11 3-Fluoro-4-(cis-3,4,5-trimethyl-piperazin-1-yl)-phenylamine

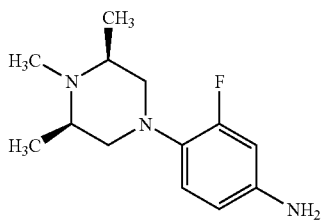

Using the method described above for the synthesis of racemic-4-(trans-2,4,5-Trimethyl-piperazin-1-yl)-phenylamine, treatment of cis-4-(2-fluoro-4-nitrophenyl)-1,2,6-trimethylpiperazine (1.39 g, 5.20 mmol) with $H_2$ and 10% Pd/C (120 mg) provided crude 3-fluoro-4-(cis-3,4,5-trimethyl-piperazin-1-yl)-phenylamine (1.04 g, 84% recovery, 96% purity as determined by LC/MS analysis @ UV 254 nm detection,). The crude product is used in the next step without further purification. LCMS-ESI (m/z): calcd for $C_{13}H_{20}FN_3$, 237; $[M+H]^+$ found, 238.

F.12 4-(cis-3,4,5-Trimethyl-piperazin-1-yl)-phenylamine

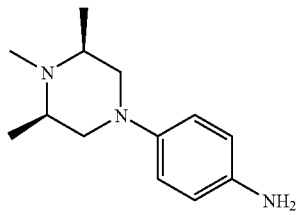

Using the method described above for the synthesis of racemic-4-(trans-2,4,5-Trimethyl-piperazin-1-yl)-phenylamine, treatment of cis-1,2,6-trimethyl-4-(4-nitrophenyl) piperazine (1.28 g, 5.13 mmol) with $H_2$ and 10% Pd/C (130 mg) provided crude 4-(cis-3,4,5-Trimethyl-piperazin-1-yl)-phenylamine (1.18 g, 101% recovery, >85% purity as determined by LC/MS analysis @ UV 254 nm detection). The crude product was used in the next step without further purification. LCMS-ESI (m/z): calcd for $C_{13}H_{21}N_3$, 219; $[M+H]^+$ found, 220.

F.13 1-Cyclopropyl-4-(4-nitrophenyl)piperazine

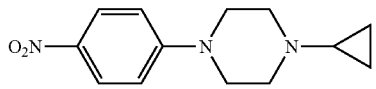

A mixture of [(1-ethoxycyclopropyl)oxy]trimethylsilane (4.5 mL. 22.4 mmol, 2 eq.), 1-(4-nitrophenyl)piperazine (2.32 g, 11.1 mmol, acetic acid (6.4 mL, 5 eq.), molecule sieves (3 A, 5 g), and sodium cyanoborohydride (2.1 g, 33.3 mmol, 3 eq.) in dry methanol (50 mL) is heated at 60-65° C. for 4 h. The reaction mixture is filtered, and the filtration is evaporated. The residue is dissolved in DCM (200 mL) and the resulting solution is washed with 2 N NaOH (100 mL), brine (100 mL×2), dried over $MgSO_4$, and evaporated to provide a yellow solid (2.75 g, 100%). The compound is used in the next reaction without further purification. $^1H$ NMR (300 MHz, DMSO-$d_6$), δ 8.02 (d, J=9.6 Hz, 2H), 7.00 (d, J=9.6 Hz, 2H), 3.38-3.42 (m, 4H), 2.60-2.68 (m, 4H), 1.60- 1.67 (m, 1H), 0.40-0.46 (m, 2H), 0.35-0.38 (m, 2H). LCMS-ESI (m/z): calcd for $C_{13}H_{17}N_3O_2$, 247.1; $[M+H]^+$ found, 248.4.

F.14 4-(4-Cyclopropyl-piperazin-1-yl)-phenylamine

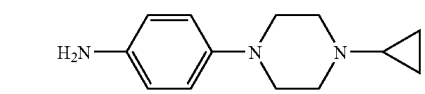

A mixture of 1-cyclopropyl-4-(4-nitrophenyl)piperazine (1.1 g, 4.4 mmol), 10% Pd/C (100 mg) in methanol (50 mL) is stirred under a hydrogen atmosphere (balloon) for 4 h. The catalyst is filtered off through a pad of Celite and the methanol solution is evaporated to give a oily product that became a reddish-brown solid on standing (0.9 g, 93%). The compound is used in the next step without further purification. LCMS-ESI (m/z): calcd for $C_{13}H_{19}N_3$, 217.1; $[M+H]^+$ found, 218.4.

F.15 1-Isopropyl-4-(4-nitrophenyl)piperazine

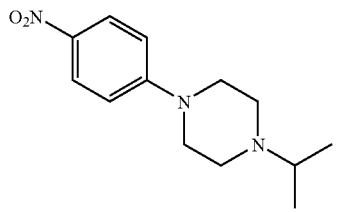

A suspension of 1-(4-nitrophenyl)piperazine (20 g, 190 mmol, 2 eq), sodium triaectoxyborohydride (41 g, 97 mmol, 2 eq), and acetone (18.8 g, 21.3 mL, 290 mmol, 3 eq) in DCE (400 mL) is stirred in a water bath at rt for 32 h. Water (100 mL) is slowly added (gas evolution) and resulting biphasic solution is stirred for 1 h. The phases are separated and the DCE extract is washed with water (2×100 mL). The combined aqueous extracts are extracted with DCE (2×50 mL), and the combined DCE extracts are filtered through a phase separation tube. The filtrate is concentrated on a rotary evaporator and the yellow oil obtained dried under vacuum for a further 2 h. The oily product obtained solidified on standing to provide 1-isopropyl-4-(4-nitrophenyl)piperazine as a yellow solid (16.5 g, 66% recovery). The product is used in the next step without further purification. LCMS Purity: 80% by ELS detection; LCMS-ESI (m/z): calcd for $C_{13}H_{19}N_3O_2$ 249.1; $[M+H]^+$ found, 250.3.

F.16 1-Isopentyl-4-(4-nitrophenyl)piperazine

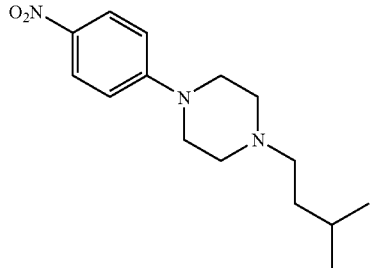

A suspension of 1-(4-nitrophenyl)piperazine (5.00 g, 24.1 mmol, 1.0 eq), sodium triaectoxyborohydride (10.23 g, 48.3 mmol, 2 eq), and isovaleraldehyde (4.16 g, 5.18 mL, 48.3 mmol) is stirred at RT for 48 h. The reaction mixture is transferred to a separatory funnel and the solution washed with 10% aqueous NaCl solution (2×50 mL) (gas evolution). A yellow precipitate formed in the separatory funnel DCM (50 mL) was added followed by a saturated aqueous solution of NaHCO$_3$ (50 mL) and the precipitate dissolved. The phases are separated and DCM phase is again washed with saturated aqueous solution of NaHCO$_3$ (50 mL). The combined aqueous NaHCO$_3$ extracts are extracted with DCM (2×50 mL), the combined DCM extracts are dried over MgSO$_4$, filtered through a filtration tube, and the solvent is evaporated to provide a viscous oil that partially solidified on standing. The residue is triturated with hexanes (25 mL) and resulting slurry stirred at room temperature for 48 h. The precipitate which forms is collected by filtration, washed with hexanes (2×25 mL), dried briefly on the frit, and then dried under vacuum for 48 h to provide 1-isopentyl-4-(4-nitrophenyl)piperazine as a yellow solid (5.15 g, 77% recovery, 92% purity as determined by LC/MS analysis @ UV 254 nm detection). The crude product was used in the next step without further purification. LCMS-ESI (m/z): calcd for $C_{15}H_{23}N_3O_2$, 277; [M+H]$^+$ found, 278.

F.17 1-(4-nitrophenyl)-4-(pentan-3-yl)piperazine:

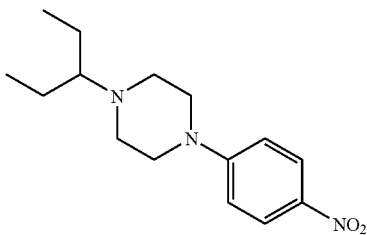

A suspension of 1-(4-nitrophenyl)piperazine (5.00 g, 24.1 mmol, 1.0 eq), sodium triacetoxyborohydride (10.23 g, 48.3 mmol, 2 eq), and pentanone (6.23 g, 72.4 mmol, 3 eq) was stirred at RT in DCM (100 mL). Due to the viscous nature of the reaction mixture a further 50 mL of DCM was added to the reaction mixture (25 mL portion added after ca. 1 h; 25 mL portion added after 4 h). After 6 d, saturated aqueous NaHCO$_3$ solution (25 mL) and 10% aqueous brine solution (25 mL) were added to the reaction mixture. The resulting mixture was stirred for 20 min, the phases separated, and the DCM extract washed with saturated aqueous NaHCO$_3$ solution (25 mL), and 0% aqueous brine solution (25 mL) (50 mL total of aqueous soln in one wash). The phases were separated and the DCM extract dried by passing through a short column of MgSO$_4$. The MgSO$_4$ was rinsed with two portions of DCM (25 mL), and the combined DCM extracts evaporated on a rotary evaporator. To the residue obtained was added hexanes (25 mL) and the slurry stirred at rt for 24 h. The yellow precipitate which formed was collected by filtration and washed with hexanes (2×25 mL). On standing the required product precipitated from the filtrate. The precipitate was collected by filtration and dried under vacuum to provide the title compound as a yellow solid (1.13 g, 16% recovery, 87% purity as determined by LC/MS analysis @ UV 254 nm detection). The crude product was used in the next step without further purification. LCMS-ESI (m/z): calcd for $C_{15}H_{23}N_3O_2$, 277; [M+H]$^+$ found, 278.

F.18 1-(4-Nitrophenyl)-4-propylpiperazine

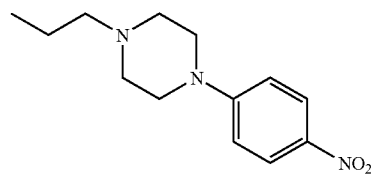

Following the general procedure described above for the synthesis of 1-isopentyl-4-(4-nitrophenyl)piperazine, treatment of 1-(4-nitrophenyl)piperazine (5.00 g, 24.1 mmol, 1.0 eq) with isovaleraldehyde (4.16 g, 5.18 mL, 48.3 mmol, 3 eq) at RT for 48 h provided the title compound as a yellow solid (5.34 g, 89% recovery, 93% purity as determined by LC/MS analysis @ UV 254 nm detection). In this case, upon addition of hexane (25 mL) to the crude residue, obtained from evaporation of the DCM extract, and stirring for 24 h the product precipitated from solution, was collected by filtration, washed with hexanes (2×25 ml), and was dried under vacuum. The crude product is used in the next step without further purification. LCMS-ESI (m/z): calcd for $C_{13}H_{19}N_3O_2$, 249; [M+H]$^+$ found, 250.

F.19 1-Cyclobutyl-4-(4-nitrophenyl)piperazine

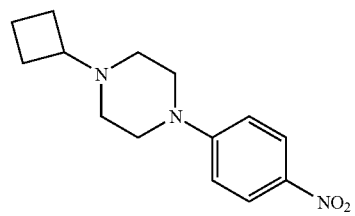

Following the general procedure described above for the synthesis of 1-(4-nitrophenyl)-4-(pentan-3-yl)piperazine, treatment of 1-(4-nitrophenyl)piperazine (5.00 g, 24.1 mmol, 1.0 equiv.) with cyclobutanone (3.38 g, 48.3 mmol, 2 equiv.) in DCM (100 mL) at RT for 72 h provided the title compound as a yellow solid (4.96 g, 99% recovery, 87% purity as determined by LC/MS analysis @ UV 254 nm detection). In this case, upon addition of hexane (25 mL) to the crude residue, obtained from evaporation of the DCM extract, and stirring for 24 h the product precipitated from solution, is collected by filtration, washed with hexanes (2×25 ml), and was dried under vacuum. The crude product is used in the next step without further purification. LCMS-ESI (m/z): calcd for $C_{14}H_{19}N_3O_2$, 261; [M+H]$^+$ found, 262.

F.20 1-Cyclohexyl-4-(4-nitrophenyl)piperazine

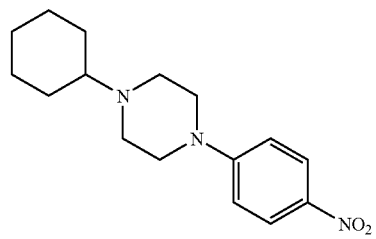

Following the general procedure described above for the synthesis of 11-(4-nitrophenyl)-4-(pentan-3-yl)piperazine, treatment of 1-(4-nitrophenyl)piperazine (5.00 g, 24.1 mmol, 1.0 equiv.) with cyclohexanone (7.10 g, 72.4 mmol, 2.0 eq) in DCM (100 mL) at rt for 72 h provided the title compound as a yellow solid (4.80 g, 68% recovery, 89% purity as determined by LC/MS analysis @ UV 254 nm detection). In this case, an additional portion (25 mL) is added to the reaction mixture after 1 h. Upon addition of hexane (25 mL) to the crude residue, obtained from evaporation of the DCM extract, and stirring for 24 h the product precipitated from solution and was collected by filtration, washed with hexanes (2×25 mL), and dried under vacuum. The crude product is used in the next step without further purification. LCMS purity: 89% by UV 254 nm detection. LCMS-ESI (m/z): calcd for $C_{16}H_{23}N_3O_2$, 289; $[M+H]^+$ found, 290.

F.21 4-(4-Isopentylpiperazin-1-yl)aniline

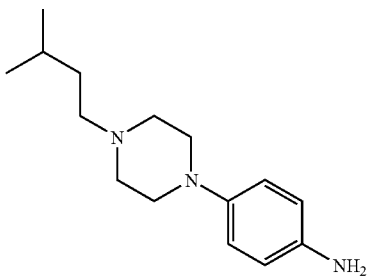

To a 250-mL round bottom flasked is added 10% Pd/C (100 mg) and 1-isopentyl-4-(4-nitrophenyl)piperazine (1.0 g, 3.6 mmol). The flask is sealed with a septum, and flushed with a slow stream of $N_2$. EtOH (30 mL) is then added via syringed into the flask. The flask is again flushed with $N_2$ and then it is fitted with a balloon of hydrogen. An outlet needle is inserted through the septum and the flask is flushed with hydrogen before the outlet needle is removed. The resulting slurry is stirred vigorously under the $H_2$ atmosphere at rt. After 24 h the yellow color of the solution dissipated and the hydrogen balloon is removed. The flask is flushed with nitrogen, DCM (10 mL) is added to the reaction mixture, and the resulting slurry stirred at rt for 1.5 h. The reaction is filtered through a filtration tube packed with a short column of Celite, the Celite washed with DCM (2×20 mL), and the combined filtrate evaporated to dryness on a rotary evaporator. The product is air dried for 48 h and then it is dried under vacuum for 2 h to provide crude 4-(4-isopentylpiperazin-1-yl)aniline (1.16 g, 120% recovery due to the incomplete removal of the solvent, >80% purity as determined by LC/MS analysis @ UV 254 nm detection). The crude product was used in the next step without further purification. LCMS-ESI (m/z): calcd for $C_{15}H_{25}N_3$, 247; $[M+H]^+$ found, 248.

F.22 4-(4-Cyclobutylpiperazin-1-yl)aniline

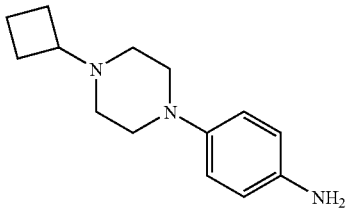

To a 250-mL round bottom flasked is added 10% Pd/C (100 mg). The flask was sealed with a septum, and flushed with a slow stream of $N_2$. 1-Cyclobutyl-4-(4-nitrophenyl)piperazine (1 g, 3.83 mmol) was dissolved in EtOH (30 mL) and transferred via syringe into the flask. The flask is again flushed with $N_2$ and then it is fitted with a balloon of hydrogen. An outlet needle is inserted through the septum and the flask is flushed with hydrogen before the outlet needle is removed. The resulting slurry is stirred vigorously under the $H_2$ atmosphere at rt. After 24 h the yellow color of the solution dissipates and the hydrogen balloon is removed. The flask is flushed with nitrogen, DCM (10 mL) is added to the reaction mixture, and the resulting slurry is stirred at rt for 1.5 h. The reaction is filtered through a filtration tube packed with a short column of Celite, the Celite washed with DCM (2×20 mL), and the combined filtrate evaporated to dryness on a rotary evaporator. The product is air dried for 48 h and then dried under vacuum for 2 h to provide crude 4-(4-cyclobutylpiperazin-1-yl)aniline (0.87 g, 98% recovery, 100% purity as determined by LC/MS analysis @ UV 254 nm detection). The crude product was used in the next step without further purification. LCMS-ESI (m/z): calcd for $C_{14}H_{21}N_3$, 231; $[M+H]^+$ found, 232.

F.23 4-(4-(pentan-3-yl)piperazin-1-yl)aniline

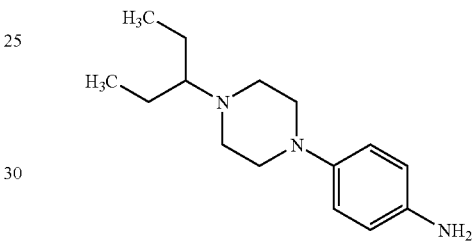

Using the method described above for the synthesis of 4-(4-isopentylpiperazin-1-yl)aniline, treatment of 4-(4-(pentan-3-yl)piperazin-1-yl)aniline (1.03 g, 3.75 mmol) with $H_2$ and 10% Pd/C provided crude 4-(4-(pentan-3-yl)piperazin-1-yl)aniline (0.91 g, 98% recovery, 91% purity as determined by LC/MS analysis @ UV 254 nm detection). The crude product is used in the next step without further purification. LCMS-ESI (m/z): calcd for $C_{15}H_{25}N_3$, 247; $[M+H]^+$ found, 248.

F.24 4-(4-Isopropylpiperazin-1-yl)aniline

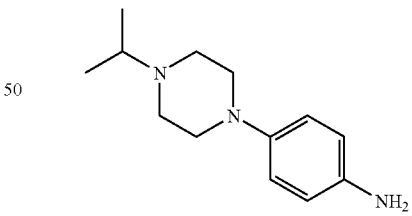

Using the method described above for the synthesis of 4-(4-isopentylpiperazin-1-yl)aniline, treatment of 1-isopropyl-4-(4-nitrophenyl)piperazine (11.0 g, 40.1 mmol) with $H_2$ and 10% Pd/C (1.0 g) at RT in EtOH (150 mL) for 24 h, followed by the addition of DCM (100 mL) to the reaction mixture and stirring for a further 3 h, provided crude 4-(4-isopropylpiperazin-1-yl)aniline (7.6 g, 86% recovery, 99% purity as determined by LC/MS analysis @ UV 254 nm detection). The crude product is used in the next step without further purification. LCMS-ESI (m/z): calcd for $C_{13}H_{21}N_3$, 219; $[M+H]^+$ found, 220.

F.25 4-(4-Propylpiperazin-1-yl)aniline

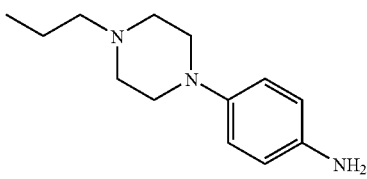

Using the method described above for the synthesis of 4-(4-isopentylpiperazin-1-yl)aniline, treatment of 1-(4-nitrophenyl)-4-propylpiperazine (1.0 g, 4.01 mmol) with $H_2$ and 10% Pd/C provided crude 4-(4-propylpiperazin-1-yl)aniline (0.99 g, 118% recovery due to incomplete removal of the solvent, >80% purity as determined by LC/MS analysis @ UV 254 nm detection,). The crude product is used in the next step without further purification. LCMS-ESI (m/z): calcd for $C_{13}H_{21}N_3$, 219; $[M+H]^+$ found, 220.

F.26 4-(4-Cyclohexylpiperazin-1-yl)aniline

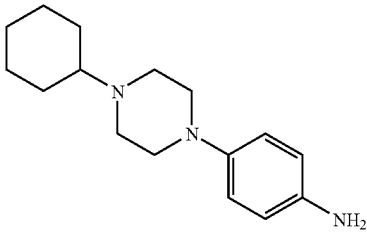

Using the method described above for the synthesis of 4-(4-isopentylpiperazin-1-yl)aniline, treatment of 1-cyclohexyl-4-(4-nitrophenyl)piperazine (1.0 g, 3.46 mmol) with $H_2$ and 10% Pd/C provided crude 4-(4-cyclohexylpiperazin-1-yl)aniline (0.89 g, 89% recovery, 78% purity as determined by LC/MS analysis @ UV 254 nm detection). The crude product is used in the next step without further purification. LCMS-ESI (m/z): calcd for $C_{16}H_{25}N_3$, 259; $[M+H]^+$ found, 260.

G: Methoxypyridine Deprotection

G.1 4-(8-(4-(4-cyclobutylpiperazin-1-yl)phenylamino)-[1,2,4]triazolo[1,5-a]pyridin-5-yl)pyridin-2(1H)-one

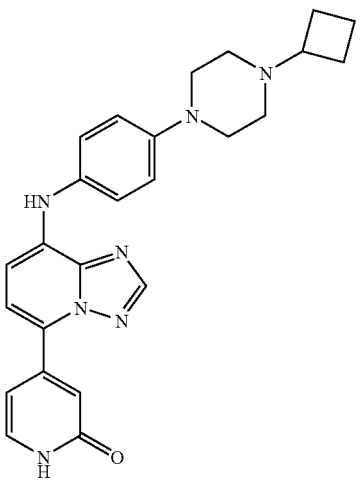

N-(4-(4-Cyclobutylpiperazin-1-yl)phenyl)-5-(2-methoxypyridin-4-yl)-[1,2,4]triazolo[1,5-c]pyridin-8-amine, pyridine hydrochloride (10.7 eq), and water (two drops) are added to a 5-mL vial. The vial is capped and heated with stirring at 150° C. for 2 h. After cooling to room temperature, the crude reaction mixture is purified by silica gel column chromatography (gradient elution with 3-5% 2 N $NH_3$ in MeOH/DCM) to provide 4-(8-(4-(4-cyclobutylpiperazin-1-yl)phenylamino)-[1,2,4]triazolo[1,5-c]pyridin-5-yl)pyridin-2(1H)-one (46 mg). $^1$H NMR (300 MHz, DMSO-$d_6$), δ 11.54 (s, 1H), 8.71 (s, 1H), 8.52 (s, 1H), 7.41 (d, J=6.9 Hz, 1H), 7.37 (d, J=8.1 Hz, 1H), 7.22 (d, J=9.0 Hz, 2H), 7.16 (d, J=1.5 Hz, 1H), 6.95 (d, J=9.0 Hz, 2H), 6.87 (d, J=8.1 Hz, 1H), 6.70 (dd, J=1.8, 7.2 Hz, 1H), 3.09 (m, 4H), 2.73 (m, 1H), 2.38 (m, 4H), 1.98 (m, 2H), 1.80 (m, 2H), 1.66 (m, 2H). LCMS Purity: 99% by UV 220 nm detection; LCMS-ESI (m/z): calcd for $C_{25}H_{27}N_7O$, 441.2; $[M+H]^+$ found, 442.6.

G.2 4-(8-(4-(4-ethylpiperazin-1-yl)phenylamino-[1,2,4]triazolo[1,5-a]pyridin-5-yl)pyridin-2(1H)-one

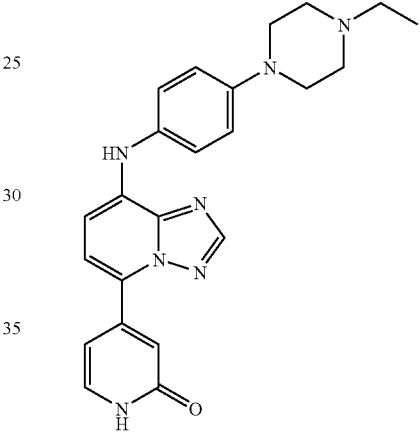

A mixture of N-(4-(4-ethylpiperazin-1-yl)phenyl)-5-(2-methoxypyridin-4-yl)-[1,2,4]triazolo[1,5-a]pyridin-8-amine (52 mg), pyridine hydrochloride (250 mg), and one drop of water are added to a 5-mL microwave vial. The vial is then capped and heated with stirring at 150° C. for 2 h. After cooling to room temperature, the crude reaction mixture is purified by silica gel column chromatography (gradient elution with 3-5% 2 N $NH_3$ in MeOH/DCM) to provide the desired product as a light yellow solid (40.1 mg, 79.6% yield). $^1$H NMR (300 MHz, DMSO-$d_6$): δ 11.61 (s, 1H), 8.78 (s, 1H), 8.56 (s, 1H), 7.45 (d, J=6.9 Hz, 1H), 7.41 (d, J=8.4 Hz, 1H), 7.26 (d, J=9.0 Hz, 2H), 7.20 (d, J=1.5 Hz, 1H), 6.97 (d, J=9.0 Hz, 2H), 6.90 (d, J=8.1 Hz, 1H), 6.73 (dd, J=1.8, 7.2 Hz, 1H), 3.12 (m, 4H), 2.50 (m, 4H), 2.38 (q, J=7.2 Hz, 2H), 1.04 (t, J=7.2 Hz, 3H); $^{13}$C NMR (75.5 MHz, DMSO-$d_6$): δ 162.53, 151.69, 147.83, 144.34, 143.66, 135.53, 134.81, 131.36, 124.99, 123.55, 117.44, 117.18, 116.19, 104.12, 103.36, 52.39, 51.66, 48.58, 12.03; LCMS-ESI (m/z): calcd for $C_{23}H_{25}N_7O$, 415; $[M+H]^+$ found, 416.

The following compounds were synthesised according to the procedure described above in G.2 of the demethylation reaction:

G.3 4-(8-(4-(4-propylpiperazin-1-yl)phenylamino-[1,2,4]triazolo[1,5-a]pyridin-5-yl)pyridin-2(1H)-one

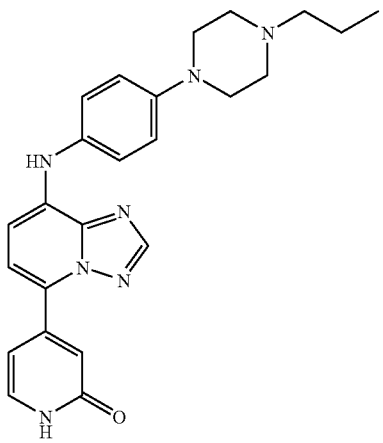

The title compound is obtained as a bright yellow solid (41.7 mg, 80% yield). $^1$H NMR (300 MHz, DMSO-$d_6$): δ 11.61 (s, 1H), 8.78 (s, 1H), 8.56 (s, 1H), 7.45 (d, J=7.2 Hz, 1H), 7.41 (d, J=8.4 Hz, 1H), 7.26 (d, J=9.0 Hz, 2H), 7.20 (d, J=1.5 Hz, 1H), 6.97 (d, J=9.0 Hz, 2H), 6.90 (d, J=8.1 Hz, 1H), 6.73 (dd, J=1.8, 7.2 Hz, 1H), 3.12 (m, 4H), 2.50 (m, 4H), 2.28 (t, J=7.2 Hz, 2H), 1.47 (sextet, J=7.2 Hz, 2H), 0.88 (t, J=7.2 Hz, 3H); LCMS-ESI (m/z): calcd for $C_{24}H_{27}N_7O$, 429; [M+H]$^+$ found, 430.

G.4 4-(8-(4-(4-(pentan-3-yl)piperazin-1-yl)phenylamino-[1,2,4]triazolo[1,5-a]pyridin-5-yl)pyridin-2(1H)-one

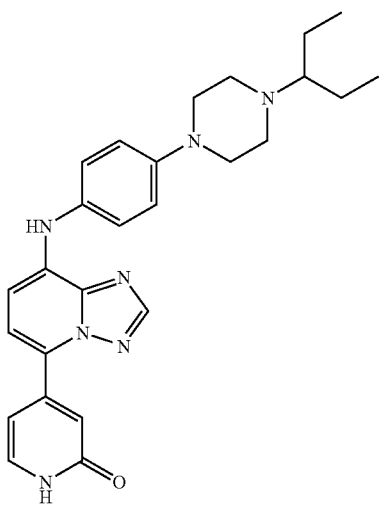

The title compound is obtained as a bright yellow solid (42.4 mg, 76% yield). NMR (300 MHz, DMSO-$d_6$): δ 11.62 (s, 1H), 8.78 (s, 1H), 8.56 (s, 1H), 7.45 (d, J=7.2 Hz, 1H), 7.41 (d, J=8.4 Hz, 1H), 7.26 (d, J=9.0 Hz, 2H), 7.20 (d, J=1.5 Hz, 1H), 6.97 (d, J=9.0 Hz, 2H), 6.90 (d, J=8.1 Hz, 1H), 6.73 (dd, J=1.8, 7.2 Hz, 1H), 3.08 (m, 4H), 2.60 (m, 4H), 2.19 (m, 1H), 1.55-1.41 (m, 2H), 1.35-1.20 (m, 2H), 0.88 (t, J=6.9 Hz, 6H); LCMS-ESI (m/z): calcd for $C_{26}H_{31}N_7O$, 457; [M+H]$^+$ found, 458.

G.5 4-(8-(4-(4-isopentylpiperazin-1-yl)phenylamino-[1,2,4]triazolo-[1,5-a]pyridin-5-yl)pyridin-2(1H)-one

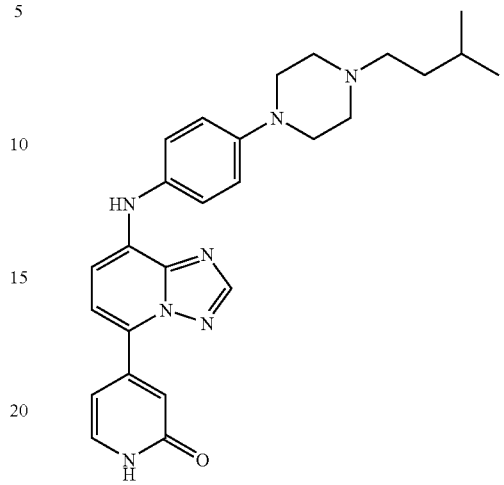

The title compound was obtained as a yellow solid (30 mg, 54.1% yield). $^1$H NMR (300 MHz, DMSO-$d_6$): δ 11.61 (s, 1H), 8.78 (s, 1H), 8.56 (s, 1H), 7.45 (d, J=6.9 Hz, 1H), 7.41 (d, J=8.7 Hz, 1H), 7.26 (d, J=9.0 Hz, 2H), 7.19 (dd, J=0.6, 2.1 Hz, 1H), 6.97 (d, J=9.0 Hz, 2H), 6.90 (d, J=8.1 Hz, 1H), 6.73 (dd, J=1.4, 7.2 Hz, 1H), 3.12 (m, 4H), 2.50 (m, 4H), 2.33 (t, J=7.5 Hz, 2H), 1.60 (m, 1H), 1.35 (m, 2H), 0.89 (d, J=6.6 Hz, 6H); LCMS-ESI (m/z): calcd for $C_{26}H_{31}N_7O$, 457; [M+H]$^+$ found, 458.

G.6 4-(8-(4-(4-cyclopropylpiperazin-1-yl)phenylamino-[1,2,4]triazolo[1,5-a]pyridin-5-yl)pyridin-2(1H)-one

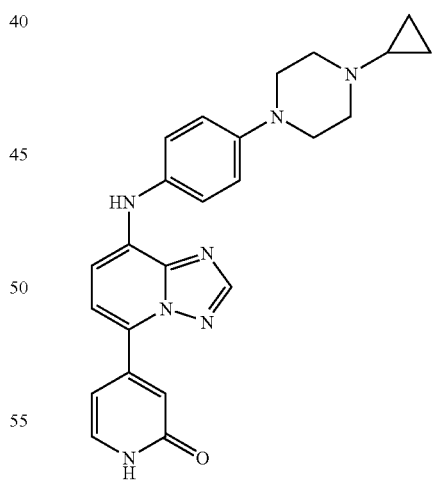

The title compound is obtained as a yellow solid (12.9 mg, 24% yield). $^1$H NMR (300 MHz, DMSO-$d_6$), δ 11.62 (s, 1H), 8.78 (s, 1H), 8.56 (s, 1H), 7.45 (d, J=6.9 Hz, 1H), 7.40 (d, J=8.4 Hz, 1H), 7.25 (d, J=8.7 Hz, 2H), 7.19 (d, J=1.5 Hz, 1H), 6.97 (d, J=8.7 Hz, 2H), 6.91 (d, J=8.4 Hz, 1H), 6.70 (dd, J=1.5, 6.9 Hz, 1H), 3.09 (m, 4H), 2.69 (m, 4H), 1.67 (m, 1H), 0.50-0.40 (m, 2H), 0.38-0.30 (m, 2H); LCMS-ESI (m/z): calcd for $C_{24}H_{25}N_7O$, 427; [M+H]$^+$ found, 428.

G.7 4-(8-(4-(4-cyclobutylpiperazin-1-yl)phenylamino-[1,2,4]triazolo[1,5-a]pyridin-5-yl)pyridin-2(1H)-one

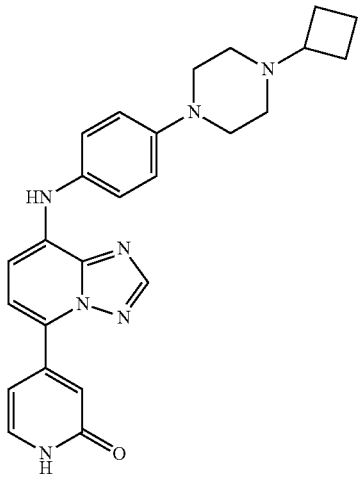

The title compound is obtained as a yellow solid (46 mg, 85.7% yield). $^1$H NMR (300 MHz, DMSO-d$_6$), δ 11.54 (s, 1H), 8.71 (s, 1H), 8.52 (s, 1H), 7.41 (d, J=6.9 Hz, 1H), 7.37 (d, J=8.1 Hz, 1H), 7.22 (d, J=9.0 Hz, 2H), 7.16 (d, J=1.5 Hz, 1H), 6.95 (d, J=9.0 Hz, 2H), 6.87 (d, J=8.1 Hz, 1H), 6.70 (dd, J=1.8, 7.2 Hz, 1H), 3.09 (m, 4H), 2.73 (m, 1H), 2.38 (m, 4H), 1.98 (m, 2H), 1.80 (m, 2H), 1.66 (m, 2H); LCMS-ESI (m/z): calcd for C$_{25}$H$_{27}$N$_7$O, 441; [M+H]$^+$ found, 442.

G.8 4-(8-(4-(4-cyclohexylpiperazin-1-yl)phenylamino-[1,2,4]triazolo[1,5-a]pyridin-5-yl)pyridin-2(1H)-one

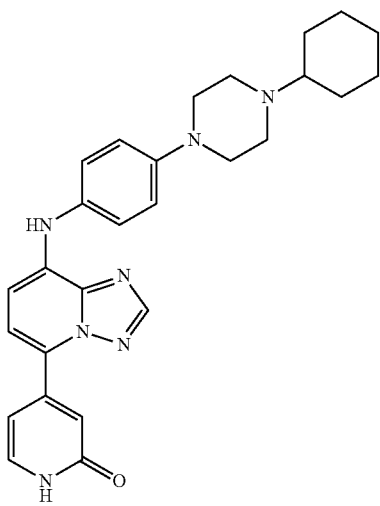

The title compound is obtained as a yellow solid (29.9 mg, 52.5%). $^1$H NMR (300 MHz, DMSO-d$_6$): δ 11.61 (s, 1H), 8.78 (s, 1H), 8.56 (s, 1H), 7.45 (d, J=7.2 Hz, 1H), 7.41 (d, J=8.4 Hz, 1H), 7.26 (d, J=9.0 Hz, 2H), 7.19 (d, J=1.8 Hz, 1H), 6.97 (d, J=9.0 Hz, 2H), 6.90 (d, J=8.1 Hz, 1H), 6.73 (dd, J=2.1, 7.2 Hz, 1H), 3.10 (m, 4H), 2.63 (m, 4H), 2.26 (m, 1H), 1.84-1.70 (m, 4H), 1.60 (m, 1H), 1.25-1.05 (m, 5H). LCMS-ESI (m/z): calcd for C$_{27}$H$_{31}$N$_7$O, 469; [M+H]$^+$ found, 470.

G.9 racemic-4-(8-(4-(trans-2,4,5-trimethylpiperazin-1-yl)phenylamino)-[1,2,4]triazolo[1,5-a]pyridin-5-yl)pyridin-2(1H)-one

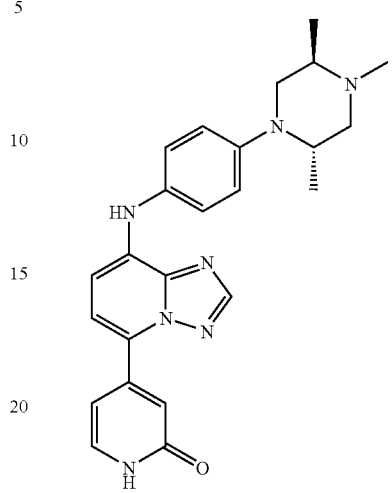

The compound is obtained as a yellow solid. $^1$H NMR (300 MHz, DMSO-d$_6$): δ 11.63 (s, 1H), 8.91 (s, 1H), 8.57 (s, 1H), 7.46 (d, J=7.2 Hz, 1H), 7.42 (d, J=8.4 Hz, 1H), 7.32 (d, J=8.7 Hz, 2H), 7.19 (d, J=1.5 Hz, 1H), 7.10 (d, J=8.7 Hz, 2H), 7.05 (d, J=8.4 Hz, 1H), 6.73 (dd, J=1.5, 7.2 Hz, 1H), 3.20 (m, 1H), 2.99 (dd, J=2.7, 11.4 Hz, 1H), 2.82 (dd, J=2.4, 11.1 Hz, 1H), 2.59 (dd, J=9.0, 10.8 Hz, 1H), 2.31 (m, 1H), 2.21 (s, 3H), 2.30 (dd, J=9.9, 9.9 Hz, 1H), 0.97 (d, J=6.3 Hz, 3H), 0.87 (d, J=6.0 Hz, 3H). LCMS-ESI (m/z): calcd for C$_{24}$H$_{27}$N$_7$O, 429; [M+H]$^+$ found, 430.

G.10 4-(8-(4-(piperazin-1-yl)phenylamino-[1,2,4]triazolo[1,5-a]pyridin-5-yl)pyridin-2(1H)-one The compound is obtained as a by-product of the demethylation of N-(4-(4-cyclopropylpiperazin-1-yl)phenyl)-5-(2-methoxypyridin-4-yl)-[1,2,4]triazolo[1,5-c]pyridin-8-amine using pyridine hydrochloride at 150° C. $^1$H NMR (300 MHz, DMSO-d$_6$): δ 12.0-11.0 (brs, 1H), 8.79 (s, 1H), 8.56 (s, 1H), 7.45 (d, J=6.9 Hz, 1H), 7.41 (d, J=8.4 Hz, 1H), 7.26 (d, J=9.0 Hz, 2H), 7.19 (d, J=2.1 Hz, 1H), 6.97 (d, J=9.0 Hz, 2H), 6.91 (d, J=8.4 Hz, 1H), 6.73 (dd, J=2.1, 7.2 Hz, 1H), 3.10 (m, 4H), 2.94 (m, 4H); LCMS-ESI (m/z): calcd for C$_{21}$H$_{21}$N$_7$O, 387; [M+H]$^+$ found, 388.

Specific Synthetic Examples

Following General Procedure A the Following Compounds were Synthesized

Example 1

4-[8-(4-Morpholin-4-yl-phenylamino)-[1,2,4]triazolo[1,5-a]pyridin-5-yl]-benzamide

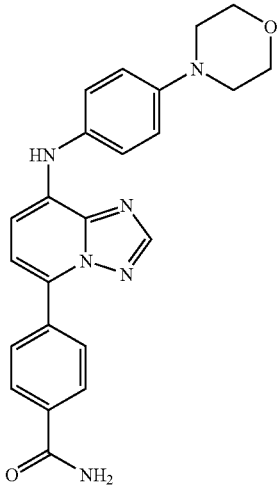

A suspension of 5-chloro-[1,2,4]triazolo[1,5-a]pyridin-8-yl)-(4-morpholin-4-yl-phenyl)-amine (70 mg, 212 µmol), 4-carbamoyl benzeneboronic acid (42 mg, 254 µmol), Pd(PPh$_3$)$_4$ (25 mg, 21 µmol) and NaO$^t$Bu (82 mg, 848 µmol) in 0.8 mL of DMF/water (3:1, degassed) is degassed for 5 min in a sealed tube. The tube is sealed and the reaction mixture heated at 90° C. overnight. After evaporation of the solvents, the residue is purified by flash chromatography (silica gel, dichloromethane/7N NH$_3$ in methanol 98:2) yielding the title compound (20 mg) as a solid.

$^1$H-NMR (400 MHz, d$_6$-DMSO) δ=3.13 (m, 4H, 2×CH$_2$), 3.79 (m, 4H, 2×CH$_2$), 7.03 (m, 3H, H$_{ar}$), 7.32 (m, 3H, H$_{ar}$), 7.47 (bs, 1H, NH), 8.03 (m, 2H, H$_{ar}$), 8.09 (m, 3H, H$_{ar}$, NH), 8.55 (s, 1H, H$_{ar}$), 8.60 (bs, 1H, NH). LCMS 99.1%, R$_t$=2.70 min, m/z 415 (M+H, AP$^+$ formic acid).

Example 2

[4-(4-Methyl-piperazin-1-yl)-phenyl]-[5-(1H-pyrazol-4-yl)-[1,2,4]triazolo[1,5-a]pyridin-8-yl]-amine

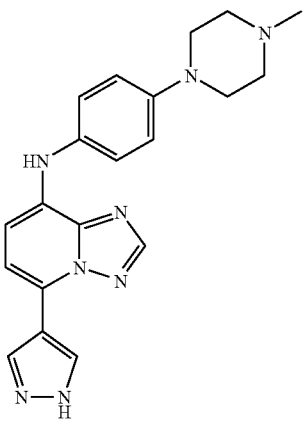

A suspension of 5-chloro-[1,2,4]triazolo[1,5-a]pyridin-8-yl)-[4-(4-methyl-piperazin-1-yl)-phenyl]-amine (50 mg, 146 µmol), 4-(4,4,5,5-tetramethyl-1,3,2-dioxaborolan-2-yl)-1H-pyrazole (57 mg, 290 µmol), Pd(PPh$_3$)$_4$ (42 mg, 40 µmol) and NaO$^t$Bu (56 mg, 580 µmol) in 1 mL of DMF/water (4:1, degassed) is degassed for 1 min in a sealed tube. The tube is sealed and the reaction mixture heated at 110° C. for three hours. After evaporation of the solvents, the residue is purified by flash chromatography (silica gel, dichloromethane/7N NH$_3$ in methanol 95:5) affording the title compound (37 mg) as a solid.

$^1$H-NMR (400 MHz, d$_6$-DMSO) δ=2.26 (s, 3H, CH$_3$), 2.52 (m, 4H, 2×CH$_2$), 3.13 (m, 4H, 2×CH$_2$), 6.99 (d, 2H, H$_{ar}$), 7.05 (d, 1H, H$_{ar}$), 7.27 (d, 2H, H$_{ar}$), 7.43 (d, 1H, H$_{ar}$), 8.33 (m, 2H, H$_{ar}$, H$_{pyrazole}$), 8.59 (s, 1H, H$_{ar}$), 8.69 (bs, 1H, H$_{pyrazole}$), 13.2 (bs, 1H, NH$_{pyrazole}$). LCMS 96.1%, R$_t$=1.86 min, m/z 375 (M+H, AP$^+$ formic acid).

Example 3

4-[5-(1H-Pyrazol-4-yl)-[1,2,4]triazolo[1,5-a]pyridin-8-ylamino]-N-pyridin-3-ylmethyl-benzamide

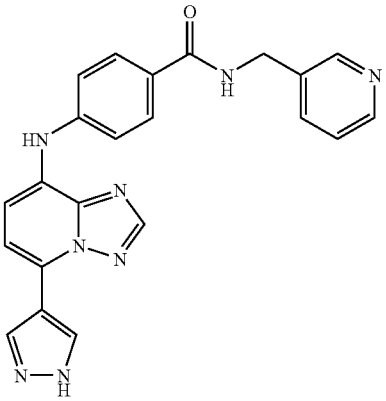

A suspension of 4-(5-chloro-[1,2,4]triazolo[1,5-a]pyridin-8-ylamino)-N-pyridin-3-ylmethyl-benzamide (50 mg, 132 µmol), 4-(4,4,5,5-tetramethyl-1,3,2-dioxaborolan-2-yl)-1H-pyrazole (51 mg, 260 µmol), Pd(PPh$_3$)$_4$ (46 mg, 40 µmol) and NaO$^t$Bu (51 mg, 530 µmol) in 1.2 mL of DMF/water (5:1, degassed) is degassed for 1 min in a sealed tube. The tube is sealed and the reaction mixture heated at 110° C. for 3.5 hours. After evaporation of the solvents and filtration through silica (dichloromethane/methanol 85:15), the residue is purified by flash chromatography (silica gel, dichloromethane/7N NH$_3$ in methanol 96:4 to 90:10) and then triturated with hot ethanol giving the title compound (24 mg) as a solid.

$^1$H-NMR (400 MHz, d$_6$-DMSO) δ=4.53 (d, 2H, CH$_2$), 7.35 (d, 2H, H$_{ar}$), 7.40 (m, 1H, H$_{ar}$), 7.52 (d, 1H, H$_{ar}$), 7.58 (d, 1H, H$_{ar}$), 7.78 (d, 1H, H$_{ar}$), 7.88 (d, 2H, H$_{ar}$), 8.43 (bs, 1H, H$_{pyrazole}$), 8.50 (m, 1H, H$_{ar}$), 8.59 (s, 1H, H$_{ar}$), 8.65 (s, 1H, H$_{ar}$), 8.78 (bs, 1H, H$_{pyrazole}$), 8.95 (t, 1H, NH), 9.01 (s, 1H, NH), 13.3 (bs, 1H, NH$_{pyrazole}$). LCMS 97.9%, R$_t$=1.85 min, m/z 411 (M+H, AP$^+$ formic acid).

Example 4

4-{8-[4-(4-Methyl-piperazin-1-yl)-phenylamino]-[1,2,4]triazolo[1,5-a]pyridin-5-yl}-1H-pyridin-2-one

4.1 [5-(2-Methoxy-pyridin-4-yl)-[1,2,4]-triazolo[1,5-a]pyridin-8-yl]-[4-(4-methyl-piperazin-1-yl)-phenyl]-amine

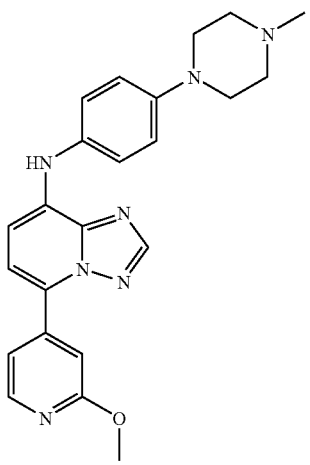

A suspension of 5-chloro-[1,2,4]triazolo[1,5-a]pyridin-8-yl)-[4-(4-methyl-piperazin-1-yl)-phenyl]-amine (50 mg, 146 µmol), 2-methoxypyridin-4-boronic acid (45 mg, 290 µmol), Pd(PPh$_3$)$_4$ (51 mg, 40 µmol) and NaO$^t$Bu (56 mg, 580 µmol) in 1.2 mL of DMF/water (5:1, degassed) is degassed for 1 min in a sealed tube. The tube is sealed and the reaction mixture heated at 110° C. for seven hours. The reaction is complete after 3 hours (HPLC). No change of composition of the reaction mixture is detected after seven hours. After evaporation of the solvents, the residue is purified by flash chromatography (silica gel, dichloromethane/7N NH$_3$ in methanol 100:0 to 96:4) affording the title compound (44 mg), which is isolated as a mixture containing 39% of product and 50% of de-chlorinated starting material (HPLC).

4.2 4-{8-[4-(4-Methyl-piperazin-1-yl)-phenylamino]-[1,2,4]triazolo[1,5-a]pyridin-5-yl}-1H-pyridin-2-one

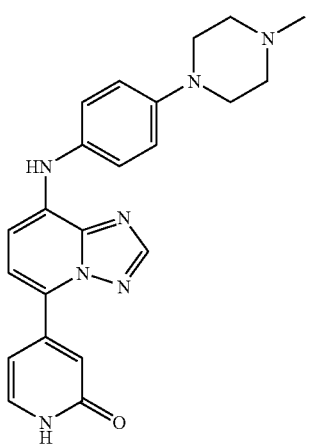

[5-(2-Methoxy-pyridin-4-yl)-[1,2,4]triazolo pyridin-8-yl]-[4-(4-methyl-piperazin-1-yl)-phenyl]-amine (44 mg, 41 µmol) is treated in a sealed tube with pyridine hydrochloride (153 mg, 1.32 mmol) and one drop of water at 150° C. for two hours. The reaction mixture is cooled and partitioned between 1 M Na$_2$CO$_3$ and ethyl acetate. The aqueous phase is extracted four times with ethyl acetate and the combined organic layers evaporated. The residue is purified by flash chromatography (silica gel, dichloromethane/7N NH$_3$ in methanol 96:4 to 90:10) affording the title compound (12 mg) as a solid.

$^1$H-NMR (400 MHz, d$_6$-DMSO) δ=2.27 (s, 3H, CH$_3$), 2.50 (m, 4H, 2×CH$_2$), 3.16 (m, 4H, 2×CH$_2$), 6.77 (d, 1H, H$_{ar}$), 6.94 (d, 1H, H$_{ar}$), 7.02 (d, 2H, H$_{ar}$), 7.22 (s, 1H, H$_{ar}$), 7.29 (d, 2H, H$_{ar}$), 7.44 (d, 1H, H$_{ar}$), 7.48 (d, 1H, H$_{ar}$), 8.59 (s, 1H, H$_{ar}$), 8.78 (bs, 1H, NH), 11.60 (bs, 1H, NH). LCMS 98.6%, R$_t$=1.74 min, m/z 402 (M+H, AP$^+$ formic acid).

Example 5

4-[5-(2-oxo-1,2-dihydro-pyridin-4-yl)-[1,2,4]triazolo[1,5-a]pyridin-8-ylamino]-N-pyridin-3-ylmethyl-benzamide

5.1 4-[5-(2-Methoxy-pyridin-4-yl)-[1,2,4]-triazolo[1,5-a]pyridin-8-ylamino]-N-pyridin-3-ylmethyl-benzamide

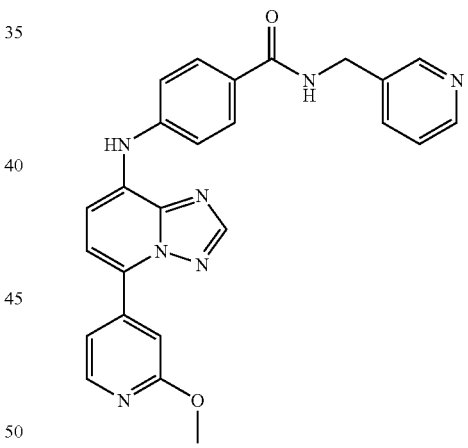

A suspension of 4-(5-chloro-[1,2,4]triazolo[1,5-a]pyridin-8-ylamino)-N-pyridin-3-ylmethyl-benzamide (50 mg, 132 µmol), 2-methoxypyridin-4-boronic acid (40 mg, 260 µmol), Pd(PPh$_3$)$_4$ (46 mg, 40 µmol) and NaO$^t$Bu (51 mg, 530 µmol) in 1.2 mL of DMF/water (5:1, degassed) is degassed for 1 min in a sealed tube. The tube is sealed and the reaction mixture heated at 110° C. for five hours. After evaporation of the solvents, the residue is purified by flash chromatography (silica gel, dichloromethane/7N NH$_3$ in methanol 97:3) affording the title compound (46 mg), which is isolated as a mixture containing 50% of product.

5.2 4-[5-(2-Oxo-1,2-dihydro-pyridin-4-yl)-[1,2,4]triazolo[1,5-a]pyridin-8-ylamino]-N-pyridin-3-ylmethyl-benzamide

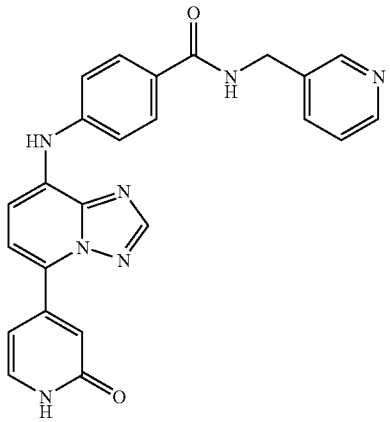

4-[5-(2-Methoxy-pyridin-4-yl)-[1,2,4]triazolo[1,5-a]pyridin-8-ylamino]-N-pyridin-3-ylmethyl-benzamide (46 mg, 51 µmol) is treated in a sealed tube with pyridine hydrochloride (153 mg, 1.32 mmol) and one drop of water at 150° C. for two hours. The reaction mixture is evaporated and the residue purified by flash chromatography (silica gel, dichloromethane/7N $NH_3$ in methanol 96:4 then 85:15) affording the title compound (14 mg) as a solid.

$^1$H-NMR (400 MHz, $d_6$-DMSO) δ=4.54 (d, 2H, $CH_2$), 6.78 (d, 1H, $H_{ar}$), 7.21 (s, 1H, $H_{ar}$), 7.40-7.53 (m, 6H, $H_{ar}$), 7.76 (d, 1H, $H_{ar}$), 7.78 (d, 1H, $H_{ar}$), 7.93 (d, 2H, $H_{ar}$), 8.50 (m, 1H, $H_{ar}$), 8.59 (s, 1H, $H_{ar}$), 8.63 (s, 1H, $H_{ar}$), 9.01 (t, 1H, NH), 9.34 (bs, 1H, NH), 11.70 (bs, 1H, NH). LCMS 99.1%, $R_t$=1.74 min, m/z 438 (M+H, AP$^+$ formic acid).

Example 6

2-Fluoro-4-{8-[4-(4-methyl-piperazin-1-yl)-phenylamino]-[1,2,4]triazolo[1,5-a]pyridin-5-yl}-benzamide

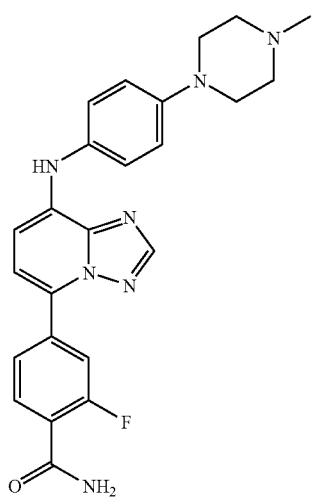

A suspension of (5-chloro-[1,2,4]triazolo[1,5-a]pyridin-8-yl)-[4-(4-methyl-piperazin-1-yl)-phenyl]-amine (50 mg, 146 µmol), 2-Fluoro-4-(4,4,5,5-tetramethyl-[1,3,2]dioxaborolan-2-yl)-benzamide (97 mg, 360 µmol), Pd(PPh$_3$)$_4$ (51 mg, 40 µmol) and NaO$^t$Bu (56 mg, 580 µmol) in 1.2 mL of DMF/water (5:1, degassed) is degassed for 1 min in a sealed tube. The tube is sealed and the reaction mixture heated at 110° C. for forty minutes in the microwave (CEM explorer) and then at the same temperature for thirty minutes in an oil bath. After evaporation of the solvents the residue is taken up in dichloromethane, filtered and evaporated. The crude product is purified by flash chromatography (silica gel, dichloromethane/7N $NH_3$ in methanol 97:3 to 90:10) and triturated (3× with ethyl acetate) affording the title compound (12 mg) as a solid.

$^1$H-NMR (400 MHz, $d_6$-DMSO) δ=2.26 (s, 3H, $CH_3$), 2.52 (m, 4H, 2×$CH_2$), 3.16 (m, 4H, 2×$CH_2$), 6.99 (m, 3H, $H_{ar}$), 7.30 (d, 2H, $H_{ar}$), 7.42 (d, 1H, $H_{ar}$), 7.76 (bs, 1H, NH), 7.82 (m, 2H, NH, $H_{ar}$), 7.93 (d, 1H, $H_{ar}$), 8.04 (d, 1H, $H_{ar}$), 8.58 (s, 1H, $H_{ar}$), 8.71 (bs, 1H, NH). LCMS 96.7%, $R_t$=1.97 min, m/z 446 (M+H, AP$^+$ formic acid).

Example 7

(4-Morpholin-4-yl-phenyl)-[5-(1H-pyrazol-4-yl)-[1,2,4]triazolo[1,5-a]pyridin-8-yl]-amine

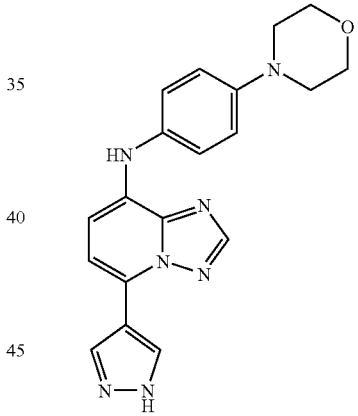

A suspension of (5-chloro-[1,2,4]triazolo[1,5-a]pyridin-8-yl)-(4-morpholin-4-yl-phenyl)-amine (60 mg, 182 µmol), 4-(4,4,5,5-tetramethyl-1,3,2-dioxaborolan-2-yl)-1H-pyrazole (71 mg, 365 µmol), Pd(PPh$_3$)$_4$ (53 mg, 46 µmol) and NaO$^t$Bu (70 mg, 739 µmol) in 3 mL of DMF/water (2:1, degassed) is degassed for 1 min in a sealed tube. The tube is sealed and the reaction mixture heated at 110° C. for 24 hours. After filtration and washing with dichloromethane the filtrate is evaporated. The solid residue is purified by chromatography (Biotage, silica gel, dichloromethane/7N $NH_3$ in methanol 100:0 to 95:5) and triturated with dichloromethane affording the title compound (28 mg) as a solid.

$^1$H-NMR (400 MHz, $d_6$-DMSO) δ=3.11 (m, 4H, 2×$CH_2$), 3.79 (m, 4H, 2×$CH_2$), 7.00 (d, 2H, $H_{ar}$), 7.07 (d, 1H, $H_{ar}$), 7.29 (d, 2H, $H_{ar}$), 7.44 (d, 1H, $H_{ar}$), 8.33 (bs, 1H, $H_{pyrazole}$), 8.37 (s, 1H, NH), 8.60 (s, 1H, $H_{ar}$), 8.69 (bs, 1H, $H_{pyrazole}$), 13.20 (bs, 1H, $NH_{pyrazole}$). LCMS 98.8%, $R_t$=2.37 min, m/z 362 (M+H, AP$^+$ formic acid).

The following Table 5 shows compounds made according to the methods described under General Scheme B.

TABLE 5

| Ex # | Structure | IUPAC name | MonoMW | $t_R$ (min) | Ion Found | Analytical Method/ Table ref # |
|---|---|---|---|---|---|---|
| 9 | 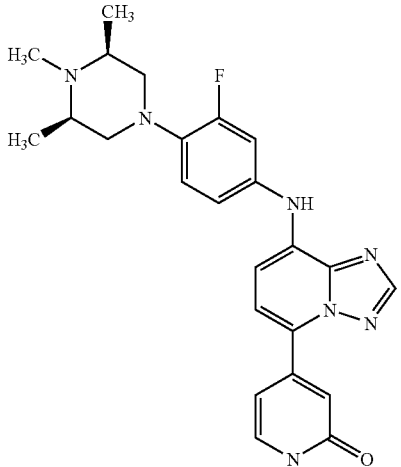 | 4-[8-({3-fluoro-4-[(3R,5S)-3,4,5-trimethylpiperazin-1-yl]phenyl}amino)[1,2,4]triazolo[1,5-a]pyridin-5-yl]pyridin-2(1H)-one | 447.2182 | 1.09 | 448 | 2 |
| 10 | 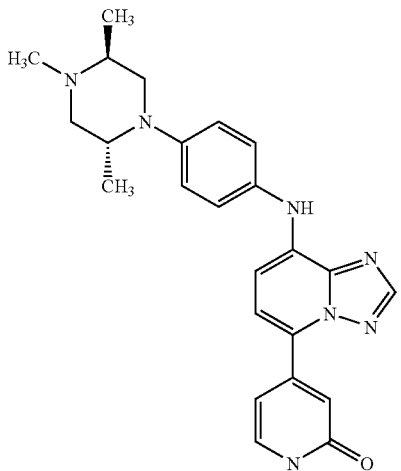 | rel-4-[8-({4-[(2R,5S)-2,4,5-trimethylpiperazin-1-yl]phenyl}amino)[1,2,4]triazolo[1,5-a]pyridin-5-yl]pyridin-2(1H)-one | 429.2277 | 1.05 | 430 | 2 |
| 11 | 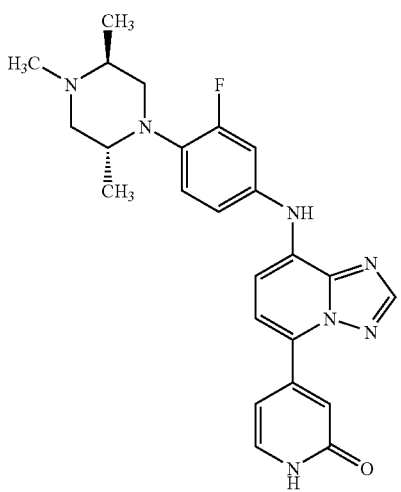 | rel-4-[8-({3-fluoro-4-[(2R,5S)-2,4,5-trimethylpiperazin-1-yl]phenyl}amino)[1,2,4]triazolo[1,5-a]pyridin-5-yl]pyridin-2(1H)-one | 447.2182 | 1.10 | 448 | 2 |

TABLE 5-continued

| Ex # | Structure | IUPAC name | MonoMW | $t_R$ (min) | Ion Found | Analytical Method/ Table ref # |
|---|---|---|---|---|---|---|
| 12 | 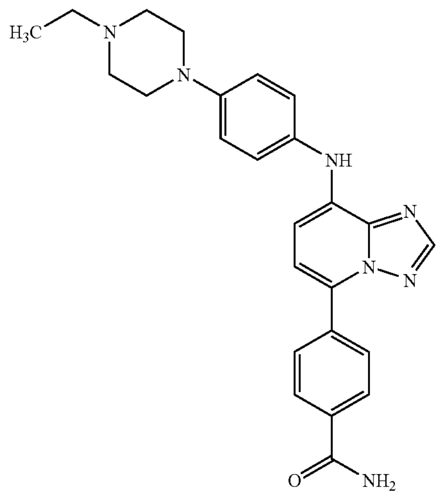 | 4-(8-{[4-(4-ethylpiperazin-1-yl)phenyl]amino}[1,2,4]triazolo[1,5-a]pyridin-5-yl)benzamide | 441.2277 | 1.66 | 442 | 4 |
| 13 | 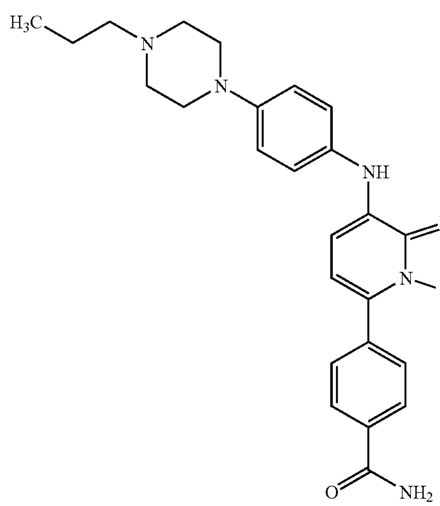 | 4-(8-{[4-(4-propylpiperazin-1-yl)phenyl]amino}[1,2,4]triazolo[1,5-a]pyridin-5-yl)benzamide | 455.2433 | 1.74 | 456 | 4 |
| 14 | 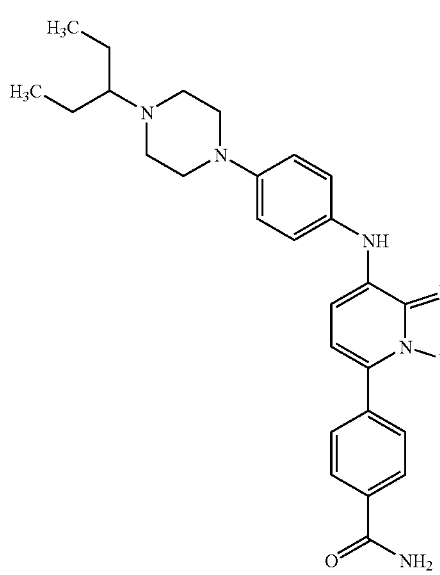 | 4-[8-({4-[4-(1-ethylpropyl)piperazin-1-yl]phenyl}amino)[1,2,4]triazolo[1,5-a]pyridin-5-yl]benzamide | 483.2746 | 1.89 | 484 | 4 |

TABLE 5-continued

| Ex # | Structure | IUPAC name | MonoMW | $t_R$ (min) | Ion Found | Analytical Method/ Table ref # |
|---|---|---|---|---|---|---|
| 15 | 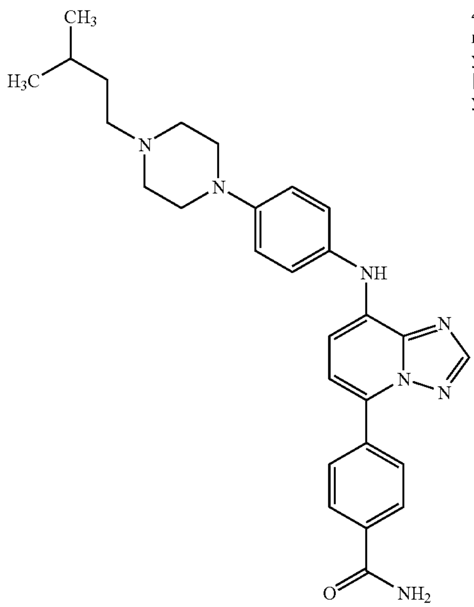 | 4-[8-({4-[4-(3-methylbutyl)piperazin-1-yl]phenyl}amino)[1,2,4]triazolo[1,5-a]pyridin-5-yl]benzamide | 483.2746 | 1.96 | 484 | 4 |
| 16 | 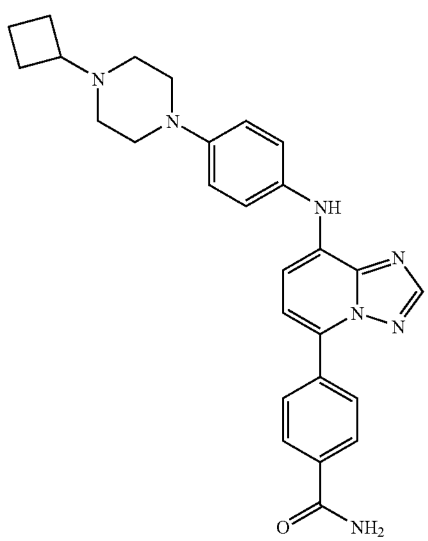 | 4-(8-{[4-(4-cyclobutylpiperazin-1-yl)phenyl]amino}[1,2,4]triazolo[1,5-a]pyridin-5-yl)benzamide | 467.2433 | 1.76 | 468 | 4 |

TABLE 5-continued

| Ex # | Structure | IUPAC name | MonoMW | $t_R$ (min) | Ion Found | Analytical Method/ Table ref # |
|---|---|---|---|---|---|---|
| 17 | 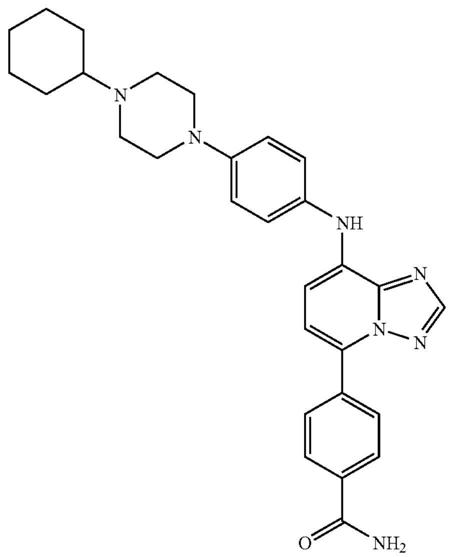 | 4-(8-{[4-(4-cyclohexylpiperazin-1-yl)phenyl]amino}[1,2,4]triazolo[1,5-a]pyridin-5-yl)benzamide | 495.2746 | 1.94 | 496 | 4 |
| 18 | 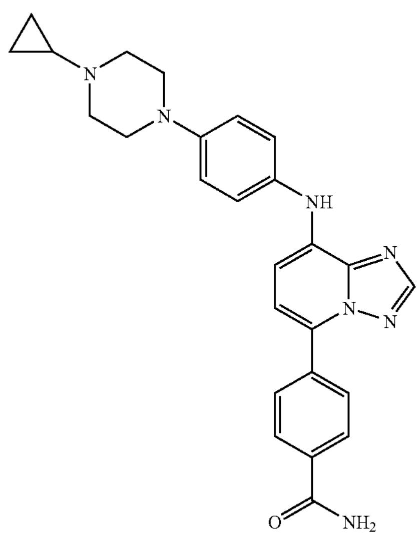 | 4-(8-{[4-(4-cyclopropylpiperazin-1-yl)phenyl]amino}[1,2,4]triazolo[1,5-a]pyridin-5-yl)benzamide | 453.2277 | 1.68 | 454 | 4 |
| 19 | 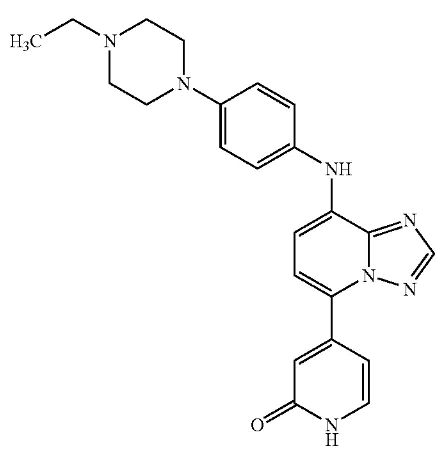 | 4-(8-{[4-(4-ethylpiperazin-1-yl)phenyl]amino}[1,2,4]triazolo[1,5-a]pyridin-5-yl)pyridin-2(1H)-one | 415.212 | 1.45 | 416 | 4 |

TABLE 5-continued
| Ex # | Structure | IUPAC name | MonoMW | $t_R$ (min) | Ion Found | Analytical Method/ Table ref # |
|---|---|---|---|---|---|---|
| 20 | 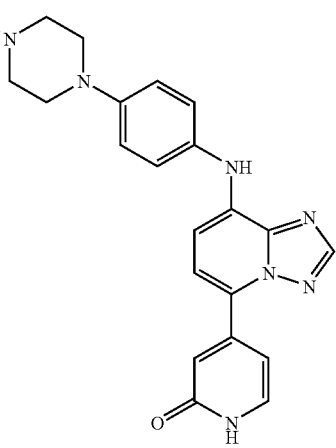 | 4-(8-{[4-(4-propylpiperazin-1-yl)phenyl]amino}[1,2,4]triazolo[1,5-a]pyridin-5-yl)pyridin-2(1H)one | 429.2277 | 1.52 | 430 | 4 |
| 21 | 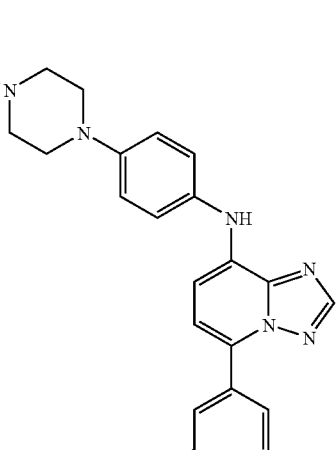 | 4-[8-({4-[4-(1-ethylpropyl)piperazin-1-yl]phenyl}amino)[1,2,4]triazolo[1,5-a]pyridin-5-yl]pyridin-2(1H)-one | 457.259 | 1.67 | 458 | 4 |
| 22 | 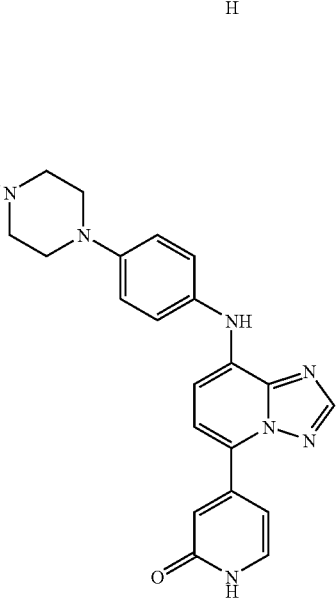 | 4-[8-({4-[4-(3-methylbutyl)piperazin-1-yl]phenyl}amino)[1,2,4]triazolo[1,5-a]pyridin-5-yl]pyridin-2(1H)-one | 457.259 | 1.75 | 458 | 4 |

TABLE 5-continued

| Ex # | Structure | IUPAC name | MonoMW | $t_R$ (min) | Ion Found | Analytical Method/ Table ref # |
|---|---|---|---|---|---|---|
| 23 | 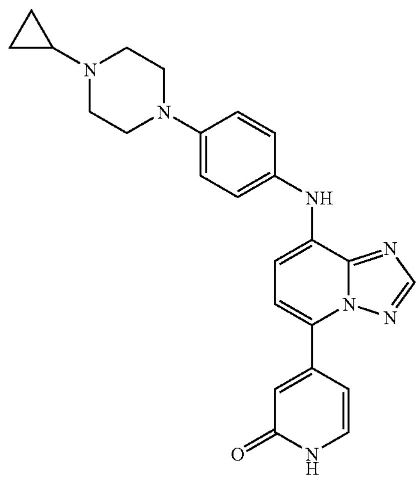 | 4-(8-{[4-(4-cyclopropylpiperazin-1-yl)phenyl]amino}[1,2,4]triazolo[1,5-a]pyridin-5-yl)pyridin-2(1H)-one | 427.212 | 1.50 | 428 | 4 |
| 24 | 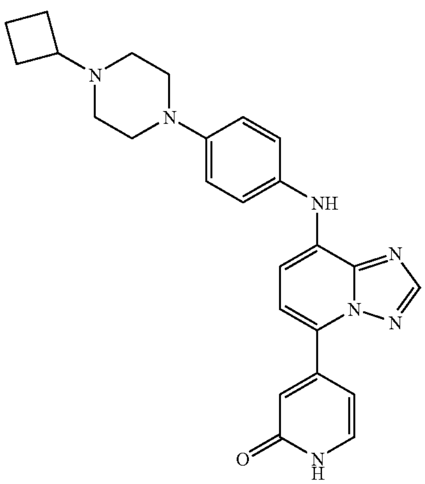 | 4-(8-{[4-(4-cyclobutylpiperazin-1-yl)phenyl]amino}[1,2,4]triazolo[1,5-a]pyridin-5-yl)pyridin-2(1H)-one | 441.2277 | 1.55 | 442 | 4 |
| 25 | 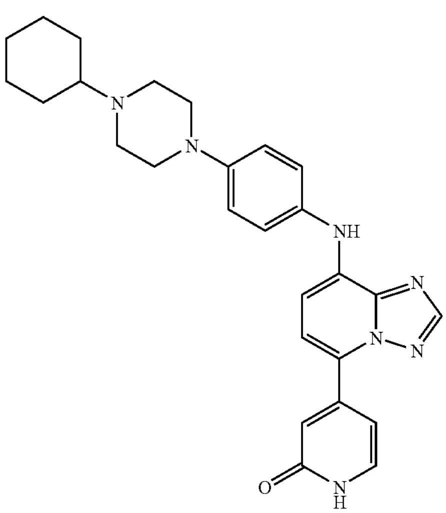 | 4-(8-{[4-(4-cyclohexylpiperazin-1-yl)phenyl]amino}[1,2,4]triazolo[1,5-a]pyridin-5-yl)pyridin-2(1H)-one | 469.259 | 1.73 | 470 | 4 |

TABLE 5-continued

| Ex # | Structure | IUPAC name | MonoMW | $t_R$ (min) | Ion Found | Analytical Method/ Table ref # |
|---|---|---|---|---|---|---|
| 26 | 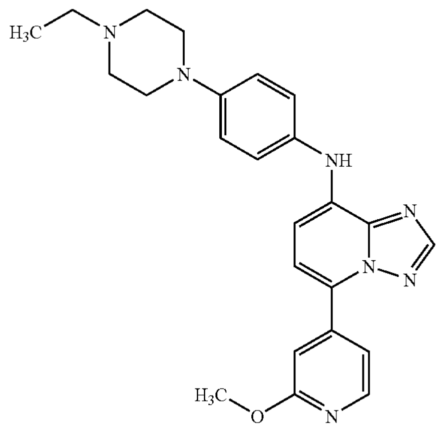 | N-[4-(4-ethylpiperazin-1-yl)phenyl]-5-(2-methoxypyridin-4-yl)[1,2,4]triazolo[1,5-a]pyridin-8-amine | 429.2277 | 1.94 | 430 | 4 |
| 27 | 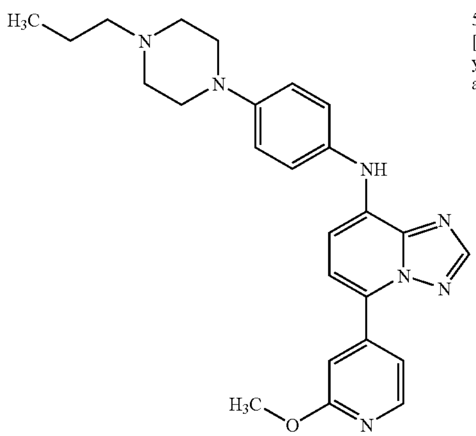 | 5-(2-methoxypyridin-4-yl)-N-[4-(4-propylpiperazin-1-yl)phenyl][1,2,4]triazolo[1,5-a]pyridin-8-amine | 443.2433 | 2.02 | 444 | 4 |
| 28 | 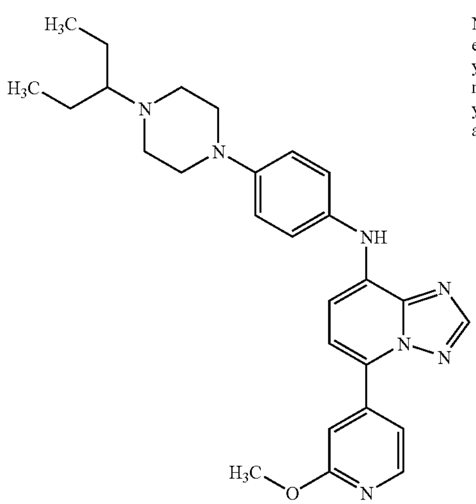 | N-{4-[4-(1-ethylpropyl)piperazin-1-yl]phenyl}-5-(2-methoxypyridin-4-yl)[1,2,4]triazolo[1,5-a]pyridin-8-amine | 471.2746 | 2.15 | 472 | 4 |

TABLE 5-continued

| Ex # | Structure | IUPAC name | MonoMW | $t_R$ (min) | Ion Found | Analytical Method/ Table ref # |
|---|---|---|---|---|---|---|
| 29 | 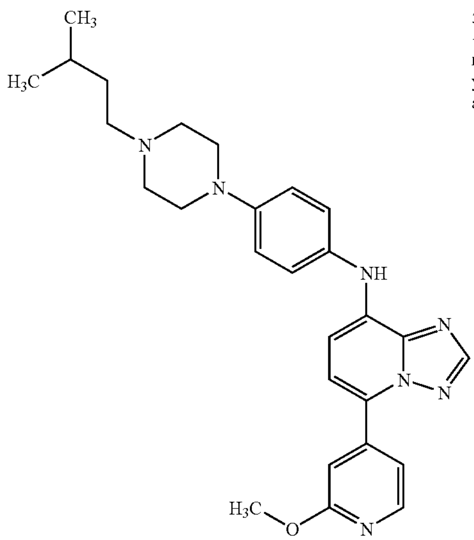 | 5-(2-methoxypyridin-4-yl)-N-{4-[4-(3-methylbutyl)piperazin-1-yl]phenyl}[1,2,4]triazolo[1,5-a]pyridin-8-amine | 471.2746 | 2.23 | 472 | 4 |
| 30 | 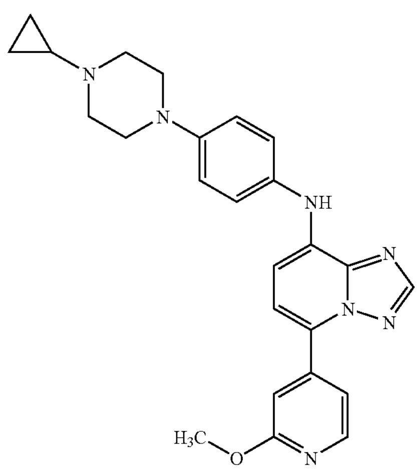 | N-[4-(4-cyclopropylpiperazin-1-yl)phenyl]-5-(2-methoxypyridin-4-yl)[1,2,4]triazolo[1,5-a]pyridin-8-amine | 441.2277 | 2.00 | 442 | 4 |
| 31 | 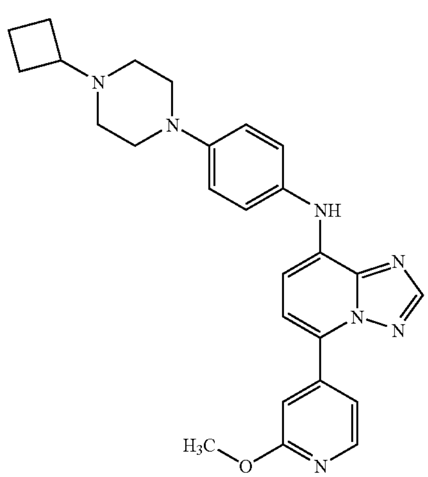 | N-[4-(4-cyclobutylpiperazin-1-yl)phenyl]-5-(2-methoxypyridin-4-yl)[1,2,4]triazolo[1,5-a]pyridin-8-amine | 455.2433 | 2.04 | 456 | 4 |

TABLE 5-continued

| Ex # | Structure | IUPAC name | MonoMW | $t_R$ (min) | Ion Found | Analytical Method/ Table ref # |
|---|---|---|---|---|---|---|
| 32 | 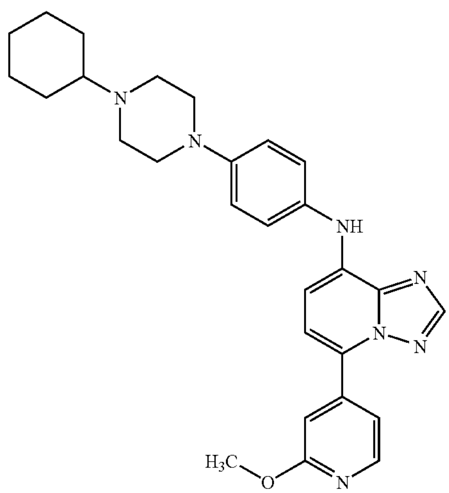 | N-[4-(4-cyclohexylpiperazin-1-yl)phenyl]-5-(2-methoxypyridin-4-yl)[1,2,4]triazolo[1,5-a]pyridin-8-amine | 483.2746 | 2.20 | 484 | 4 |
| 33 | 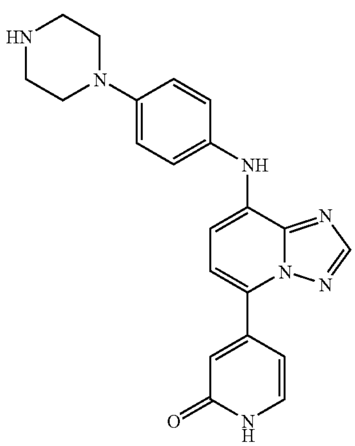 | 4-{8-[(4-piperazin-1-ylphenyl)amino][1,2,4]triazolo[1,5-a]pyridin-5-yl}pyridin-2(1H)-one | 387.1807 | 1.40 | 388 | 4 |
| 34 | 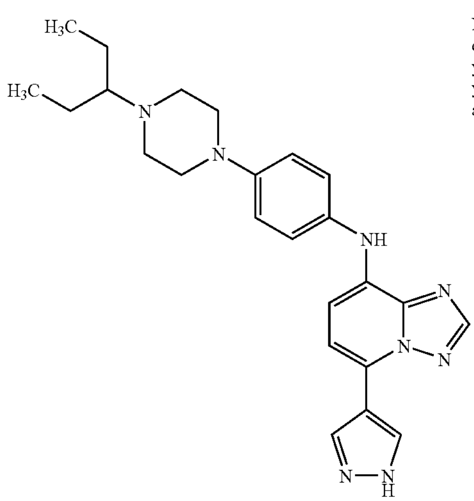 | N-{4-[4-(1-ethylpropyl)piperazin-1-yl]phenyl}-5-(1H-pyrazol-4-yl)[1,2,4]triazolo[1,5-a]pyridin-8-amine | 430.2593 | 1.82 | 431 | 4 |

TABLE 5-continued

| Ex # | Structure | IUPAC name | MonoMW | $t_R$ (min) | Ion Found | Analytical Method/ Table ref # |
|---|---|---|---|---|---|---|
| 35 | 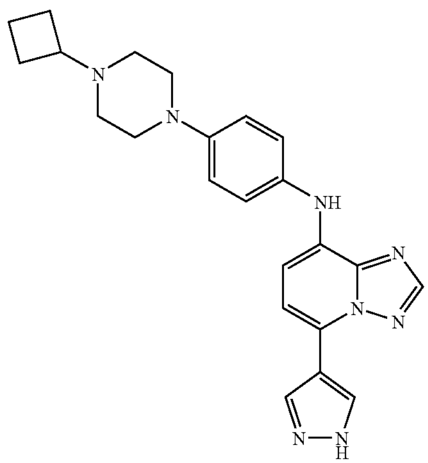 | N-[4-(4-cyclobutylpiperazin-1-yl)phenyl]-5-(1H-pyrazol-4-yl)[1,2,4]triazolo[1,5-a]pyridin-8-amine | 414.228 | 1.69 | 415 | 4 |
| 36 | 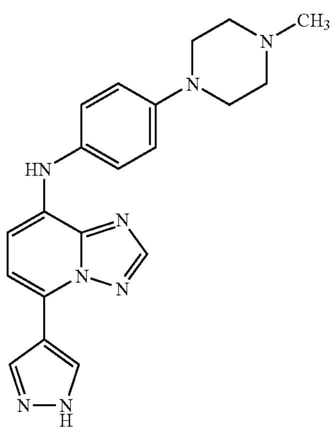 | N-[4-(4-methylpiperazin-1-yl)phenyl]-5-(1H-pyrazol-4-yl)[1,2,4]triazolo[1,5-a]pyridin-8-amine | 374.1967 | 1.82 | 375 | 3 |
| 37 | 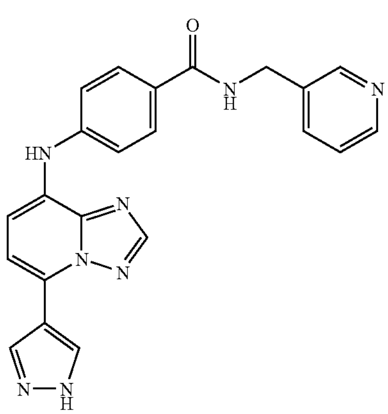 | 4-{[5-(1H-pyrazol-4-yl)[1,2,4]triazolo[1,5-a]pyridin-8-yl]amino}-N-(pyridin-3-ylmethyl)benzamide | 410.1603 | 1.88 | 411 | 3 |

TABLE 5-continued

| Ex # | Structure | IUPAC name | MonoMW | $t_R$ (min) | Ion Found | Analytical Method/ Table ref # |
|---|---|---|---|---|---|---|
| 38 | 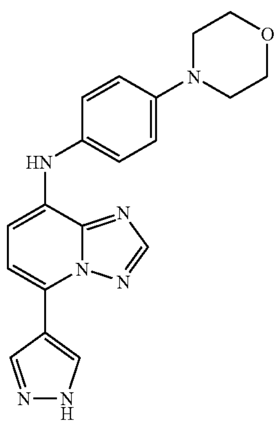 | N-(4-morpholin-4-ylphenyl)-5-(1H-pyrazol-4-yl)[1,2,4]triazolo[1,5-a]pyridin-8-amine | 361.1651 | 2.52 | 362 | 3 |
| 39 | 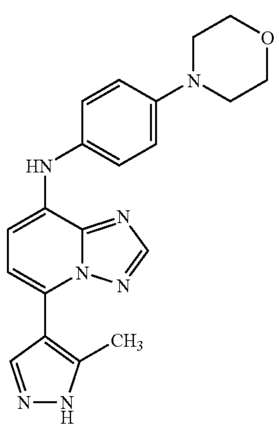 | 5-(5-methyl-1H-pyrazol-4-yl)-N-(4-morpholin-4-ylphenyl)[1,2,4]triazolo[1,5-a]pyridin-8-amine | 375.1807 | 2.51 | 376 | 3 |
| 40 | 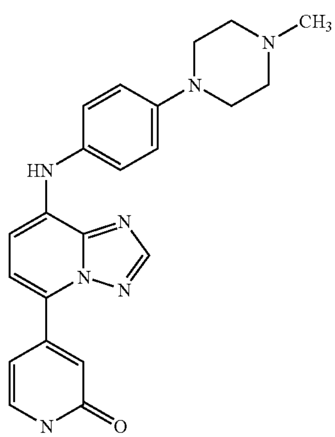 | 4-(8-{[4-(4-methylpiperazin-1-yl)phenyl]amino}[1,2,4]triazolo[1,5-a]pyridin-5-yl)pyridin-2(1H)-one | 401.1964 | 1.72 | 402 | 3 |

TABLE 5-continued

| Ex # | Structure | IUPAC name | MonoMW | $t_R$ (min) | Ion Found | Analytical Method/ Table ref # |
|---|---|---|---|---|---|---|
| 41 | 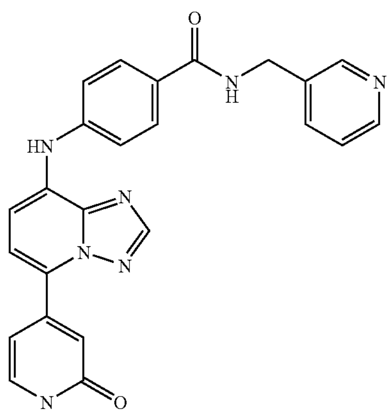 | 4-{[5-(2-oxo-1,2-dihydropyridin-4-yl)[1,2,4]triazolo[1,5-a]pyridin-8-yl]amino}-N-(pyridin-3-ylmethyl)benzamide | 437.16 | 1.78 | 438 | 3 |
| 42 | 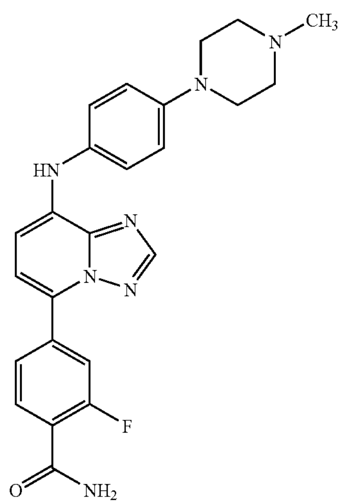 | 2-fluoro-4-(8-{[4-(4-methylpiperazin-1-yl)phenyl]amino}[1,2,4]triazolo[1,5-a]pyridin-5-yl)benzamide | 445.2026 | 1.94 | 446 | 3 |
| 43 | 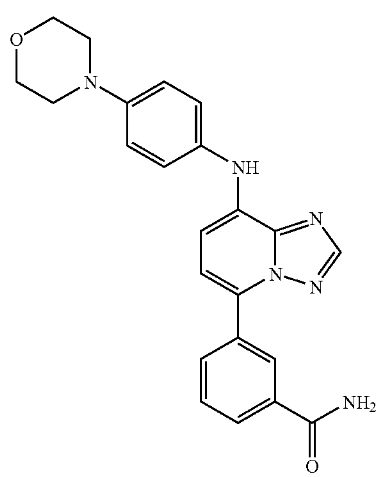 | 3-{8-[(4-morpholin-4-ylphenyl)amino][1,2,4]triazolo[1,5-a]pyridin-5-yl}benzamide | 414.1804 | 1.87 | 415 | 2 |

TABLE 5-continued
| Ex # | Structure | IUPAC name | MonoMW | $t_R$ (min) | Ion Found | Analytical Method/ Table ref # |
|---|---|---|---|---|---|---|
| 44 | 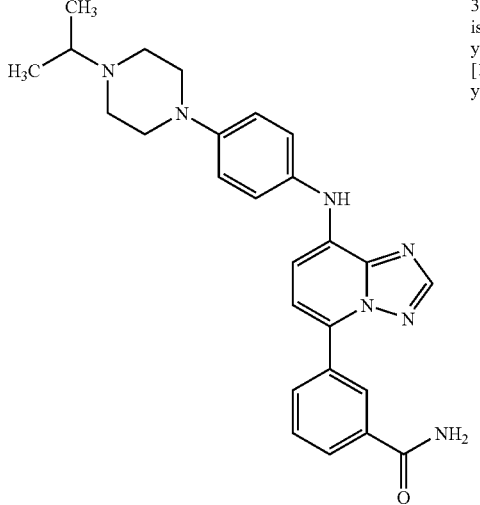 | 3-(8-{[4-(4-isopropylpiperazin-1-yl)phenyl]amino}[1,2,4]triazolo[1,5-a]pyridin-5-yl)benzamide | 455.2433 | 1.21 | 456 | 2 |
| 45 | 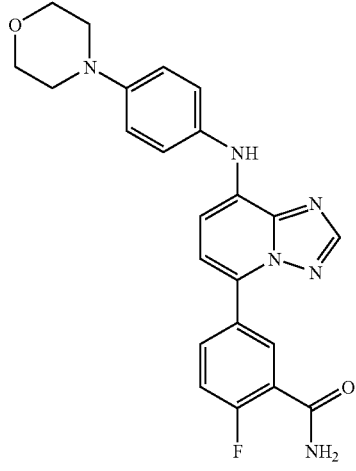 | 2-fluoro-5-{8-[(4-morpholin-4-ylphenyl)amino][1,2,4]triazolo[1,5-a]pyridin-5-yl}benzamide | 432.171 | 1.97 | 433 | 2 |
| 46 | 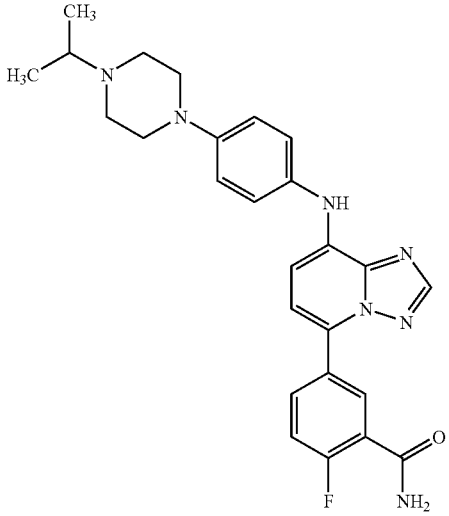 | 2-fluoro-5-(8-{[4-(4-isopropylpiperazin-1-yl)phenyl]amino}[1,2,4]triazolo[1,5-a]pyridin-5-yl)benzamide | 473.2339 | 1.27 | 474 | 2 |

TABLE 5-continued

| Ex # | Structure | IUPAC name | MonoMW | $t_R$ (min) | Ion Found | Analytical Method/ Table ref # |
|---|---|---|---|---|---|---|
| 47 | 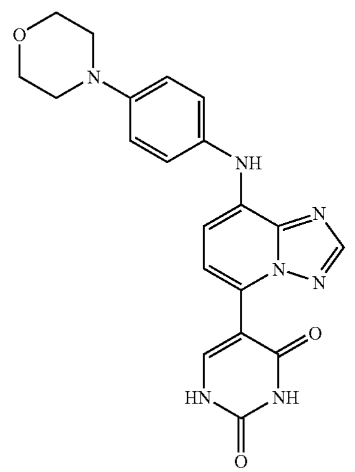 | 5-{8-[(4-morpholin-4-ylphenyl)amino][1,2,4]triazolo[1,5-a]pyridin-5-yl}pyrimidine-2,4(1H,3H)-dione | 405.1549 | 1.27 | 406 | 2 |
| 48 | 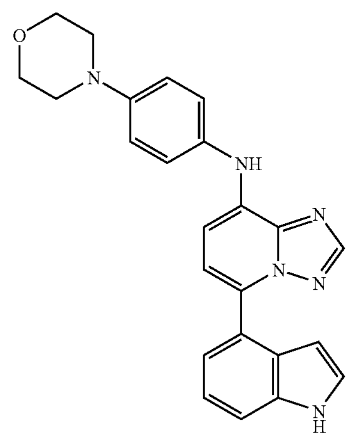 | 5-(1H-indol-4-yl)-N-(4-morpholin-4-ylphenyl)[1,2,4]triazolo[1,5-a]pyridin-8-amine | 410.1855 | 2.45 | 411 | 2 |
| 49 | 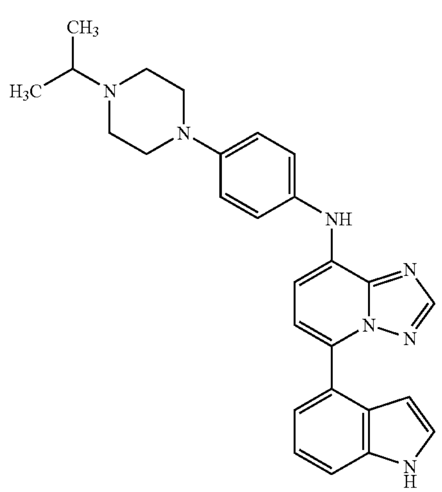 | 5-(1H-indol-4-yl)-N-[4-(4-isopropylpiperazin-1-yl)phenyl][1,2,4]triazolo[1,5-a]pyridin-8-amine | 451.2484 | 1.45 | 452 | 2 |

TABLE 5-continued

| Ex # | Structure | IUPAC name | MonoMW | $t_R$ (min) | Ion Found | Analytical Method/ Table ref # |
|---|---|---|---|---|---|---|
| 50 | 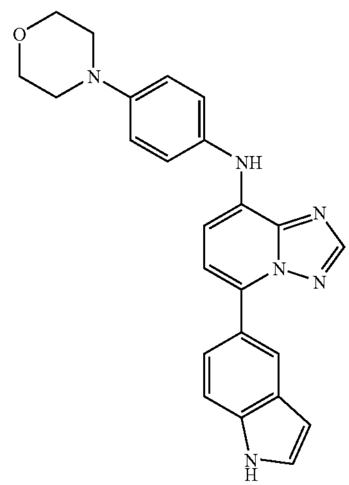 | 5-(1H-indol-5-yl)-N-(4-morpholin-4-ylphenyl)[1,2,4]triazolo[1,5-a]pyridin-8-amine | 410.1855 | 2.54 | 411 | 2 |
| 51 | 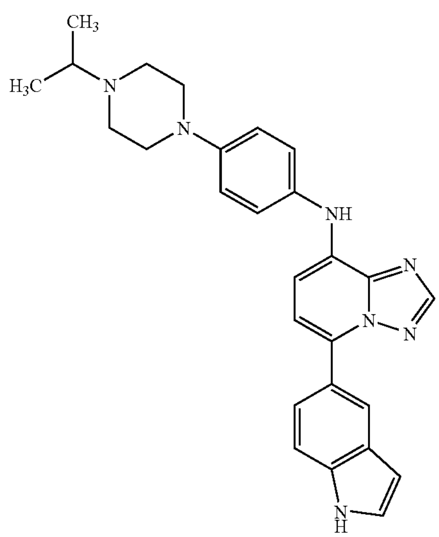 | 5-(1H-indol-5-yl)-N-[4-(4-isopropylpiperazin-1-yl)phenyl][1,2,4]triazolo[1,5-a]pyridin-8-amine | 451.2484 | 1.50 | 452 | 2 |
| 52 | 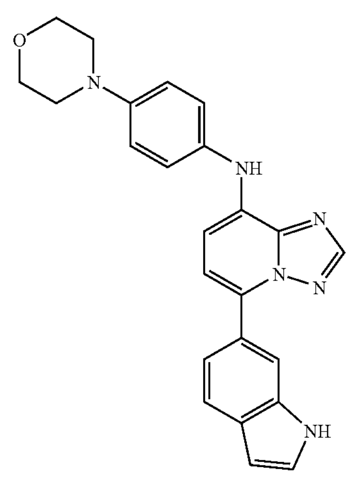 | 5-(1H-indol-6-yl)-N-(4-morpholin-4-ylphenyl)[1,2,4]triazolo[1,5-a]pyridin-8-amine | 410.1855 | 2.65 | 411 | 2 |

| Ex # | Structure | IUPAC name | MonoMW | $t_R$ (min) | Ion Found | Analytical Method/ Table ref # |
|---|---|---|---|---|---|---|
| 53 | 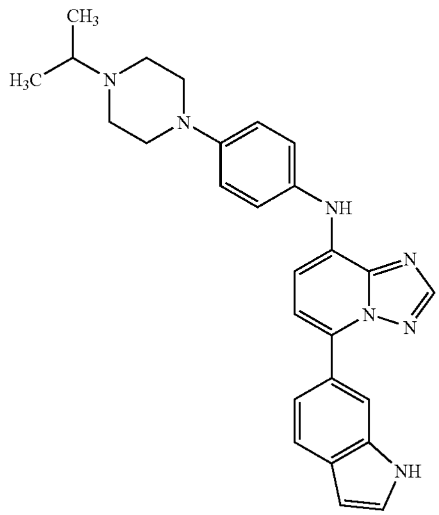 | 5-(1H-indol-6-yl)-N-[4-(4-isopropylpiperazin-1-yl)phenyl][1,2,4]triazolo[1,5-a]pyridin-8-amine | 451.2484 | 1.58 | 452 | 2 |
| 54 | 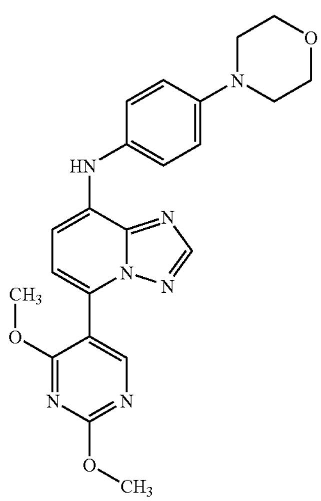 | 5-(2,4-dimethoxypyrimidin-5-yl)-N-(4-morpholin-4-ylphenyl)[1,2,4]triazolo[1,5-a]pyridin-8-amine | 433.1862 | 2.23 | 434 | 2 |
| 55 | 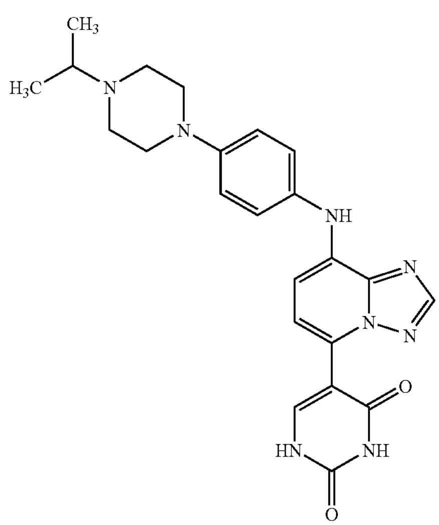 | 5-(8-{[4-(4-isopropylpiperazin-1-yl)phenyl]amino}[1,2,4]triazolo[1,5-a]pyridin-5-yl)pyrimidine-2,4(1H,3H)-dione | 446.2178 | 1.63 | 447 | 1 |

TABLE 5-continued

| Ex # | Structure | IUPAC name | MonoMW | $t_R$ (min) | Ion Found | Analytical Method/ Table ref # |
|---|---|---|---|---|---|---|
| 56 | 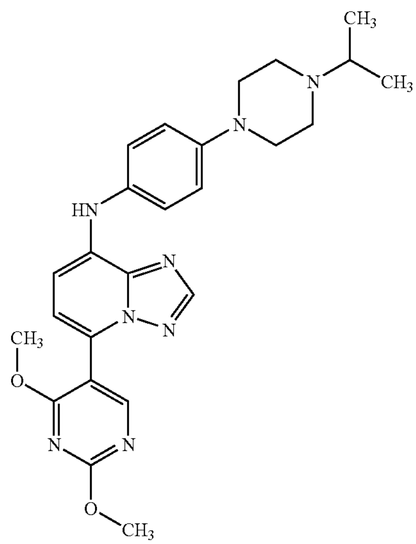 | 5-(2,4-dimethoxypyrimidin-5-yl)-N-[4-(4-isopropylpiperazin-1-yl)phenyl][1,2,4]triazolo[1,5-a]pyridin-8-amine | 474.2491 | 2.69 | 475 | 1 |
| 57 | 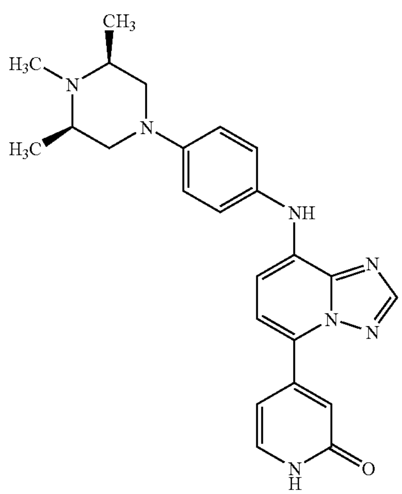 | 4-[8-({4-[(3R,5S)-3,4,5-trimethylpiperazin-1-yl]phenyl}amino)[1,2,4]triazolo[1,5-a]pyridin-5-yl]pyridin-2(1H)-one | 429.2277 | 1.89 | 430 | 1 |
| 58 | 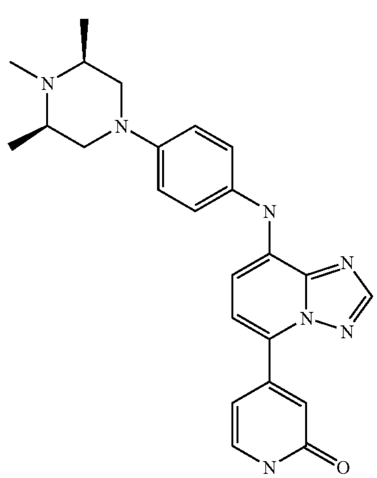 | 4-[8-({4-[cis-3,4,5-trimethylpiperazin-1-yl]phenyl}amino)[1,2,4]triazolo[1,5-a]pyridin-5-yl]pyridin-2(1H)-one | 429 | 1.89 | 430 | 1 |

TABLE 5-continued

| Ex # | Structure | IUPAC name | MonoMW | $t_R$ (min) | Ion Found | Analytical Method/ Table ref # |
|---|---|---|---|---|---|---|
| 59 | 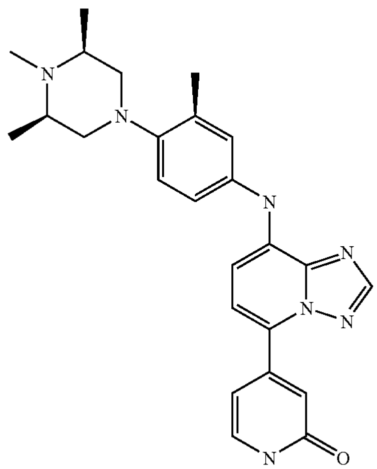 | 4-[8-({3-fluoro-4-[cis-3,4,5-trimethylpiperazin-1-yl]phenyl}amino)[1,2,4]triazolo[1,5-a]pyridin-5-yl]pyridin-2(1H)-one | 447 | 1.09 | 448 | 2 |
| 60 | 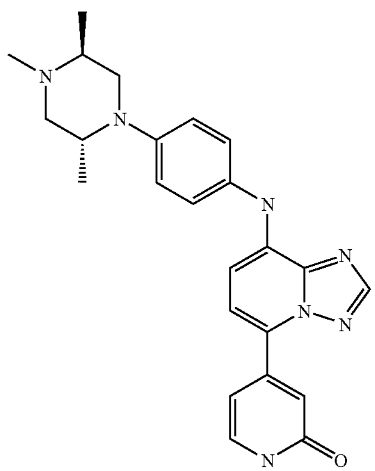 | racemic-4-[8-({4-[trans-2,4,5-trimethylpiperazin-1-yl]phenyl}amino)[1,2,4]triazolo[1,5-a]pyridin-5-yl]pyridin-2(1H)-one | 429 | 1.05 | 430 | 2 |
| 61 | 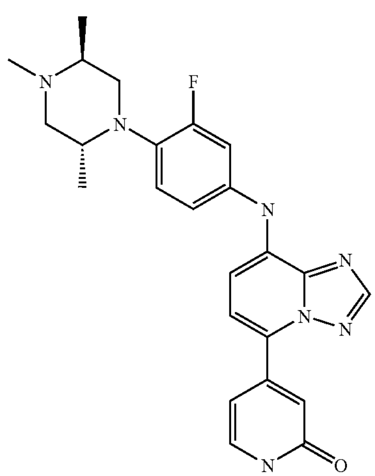 | racemic-4-[8-({3-fluoro-4-[trans-2,4,5-trimethylpiperazin-1-yl]phenyl}amino)[1,2,4]triazolo[1,5-a]pyridin-5-yl]pyridin-2(1H)-one | 447 | 1.10 | 448 | 2 |

Biological Activity Assays

To identify compounds that decrease the ECM-degrading activity of cells, the ECM-degrading activity of cells may be induced to allow proper detection of this activity, and to achieve a clearer read-out. In the context of RA, the cells of choice are mammalian synovial fibroblasts and the triggers that may be used to induce the ECM-degrading activity are cytokines or combination of cytokines relevant in the field of arthritis: for instance TNF-α, IL1β, IL6, OSM, IL17, and MIF1-α. This list is not comprehensive due to the plethora of cytokines potentially involved in the RA pathogenesis (Smolen and Steiner, 2003). To set up an in vitro assay that is as close as possible to the complexity of the pathology, the trigger applied should be a mixture of factors generated by contacting cytokine-producing cells relevant in the field of arthritis, such as monocytes, macrophages, T-cells, and B-cells, with a trigger. The cytokine-producing cells will respond to the contact by producing a complex and unbiased mixture of factors. If the cytokine-producing cell used is also found in a pannus, and the cytokine applied to produce this trigger is found in the synovial fluid of rheumatoid arthritis patients, the mixture of factors ultimately produced will contain part of the factors that are present in the joints of arthritis patients.

Principle of the 'MMP Assay'

Matrix Metallo Proteases (MMPs) possess various physiological roles, as e.g. the maturation of other proteases, growth factors, and the degradation of extra-cellular matrix components. MMP1 is one of the members of the MMP family that is able to degrade native collagen, the main component of bone and cartilage. An increased expression of MMP1 by synovial fibroblasts (SFs) is diagnostic for the progression of the arthritic disease and is predictive for erosive processes in the joint (Cunnane et al., 2001). The expression of MMP1 by SFs can be increased by the activation of SFs with triggers relevant for rheumatoid arthritis, as cytokines like TNF-α or IL1β (Andreakos et al., 2003). Taken together, measurement of the levels of MMP1 produced by activated SFs is a readout that is highly relevant in the context of RA as this event reflects the level of activation of SFs towards an erosive phenotype as it is seen in the pannus. Compounds that are able to reduce MMP1 expression in activated SFs are thus potential drug candidates for the treatment of RA. Compounds can reduce MMP1 expression because they are inhibiting targets involved in pathways resulting in increased MMP1 expression. One class of targets are kinases. Kinases that are inhibited with reasonable potency by compounds that inhibit MMP1 expression in activated SFs and that can be proven to be involved in MMP1 regulation are likely to be the drug target for the compounds and considered a relevant RA drug target. Proof that a kinase is involved in MMP1 regulation can come from experiments that show that reduced expression and/or activity of a candidate drug target in activated SFs leads to reduction in MMP1 expression by these cells. Several state of the art methods can be used like but not limited to use of siRNA or dominant negatives. In the following examples, the development of an assay, further referred to as 'MMP assay', monitors the MMP1 production by synovial fibroblasts (SFs) in response to diverse activating triggers (Example 2.1). The use of this assay is then described for the testing of compounds and exemplifying that the triazolopyridine compounds of the present invention are inhibiting MMP1 expression from activated SFs. In a further aspect, we show that the triazolopyridine compounds of the present invention possess TAK1 inhibiting activity. See Table 6.

2.1 Development of the MMP Assay

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 µg/mL anti-MMP1 antibody MAB1346 (Chemicon). The antibody is diluted in buffer 40 (1.21 g Tris base (Sigma), 0.58 g NaCl (Calbiochem) and 5 mL 10% $NaN_3$ (Sigma) in 1 L milliQ water and adjusted to pH 8.5). After overnight incubation at 4° C., plates are washed with PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well Casein buffer (2% Casein (VWR International) in PBS). Next day, casein buffer is removed from ELISA plates and replaced by 50 µL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 mL 0.5 M EDTA pH 8 (Invitrogen), 5 mL 10% $NaN_3$ in 1 L milliQ and adjusted to pH 7.0). 0.25 mM DTT (Sigma) is added to the thawed sample plates. After removal of the EC buffer, 20 µL of sample is transferred to the ELISA plates. After overnight incubation at 4° C. plates are washed twice with PBS and once with PBST (PBS with 0.05% Tween-20 (Sigma)) and incubated with 35 µL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0.5M EDTA pH 8 in 2 L milliQ and adjusted to pH 7.0) at a concentration of 5 µg/mL. After 2 h of incubation at RT, plates are washed as described above and incubated with 50 µL/well streptavidin-HRP conjugate (Biosource). Streptavidin-HRP conjugate is diluted in buffer C at a concentration of 0.25 µg/mL. After 45 min, plates are washed as described above and incubated for 5 min with 50 µL/well BM Chem ELISA Substrate (Roche). Readout is performed on the Luminoscan Ascent Luminometer (Labsystems) with an integration time of 200 msec or with an Envision reader (Perkin Elmer).

Figure 2:
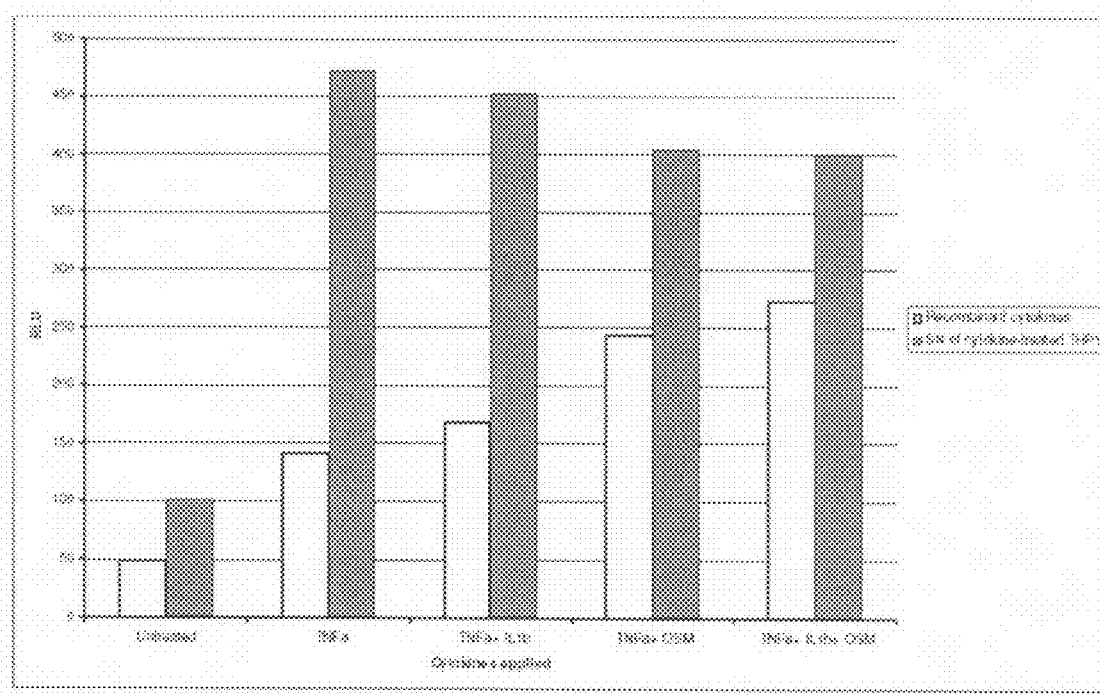
FIG. 2. This chart shows the increased expression of MMP1 in synovial fibroblasts triggered with cytokines involved in rheumatoid arthritis pathology.

The increase of MMP1 expression by SFs upon treatment with cytokines relevant in the field of RA (TNF-α, IL1β and OSM) or a combination thereof is shown in FIG. 2 as white bars. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/mL. 72 h after cytokine addition, the supernatant is collected and processed in the MMP1 ELISA as described in the protocol given above. In parallel with this experiment, SFs are triggered, using the same protocol, with the supernatant of THP1 cells (2-fold diluted in M199+1% FBS) treated with the same cytokines or combinations of cytokines for 48 h in M199 medium+1% FBS. MMP1 levels for these samples are shown in FIG. 2 as grey bars. The induction of the MMP1 expression by SFs triggered with the supernatants of TNF-α-treated THP1 cells is stronger (>4.5 fold induction) as compared to the SFs triggered with recombinant TNF-α alone (3-fold induction) and almost equals the 5-fold induction obtained by a mixture of 3 purified cytokines (TNF-α, IL1βb, OSM). This result indicates that the supernatant of TNF-a-induced THP1 cells contains, besides TNF-α, additional pro-inflammatory factors that activate SFs towards MMP1 expression. As the role of TNF-α in the RA pathogenesis is validated (TNF-α-blockers as Infliximab and Ethanercept show some efficacy in the treatment of RA patients) and the THP-1 cells are representative for monocytes/macrophages present in the joint of RA patients, the TNF-α-based trigger mixture prepared by contacting THP-1 cells with TNF-α will contain factors present in the joints of RA patients and subsequently is relevant to RA. This TNF-α-based complex trigger, further referred to as the 'complex trigger', will further be used as basis for the 'MMP assay'. For preparing a stock of this 'complex trigger', THP-1 cells are used between passage 8 and 16. THP-1 cells are routinely grown in suspension cultures in RPMI supplemented with 10% heat-inactivated FBS (Invitrogen). The cultures are diluted twice a week to a cell density of 2E5 cells/mL, avoiding cell density to exceed 1.5E5 cells/mL. For production of the complex trigger mixture, THP1 cells are seeded in M199 medium supplemented with 1% heat-inactivated FBS at a density of 1E6 cells/ml. Recombinant human TNF-α (Pepro-Tech) is added to final concentration of 50 ng/mL and cells are incubated at 37° C., 5% CO2. After 72 hr, the supernatant was collected by centrifugation, filtered through a 0.22 um Nalgene filter and stored at −80° C. in aliquots till further use. Every new batch of "complex trigger" was characterized for its efficacy at inducing MMP1 expression by SFs.

Figure 3:
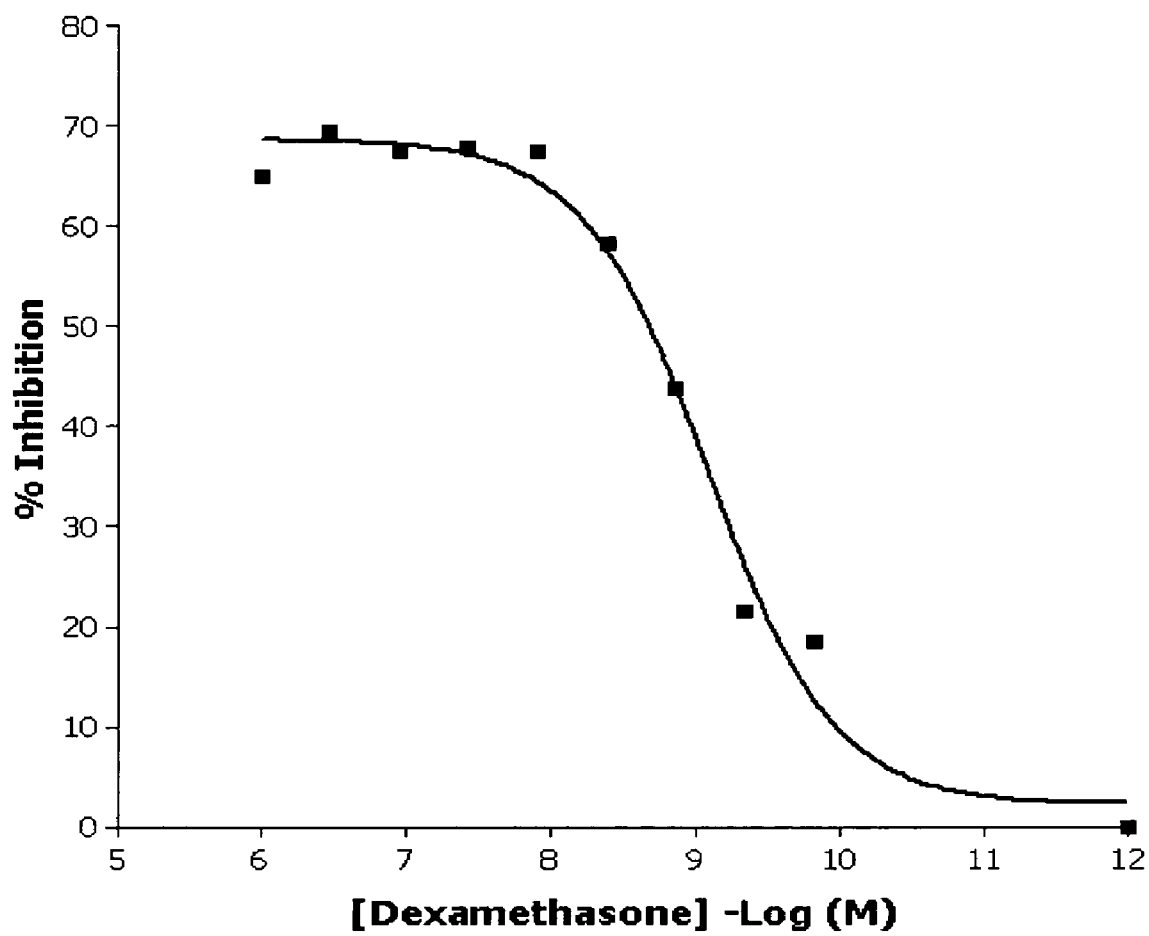
FIG. 3. This graph shows the dose-dependent inhibition of the "TNF-α-based trigger"-induced expression of MMP1 by SFs by a known anti-inflammatory compound.

Inhibition of the activation of SF by the 'complex trigger' is shown using dexamethasone, a potent anti-inflammatory agent that also strongly reduces collagen-induced arthritis in rodents (Yang et al., 2004) (FIG. 3). Dexamethasone is shown to dose-dependently reduce amounts of MMP1 produced by complex trigger activated SFs. SFs are seeded at a density of 3000 cells/well in 96 well plates. 24 hrs after seeding, increasing concentrations of dexamethasone are added to the cells. After overnight incubation, medium of every well is refreshed to supernatant of THP-1 cells treated with TNF-a (50% diluted in M199+0.5% FBS), and the same concentration of dexamethasone as added the day before. 48 hrs after treatment, the supernatant is collected and subjected to the MMP1 ELISA described above. The addition of dexamethasone clearly reduced the MMP1 expression by SFs, with an $IC_{50}$ value of about 1 nM (see FIG. 3). These data show that the MMP1 expression by activated SFs can be reduced by the addition of a physiologically relevant inhibitor and represent a proof of principle for the 'MMP assay'.

2.2 Compounds of the Present Invention Inhibit MMP1 Expression from Activated SFs SFs were acquired at passage 1 from a commercial supplier (Cell applications, Inc.). SFs are cultured in DMEM supplemented with 10% heat-inactivated FBS, 1× penicillin/streptomycin (Invitrogen) at 37° C., 10% $CO_2$ until passage 6. Aliquots of the cells are frozen and cryopreserved in liquid nitrogen. Starting from a cryopreserved aliquot, cells are further expanded by sub-culturing cells at 1/3 ratio every week. Cells between passage 10 and 12 are routinely used in compound testing according to following protocol.

Starting from the compound master stocks (all at 10 mM concentration in 100% DMSO) a 3-fold serial dilution is made in 96-well plates in 100% DMSO. Then, plates are further diluted 45-fold in M199 medium supplemented with 1% heat-inactivated FBS to obtain a intermediate work stock.

At day 1, RASFs are seeded in 96 well plates (flat bottom, tissue culture treated, Greiner) at a density of 3000 cells/well in complete synovial growth medium (Cell Applications). Day 5, the medium is completely removed from the cells, and replaced by 81 µL of M199 medium supplemented with 1% heat-inactivated FBS followed by addition of 10 µL compound out of the intermediate work stock. After an incubation period of 90 minutes, which allows the compounds to equilibrate and enter the cells, cells are stimulated with either TNF-α or 'complex trigger'. TNF-α trigger is added in a volume of 10 to obtain final concentration of 10 ng/mL. For that, TNF-α stock (PeproTech) at 10 µg/mL was diluted to 100 ng/mL TNF-a in M199 medium supplemented with 1% FBS. 'Complex trigger' mix is added in a volume of 20 µL to obtain a final concentration of 12.5%. For that, 'complex trigger' mix, is diluted to 80% with M199 medium supplemented with 1% FBS. After incubation for 48 hrs, 20 µL of the cell supernatant is then processed in the MMP1 ELISA as described above, delivering raw data (RLU: relative luminescence units). The following controls are included in the experiments, a maximal signal control, in which the cells are activated by TNF-α (or the complex trigger) but only the 0.2% DMSO vehicle (and thus no compound) is added. This control indicates the maximal level of MMP1 that can be achieved in the test. A minimal signal control is also included in these experiments. Here, cells are not triggered. This control returns the basal MMP1 levels produced by the RASFs. The percent inhibition of the MMP1 expression achieved by the compounds is then calculated based on the RLU data returned by the ELISA with following formula: [[(maximal MMP1 levels−minimal MMP1 levels)−(MMP1 level compound X at concentration Y−minimal MMP1 levels)]/(maximal MMP1 levels−minimal MMP1 levels)]×100. Based on these percent inhibition data obtained in at least two independent experiments for the compounds, compounds are ranked as inactive (−), active (+), more active (++) and strongly active (+++). See Table 6.

2.3 In Vitro TAK1 Kinase Assay

For assessing TAK1 inhibition, active TAK1-TAB1 fusion protein was used from Upstate (Cat. No, 14-600). Kinase reactions are set up in 96-well polypropylene plates in 25 µL containing 0.5 mU TAK1-TAB1 fusion protein, 5mM ATP, 0.01 µCi/µL [$^{33}$P]-γ-ATP, 0.1 mg/mL casein substrate in 1× reaction buffer containing 10 mM MOPS pH 7.0, 1 mM EDTA.

Starting from the compound master stocks (all at 10 mM concentration in 100% DMSO) a 3-fold serial dilution is made in 96-well plates in 100% DMSO. Plates are further diluted 66-fold in $H_2O$ containing 3.5% DMSO, to obtain an intermediate work stock with compounds at 5× the final assay concentration in 5% DMSO.

5 µL of the intermediate stock is transferred into V-bottom 96 well polypropylene plates and 11 µL of Enzyme mix is added. Enzyme mix is made by combining 5 µL 5× reaction buffer (40 mM MOPS pH 7.0, 1 mM EDTA), 5 µL casein (Sigma) diluted in $H_2O$ to 0.5 mg/mL and 1 µL of TAK1-TAB1 fusion protein that was prediluted to 0.5 mU/µL in 1× enzyme dilution buffer (20 mM MOPS pH 7.0, 0.1 mM EDTA, 0.01% Brij-35, 5% glycerol, 1 mM DTT, 1 mg/ml BSA).

The reactions are started by the addition of 9 µL of mixture containing ATP (20.83 uM) and [$^{33}$P]-γ-ATP (0.028 µCi/µL).

The assay is stopped 90 minutes after incubation at 30° C. by the addition of 25 µL phosphoric acid (150 mM). The label incorporated into the casein substrate is separated from labeled unincorporated ATP by filtration onto 96-well filter plates using a harvester device. After 6 washes with 75 mM phosphoric acid, the bottom of the filter plates are sealed, and incorporated label is quantified after addition of 40 µL scintillation fluid using TopCount. Percent inhibition is calculated relative to control reactions which do not contain inhibitor.

Based on these percent inhibition data obtained in at least two independent experiments for the compounds, compounds are ranked as inactive (−), active (+), more active (++) and strongly active (+++). See Table 6.

It should be understood that factors such as the differential cell penetration capacity of the various compounds can contribute to discrepancies between the activity of the compounds in the in vitro biochemical and cellular MMP assays.

Semi-Quantitative Score:

−>10001 nM

+5001-10000 nM

++1001-5000 nM

+++501-1000 nM

++++<500 nM

TABLE 6

| EXAMPLE # | NAME | REDUCTION MMP1/TNFa | Reduction MMP1/THP1 | POTENCY TAK1 (MAP3K7) |
|---|---|---|---|---|
| 1 | 4-[8-(4-Morpholin-4-yl-phenylamino)-[1,2,4]triazolo[1,5-a]pyridin-5-yl]-benzamide | +++ | − | − |
| 2 | [4-(4-Methyl-piperazin-1-yl)-phenyl]-[5-(1H-pyrazol-4-yl)-[1,2,4]triazolo[1,5-a]pyridin-8-yl]-amine | +++ | + | +++ |
| 3 | 4-[5-(1H-Pyrazol-4-yl)-[1,2,4]triazolo[1,5-a]pyridin-8-ylamino]-N-pyridin-3-ylmethyl-benzamide | +++ | ++ | +++ |
| 4 | 4-{8-[4-(4-Methyl-piperazin-1-yl)-phenylamino]-[1,2,4]triazolo[1,5-a]pyridin-5-yl}-1H-pyridin-2-one | +++ | ++ | +++ |
| 5 | 4-[5-(2-Oxo-1,2-dihydro-pyridin-4-y-1)-[1,2,4]triazolo[1,5-a]pyridin-8-ylamino]-N-pyridin-3-ylmethyl-benzamide | +++ | − | +++ |
| 6 | 2-Fluoro-4-{8-[4-(4-methyl-piperazin-1-yl)-phenylamino]-[1,2,4]triazolo[1,5-a]pyridin-5-yl}-benzamide | +++ | − | ++ |
| 7 | (4-Morpholin-4-yl-phenyl)-[5-(1H-pyrazol-4-yl)-[1,2,4]triazolo[1,5-a]pyridin-8-yl]-amine | +++ | + | +++ |
| 8 | [5-(5-Methyl-1H-pyrazol-4-yl)-[1,2,4]triazolo[1,5-a]pyridin-8-yl]-(4-morpholin-4-yl-phenyl)-amine | ++ | + | ++ |
| 9 | 4-[8-({3-fluoro-4-[(3R,5S)-3,4,5-trimethylpiperazin-1-yl]phenyl}amino)[1,2,4]triazolo[1,5-a]pyridin-5-yl]pyridin-2(1H)-one | ++ | | +++ |
| 10 | rel-4-[8-({4-[(2R,5S)-2,4,5-trimethylpiperazin-1-yl]phenyl}amino)[1,2,4]triazolo[1,5-a]pyridin-5-yl]pyridin-2(1H)-one | +++ | | ++++ |
| 11 | rel-4-[8-({3-fluoro-4-[(2R,5S)-2,4,5-trimethylpiperazin-1-yl]phenyl}amino)[1,2,4]triazolo[1,5-a]pyridin-5-yl]pyridin-2(1H)-one | ++ | | ++++ |
| 12 | 4-(8-{[4-(4-ethylpiperazin-1-yl)phenyl]amino}[1,2,4]triazolo[1,5-a]pyridin-5-yl)benzamide | ++++ | | ++++ |
| 13 | 4-(8-{[4-(4-propylpiperazin-1-yl)phenyl]amino}[1,2,4]triazolo[1,5-a]pyridin-5-yl)benzamide | − | | ++++ |
| 14 | 4-[8-({4-[4-(1-ethylpropyl)piperazin-1-yl]phenyl}amino)[1,2,4]triazolo[1,5-a]pyridin-5-yl]benzamide | − | | ++++ |
| 15 | 4-[8-({4-[4-(3-methylbutyl)piperazin-1-yl]phenyl}amino)[1,2,4]triazolo[1,5-a]pyridin-5-yl]benzamide | ++ | | ++++ |
| 16 | 4-(8-{[4-(4-cyclobutylpiperazin-1-yl)phenyl]amino}[1,2,4]triazolo[1,5-a]pyridin-5-yl)benzamide | + | | ++++ |
| 17 | 4-(8-{[4-(4-cyclohexylpiperazin-1-yl)phenyl]amino}[1,2,4]triazolo[1,5-a]pyridin-5-yl)benzamide | | | |
| 18 | 4-(8-{[4-(4-cyclopropylpiperazin-1-yl)phenyl]amino}[1,2,4]triazolo[1,5-a]pyridin-5-yl)benzamide | ++ | | ++ |
| 19 | 4-(8-{[4-(4-ethylpiperazin-1-yl)phenyl]amino}[1,2,4]triazolo[1,5-a]pyridin-5-yl)pyridin-2(1H)-one | ++ | | ++++ |
| 20 | 4-(8-{[4-(4-propylpiperazin-1-yl)phenyl]amino}[1,2,4]triazolo[1,5-a]pyridin-5-yl)pyridin-2(1H)-one | ++ | | ++++ |
| 21 | 4-[8-({4-[4-(1-ethylpropyl)piperazin-1-yl]phenyl}amino)[1,2,4]triazolo[1,5-a]pyridin-5-yl]pyridin-2(1H)-one | − | | ++++ |

TABLE 6-continued

| EXAMPLE # | NAME | REDUCTION MMP1/TNFa | Reduction MMP1/THP1 | POTENCY TAK1 (MAP3K7) |
|---|---|---|---|---|
| 22 | 4-[8-({4-[4-(3-methylbutyl)piperazin-1-yl]phenyl}amino)[1,2,4]triazolo[1,5-a]pyridin-5-yl]pyridin-2(1H)-one | ++ | | ++++ |
| 23 | 4-(8-{[4-(4-cyclopropylpiperazin-1-yl)phenyl]amino}[1,2,4]triazolo[1,5-a]pyridin-5-yl)pyridin-2(1H)-one | ++ | | ++++ |
| 24 | 4-(8-{[4-(4-cyclobutylpiperazin-1-yl)phenyl]amino}[1,2,4]triazolo[1,5-a]pyridin-5-yl)pyridin-2(1H)-one | ++ | | ++++ |
| 25 | 4-(8-{[4-(4-cyclohexylpiperazin-1-yl)phenyl]amino}[1,2,4]triazolo[1,5-a]pyridin-5-yl)pyridin-2(1H)-one | ++ | | ++++ |
| 26 | N-[4-(4-ethylpiperazin-1-yl)phenyl]-5-(2-methoxypyridin-4-yl)[1,2,4]triazolo[1,5-a]pyridin-8-amine | ++ | | − |
| 27 | 5-(2-methoxypyridin-4-yl)-N-[4-(4-propylpiperazin-1-yl)phenyl][1,2,4]triazolo[1,5-a]pyridin-8-amine | ++ | | − |
| 28 | N-{4-[4-(1-ethylpropyl)piperazin-1-yl]phenyl}-5-(2-methoxypyridin-4-yl)[1,2,4]triazolo[1,5-a]pyridin-8-amine | ++ | | − |
| 29 | 5-(2-methoxypyridin-4-yl)-N-{4-[4-(3-methylbutyl)piperazin-1-yl]phenyl}[1,2,4]triazolo[1,5-a]pyridin-8-amine | ++ | | − |
| 30 | N-[4-(4-cyclopropylpiperazin-1-yl)phenyl]-5-(2-methoxypyridin-4-yl)[1,2,4]triazolo[1,5-a]pyridin-8-amine | ++ | | − |
| 31 | N-[4-(4-cyclobutylpiperazin-1-yl)phenyl]-5-(2-methoxypyridin-4-yl)[1,2,4]triazolo[1,5-a]pyridin-8-amine | + | | − |
| 32 | N-[4-(4-cyclohexylpiperazin-1-yl)phenyl]-5-(2-methoxypyridin-4-yl)[1,2,4]triazolo[1,5-a]pyridin-8-amine | + | | − |
| 33 | 4-{8-[(4-piperazin-1-ylphenyl)amino][1,2,4]triazolo[1,5-a]pyridin-5-yl}pyridin-2(1H)-one | ++ | | ++++ |
| 34 | N-{4-[4-(1-ethylpropyl)piperazin-1-yl]phenyl}-5-(1H-pyrazol-4-yl)[1,2,4]triazolo[1,5-a]pyridin-8-amine | ++ | | ++++ |
| 35 | N-[4-(4-cyclobutylpiperazin-1-yl)phenyl]-5-(1H-pyrazol-4-yl)[1,2,4]triazolo[1,5-a]pyridin-8-amine | − | | ++++ |
| 36 | N-[4-(4-methylpiperazin-1-yl)phenyl]-5-(1H-pyrazol-4-yl)[1,2,4]triazolo[1,5-a]pyridin-8-amine | ++ | − | ++++ |
| 37 | 4-{[5-(1H-pyrazol-4-yl)[1,2,4]triazolo[1,5-a]pyridin-8-yl]amino}-N-(pyridin-3-ylmethyl)benzamide | ++++ | ++ | +++ |
| 38 | N-(4-morpholin-4-ylphenyl)-5-(1H-pyrazol-4-yl)[1,2,4]triazolo[1,5-a]pyridin-8-amine | | | |
| 39 | 5-(5-methyl-1H-pyrazol-4-yl)-N-(4-morpholin-4-ylphenyl)[1,2,4]triazolo[1,5-a]pyridin-8-amine | + | − | ++ |
| 40 | 4-(8-{[4-(4-methylpiperazin-1-yl)phenyl]amino}[1,2,4]triazolo[1,5-a]pyridin-5-yl)pyridin-2(1H)-one | ++ | ++ | ++++ |
| 41 | 4-{[5-(2-oxo-1,2-dihydropyridin-4-yl)[1,2,4]triazolo[1,5-a]pyridin-8-yl]amino}-N-(pyridin-3-ylmethyl)benzamide | ++ | − | ++ |

TABLE 6-continued

| EXAMPLE # | NAME | REDUCTION MMP1/TNFa | Reduction MMP1/THP1 | POTENCY TAK1 (MAP3K7) |
|---|---|---|---|---|
| 42 | 2-fluoro-4-(8-{[4-(4-methylpiperazin-1-yl)phenyl]amino}[1,2,4]triazolo[1,5-a]pyridin-5-yl)benzamide | +++ | − | ++ |
| 43 | 3-{8-[(4-morpholin-4-ylphenyl)amino][1,2,4]triazolo[1,5-a]pyridin-5-yl}benzamide | − | − | |
| 44 | 3-(8-{[4-(4-isopropylpiperazin-1-yl)phenyl]amino}[1,2,4]triazolo[1,5-a]pyridin-5-yl)benzamide | ++ | − | |
| 45 | 2-fluoro-5-{8-[(4-morpholin-4-ylphenyl)amino][1,2,4]triazolo[1,5-a]pyridin-5-yl}benzamide | − | − | |
| 46 | 2-fluoro-5-(8-{[4-(4-isopropylpiperazin-1-yl)phenyl]amino}[1,2,4]triazolo[1,5-a]pyridin-5-yl)benzamide | − | − | |
| 47 | 5-{8-[(4-morpholin-4-ylphenyl)amino][1,2,4]triazolo[1,5-a]pyridin-5-yl}pyrimidine-2,4(1H,3H)-dione | | | |
| 48 | 5-(1H-indol-4-yl)-N-(4-morpholin-4-ylphenyl)[1,2,4]triazolo[1,5-a]pyridin-8-amine | ++ | − | |
| 49 | 5-(1H-indol-4-yl)-N-[4-(4-isopropylpiperazin-1-yl)phenyl][1,2,4]triazolo[1,5-a]pyridin-8-amine | − | | ++ |
| 50 | 5-(1H-indol-5-yl)-N-(4-morpholin-4-ylphenyl)[1,2,4]triazolo[1,5-a]pyridin-8-amine | ++ | − | |
| 51 | 5-(1H-indol-5-yl)-N-[4-(4-isopropylpiperazin-1-yl)phenyl][1,2,4]triazolo[1,5-a]pyridin-8-amine | − | − | |
| 52 | 5-(1H-indol-6-yl)-N-(4-morpholin-4-ylphenyl)[1,2,4]triazolo[1,5-a]pyridin-8-amine | − | − | |
| 53 | 5-(1H-indol-6-yl)-N-[4-(4-isopropylpiperazin-1-yl)phenyl][1,2,4]triazolo[1,5-a]pyridin-8-amine | − | − | |
| 54 | 5-(2,4-dimethoxypyrimidin-5-yl)-N-(4-morpholin-4-ylphenyl)[1,2,4]triazolo[1,5-a]pyridin-8-amine | − | − | |
| 55 | 5-(8-{[4-(4-isopropylpiperazin-1-yl)phenyl]amino}[1,2,4]triazolo[1,5-a]pyridin-5-yl)pyrimidine-2,4(1H,3H)-dione | − | − | |
| 56 | 5-(2,4-dimethoxypyrimidin-5-yl)-N-[4-(4-isopropylpiperazin-1-yl)phenyl][1,2,4]triazolo[1,5-a]pyridin-8-amine | − | − | |
| 57 | 4-[8-({4-[(3R,5S)-3,4,5-trimethylpiperazin-1-yl]phenyl}amino)[1,2,4]triazolo[1,5-a]pyridin-5-yl]pyridin-2(1H)-one | ++ | | ++++ |

REFERENCES

Andreakos E, et al. (2003). Arthritis Rheum. 48: 1901-12.
Blonska M., Shambharkar P B., Kobayashi M., Zhang D., Sakurai H., Su B. and Lin X. (2005) J. Biol. Chem. 280: 43056-43063
Boutros M., Agaisse H. and Perrimon M. (2002) Dev. Cell 13: 711-722
Choy E H, Panayi G S. (2001). N Engl J Med. 344: 907-16.
Coussens L M, et al. (2002). Science 295: 2387-92.
Creemers E E, et al. (2001). Circ Res. 2001 89:201-10
Cunnane G, et al. (2001). Arthritis Rheum 44: 2263-74.
Dong W., Liu Y., Peng J., Chen L. Zou T. Xiao H., Liu Z., Li W., Bu Y. and Qi, Y. (2006) J. Biol. Chem. 281: 26029-26040
Edwards J. C. W., Szczepanski L., Szechinski J., Filipowicz-Sosnowska A., Emery P., Close D. R., Stevens R. M., Shaw T. (2004) N Engl J Med. 350:2572-2581.
EMBO J. 23:4780-91.
Firestein G S. (2003). Nature. 423:356-61.
Gapski R, et al. (2004). J Periodontol. 75:441-52.
Gomez-Reino J J, et al. (2003). Arthritis Rheum. 48: 2122-7.
Huang H., Ryu J., Ha J., Chang E J., Kim H J., Kim H M., Kitamura T., Lee Z H. And Kim H H. (2006) Cell Death Differ. 13: 1879-1891

Irie T., Muta T. and Takeshige K. (2000) FEBS Lett. 467: 160-164

Klatt A R., Klinger G., Neumuller O., Eidenmuller B., Wagner I., Achenbach T., Aigner T. and Bartnik E. (2006) Biomedicine & Pharmacotherapy 60: 55-61

Kremer J. M., Westhovens R., Leon M., Di Giorgio E., Alten R., Steinfeld S., Russell A., Dougados M., Emery P., Nuamah I. F., Williams G. R., Becker J.-C., Hagerty D. T., Moreland L. W. (2003) N Engl J Med. 349:1907-1915.

Lee D M, Weinblatt M E (2001). Lancet. 358: 903-11.

Mizukami J., Takaesu G., Akatsuka H., Sakurai H., Ninomiya-Tsuji J., Matsumoto K. and Sakurai N. (2002) Mol. Cell Biol. 22: 992-1000

New L, Jiang Y, Han J. (2003) Regulation of PRAK subcellular location by p38 MAP kinases. Mol Biol Cell. 14(6): 2603-16.

Ninomiya-Tsuji J., Kishimoto K., Hiyama A., Inoue J., Cao Z. and Matsumoto K. (1999) Nature 398: 252-256

O'Dell J R, Leff R, Paulsen G, Haire C, Mallek J, Eckhoff P J, Fernandez A, Blakely K, Wees S, Stoner J, Hadley S, Felt J, Palmer W, Waytz P, Churchill M, Klassen L, Moore G. (2002) Arthritis Rheum. 46:1164-70.

O'Dell J R. (2004) Therapeutic strategies for rheumatoid arthritis. N Engl J Med. 350(25):2591-602.

Reif S, Somech R, Brazovski E, Reich R, Belson A, Konikoff F M, Kessler A. (2005) Digestion. 71:124-130.

Rosenberg G A. (2002). Glia. 39:279-91.

Sakurai H., Miyoshi H., Toriumi W. and Sugita T. (1999) J. Biol. Chem. 274: 10641-10648

Sato S., Sanjo H., Takeda K., Ninomiya-Tsuji J., Yamamoto M., Kawai T., Matsumoto K., Takeuchi O. and Akira S. (2005) Nat. Immunol 6: 1087-1095

Schanstra J P, et al. (2002). J Clin Invest. 110:371-9.

Seternes O M, Mikalsen T, Johansen B, Michaelsen E, Armstrong C G, Morrice N A, Turgeon B, Meloche S, Moens U, Keyse S M. (2004) Activation of MK5/PRAK by the atypical MAP kinase ERK3 defines a novel signal transduction pathway.

Shi Y, Kotlyarov A, Laabeta K, Gruber A D, Butt E, Marcus K, Meyer H E, Friedrich A, Volk H D, Gaestel M. (2003) Elimination of protein kinase MK5/PRAK activity by targeted homologous recombination. Mol Cell Biol. 23:7732-41.

Shibuya H., Iwata H., Masuyama N., Gotoh Y., Yamaguchi K., Irie K., Matsumoto K., Nishida E. and Ueno N. (1998) EMBO J. 17: 1019-1028

Shim J H., Xiao C., Paschal A E., Bailey S T., Rao P., Hayden M S., Lee K Y., Bussey C., Steckel M., Tanaka N., Yamada G., Akira S., Matsumoto K., Ghosh S. (2005) Genes Dev. 19:2668-2681

Smolen J S, Steiner G. (2003). Nat Rev Drug Discov. 2: 473-88.

St Clair E W, van der Heijde D M, Smolen J S, Maini R N, Bathon J M, Emery P, Keystone E, Schiff M, Kalden J R, Wang B, Dewoody K, Weiss R, Baker D; (2004) Combination of infliximab and methotrexate therapy for early rheumatoid arthritis: a randomized, controlled trial. Arthritis Rheum. 50:3432-43.

Suzuki R, et al. (2004). Treat Respir Med. 3:17-27.

Vidal S., Khush R. S., Leulier F., Tzou P., Nakamura M. and Lemaitre B. (2001) Genes & Dev. 15: 1900-1912

Wan Y Y., Chi H., Xie M., Schneider M D. And Flavell R A. (2006) Nat. Immunol 7: 851-858

Yamagushi K., Shirakabe K., Shibuya H., Irie K., Oishi I., Ueno N., Taniguchi T., Nishida E. and Matsumoto K. (1995) Science 270: 2008-2011

Yang Y H, Morand E F, Getting S J, Paul-Clark M, Liu D L, Yona S, Hannon R, Buckingham J C, Perretti M and Flower R J (2004) Arthritis Rheum. 50:976-84.

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

We claim:

1. A compound according to formula III:

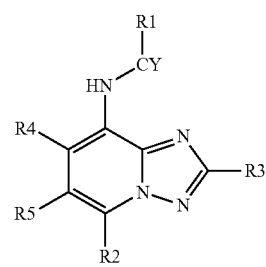

wherein $R^1$ represents H, halogen, $C_1$-$C_6$ alkyl, $C_1$-$C_6$ alkoxy, $CF_3$, CN, heterocycloalkyl, unsubstituted, or substituted with $C_1$-$C_6$ alkyl, $C_1$-$C_8$ cycloalkyl, $C_1$-$C_6$ alkoxy, $C_1$-$C_6$ haloalkyl, hydroxy, carboxamido, cyano, or halo, cycloalkyl, unsubstituted, or substituted with $C_1$-$C_6$ alkyl, $C_1$-$C_6$ alkoxy, $C_1$-$C_6$ haloalkyl, hydroxy, carboxamido, cyano, or halo, monocyclic aryl, unsubstituted, or substituted with $C_1$-$C_6$ alkyl, $C_1$-$C_6$ alkoxy, $C_1$-$C_6$ haloalkyl, hydroxy, carboxamido, cyano, or halo, monocyclic heteroaryl, unsubstituted, or substituted with $C_1$-$C_6$ alkyl, $C_1$-$C_6$ alkoxy, $C_1$-$C_6$ haloalkyl, hydroxy, carboxamido, cyano, or halo, C(=NH)NR$^a$R$^b$, —COR$^a$, —OR$^a$, —OC(O)—$C_1$-$C_6$ alkyl, (CH$_2$)$_a$COOR$^a$, C(O)NR$^a$R$^b$, S(O)$_2$(CH$_2$)$_a$N (R$^a$R$^b$), SR$^a$, SO(CH$_2$)$_a$NR$^a$R$^b$, S(O)$_2$—R$^a$, SOR$^a$, (CH$_2$)$_a$NR$^a$R$^b$, (CH$_2$)$_a$N(R$^a$)S(O)$_2$—$C_1$-$C_6$ alkyl, (CH$_2$)$_a$NR$^a$S(O)—$C_1$-$C_6$ alkyl, NR$^a$CO—R$^b$, and NH—CO—CO—OR$^a$; each of which may be optionally substituted with one or more groups selected from H, halogen, OH, $C_1$-$C_6$ alkyl, NH$_2$, N($C_1$-$C_6$ alkyl)($C_1$-$C_6$alkyl), heterocycloalkyl, cycloalkyl and $CF_3$;

R² is selected from heteroaryl, unsubstituted, or substituted with C₁-C₆ alkyl, C₁-C₆ alkoxy, C₁-C₆ haloalkyl, hydroxy, cyano, or halo;

R³, R⁴ and R⁵ are independently selected from H, OH, OMe, OC₂H₅, F, Cl, Me, Et, SO₂Me, CF₃ and OCF₃;

CY—R¹ is

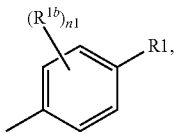

the subscript n1 is 1, 2, 3, or 4; and each $R^{1b}$ is independently selected from hydrogen, C₁-C₆ alkyl, C₁-C₆ alkoxy, C₁-C₆ haloalkyl, cyano, and halo;

$R^a$ and $R^b$ each independently represent H, halogen, C₁-C₆ alkyl, $(CH_2)_a$—N(C₁-C₆ alkyl)(C₁-C₆-alkyl), $(CH_2)_a$-monocyclic aryl, $(CH_2)_a$-monocyclic heteroaryl, $(CH_2)_a$-cycloalkyl or $(CH_2)_a$-heterocycloalkyl, each of which may be optionally substituted with one or more groups selected from halogen, —OH, C₁-C₆ alkyl, C₁-C₆ alkyl-O—C₁-C₆ alkyl, C₁-C₆ alkoxy, —NH₂, —NR$^c$R$^d$, NR$^c$COR$^d$, heteroaryl, heterocycloalkyl, or —CF₃; or $R^a$ and $R^b$ may, if joined to the same atom, represent together with the nitrogen to which they are attached a heterocycloalkyl group which may be optionally substituted with one or more groups selected from halogen, —OH, C₁-C₆ alkyl, C₁-C₆ alkoxy, —NH₂, —NR$^c$R$^d$, —NR$^c$COR$^d$, —C(O)NR$^c$R$^d$, aryl, aralkyl, heteroaryl, cycloalkyl or —CF₃;

$R^c$ and $R^d$ each independently represent H, or C₁-C₆ alkyl; and

"a" is 0, 1, 2 or 3;

or a pharmaceutically acceptable salt, stereoisomer, or tautomer thereof.

2. The compound according to claim 1, wherein each of R³, R⁴ and R⁵ is H.

3. A compound according to claim 1, wherein the compound is according to formula XXIIc, or XXIId:

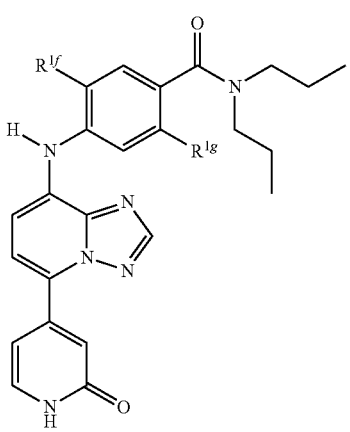

XXIIc

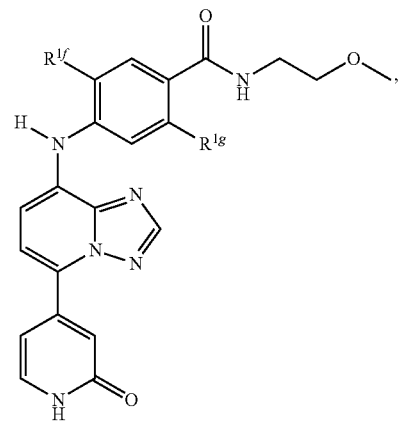

XXIId and wherein each $R^{1f}$ and $R^{1g}$ is hydrogen or F.

4. The compound according to claim 1, wherein the compound is according to formula IXa or IXb:

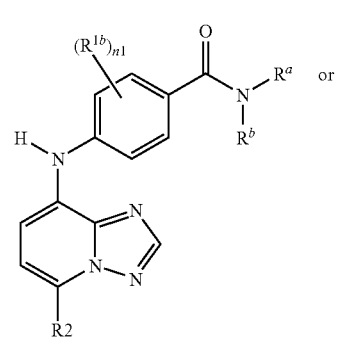

IXa

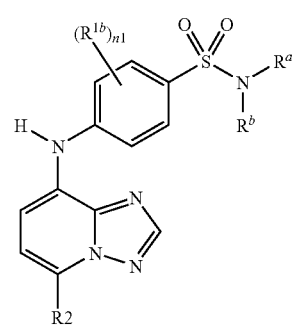

IXb and wherein $R^{1b}$ is independently selected from hydrogen, C₁-C₆ alkyl, C₁-C₆ alkoxy, C₁-C₆ haloalkyl, cyano, and halo; n1 is 1, 2, 3, or 4; R² is selected from heteroaryl, unsubstituted, or substituted with C₁-C₆ alkyl, C₁-C₆ alkoxy, C₁-C₆ haloalkyl, hydroxy, cyano, or halo; and $R^a$ and $R^b$ each independently represent H, halogen, C₁-C₆ alkyl, $(CH_2)_a$—N(C₁-C₆ alkyl)(C₁-C₆-alkyl), $(CH_2)_a$-monocyclic aryl, $(CH_2)_a$-monocyclic heteroaryl, $(CH_2)_a$-cycloalkyl or $(CH_2)_a$-heterocycloalkyl, each of which may be optionally substituted with one or more groups selected from halogen, —OH, C₁-C₆ alkyl, C₁-C₆ alkyl-O—C₁-C₆ alkyl, C₁-C₆ alkoxy, —NH₂, —NR$^c$R$^d$, NR$^c$COR$^d$, heteroaryl, heterocycloalkyl, or —CF₃; or $R^a$ and $R^b$ may, if joined to the same atom, represent together with the nitrogen to which they are attached a heterocycloalkyl group; which may be optionally substituted with one or more groups selected from halogen, —OH, $C_1$-$C_6$ alkyl, $C_1$-$C_6$ alkoxy, —$NH_2$, —$NR^cR^d$, —$NR^cCOR^d$, —$C(O)NR^cR^d$, aryl, aralkyl, heteroaryl, cycloalkyl or —$CF_3$; and "a" is 0, 1, 2, or 3.

5. A compound according to claim 4, wherein $R^a$ is H, and $R^b$ is Me, Et, Pr, i-Pr, t-Bu, i-Bu, i-pentyl, cyclopropyl, cyclobutyl, cyclopentyl, cyclohexyl, cyclopropylmethyl, phenyl, benzyl, or pyridylmethyl.

6. A pharmaceutical composition comprising a therapeutically effective amount of a compound according to claim 1, in admixture with a pharmaceutically acceptable carrier.

7. A compound according the following formula,

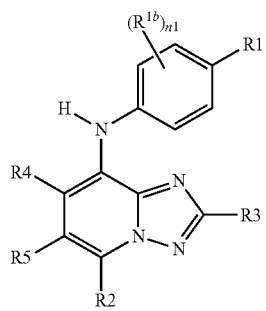

wherein
each $R^{1b}$ is independently selected from hydrogen, $C_1$-$C_6$ alkyl, $C_1$-$C_6$ alkoxy, $C_1$-$C_6$ haloalkyl, $OCF_3$, cyano, and halo; and the subscript n1 is 1, 2, 3, or 4;
$R^1$ is
-L-$R^{1a}$; and wherein
L is selected from a single bond, alkylene, —CO—, and —$SO_2$—;
$R^{1a}$ is selected from $C_1$-$C_6$ alkyl, $C_1$-$C_6$ haloalkyl,
cycloalkyl, unsubstituted, or substituted with $C_1$-$C_6$ alkyl, $C_1$-$C_6$ alkoxy, $C_1$-$C_6$ haloalkyl, hydroxy, $C_1$-$C_6$ haloalkoxy, CN, cycloalkyl, heterocycloalkyl, aryl, heteroaryl, aralkyl, cycloalkylalkyl, or halo,
aryl, unsubstituted, or substituted with $C_1$-$C_6$ alkyl, $C_1$-$C_6$ alkoxy, $C_1$-$C_6$ haloalkyl, hydroxy, cyano, or halo,
heterocycloalkyl unsubstituted, or substituted with $C_1$-$C_6$ alkyl, $C_1$-$C_6$ alkoxy, $C_1$-$C_6$ haloalkyl, hydroxy, $C_1$-$C_6$ haloalkoxy, CN, cycloalkyl, heterocycloalkyl, aryl, heteroaryl, aralkyl, cycloalkylalkyl, or halo,
heteroaryl, unsubstituted or substituted with $C_1$-$C_6$ alkyl, $C_1$-$C_6$ alkoxy, $C_1$-$C_6$ haloalkyl, hydroxy, cyano, or halo,
amino, unsubstituted or substituted with $C_1$-$C_6$ alkyl,
aralkyl, unsubstituted or substituted with $C_1$-$C_6$ alkyl, $C_1$-$C_6$ alkoxy, $C_1$-$C_6$ haloalkyl, hydroxy, or halo,
heteroarylalkyl, unsubstituted or substituted with $C_1$-$C_6$ alkyl, $C_1$-$C_6$ alkoxy, $C_1$-$C_6$ haloalkyl, hydroxy, or halo, and
aminoalkyl;

or $R^1$ is
-L-$R^{1a}$; and L is —CO—, and —$SO_2$—; and $R^{1a}$ is amino, alkylamino, dialkylamino, cycloalkylamino, cycloalkylalkylamino, arylamino, aralkylamino, heteroarylamino, and heteroarylalkylamino;
$R^2$ is selected from heteroaryl, unsubstituted, or substituted with $C_1$-$C_6$ alkyl, $C_1$-$C_6$ alkoxy, $C_1$-$C_6$ haloalkyl, hydroxy, carboxamido, cyano, or halo; and
$R^3$, $R^4$ and $R^5$ are independently selected from H, OH, OMe, $OC_2H_5$, F, Cl, Me, Et, $SO_2$Me, $CF_3$ and $OCF_3$.

8. The compound according to claim 7, wherein the compound is according to formula Va:

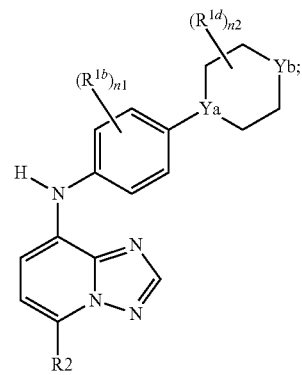

and wherein Ya is C or N; Yb is C—$R^{1c}$, O, S, $SO_2$ or N—$R^{1c}$; each $R^{1b}$ is independently selected from H, Me, Et, n-Pr, iso-Pr, Cl, F, CN, OMe, OEt, $CF_3$, $CF_2CF_3$ and $OCF_3$; $R^{1c}$ is selected from hydrogen, alkyl, cycloalkyl, and heterocycloalkyl; each $R^{1d}$ is independently selected from H, Me, Et, n-Pr, iso-Pr, Cl, F, CN, OMe, OEt, $CF_3$, $CF_2CF_3$ and $OCF_3$; and each n1 and n2 is independently 1 or 2.

9. The compound according to claim 7, wherein $R^2$ is heteroaryl.

10. The compound according to claim 7, wherein $R^2$ is selected from pyridyl, indolyl, isoindolyl, pyrrolyl, furanyl, thienyl, pyrazolyl, oxazolyl, and thiazolyl.

11. The compound according to claim 7, wherein $R^2$ is

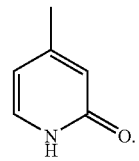

12. The compound according to claim 7, wherein $R^2$ is

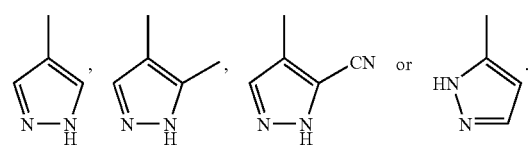

13. The compound according to claim 7, wherein the compound is according to formula XIVa, or XIVb:

XIVa

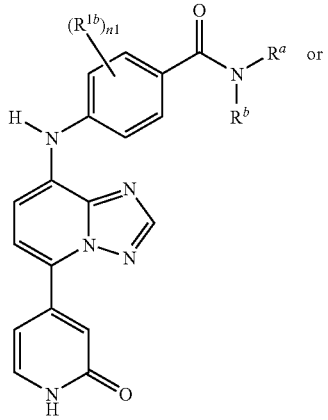

XIVb and wherein $R^{1b}$ is independently selected from hydrogen, $C_1$-$C_6$ alkyl, $C_1$-$C_6$ alkoxy, $C_1$-$C_6$ haloalkyl, cyano, and halo; n1 is 1, 2, 3, or 4; each $R^a$ and $R^b$ is independently selected from hydrogen, $C_1$-$C_6$ alkyl, aryl, aralkyl, heteroaryl, heteroarylalkyl, cycloalkyl, and cycloalkylalkyl.

14. The compound according to claim 13, wherein $R^a$ is H; and $R^b$ is Me, Et, Pr, i-Pr, t-Bu, i-Bu, i-pentyl, cyclopropyl, cyclobutyl, cyclopentyl, cyclohexyl, cyclopropylmethyl, phenyl, benzyl, or pyridylmethyl.

15. A compound according to claim 7, wherein L is —$CH_2$—.

16. A compound according to claim 7, wherein the compound is according to formula XIa, XId, XIg, or XIj

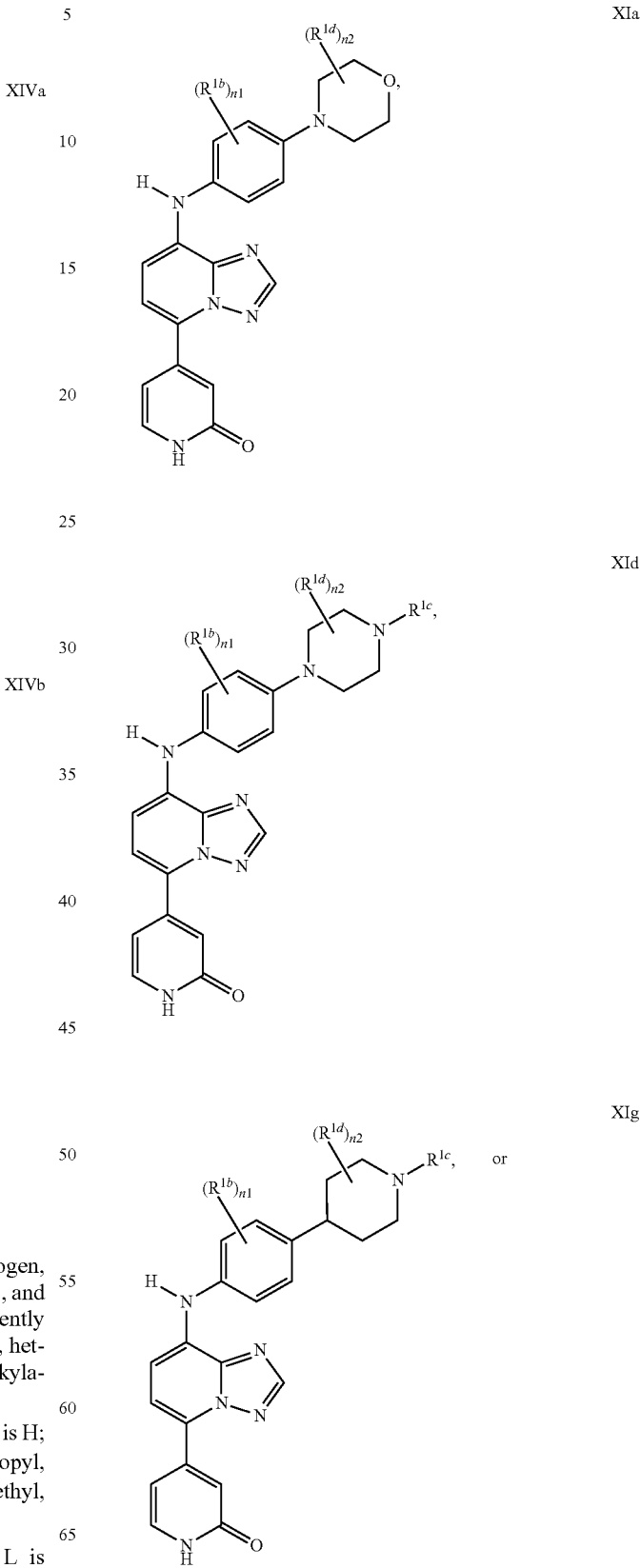

-continued

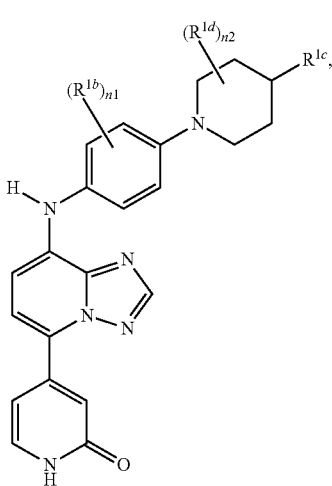

and wherein $R^{1c}$ is hydrogen, alkyl, cycloalkyl, or heterocycloalkyl; each $R^{1b}$ is independently selected from H, Me, Et, n-Pr, iso-Pr, Cl, F, CN, OMe, OEt, $CF_3$, $CF_2CF_3$ and $OCF_3$; each $R^{1d}$ is independently selected from H, Me, Et, n-Pr, iso-Pr, Cl, F, CN, OMe, OEt, $CF_3$, $CF_2CF_3$ and $OCF_3$; and each n1 and n2 is independently 1 or 2.

17. The compound according to claim 16 wherein each $R^{1d}$ is H.

18. The compound according to claim 7, wherein the compound is according to formula IIIa:

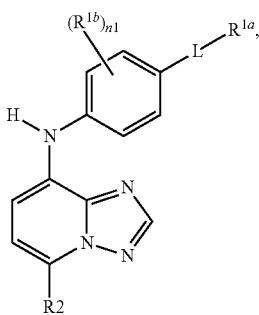

IIIa wherein L, $R^{1a}$, and $R^2$ are as defined in claim 13, the subscript n1 is 1, 2, 3, or 4;

and each $R^{1b}$ is independently selected from hydrogen, $C_1$-$C_6$ alkyl, $C_1$-$C_6$ alkoxy, $C_1$-$C_6$ haloalkyl, cyano, and halo.

19. The compound according to claim 18, wherein L is —CO— or $SO_2$—; and $R^{1a}$ is amino.

20. The compound according to claim 18, wherein L is —CO— or $SO_2$—; and $R^{1a}$ is alkylamino, dialkylamino, cycloalkylamino, arylamino, aralkylamino, heteroarylamino, and heteroarylalkylamino.

21. The compound according to claim 18, wherein L is a single bond.

22. The compound according to claim 18, wherein L is —CO—.

23. The compound according to claims 7 or 18, wherein L is a single bond, —CO—, $SO_2$, and —$(CH_2)_{m1}$—; the subscript m1 is 1, 2, 3, or 4; and $R^{1a}$ is

XIj and wherein the ring P is heterocycloalkyl, unsubstituted, or substituted with $C_1$-$C_6$ alkyl, $C_1$-$C_6$ alkoxy, $C_1$-$C_6$ haloalkyl, hydroxy, or halo.

24. A compound according to formula VIa, VId, VIg, or VIj:

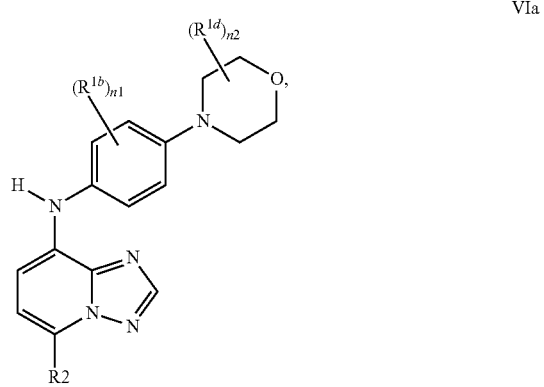

VIa

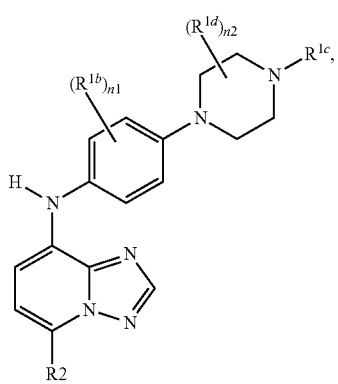

VId

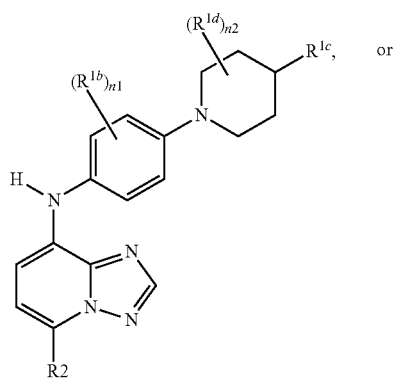

VIg or

VIj

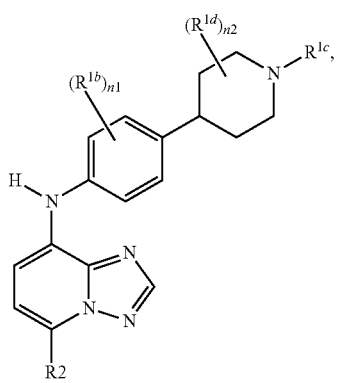

and wherein $R^2$ is selected from heteroaryl, unsubstituted, or substituted with $C_1$-$C_6$ alkyl, $C_1$-$C_6$ alkoxy, $C_1$-$C_6$ haloalkyl, hydroxy, carboxamido, cyano, or halo; each $R^{1b}$ is independently selected from H, Me, Et, n-Pr, iso-Pr, Cl, F, CN, OMe, OEt, $CF_3$, $CF_2CF_3$ and $OCF_3$; $R^{1c}$ is selected from hydrogen, alkyl, cycloalkyl, and heterocycloalkyl; each $R^{1d}$ is independently selected from H, Me, Et, n-Pr, iso-Pr, Cl, F, CN, OMe, OEt, $CF_3$, $CF_2CF_3$ and $OCF_3$; and each n1 and n2 is independently 1 or 2.

25. The compound according to any one of claims 24, 4 or 16, wherein each $R^{1b}$ is H.

26. The compound according to any one of claims 24, 4 or 16, wherein n1 is 1 or 2; and each $R^{1b}$ is independently selected from Me, Et, Pr, iso-Pr, Cl, F, CN, OMe, OEt, $CF_3$, $CF_2CF_3$ and $OCF_3$.

27. The compound according to any one of claims 24, 4 or 16, wherein n1 is 1 or 2; and each $R^{1b}$ is independently selected from Me, F, $C_1$ and $CF_3$.

28. The compound according to either of claims 24 or 16, with respect to compounds of formulae VId, VIg, VIj, XId, XIg, or XIj, wherein $R^{1c}$ is Me, Et, Pr, i-Pr, t-Bu, i-Bu, i-pentyl, cyclopropyl, cyclobutyl, cyclopentyl, cyclohexyl, cyclopropylmethyl, or piperidinyl.

29. A compound according to formula VIIIa, VIIId, or VIIIg:

VIIIa

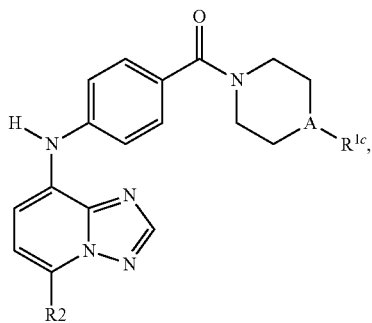

VIIId

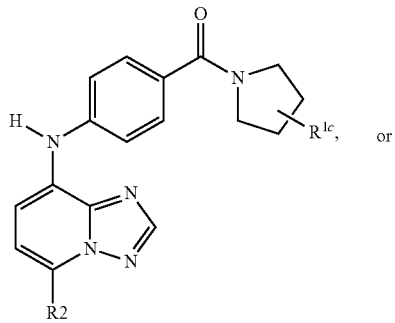

or

VIIIg

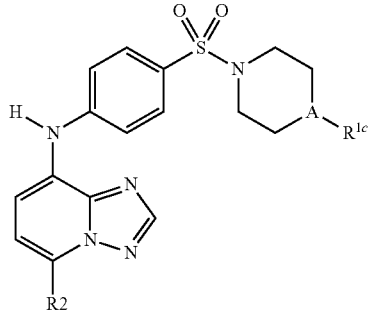

and wherein $R^2$ is selected from heteroaryl, unsubstituted, or substituted with $C_1$-$C_6$ alkyl, $C_1$-$C_6$ alkoxy, $C_1$-$C_6$ haloalkyl, hydroxy, carboxamido, cyano, or halo; A is CH or N; and $R^{1c}$ is hydrogen, unsubstituted alkyl, unsubstituted aryl, unsubstituted aralkyl, unsubstituted heteroaryl or unsubstituted cycloalkyl.

30. A compound according to formula XXIIa, XXIIb, or XXIIf:

XXIIa

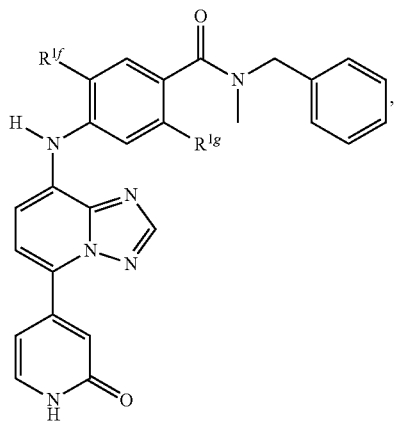

-continued

XXIIb

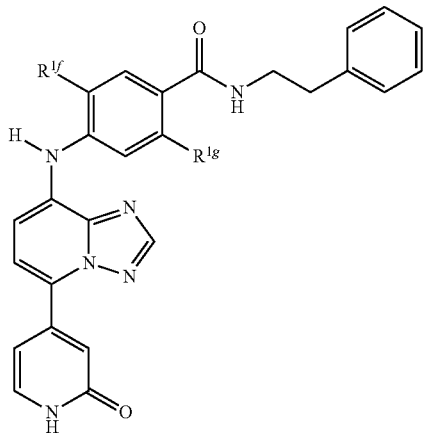

or

XXIIf

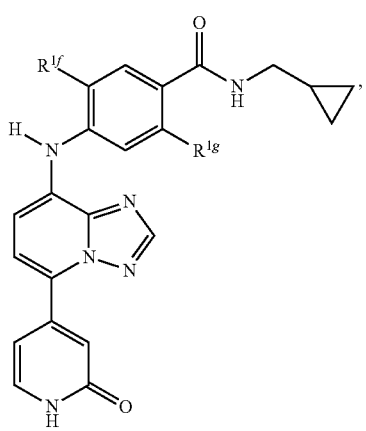

and wherein each $R^{1f}$ and $R^{1g}$ is hydrogen or F.

31. A compound according to formula XXIIe:

XXIIe

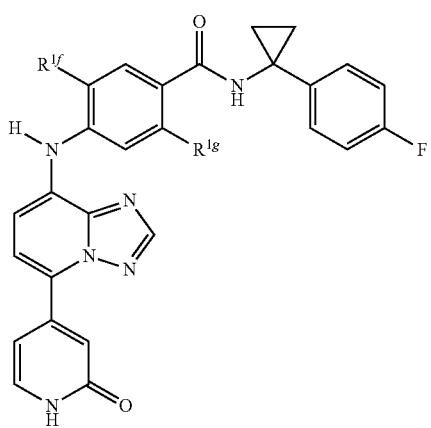

and wherein each $R^{1f}$ and $R^{1g}$ is hydrogen or F.

32. A compound selected from:
[4-(4-Methyl-piperazin-1-yl)-phenyl]-[5-(1H-pyrazol-4-yl)-[1,2,4]triazolo[1,5-a]pyridin-8-yl]-amine;
4-[5-(1H-Pyrazol-4-yl)-[1,2,4]triazolo[1,5-a]pyridin-8-ylamino]-N-pyridin-3-ylmethyl-benzamide;
4-{8-[4-(4-Methyl-piperazin-1-yl)-phenylamino]-[1,2,4]-triazolo[1,5-a]pyridin-5-yl}-1H-pyridin-2-one;
4-[5-(2-oxo-1,2-dihydro-pyridin-4-yl)-[1,2,4]triazolo[1,5-a]pyridin-8-ylamino]-N-pyridin-3-ylmethyl-benzamide;
(4-Morpholin-4-yl-phenyl)-[5-(1H-pyrazol-4-yl)-[1,2,4]-triazolo[1,5-a]pyridin-8-yl]-amine;
4-[8-({3-fluoro-4-[(3R,5S)-3,4,5-trimethylpiperazin-1-yl]phenyl}amino)[1,2,4]triazolo[1,5-a]pyridin-5-yl]pyridin-2(1H)-one;
4-[8-({4-[(2R,5S)-2,4,5-trimethylpiperazin-1-yl]phenyl}amino)[1,2,4]triazolo[1,5-a]pyridin-5-yl]pyridin-2(1H)-one;
4-[8-({3-fluoro-4-[(2R,5S)-2,4,5-trimethylpiperazin-1-yl]phenyl}amino)[1,2,4]triazolo[1,5-a]pyridin-5-yl]pyridin-2(1H)-one;
4-(8-{[4-(4-ethylpiperazin-1-yl)phenyl]amino}[1,2,4]triazolo[1,5-a]pyridin-5-yl)pyridin-2(1H)-one;
4-(8-{[4-(4-propylpiperazin-1-yl)phenyl]amino}[1,2,4]triazolo[1,5-a]pyridin-5-yl)pyridin-2(1H)-one;
4-(8-({4-[4-(1-ethylpropyl)piperazin-1-yl]phenyl}amino)[1,2,4]triazolo[1,5-a]pyridin-5-yl)pyridin-2(1H)-one;
4-[8-({4-[4-(3-methylbutyl)piperazin-1-yl]phenyl}amino)[1,2,4]triazolo[1,5-a]pyridin-5-yl]pyridin-2(1H)-one;
4-(8-{[4-(4-cyclopropylpiperazin-1-yl)phenyl]amino}[1,2,4]triazolo[1,5-a]pyridin-5-yl)pyridin-2(1H)-one;
4-(8-{[4-(4-cyclobutylpiperazin-1-yl)phenyl]amino}[1,2,4]triazolo[1,5-a]pyridin-5-yl)pyridin-2(1H)-one;
4-(8-{[4-(4-cyclohexylpiperazin-1-yl)phenyl]amino}[1,2,4]triazolo[1,5-a]pyridin-5-yl)pyridin-2(1H)-one;
N-[4-(4-ethylpiperazin-1-yl)phenyl]-5-(2-methoxypyridin-4-yl)[1,2,4]triazolo[1,5-a]pyridin-8-amine;
5-(2-methoxypyridin-4-yl)-N-[4-(4-propylpiperazin-1-yl)phenyl][1,2,4]triazolo[1,5-a]pyridin-8-amine;
N-{4-[4-(1-ethylpropyl)piperazin-1-yl]phenyl}-5-(2-methoxypyridin-4-yl)[1,2,4]-triazolo[1,5-a]pyridin-8-amine;
5-(2-methoxypyridin-4-yl)-N-{4-[4-(3-methylbutyl)piperazin-1-yl]phenyl}[1,2,4]triazolo[1,5-a]pyridin-8-amine;
N-[4-(4-cyclopropylpiperazin-1-yl)phenyl]-5-(2-methoxypyridin-4-yl)[1,2,4]-triazolo[1,5-a]pyridin-8-amine;
N-[4-(4-cyclobutylpiperazin-1-yl)phenyl]-5-(2-methoxypyridin-4-yl)[1,2,4]triazolo[1,5-a]pyridin-8-amine;
N-[4-(4-cyclohexylpiperazin-1-yl)phenyl]-5-(2-methoxypyridin-4-yl)[1,2,4]triazolo[1,5-a]pyridin-8-amine;
4-{8-[(4-piperazin-1-ylphenyl)amino][1,2,4]-triazolo[1,5-a]pyridin-5-yl}pyridin-2(1H)-one;
N-{4-[4-(1-ethylpropyl)piperazin-1-yl]phenyl}-5-(1H-pyrazol-4-yl)[1,2,4]triazolo[1,5-a]pyridin-8-amine;
N-[4-(4-cyclobutylpiperazin-1-yl)phenyl]-5-(1H-pyrazol-4-yl)[1,2,4]triazolo[1,5-a]pyridin-8-amine;
N-[4-(4-methylpiperazin-1-yl)phenyl]-5-(1H-pyrazol-4-yl)[1,2,4]triazolo[1,5-a]pyridin-8-amine;
4-{[5-(1H-pyrazol-4-yl)[1,2,4]-triazolo[1,5-a]pyridin-8-yl]amino}-N-(pyridin-3-ylmethyl)benzamide;
N-(4-morpholin-4-ylphenyl)-5-(1H-pyrazol-4-yl)[1,2,4]triazolo[1,5-a]pyridin-8-amine;
5-(5-methyl-1H-pyrazol-4-yl)-N-(4-morpholin-4-ylphenyl)[1,2,4]-triazolo[1,5-a]pyridin-8-amine;
4-(8-{[4-(4-methylpiperazin-1-yl)phenyl]amino}[1,2,4]triazolo[1,5-a]pyridin-5-yl)pyridin-2(1H)-one;
4-{[5-(2-oxo-1,2-dihydropyridin-4-yl)-[1,2,4]-triazolo[1,5-a]pyridin-8-yl]amino}-N-(pyridin-3-ylmethyl)benzamide;
5-{8-[(4-morpholin-4-ylphenyl)amino][1,2,4]triazolo[1,5-a]pyridin-5-yl}pyrimidine-2,4(1H,3H)-dione;

5-(1H-indol-4-yl)-N-(4-morpholin-4-ylphenyl)[1,2,4]-triazolo[1,5-a]pyridin-8-amine;
5-(1H-indol-4-yl)-N-[4-(4-isopropylpiperazin-1-yl)phenyl][1,2,4]triazolo[1,5-a]pyridin-8-amine;
5-(1H-indol-5-yl)-N-(4-morpholin-4-ylphenyl)[1,2,4]triazolo[1,5-a]pyridin-8-amine;
5-(1H-indol-5-yl)-N-[4-(4-isopropylpiperazin-1-yl)phenyl][1,2,4]-triazolo[1,5-a]pyridin-8-amine;
5-(1H-indol-6-yl)-N-(4-morpholin-4-ylphenyl)[1,2,4]triazolo[1,5-a]pyridin-8-amine;
5-(1H-indol-6-yl)-N-[4-(4-isopropylpiperazin-1-yl)phenyl][1,2,4]triazolo[1,5-a]pyridin-8-amine;
5-(2,4-dimethoxypyrimidin-5-yl)-N-(4-morpholin-4-ylphenyl)[1,2,4]-triazolo[1,5-a]pyridin-8-amine;
5-(8-{[4-(4-isopropylpiperazin-1-yl)phenyl]amino}[1,2,4]triazolo[1,5-a]pyridin-5-yl)pyrimidine-2,4(1H,3H)-dione;
5-(2,4-dimethoxypyrimidin-5-yl)-N-[4-(4-isopropylpiperazin-1-yl)phenyl][1,2,4]triazolo[1,5-a]pyridin-8-amine;
4-[8-({4-[(3R,5S)-3,4,5-trimethylpiperazin-1-yl]phenyl}amino)[1,2,4]triazolo[1,5-a]pyridin-5-yl]pyridin-2(1H)-one;
4-[8-({4-[cis-3,4,5-trimethylpiperazin-1-yl]phenyl}amino)[1,2,4]-triazolo[1,5-a]pyridin-5-yl]pyridin-2(1H)-one;
4-[8-({3-fluoro-4-[cis-3,4,5-trimethylpiperazin-1-yl]phenyl}amino)[1,2,4]triazolo[1,5-a]pyridin-5-yl]pyridin-2(1H)-one;
racemic-4-[8-({4-[trans-2,4,5-trimethylpiperazin-1-yl]phenyl}amino)[1,2,4]triazolo[1,5-a]pyridin-5-yl]pyridin-2(1H)-one; and
racemic-4-[8-({3-fluoro-4-[trans-2,4,5-trimethylpiperazin-1-yl]phenyl}amino)[1,2,4]-triazolo[1,5-a]pyridin-5-yl]pyridin-2(1H)-one.

\* \* \* \* \*